US012570644B2

(12) United States Patent
Jin

(10) Patent No.: US 12,570,644 B2
(45) Date of Patent: Mar. 10, 2026

(54) LIGHT EMITTING DEVICE AND AMINE COMPOUND FOR THE SAME

(71) Applicant: Samsung Display Co., Ltd., Yongin-si (KR)

(72) Inventor: Xiulan Jin, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 802 days.

(21) Appl. No.: 17/380,569

(22) Filed: Jul. 20, 2021

(65) Prior Publication Data

US 2022/0190255 A1 Jun. 16, 2022

(30) Foreign Application Priority Data

Dec. 8, 2020 (KR) ........................ 10-2020-0170692

(51) Int. Cl.
*H01L 51/00* (2006.01)
*C07D 209/86* (2006.01)
(Continued)

(52) U.S. Cl.
CPC ......... *C07D 409/12* (2013.01); *C07D 209/86* (2013.01); *C07D 405/12* (2013.01);
(Continued)

(58) Field of Classification Search
None
See application file for complete search history.

(56) References Cited

U.S. PATENT DOCUMENTS 9,843,005 B2 12/2017 Miyata
9,887,366 B2 2/2018 Cho et al.
(Continued)

FOREIGN PATENT DOCUMENTS

CN 111747905 A 10/2020
JP 2004071550 A * 3/2004
(Continued)

OTHER PUBLICATIONS

Search Report dated Jul. 25, 2025 from the Office Action for Chinese Application No. 202111482783.8 issued Jul. 29, 2025. 9 pages. (see p. 8-9, categorizing the cited references).

*Primary Examiner* — Tae H Yoon
(74) *Attorney, Agent, or Firm* — Lerner David LLP

(57) ABSTRACT

Provided is a light emitting device that includes a first electrode, a second electrode disposed on the first electrode, and at least one functional layer disposed between the first electrode and the second electrode. The at least one functional layer includes an amine compound represented by Formula 1 below, thereby exhibiting high luminous efficiency and improved service life characteristics.

[Formula 1]

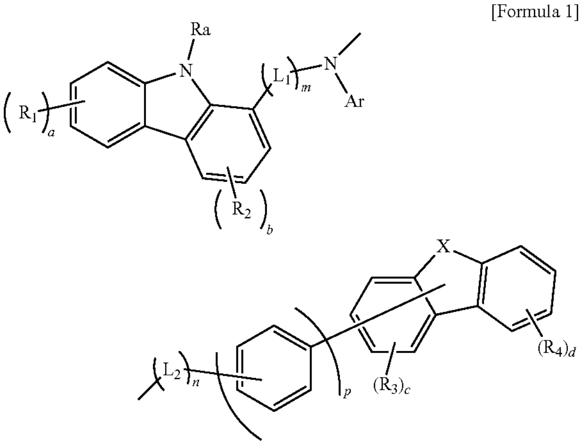

7 Claims, 6 Drawing Sheets

(51) Int. Cl.

| | |
|---|---|
| ***C07D 405/12*** | (2006.01) |
| ***C07D 409/12*** | (2006.01) |
| ***C07D 409/14*** | (2006.01) |
| ***C09K 11/06*** | (2006.01) |
| ***H10K 85/60*** | (2023.01) |
| *H10K 50/11* | (2023.01) |
| *H10K 50/15* | (2023.01) |
| *H10K 50/17* | (2023.01) |
| *H10K 50/18* | (2023.01) |
| *H10K 101/10* | (2023.01) |

(52) U.S. Cl.

CPC ............ *C07D 409/14* (2013.01); *C09K 11/06* (2013.01); *H10K 85/633* (2023.02); *H10K 85/636* (2023.02); *C07B 2200/05* (2013.01); *C09K 2211/1018* (2013.01); *H10K 50/11* (2023.02); *H10K 50/15* (2023.02); *H10K 50/17* (2023.02); *H10K 50/181* (2023.02); *H10K 85/615* (2023.02); *H10K 85/6572* (2023.02); *H10K 85/6574* (2023.02); *H10K 85/6576* (2023.02); *H10K 2101/10* (2023.02)

(56) References Cited

U.S. PATENT DOCUMENTS

| | | | |
|---|---|---|---|
| 10,134,999 | B2 | 11/2018 | Ito et al. |
| 10,246,441 | B2 | 4/2019 | Kato |
| 10,461,260 | B2 | 10/2019 | Hung et al. |
| 2015/0221874 | A1 | 8/2015 | Kim et al. |
| 2017/0179416 | A1 | 6/2017 | Lim et al. |
| 2018/0123051 | A1 | 5/2018 | Lee et al. |
| 2019/0131537 | A1 | 5/2019 | Kim et al. |
| 2019/0185460 | A1 | 6/2019 | Kim et al. |

FOREIGN PATENT DOCUMENTS

| | | | | |
|---|---|---|---|---|
| KR | 10-2006-0120040 | | * | 11/2006 |
| KR | 10-1446401 | | | 10/2014 |
| KR | 10-2016-0116219 | | | 10/2016 |
| KR | 10-2017-0075116 | | | 7/2017 |
| KR | 10-1786749 | | | 10/2017 |
| KR | 10-1847343 | | | 4/2018 |
| KR | 20180063707 | A | | 6/2018 |
| KR | 20180096458 | A | | 8/2018 |
| KR | 10-2022391 | | | 9/2019 |
| KR | 10-2050501 | | | 11/2019 |
| KR | 20200075566 | A | | 6/2020 |
| KR | 10-2020-0090091 | | | 7/2020 |
| WO | 2014/030872 | | | 2/2014 |
| WO | 2015/163584 | | | 10/2015 |
| WO | 2016/013735 | | | 1/2016 |
| WO | 2016/105123 | | | 6/2016 |
| WO | 2016/122150 | | | 8/2016 |
| WO | WO 2016/175533 | A2 | * | 11/2016 |
| WO | 2018/101490 | | | 6/2018 |
| WO | 2019/212290 | | | 11/2019 |
| WO | 2020130529 | A1 | | 6/2020 |
| WO | WO 2020/149521 | A1 | * | 7/2020 |

* cited by examiner

LIGHT EMITTING DEVICE AND AMINE COMPOUND FOR THE SAME

CROSS-REFERENCE TO RELATED APPLICATION(S)

This application claims priority to and benefits of Korean Patent Application No. 10-2020-0170692 under 35 U.S.C. § 119, filed on Dec. 8, 2020 in the Korean Intellectual Property Office, the entire contents of which are incorporated herein by reference.

BACKGROUND

1. Technical Field

The disclosure herein relates to an amine compound used in a hole transport region and a light emitting device including the same.

2. Description of the Related Art

Active development continues for an organic electroluminescence display as an image display apparatus. The organic electroluminescence display includes a so-called self-luminescent light emitting device in which holes and electrons respectively injected from a first electrode and a second electrode recombine in an emission layer, and thus a luminescent material of the emission layer emits light to implement display.

In the application of a light emitting device to a display apparatus, there is a demand for a light emitting device having a low driving voltage, a high luminous efficiency, and a long service life, and continuous development is required for materials for a light emitting device which stably achieves such characteristics.

In order to implement a light emitting device with high efficiency, development is being conducted on materials of a hole transport region for suppressing the diffusion of exciton energy of the emission layer.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

The disclosure provides a light emitting device exhibiting excellent luminous efficiency and long service life characteristics.

The disclosure also provides an amine compound which is a material for a light emitting device having high efficiency and long service life characteristics.

In an embodiment, an amine compound may be represented by Formula 1 below:

[Formula 1]

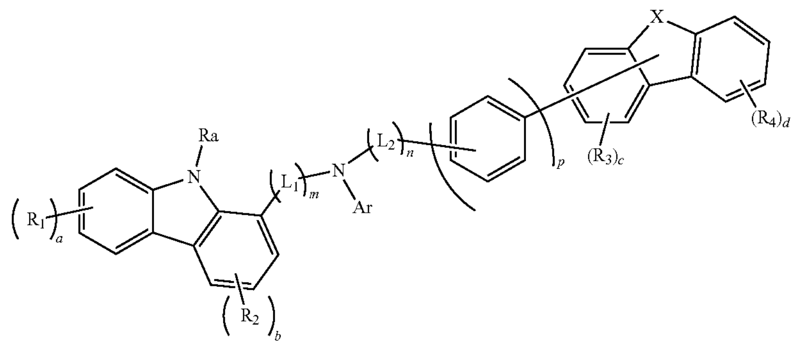

In Formula 1 above, $R_a$ may be an unsubstituted aryl group having 6 to 40 ring-forming carbon atoms, and X may be O, S, or N. In Formula 1, Ar may be a substituted or unsubstituted aryl group having 6 to 40 ring-forming carbon atoms, or a substituted or unsubstituted heteroaryl group having 2 to 40 ring-forming carbon atoms. In Formula 1, a, c, and d may each independently be an integer from 0 to 4, and b may be an integer from 0 to 3. In Formula 1, $R_1$ and $R_2$ may each independently be a hydrogen atom, a deuterium atom, a halogen atom, or a substituted or unsubstituted alkyl group having 1 to 20 carbon atoms, and $R_3$ and $R_4$ may each independently be a hydrogen atom, a deuterium atom, a halogen atom, a substituted or unsubstituted alkyl group having 1 to 20 carbon atoms, a substituted or unsubstituted alkenyl group having 2 to 20 carbon atoms, or a substituted or unsubstituted aryl group having 6 to 40 ring-forming carbon atoms, or are bonded to an adjacent group to form a ring. In Formula 1, m, n, and p may each independently be 0 or 1, and $L_2$ and $L_2$ may each independently be a direct linkage, a substituted or unsubstituted arylene group having 6 to 30 ring-forming carbon atoms, or a substituted or unsubstituted heteroarylene group having 5 to 30 ring-forming carbon atoms.

In an embodiment, Formula 1 above may be represented by Formula 1-1 or Formula 1-2 below:

[Formula 1-1]

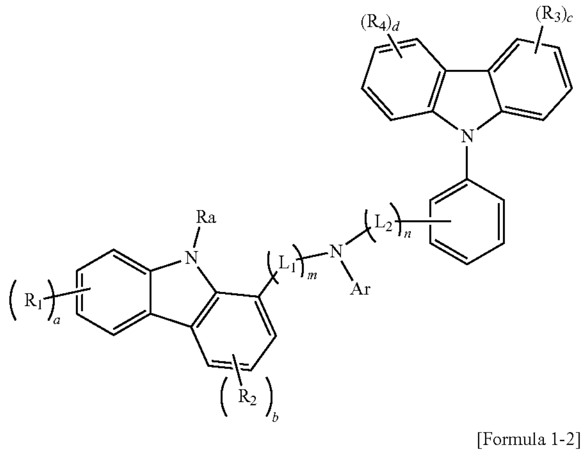

[Formula 1-2]

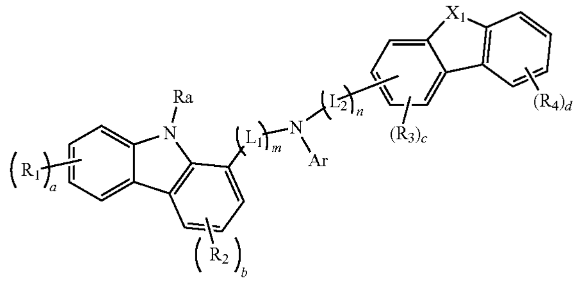

In Formula 1-2 above, $X_1$ may be O or S. In Formula 1-1 and Formula 1-2 above, Ra, Ar, a to d, $R_1$ to $R_4$, $L_1$, $L_2$, m, and n may be the same as defined in connection with Formula 1 above.

In an embodiment, when m is 1, $L_1$ may be a substituted or unsubstituted divalent phenyl group, or a substituted or unsubstituted divalent dibenzofuran group.

In an embodiment, when m is 1 and $L_1$ is a substituted or unsubstituted divalent phenyl group, Formula 1 may be represented by Formula 1A or Formula 1B below:

[Formula 1A]

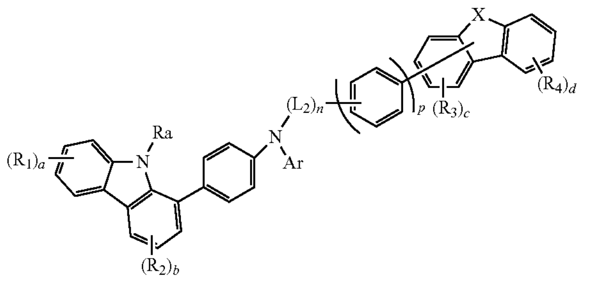

-continued

[Formula 1B]

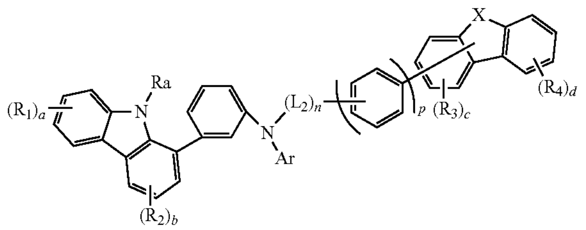

In Formula 1A and Formula 1B above, Ra, X, Ar, a to d, $R_1$ to $R_4$, $L_2$, n, and p may be the same as defined in connection with Formula 1 above.

In an embodiment, at least one of n and p may be 0.

In an embodiment, Ar may be a substituted or unsubstituted phenyl group, a substituted or unsubstituted naphthyl group, a substituted or unsubstituted biphenyl group, a substituted or unsubstituted phenanthrene group, a substituted or unsubstituted terphenyl group, a substituted or unsubstituted quaterphenyl group, a substituted or unsubstituted carbazole group, a substituted or unsubstituted dibenzofuran group, a substituted or unsubstituted dibenzothiophene group, a substituted or unsubstituted benzo naphtho furan group, or a substituted or unsubstituted benzo naphtho thiophene group.

In an embodiment, $R_a$ may be an unsubstituted phenyl group.

In an embodiment, at least one of $R_1$ to $R_4$ may be a deuterium atom, or Ar may be substituted with at least one deuterium atom.

In an embodiment, a light emitting device may include a first electrode, a second electrode disposed on the first electrode, and at least one functional layer disposed between the first electrode and the second electrode and including the amine compound of an embodiment represented by Formula 1.

In an embodiment, the at least one functional layer may include an emission layer, a hole transport region disposed between the first electrode and the emission layer, and an electron transport region disposed between the emission layer and the second electrode, and the hole transport region may include the amine compound of an embodiment.

In an embodiment, the hole transport region may include at least one of a hole injection layer, a hole transport layer, and an electron blocking layer, and at least one of the hole injection layer, the hole transport layer, and the electron blocking layer may include the amine compound of an embodiment.

In an embodiment, the emission layer may include a compound represented by Formula E-1 below:

[Formula E-1]

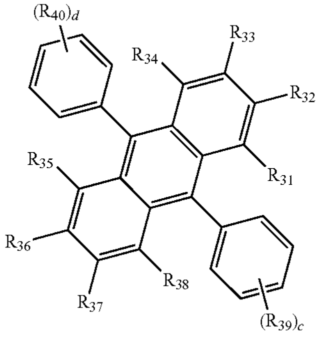

In Formula E-1, c and d may each independently be an integer from 0 to 5, and $R_{31}$ to $R_{40}$ may each independently be a hydrogen atom, a deuterium atom, a halogen atom, a substituted or unsubstituted silyl group, a substituted or unsubstituted alkyl group having 1 to 20 carbon atoms, a substituted or unsubstituted alkenyl group having 2 to 20 carbon atoms, a substituted or unsubstituted oxy group, a substituted or unsubstituted thiol group, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In an embodiment, the emission layer may emit blue light or green light.

BRIEF DESCRIPTION OF THE DRAWINGS

The accompanying drawings are included to provide a further understanding of the embodiments and are incorporated in and constitute a part of this specification. The drawings illustrate embodiments of the disclosure and principles thereof. The above and other aspects and features of the disclosure will become more apparent by describing in detail embodiments thereof with reference to the attached drawings, in which.

DETAILED DESCRIPTION OF THE EMBODIMENTS

Figure 1:
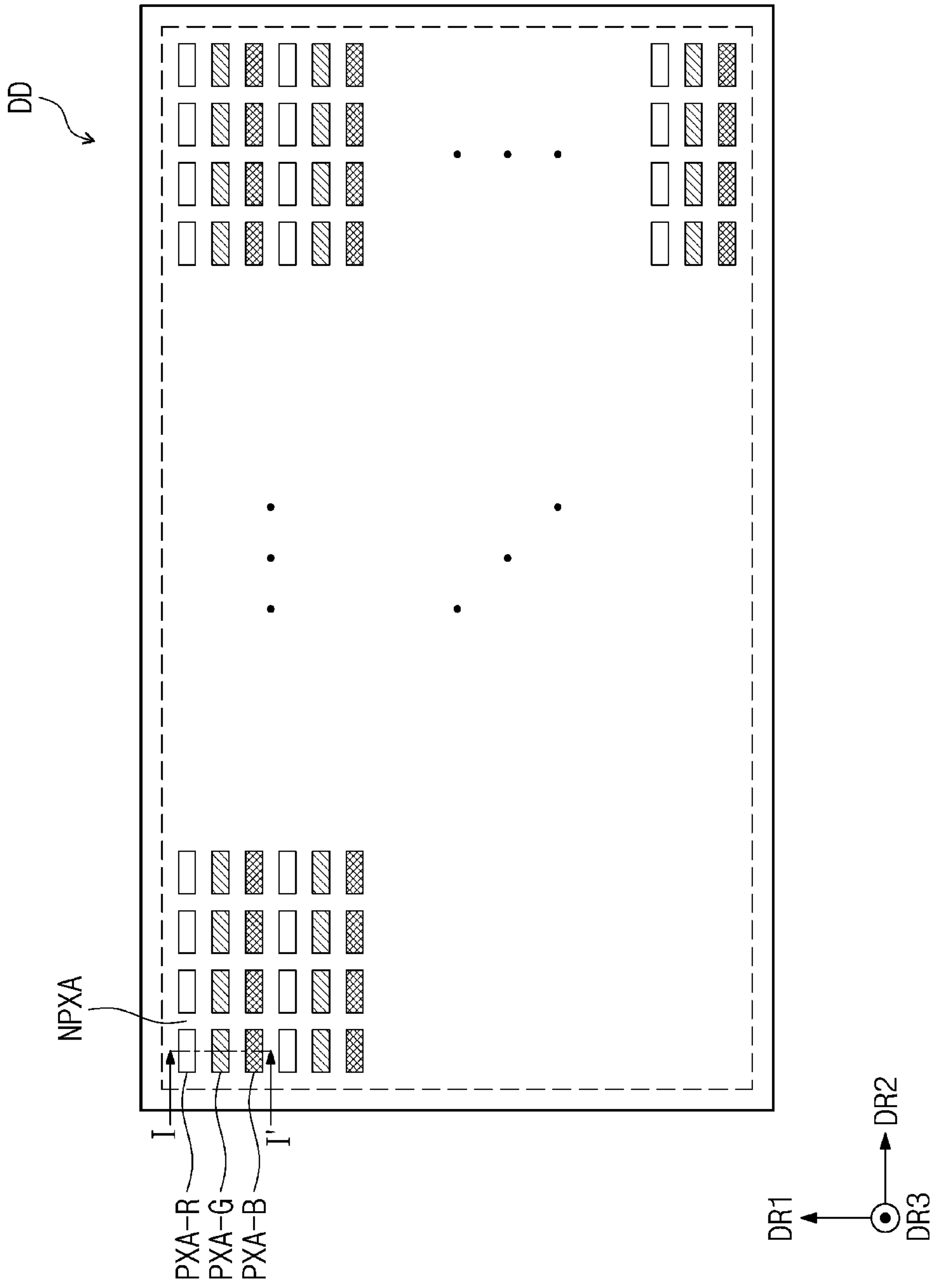
FIG. 1 is a plan view illustrating a display apparatus according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being “on”, “connected to”, or “coupled to” another element, it can be directly on, connected to, or coupled to the other element, or one or more intervening elements may be present therebetween. In a similar sense, when an element (or region, layer, part, etc.) is described as “covering” another element, it can directly cover the other element, or one or more intervening elements may be present therebetween.

In the description, when an element is “directly on,” “directly connected to,” or “directly coupled to” another element, there are no intervening elements present. For example, “directly on” may mean that two layers or two elements are disposed without an additional element such as an adhesion element therebetween.

As used herein, the expressions used in the singular such as “a,” “an,” and “the,” are intended to include the plural forms as well, unless the context clearly indicates otherwise.

As used herein, the term “and/or” includes any and all combinations of one or more of the associated listed items. For example, “A and/or B” may be understood to mean “A, B, or A and B.” The terms “and” and “or” may be used in the conjunctive or disjunctive sense and may be understood to be equivalent to “and/or”.

The term “at least one of” is intended to include the meaning of “at least one selected from” for the purpose of its meaning and interpretation. For example, “at least one of A and B” may be understood to mean “A, B, or A and B.” When preceding a list of elements, the term, “at least one of,” modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms “below”, “beneath”, “lower”, “above”, “upper”, or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned “below” or “beneath” another device may be placed “above” another device. Accordingly, the illustrative term “below” may include both the lower and upper positions. The device may also be oriented in other directions and thus the spatially relative terms may be interpreted differently depending on the orientations.

The terms “about” or “approximately” as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, “about” may mean within one or more standard deviations, or within ±20%, 10%, or 5% of the stated value.

It should be understood that the terms “comprises,” “comprising,” “includes,” “including,” “have,” “having,” “contains,” “containing,” and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

In the specification, the term “substituted or unsubstituted” may mean substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. Each of the substituents listed above may themselves be substituted or unsubstituted. For example, a biphenyl group may be interpreted as an aryl group or a phenyl group substituted with a phenyl group.

In the specification, the term “bonded to an adjacent group to form a ring” may mean a group that is bonded to an adjacent group to form a substituted or unsubstituted hydrocarbon ring, or a substituted or unsubstituted heterocycle. The hydrocarbon ring may include an aliphatic hydrocarbon ring and an aromatic hydrocarbon ring. The heterocycle may include an aliphatic heterocycle and an aromatic heterocycle. The hydrocarbon ring and the heterocycle may each be monocyclic or polycyclic. A ring formed adjacent groups being bonded to each other may be connected to another ring to form a spiro structure.

In the specification, the term “adjacent group” may mean a substituent substituted for an atom which is directly bonded to an atom substituted with a corresponding substituent, another substituent substituted for an atom which is substituted with a corresponding substituent, or a substituent sterically positioned at the nearest position to a corresponding substituent. For example, two methyl groups in 1,2-dimethylbenzene may be interpreted as “adjacent groups” to each other and two ethyl groups in 1,1-diethylcyclopentane may be interpreted as “adjacent groups” to each other. For example, two methyl groups in 4,5-dimethylphenanthrene may be interpreted as “adjacent groups” to each other.

In the specification, examples of a halogen atom may include a fluorine atom, a chlorine atom, a bromine atom, and an iodine atom.

In the specification, an alkyl group may be a linear, a branched, or a cyclic type. The number of carbon atoms in the alkyl group may be 1 to 50, 1 to 30, 1 to 20, 1 to 10, or 1 to 6. Examples of the alkyl group may include a methyl group, an ethyl group, an n-propyl group, an isopropyl group, an n-butyl group, an s-butyl group, a t-butyl group, an i-butyl group, a 2-ethylbutyl group, a 3,3-dimethylbutyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclohexyl group, a 4-t-butylcyclohexyl group, an n-heptyl group, a 1-methylheptyl group, a 2,2-dimethylheptyl group, a 2-ethylheptyl group, a 2-butylheptyl group, an n-octyl group, a t-octyl group, a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldocecyl group, a 2-octyldodecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-heneicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, etc., but embodiments are not limited thereto.

In the specification, a hydrocarbon ring group may be any functional group or substituent derived from an aliphatic hydrocarbon ring. The hydrocarbon ring group may be a saturated hydrocarbon ring group having 5 to 20 ring-forming carbon atoms.

In the specification, an aryl group may be any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexiphenyl group, a triphenylenyl group, a pyrenyl group, a benzofluoranthenyl group, a chrysenyl group, etc., but embodiments are not limited thereto.

In the specification, a fluorenyl group may be substituted, and two substituents may be bonded to each other to form a spiro structure. Examples of substituted fluorenyl groups are as follows. However, embodiments are not limited thereto.

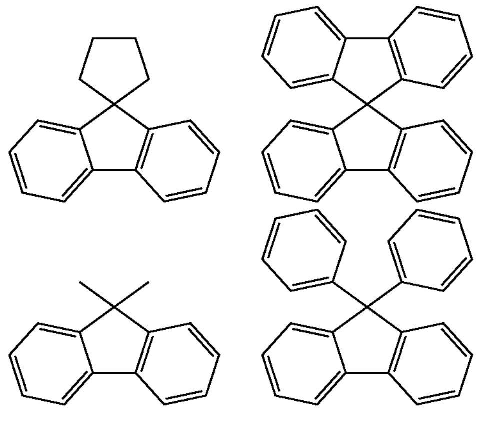

In the specification, a heterocyclic group may be any functional group or substituent derived from a ring including at least one of B, O, N, P, Si, and Se as a heteroatom. The heterocyclic group may include an aliphatic heterocyclic group and an aromatic heterocyclic group. The aromatic heterocyclic group may be a heteroaryl group. The aliphatic heterocycle and the aromatic heterocycle may each be monocyclic or polycyclic.

In the specification, a heterocyclic group may include at least one of B, O, N, P, Si, and S as a heteroatom. If the heterocyclic group includes two or more heteroatoms, the two or more heteroatoms may be the same as or different from each other. The heterocyclic group may be a monocyclic heterocyclic group or a polycyclic heterocyclic group and may be a heteroaryl group. The number of ring-forming carbon atoms in the heterocyclic group may be 2 to 30, 2 to 20, or 2 to 10.

In the specification, an aliphatic heterocyclic group may include at least one of B, O, N, P, Si, and S as a heteroatom. The number of ring-forming carbon atoms in the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., but embodiments are not limited thereto.

In the specification, a heteroaryl group may include at least one of B, O, N, P, Si, and S as a heteroatom. When the heteroaryl group contains two or more heteroatoms, the two or more heteroatoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Examples of the heteroaryl group may include a thiophene group, a furan group, a pyrrole group, an imidazole group, a triazole group, a pyridine group, a bipyridine group, a pyrimidine group, a triazine group, a triazole group, an acridyl group, a pyridazine group, a pyrazinyl group, a quinoline group, a quinazoline group, a quinoxaline group, a phenoxazine group, a phthalazine group, a pyrido pyrimidine group, a pyrido pyrazine group, a pyrazino pyrazine group, an isoquinoline group, an indole group, a carbazole group, an N-arylcarbazole group, an N-heteroarylcarbazole group, an N-alkylcarbazole group, a benzoxazole group, a benzoimidazole group, a benzothiazole group, a benzocarbazole group, a benzothiophene group, a dibenzothiophene group, a thienothiophene group, a benzofuran group, a phenanthroline group, a thiazole group, an isoxazole group, an oxazole group, an oxadiazole group, a thiadiazole group, a phenothiazine group, a dibenzosilole group, a dibenzofuran group, etc., but embodiments are not limited thereto.

In the specification, the above description with respect to the aryl group may be applied to an arylene group, except that the arylene group is a divalent group. The explanation on the aforementioned heteroaryl group may be applied to the heteroarylene group, except that the heteroarylene group is a divalent group.

In the specification, a silyl group may include an alkylsilyl group and an arylsilyl group. Examples of the silyl group may include trimethylsilyl, triethylsilyl, t-butyldimethylsilyl, propyldimethylsilyl, triphenylsilyl, diphenylsilyl, phenylsilyl, etc. However, embodiments are not limited thereto.

In the specification, the number of carbon atoms in an amino group is not specifically limited, but may be 1 to 30. The amino group may include an alkyl amino group, an aryl amino group, or a heteroaryl amino group. Examples of the amino group may include a methylamino group, a dimethylamino group, a phenylamino group, a diphenylamino group, a naphthylamino group, a 9-methyl-anthracenylamino group, a triphenylamino group, etc., but embodiments are not limited thereto.

In the specification, the number of ring-forming carbon atoms in a carbonyl group is not specifically limited, but may be 1 to 40, 1 to 30, or 1 to 20. For example, a carbonyl group may have one of the following structures, but embodiments are not limited thereto.

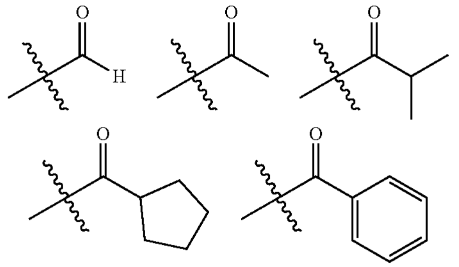

In the specification, the number of carbon atoms in a sulfinyl group and a sulfonyl group is not particularly limited, but may be 1 to 30. The sulfinyl group may include an alkyl sulfinyl group and an aryl sulfinyl group. The sulfonyl group may include an alkyl sulfonyl group and an aryl sulfonyl group.

In the specification, a thio group may include an alkylthio group and an arylthio group. The thio group may be a sulfur atom that is bonded to an alkyl group or an aryl group as defined above. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, but embodiments are not limited thereto.

In the specification, an oxy group may be an oxygen atom that is bonded to an alkyl group or an aryl group as defined above. The oxy group may include an alkoxy group and an aryl oxy group. The alkoxy group may be a linear chain, a branched chain, or a ring chain. The number of carbon atoms in an alkoxy group is not specifically limited, but may be, for example, 1 to 20 or 1 to 10. Examples of an oxy group may include methoxy, ethoxy, n-propoxy, isopropoxy, butoxy, pentyloxy, hexyloxy, octyloxy, nonyloxy, decyloxy, benzyloxy, etc., but embodiments are not limited thereto.

In the specification, a boron group may be a boron atom that is bonded to an alkyl group or an aryl group as defined above. The boron group may include an alkyl boron group and an aryl boron group. Examples of the boron group may include a trimethylboron group, a triethylboron group, a t-butyldimethylboron group, a triphenylboron group, a diphenylboron group, a phenylboron group, etc., but embodiments are not limited thereto.

In the specification, an alkenyl group may be linear or branched. The number of carbon atoms in an alkenyl group is not specifically limited, but may be 2 to 30, 2 to 20, or 2 to 10. Examples of an alkenyl group may include a vinyl group, a 1-butenyl group, a 1-pentenyl group, a 1,3-butadienyl aryl group, a styrenyl group, a styryl vinyl group, etc., but embodiments are not limited thereto.

In the specification, the number of carbon atoms in an amine group is not specifically limited, but may be 1 to 30.

The amine group may include an alkyl amine group and an aryl amine group. Examples of the amine group may include a methylamine group, a dimethylamine group, a phenylamine group, a diphenylamine group, a naphthylamine group, a 9-methyl-anthracenylamine group, etc., but embodiments are not limited thereto.

In the specification, an alkyl group within an alkylthio group, an alkylsulfoxy group, an alkylaryl group, an alkylamino group, an alkyl boron group, an alkyl silyl group, and an alkyl amine group may be the same as the examples of the alkyl group described above.

In the specification, an aryl group within an aryloxy group, an arylthio group, an arylsulfoxy group, an arylamino group, an arylboron group, an arylsilyl group, and an arylamine group may be the same as the examples of the aryl group described above.

In the specification, a direct linkage may be a single bond.

In the specification,

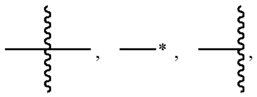

etc. each represent a binding site to a neighboring atom.

Hereinafter, embodiments will be described with reference to the accompanying drawings.

Figure 2:
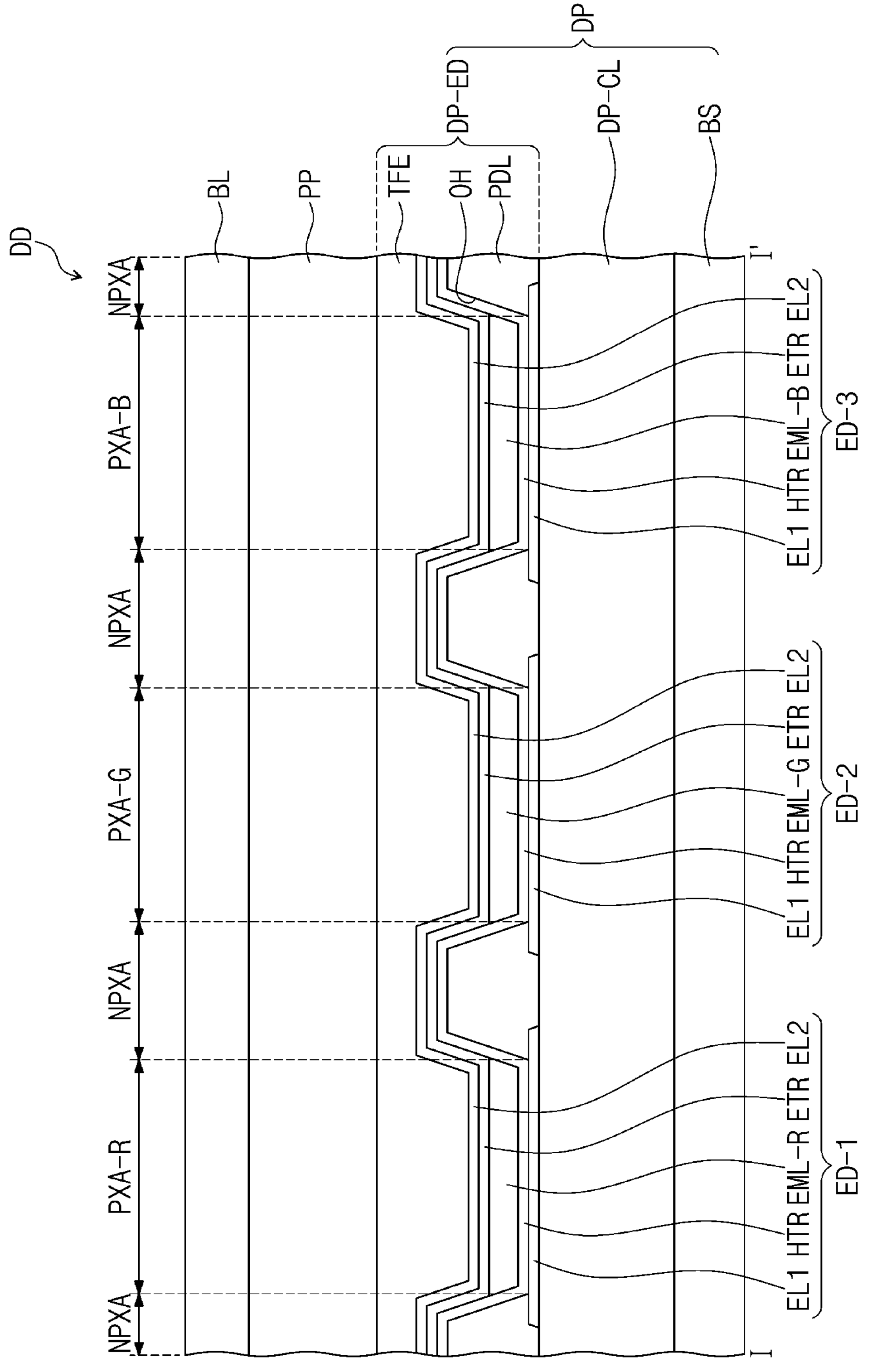
FIG. 2 is a schematic cross-sectional view of a display apparatus according to an embodiment.

FIG. 1 is a plan view illustrating an embodiment of a display apparatus DD. FIG. 2 is a schematic cross-sectional view of the display apparatus DD of the embodiment. FIG. 2 is a schematic cross-sectional view illustrating a part taken along line I-I' of FIG. 1.

The display apparatus DD may include a display panel DP and an optical layer PP disposed on the display panel DP. The display panel DP includes light emitting devices ED-1, ED-2, and ED-3. The display apparatus DD may include multiple light emitting devices ED-1, ED-2, and ED-3. The optical layer PP may be disposed on the display panel DP and may control light reflected from an external light at the display panel DP. The optical layer PP may include, for example, a polarization layer or a color filter layer. Although not shown in the drawing, in an embodiment, the optical layer PP may be omitted from the display apparatus DD.

A base substrate BL may be disposed on the optical layer PP. The base substrate BL may provide a base surface on which the optical layer PP disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawing, in an embodiment, the base substrate BL may be omitted.

The display apparatus DD according to an embodiment may further include a filling layer (not shown). The filling layer (not shown) may be disposed between a display device layer DP-ED and a base substrate BL. The filling layer (not shown) may include an organic material layer. The filling layer (not shown) may include at least one of an acrylic-based resin, a silicone-based resin, and an epoxy-based resin.

The display panel DP may include a base layer BS, a circuit layer DP-CL provided on the base layer BS, and a display element layer DP-ED. The display element layer DP-ED may include a pixel defining film PDL, the light emitting devices ED-1, ED-2, and ED-3 disposed between portions of the pixel defining film PDL, and an encapsulation layer TFE disposed on the light emitting devices ED-1, ED-2, and ED-3.

The base layer BS may provide a base surface on which the display element layer DP-ED is disposed. The base layer BS may be a glass substrate, a metal substrate, a plastic substrate, etc. However, embodiments are not limited thereto, and the base layer BS may include an inorganic layer, an organic layer, or a composite material layer.

In an embodiment, the circuit layer DP-CL is disposed on the base layer BS, and the circuit layer DP-CL may include transistors (not shown). Each of the transistors (not shown) may include a control electrode, an input electrode, and an output electrode. For example, the circuit layer DP-CL may include a switching transistor and a driving transistor in order to drive the light emitting devices ED-1, ED-2, and ED-3 of the display element layer DP-ED.

Each of the light emitting devices ED-1, ED-2, and ED-3 may have a structure of a light emitting device ED of an embodiment according to FIGS. 3 to 6, which will be described later. Each of the light emitting devices ED-1, ED-2, and ED-3 may include a first electrode EL1, a hole transport region HTR, emission layers EML-R, EML-G, and EML-B, an electron transport region ETR, and a second electrode EL2.

FIG. 2 illustrates an embodiment in which the emission layers EML-R, EML-G, and EML-B of the light emitting devices ED-1, ED-2, and ED-3 are disposed in the openings OH defined in the pixel defining film PDL, and the hole transport region HTR, the electron transport region ETR, and the second electrode EL2 are each provided as a common layer in the light emitting devices ED-1, ED-2, and ED-3. However, embodiments are not limited thereto. Although not shown in FIG. 2, in an embodiment, the hole transport region HTR and the electron transport region ETR may each be provided by being patterned inside the openings OH defined in the pixel defining film PDL. For example, the hole transport region HTR, the emission layers EML-R, EML-G, and EML-B, and the electron transport region ETR of the light emitting devices ED-1, ED-2, and ED-3 in an embodiment may each be provided by being patterned in an inkjet printing method.

An encapsulation layer TFE may cover the light emitting devices ED-1, ED-2, and ED-3. The encapsulation layer TFE may seal the display element layer DP-ED. The encapsulation layer TFE may be a thin film encapsulation layer. The encapsulation layer TFE may be formed by laminating one layer or multiple layers. The encapsulation layer TFE may include at least one insulation layer. The encapsulation layer TFE according to an embodiment may include at least one inorganic film (hereinafter, an encapsulation-inorganic film). The encapsulation layer TFE according to an embodiment may also include at least one organic film (hereinafter, an encapsulation-organic film) and at least one encapsulation-inorganic film.

The encapsulation-inorganic film may protect the display element layer DP-ED from moisture and/or oxygen, and the encapsulation-organic film may protect the display element layer DP-ED from foreign substances such as dust particles. The encapsulation-inorganic film may include silicon nitride, silicon oxynitride, silicon oxide, titanium oxide, aluminum oxide, or the like, but embodiments are not limited thereto. The encapsulation-organic film may include an acrylic-based compound, an epoxy-based compound, or the like. The encapsulation-organic film may include a photopolymerizable organic material, but embodiments are not particularly limited thereto.

The encapsulation layer TFE may be disposed on the second electrode EL2 and may be disposed to fill the openings OH.

Referring to FIGS. 1 and 2, the display apparatus DD may include a non-light emitting region NPXA and light emitting regions PXA-R, PXA-G, and PXA-B. The light emitting regions PXA-R, PXA-G, and PXA-B may each be a region which emits light generated from the light emitting devices ED-1, ED-2, and ED-3, respectively. The light emitting regions PXA-R, PXA-G, and PXA-B may be spaced apart from each other in a plane.

Each of the light emitting regions PXA-R, PXA-G, and PXA-B may be a region divided by a pixel defining film PDL. The non-light emitting regions NPXA may be regions between the adjacent light emitting regions PXA-R, PXA-G, and PXA-B, which correspond to portions of the pixel defining film PDL. In the specification, each of the light emitting regions PXA-R, PXA-G, and PXA-B may correspond to a pixel. The pixel defining film PDL may separate the light emitting devices ED-1, ED-2, and ED-3. The emission layers EML-R, EML-G, and EML-B of the light emitting devices ED-1, ED-2 and ED-3 may be disposed in openings OH defined by the pixel defining film PDL and separated from each other.

The light emitting regions PXA-R, PXA-G, and PXA-B may be divided into groups according to the color of light generated from the light emitting devices ED-1, ED-2, and ED-3. In the display apparatus DD of an embodiment shown in FIGS. 1 and 2, three light emitting regions PXA-R, PXA-G, and PXA-B which emit red light, green light, and blue light, respectively are illustrated. For example, the display apparatus DD of an embodiment may include the red light emitting region PXA-R, the green light emitting region PXA-G, and the blue light emitting region PXA-B which are separated from one another.

In the display apparatus DD according to an embodiment, the light emitting devices ED-1, ED-2, and ED-3 may emit light having wavelengths different from one another. For example, in an embodiment, the display apparatus DD may include a first light emitting device ED-1 that emits red light, a second light emitting device ED-2 that emits green light, and a third light emitting device ED-3 that emits blue light. For example, the red light emitting region PXA-R, the green light emitting region PXA-G, and the blue light emitting region PXA-B of the display apparatus DD may correspond to the first light emitting device ED-1, the second light emitting device ED-2, and the third light emitting device ED-3, respectively.

However, embodiments are not limited thereto, and the first to third light emitting devices ED-1, ED-2, and ED-3 may emit light in a same wavelength range or at least one light emitting device may emit light in a wavelength range different from the others. For example, the first to third light emitting devices ED-1, ED-2, and ED-3 may all emit blue light.

The light emitting regions PXA-R, PXA-G, and PXA-B in the display apparatus DD according to an embodiment may be arranged in a stripe form. Referring to FIG. 1, the red light emitting regions PXA-R, the green light emitting regions PXA-G, and the blue light emitting regions PXA-B each may be arranged along a second directional axis DR2. The red light emitting region PXA-R, the green light emitting region PXA-G, and the blue light emitting region PXA-B may be alternately arranged in this order along a first directional axis DR1.

FIGS. 1 and 2 illustrate that all the light emitting regions PXA-R, PXA-G, and PXA-B have similar area, but embodiments are not limited thereto, and the light emitting regions PXA-R, PXA-G, and PXA-B may have different areas from each other according to a wavelength range of the emitted light. The areas of the light emitting regions PXA-R, PXA-G, and PXA-B may be areas in a plan view that are defined by the first directional axis DR1 and the second directional axis DR2.

The arrangement of the light emitting regions PXA-R, PXA-G, and PXA-B is not limited to the feature illustrated in FIG. 1, and the order in which the red light emitting region PXA-R, the green light emitting region PXA-G, and the blue light emitting region PXA-B are arranged may be variously combined and provided according to characteristics of a display quality required in the display apparatus DD. For example, the arrangement form of the light emitting regions PXA-R, PXA-G, and PXA-B may be a PenTile® arrangement form or a diamond arrangement form.

The areas of the light emitting regions PXA-R, PXA-G, and PXA-B may be different from each other. For example, in an embodiment, an area of the green light emitting region PXA-G may be smaller than that of the blue light emitting region PXA-B, but embodiments are not limited thereto.

Hereinafter, FIGS. 3 to 6 are each a schematic cross-sectional view illustrating light emitting devices according to embodiments. The light emitting devices ED according to embodiments may each include a first electrode EL1, a second electrode EL2 facing and disposed on the first electrode EL1, and at least one functional layer disposed between the first electrode EL1 and the second electrode EL2. The at least one functional layer may include a hole transport region HTR, an emission layer EML, and an electron transport region ETR that are sequentially stacked. For example, each of the light emitting devices ED of embodiments may include a first electrode EL1, a hole transport region HTR, an emission layer EML, an electron transport region ETR, and a second electrode EL2 that are sequentially stacked.

Figure 3:
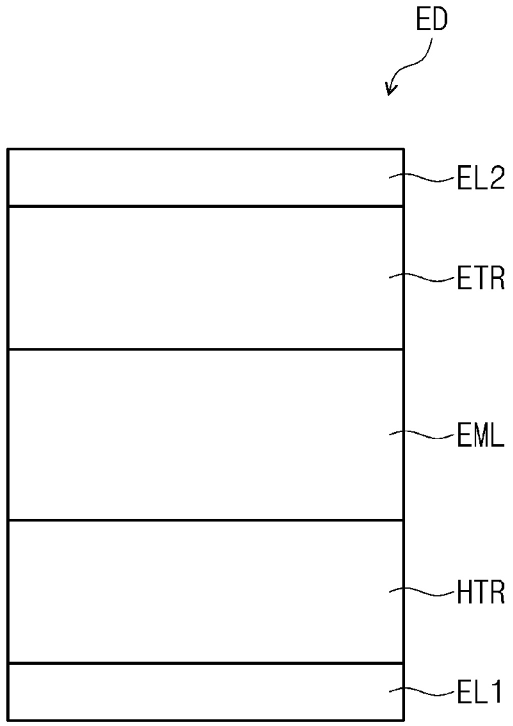
FIG. 3 is a schematic cross-sectional view illustrating a light emitting device according to an embodiment.
Figure 4:
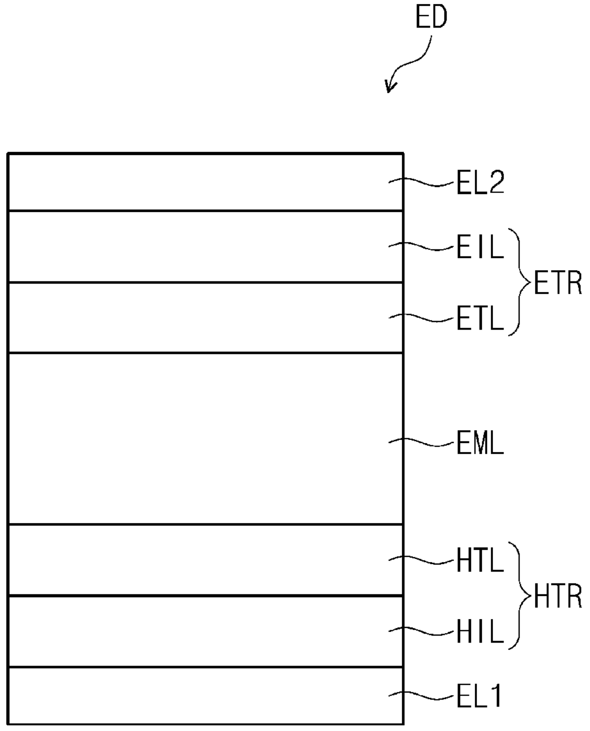
FIG. 4 is a schematic cross-sectional view illustrating a light emitting device according to an embodiment.
Figure 5:
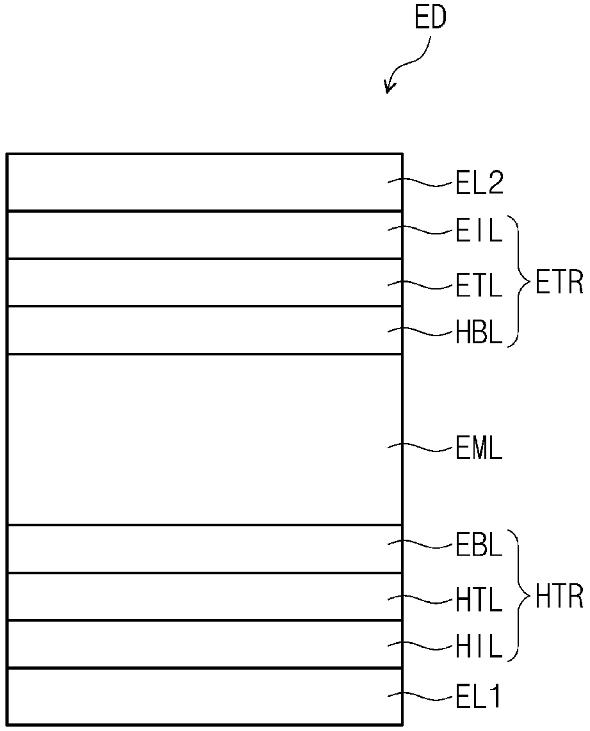
FIG. 5 is a schematic cross-sectional view illustrating a light emitting device according to an embodiment.
Figure 6:
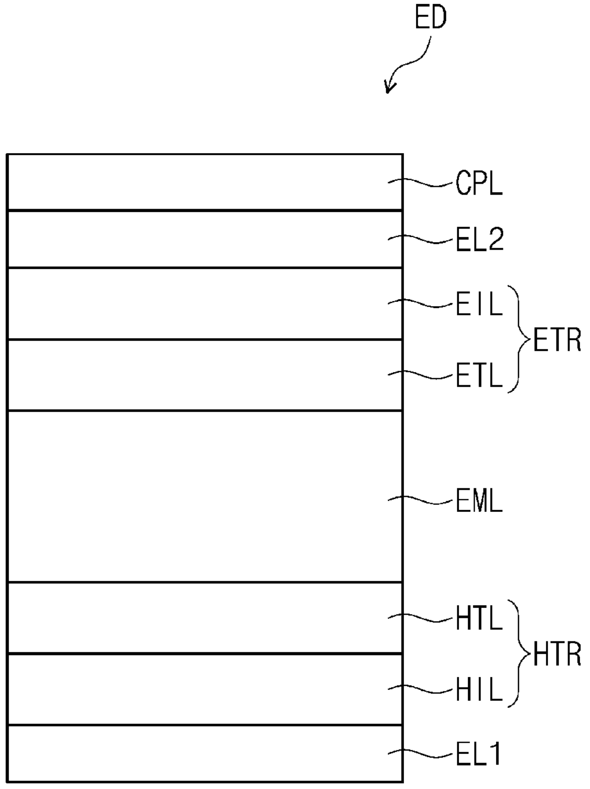
FIG. 6 is a schematic cross-sectional view illustrating a light emitting device according to an embodiment.

In comparison to FIG. 3, FIG. 4 illustrates a schematic cross-sectional view of a light emitting device ED of an embodiment, in which a hole transport region HTR includes a hole injection layer HIL and a hole transport layer HTL, and an electron transport region ETR includes an electron injection layer EIL and an electron transport layer ETL. In comparison to FIG. 3, FIG. 5 illustrates a schematic cross-sectional view of a light emitting device ED of an embodiment, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 4, FIG. 6 illustrates a schematic cross-sectional view of a light emitting device ED of an embodiment including a capping layer CPL disposed on a second electrode EL2.

The light emitting device ED of an embodiment may include the amine compound of an embodiment, which will be described below, in at least one functional layer of the hole transport region HTR, the emission layer EML, the electron transport region ETR, or the like. The emission layer EML in the light emitting device ED of an embodiment may emit blue light or green light.

In the light emitting device ED according to an embodiment, the first electrode EL1 has conductivity. The first electrode EL1 may be formed of a metal material, a metal alloy, or a conductive compound. The first electrode EL1 may be an anode or a cathode. However, embodiments are not limited thereto. In an embodiment, the first electrode EL1 may be a pixel electrode. The first electrode EL1 may be a transmissive electrode, a transflective electrode, or a reflective electrode. If the first electrode EL1 is a transmissive electrode, the first electrode EL1 may be formed using a transparent metal oxide such as indium tin oxide (ITO), indium zinc oxide (IZO), zinc oxide (ZnO), and indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF, Mo, Ti, W, a compound thereof, or a mixture thereof (e.g., a mixture of Ag and Mg, a mixture of LiF and Ca, a mixture of LiF and Al, etc.). In an embodiment, the first electrode EL1 may have a multilayer structure including a reflective film or a transflective film formed of the above-described materials, and a transparent conductive film formed of ITO, IZO, ZnO, ITZO, etc. For example, the first electrode EL1 may have a three-layer structure of ITO/Ag/ITO, but embodiments are not limited thereto. For example, in an embodiment, the first electrode EL1 may include the above-described metal materials, combinations of at least two metal materials of the above-described metal materials, oxides of the above-described metal materials, or the like. A thickness of the first electrode EL1 may be in a range of about 700 Å to about 10,000 Å. For example, the thickness of the first electrode EL1 may be in a range of about 1,000 Å to about 3,000 Å.

The hole transport region HTR may be provided on the first electrode EL1. The hole transport region HTR may include at least one of a hole injection layer HIL, a hole transport layer HTL, a buffer layer (not shown), an emission-auxiliary layer (not shown), and an electron blocking layer EBL. A thickness of the hole transport region HTR may be, for example, in a range of about 50 Å to about 15,000 Å.

The hole transport region HTR may have a single layer formed of a single material, a single layer formed of different materials, or a multilayer structure including layers formed of different materials.

For example, the hole transport region HTR may have a single layer structure of the hole injection layer HIL or the hole transport layer HTL, and may have a single layer structure formed of a hole injection material and a hole transport material. The hole transport region HTR may have a single layer structure formed of different materials, or a structure in which a hole injection layer HIL/hole transport layer HTL, a hole injection layer HIL/hole transport layer HTL/buffer layer (not shown), a hole injection layer HIL/buffer layer (not shown), a hole transport layer HTL/buffer layer (not shown), or a hole injection layer HIL/hole transport layer HTL/electron blocking layer EBL are stacked in order from the first electrode EL1, but embodiments are not limited thereto.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR in the light emitting device ED of an embodiment may include an amine compound represented by Formula 1 below. The hole transport region HTR in the light emitting device ED of an embodiment may include at least one of a hole injection layer HIL, a hole transport layer HTL, and an electron blocking layer EBL, and at least one of the hole injection layer HIL, the hole transport layer HTL, and the electron blocking layer EBL may include the amine compound represented by Formula 1 according to an embodiment. For example, the hole transport layer HTL in the light emitting device ED of an embodiment may include an amine compound represented by Formula 1 below:

[Formula 1]

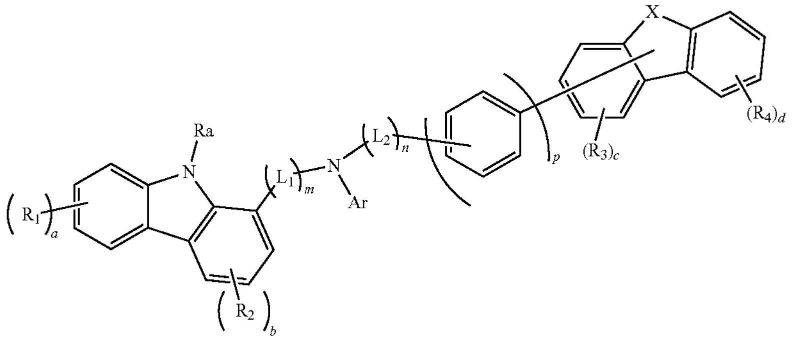

The amine compound represented by Formula 1 corresponds to a structure in which an amine derivative contains at least one dibenzoheterole group and a carbazole moiety represented by

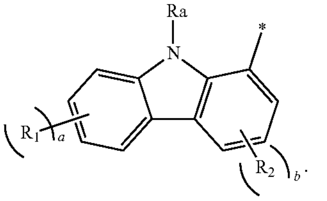

The amine group of the amine derivative containing at least one dibenzoheterole group may be directly or indirectly bonded to the carbazole moiety at an ortho-position to the N (nitrogen atom) of the carbazole moiety.

In Formula 1, $R_a$ may be an unsubstituted aryl group having 6 to 40 ring-forming carbon atoms. For example, in an embodiment, $R_a$ may be an unsubstituted phenyl group.

In Formula 1, a may be an integer from 0 to 4, and b may be an integer from 0 to 3. In an embodiment, $R_1$ and $R_2$ may each independently be a hydrogen atom, a deuterium atom, a halogen atom, a substituted or unsubstituted alkyl group having 1 to 20 carbon atoms. When a is 2 or greater, multiple $R_1$ groups may all be the same or at least one may be different from the rest. When b is 2 or greater, multiple $R_2$ groups may all be the same or at least one may be different from the rest. For example, multiple $R_1$ and multiple $R_2$ groups may all be hydrogen atoms. In an embodiment, at least one of $R_1$ and $R_2$ may be a deuterium atom. However, embodiments are not limited thereto.

In Formula 1, X may be O, S, or N. For example, the amine compound according to an embodiment may include a dibenzofuran group, a dibenzothiophene group, or a carbazole group as a dibenzoheterole group in the amine derivative.

In Formula 1, Ar may be a substituted or unsubstituted aryl group having 6 to 40 ring-forming carbon atoms, or a substituted or unsubstituted heteroaryl group having 2 to 40 ring-forming carbon atoms. For example, in an embodiment, Ar may be a substituted or unsubstituted phenyl group, a substituted or unsubstituted naphthyl group, a substituted or unsubstituted biphenyl group, a substituted or unsubstituted phenanthrene group, a substituted or unsubstituted terphenyl group, a substituted or unsubstituted quaterphenyl group, a substituted or unsubstituted carbazole group, a substituted or unsubstituted dibenzofuran group, a substituted or unsubstituted dibenzothiophene group, a substituted or unsubstituted benzo naphtho furan group, or a substituted or unsubstituted benzo naphtho thiophene group. However, the embodiments are not limited thereto.

In Formula 1, c and d may be each independently an integer from 0 to 4. $R_3$ and $R_4$ may each independently be a hydrogen atom, a deuterium atom, a halogen atom, a substituted or unsubstituted alkyl group having 1 to 20 carbon atoms, a substituted or unsubstituted alkenyl group having 2 to 20 carbon atoms, or a substituted or unsubstituted aryl group having 6 to 40 ring-forming carbon atoms, or may be bonded to an adjacent group to form a ring. For example, multiple $R_3$ groups or multiple $R_4$ groups may be bonded to each other to form a condensed ring with a dibenzoheterole group.

In an embodiment, $R_3$ and $R_4$ may each be hydrogen atoms, or at least one of $R_3$ and $R_4$ may be a deuterium atom. However, embodiments are not limited thereto.

In an embodiment, in the amine compound represented by Formula 1, at least one of $R_1$ to $R_4$ may be a deuterium atom, or Ar may be substituted with at least one deuterium atom.

In Formula 1, m, n, and p may each independently be 0 or 1. In Formula 1, $L_1$ and $L_2$ may each independently be a direct linkage, a substituted or unsubstituted arylene group having 6 to 30 ring-forming carbon atoms, or a substituted or unsubstituted heteroarylene group having 5 to 30 ring-forming carbon atoms except for carbazole.

In an embodiment, when m is 1, $L_1$ may be a substituted or unsubstituted divalent phenyl group, or a substituted or unsubstituted divalent dibenzofuran group. In the amine compound of an embodiment, when m is 0, the amine group of the amine derivative may be directly bonded to the carbazole moiety at an ortho-position to the nitrogen atom of the carbazole moiety. When m is 1, the amine group of the amine derivative may be indirectly bonded, via $L_1$ as a linker, to the carbazole moiety at an ortho-position to the nitrogen atom of the carbazole moiety.

In the amine compound represented by Formula 1 of an embodiment, at least one of n and p may be 0. For example, n may be 0 and p may be 1, or n may be 1 and p may be 0, or both n and p may be 0.

In an embodiment, when X is O or S, n and p may each be 0. For example, when X is O or S, the benzene ring of the dibenzoheterole group including X as a ring-forming atom may be directly bonded to the nitrogen atom of the amine.

In an embodiment, the amine compound represented by Formula 1 may be represented by Formula 1-1 or Formula 1-2 below:

[Formula 1-1]

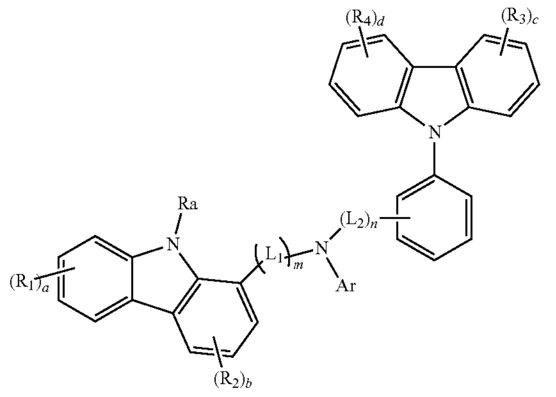

[Formula 1-2]

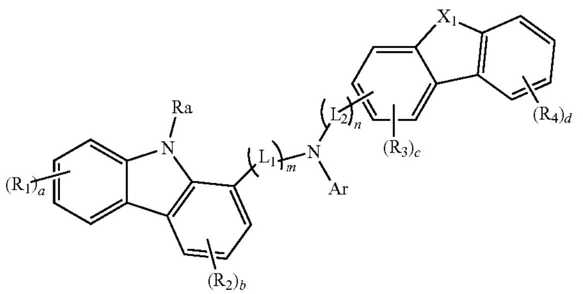

Formula 1-1 corresponds to the case where X is N in Formula 1. In the amine compound represented by Formula 1 of an embodiment, when X is N, p may be 1. In the amine compound represented by Formula 1-1, Ra, Ar, a to d, $R_1$ to $R_4$, $L_1$, $L_2$, m, and n may be the same as defined in connection with Formula 1 above.

Formula 1-2 corresponds to the case where p is 0 in Formula 1 as described above. In the amine compound represented by Formula 1-2, $X_1$ may be O or S. In the amine compound represented by Formula 1-2, Ra, Ar, a to d, $R_1$ to $R_4$, $L_1$, $L_2$, m, and n may be the same as defined in connection with Formula 1 above.

In an embodiment, when m is 1 and $L_1$ is a substituted or unsubstituted divalent phenyl group, Formula 1 may be represented by Formula 1A or Formula 1B below:

[Formula 1A]

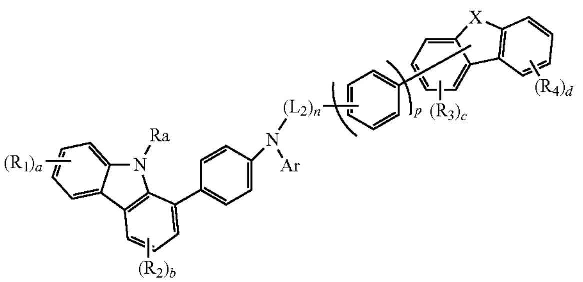

-continued

[Formula 1B]

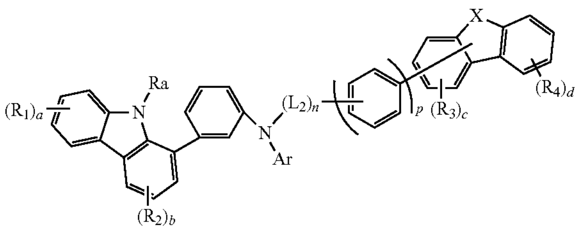

In the amine compound of an embodiment, when $L_1$ is a phenylene linker, the carbazole moiety may be bonded to the phenylene linker at a para-position to the amine group of the amine derivative as in the case of Formula 1A, or the carbazole moiety may be bonded to the phenylene linker at a meta-position to the amine group of the amine derivative as in the case of Formula 1B. In Formula 1A and Formula 1B, Ra, X, Ar, a to d, $R_1$ to $R_4$, $L_2$, n, and p may be the same as defined in connection with Formula 1 above.

In an embodiment, in the amine compound represented by Formula 1, when m is 1, $L_1$ may be an unsubstituted divalent dibenzofuran group.

In an embodiment, the amine compound represented by Formula 1 may be any one selected from Compound Group 1 below. The hole transport region HTR of the light emitting device ED of an embodiment may include at least one among the amine compounds disclosed in Compound Group 1 below:

[Compound Group 1]

1

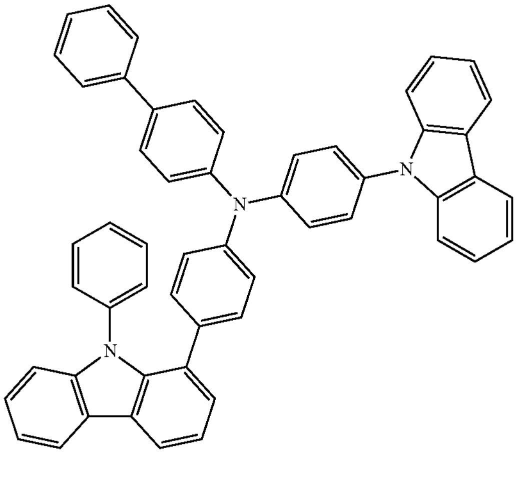

-continued

2

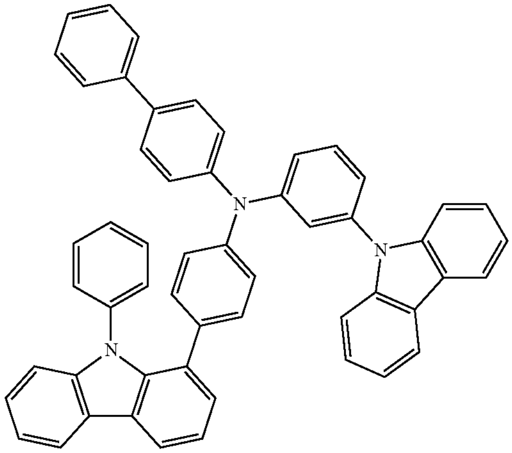

3

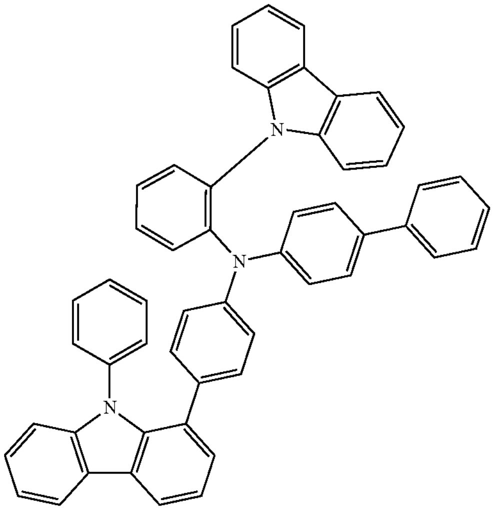

4

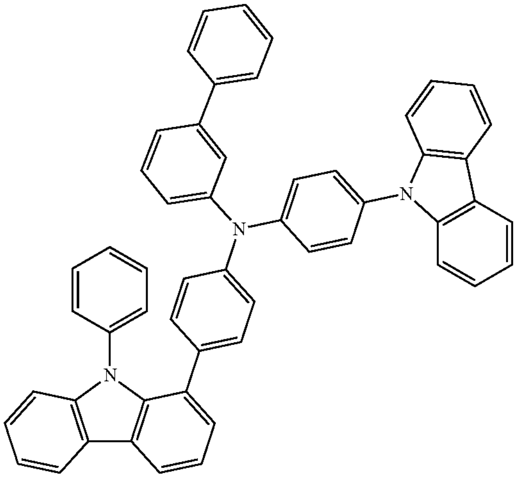

-continued
5
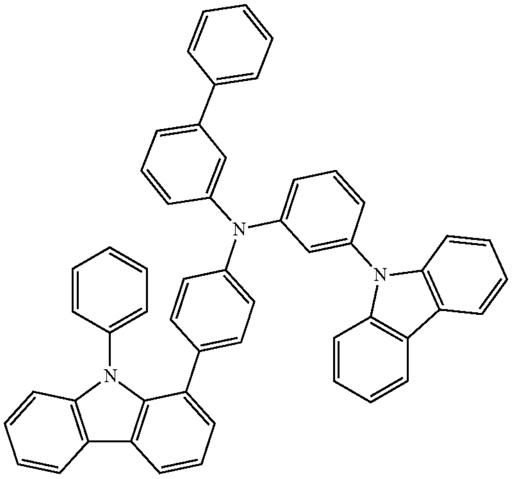
6
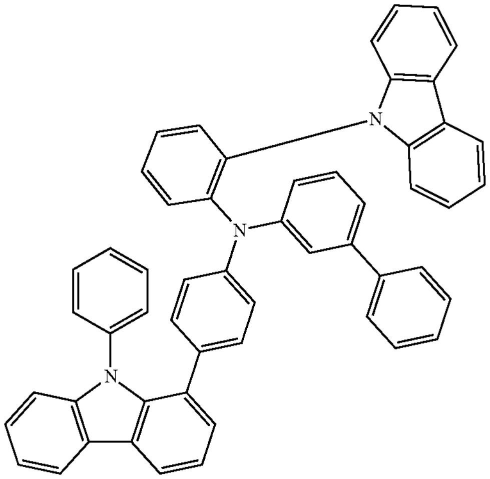
7
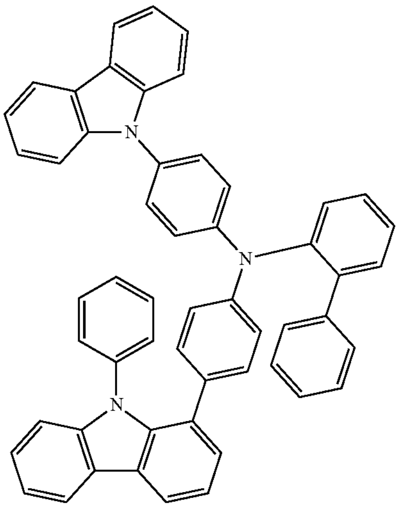
-continued
8
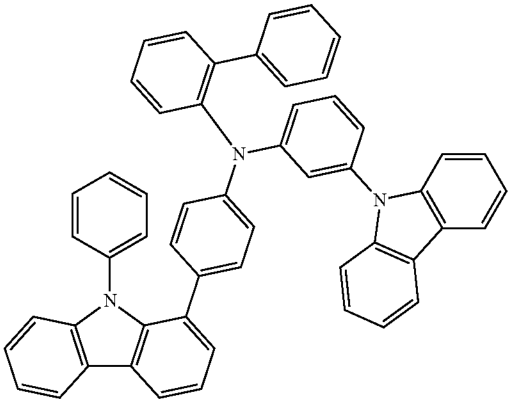
9
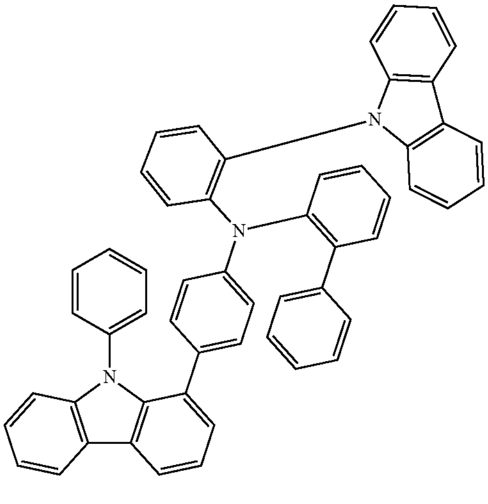
10
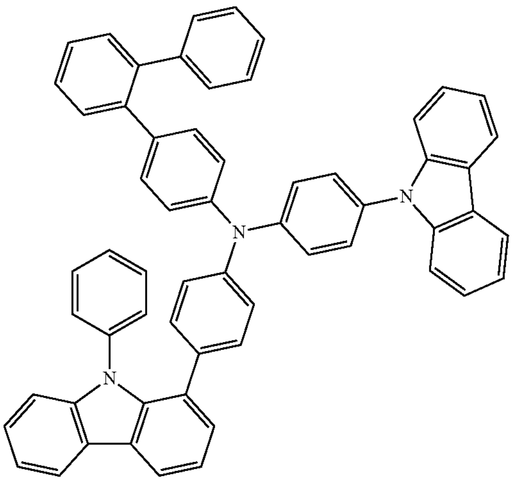

-continued
11
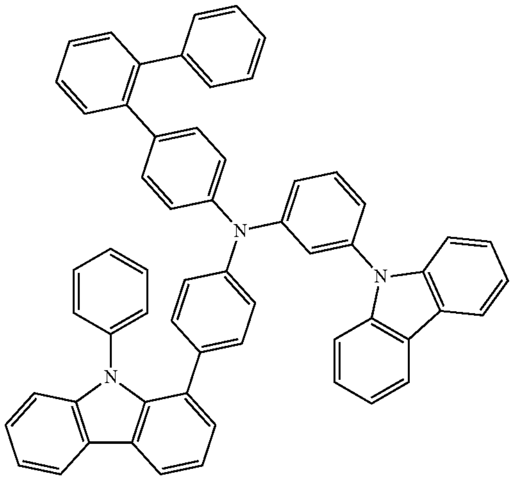
12
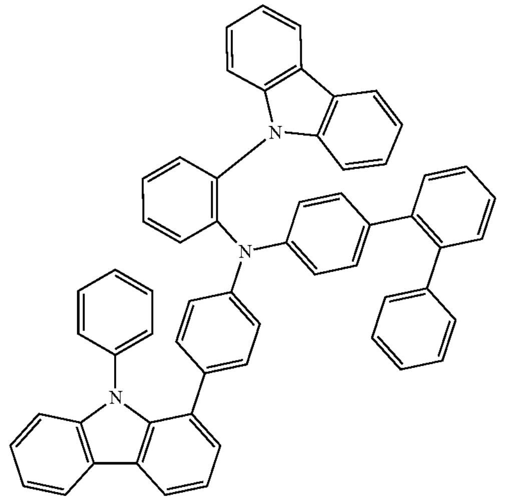
13
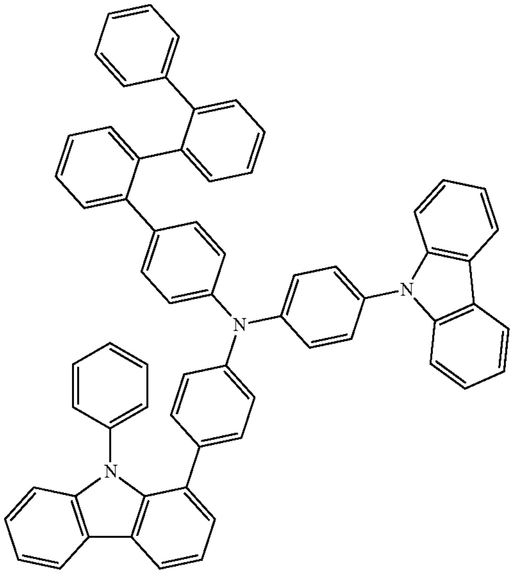
-continued
14
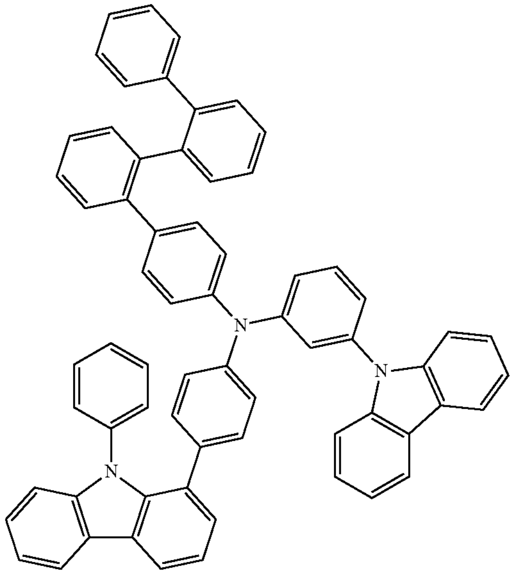
15
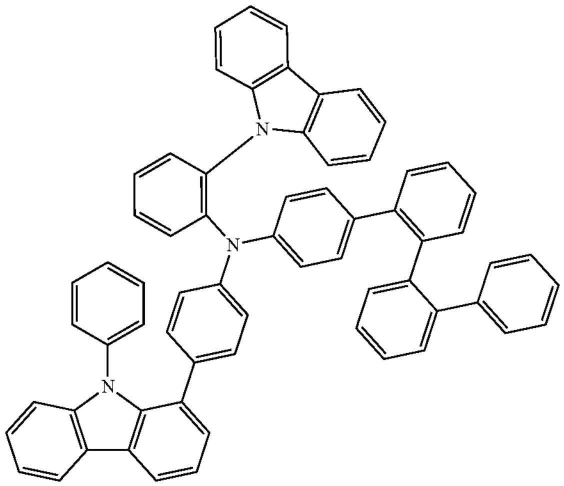
16
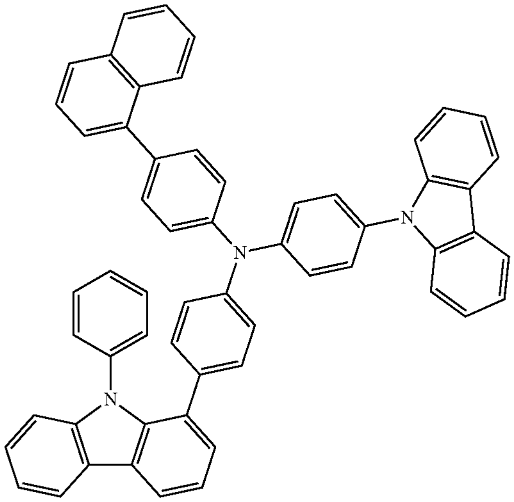

17
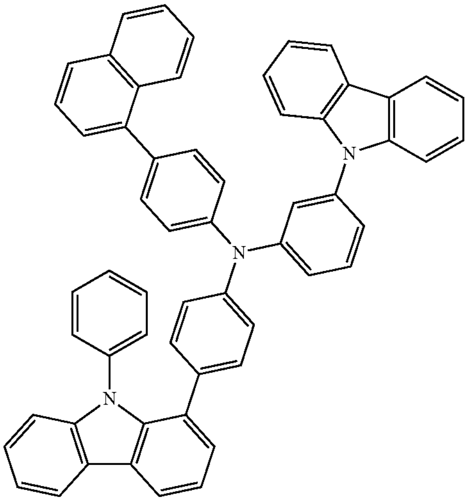
18
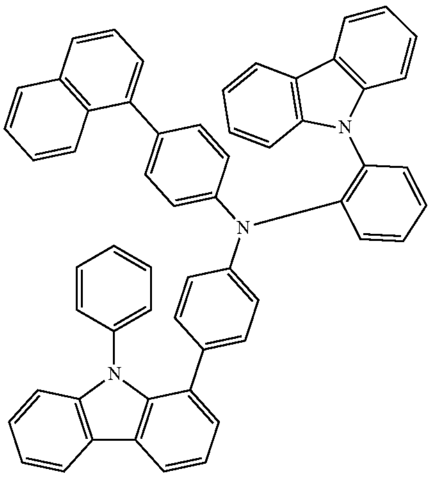
19
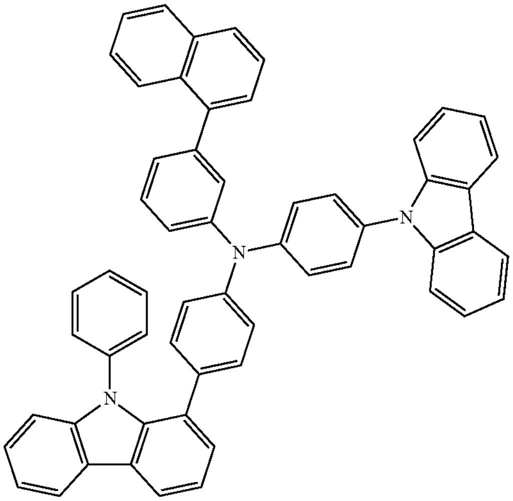
20
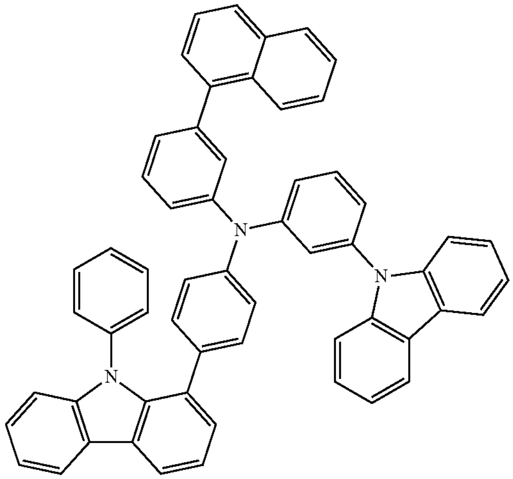
21
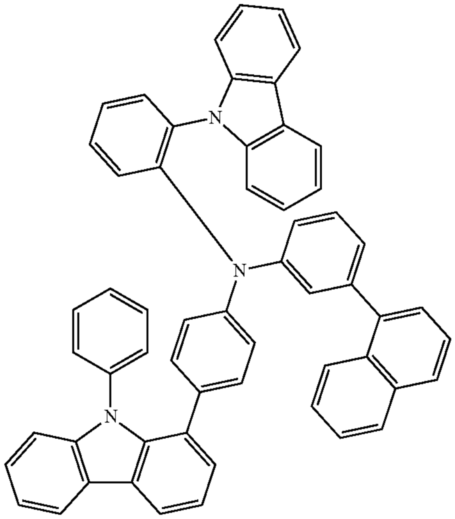
22
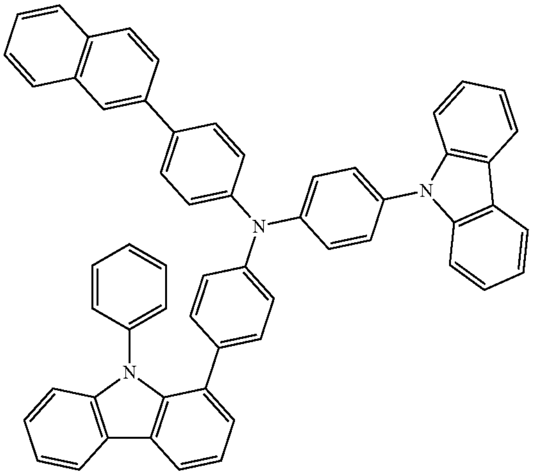

-continued
23
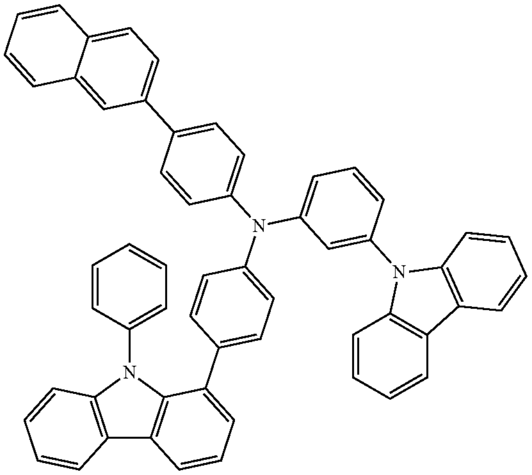
24
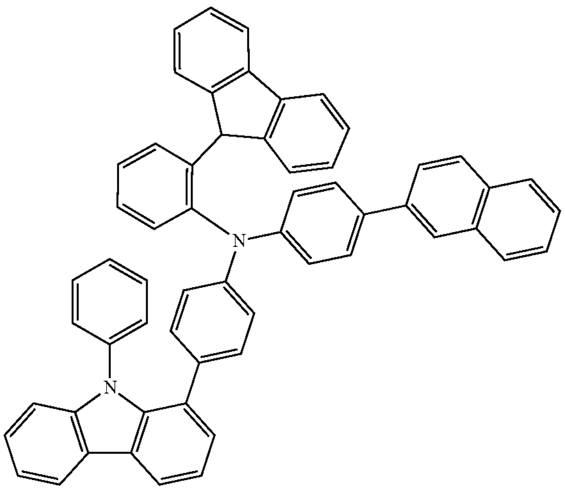
25
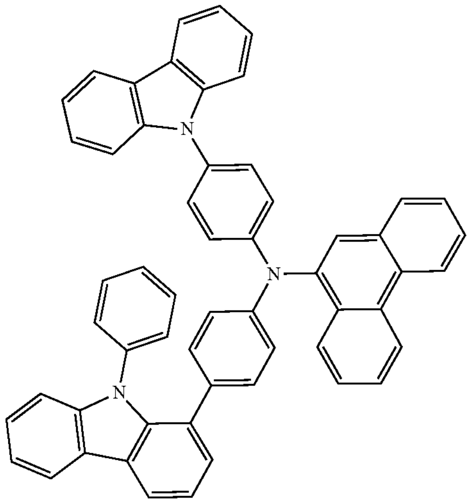
-continued
26
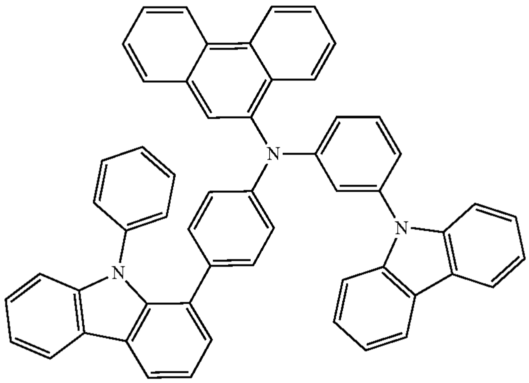
27
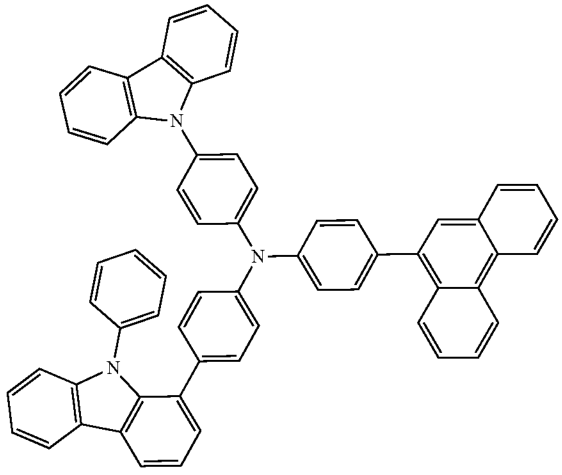
28
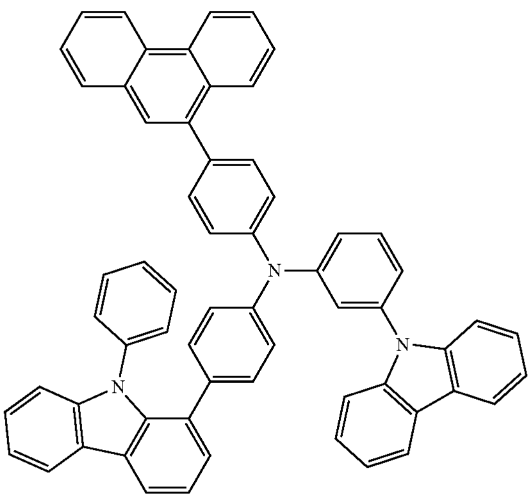

-continued
29
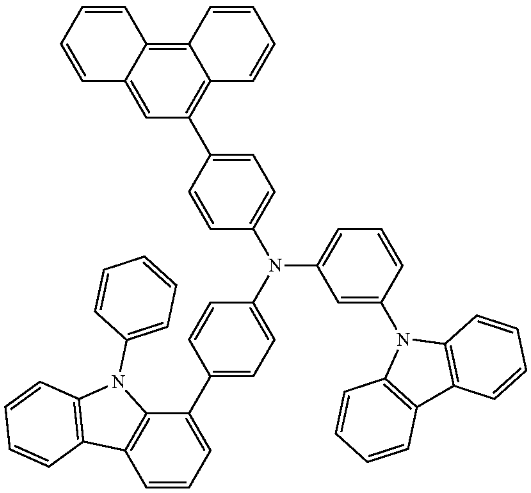
30
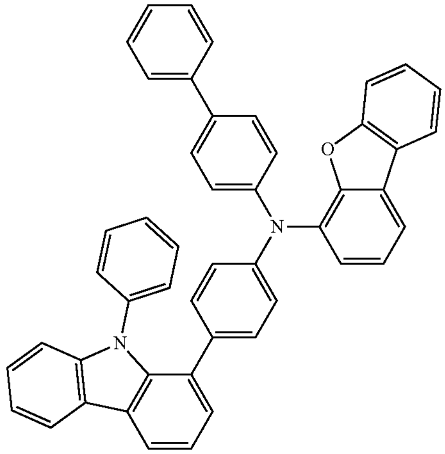
31
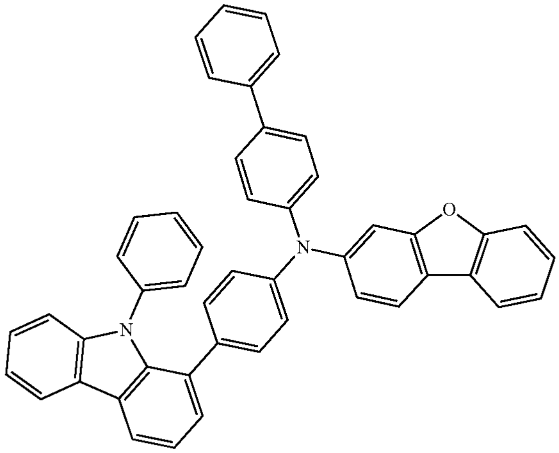
-continued
32
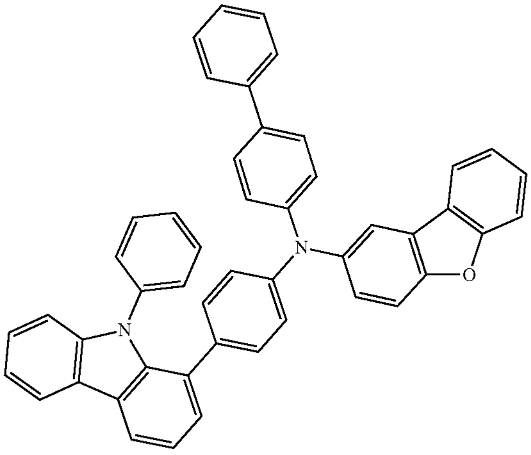
33
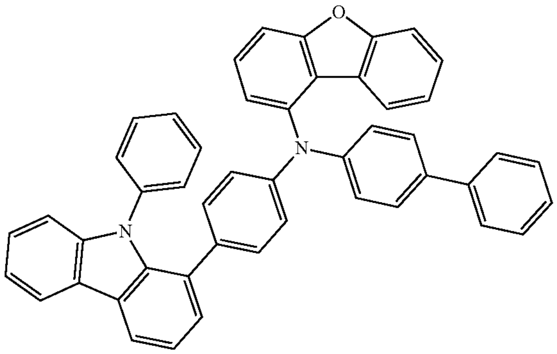
34
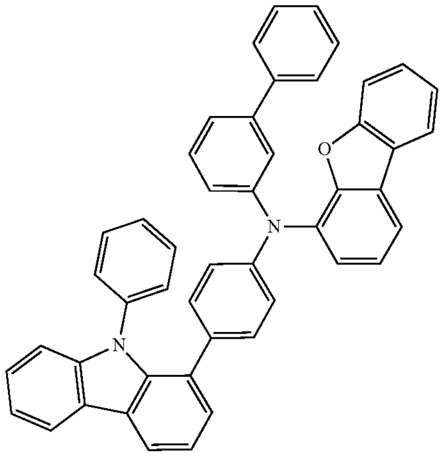

-continued
35
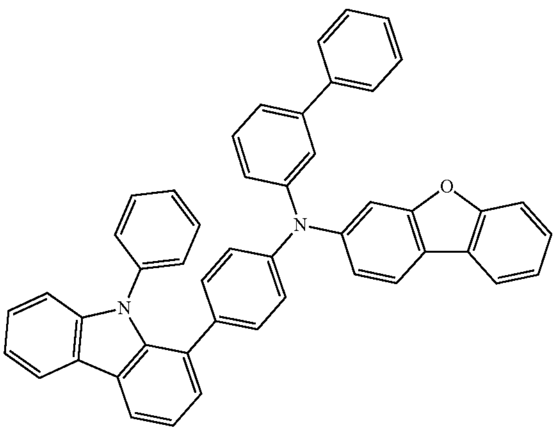
36
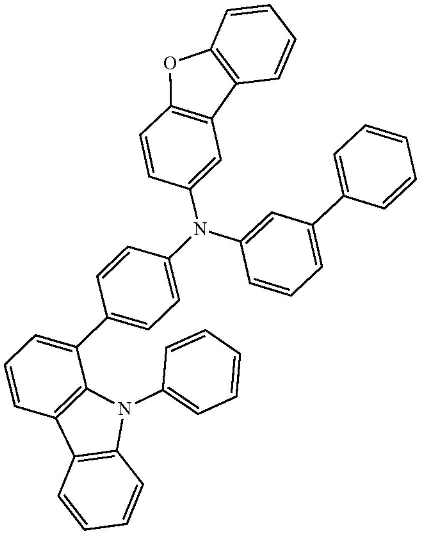
37
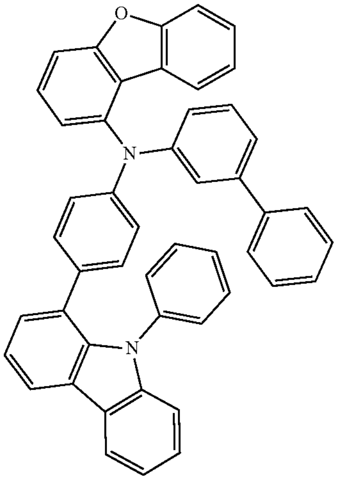
-continued
38
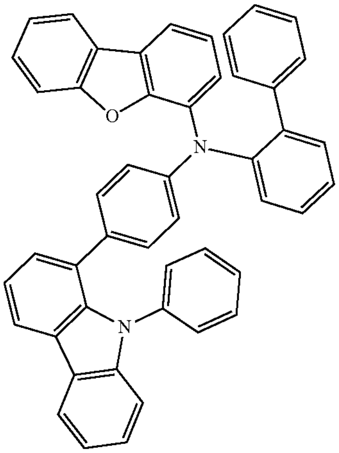
39
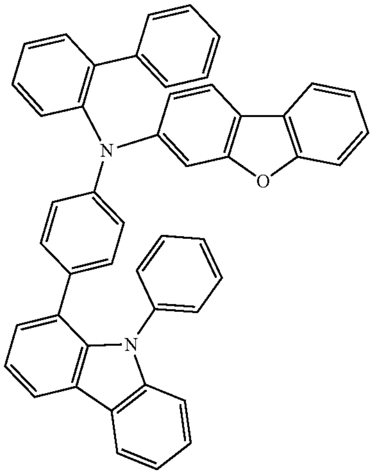
40
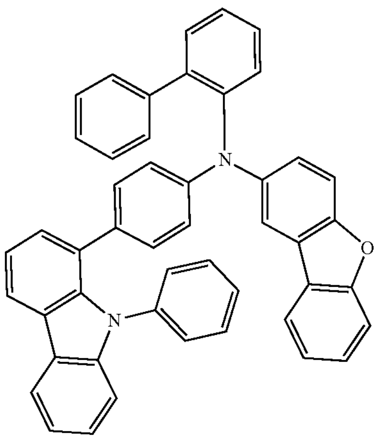

-continued
41
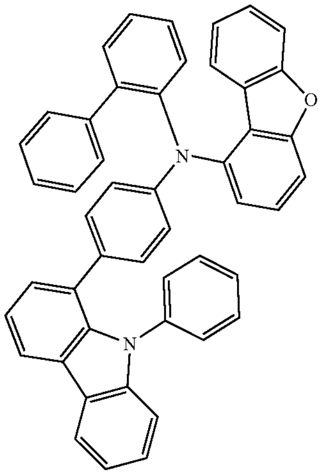
42
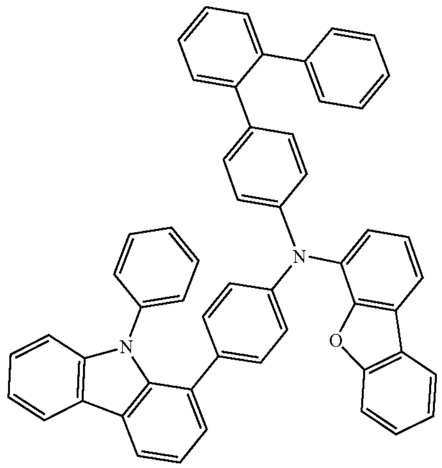
43
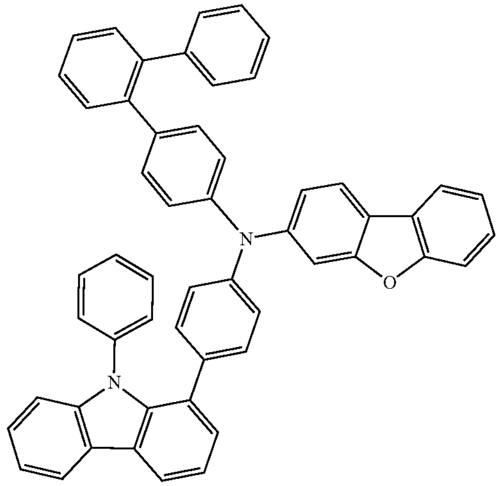
-continued
44
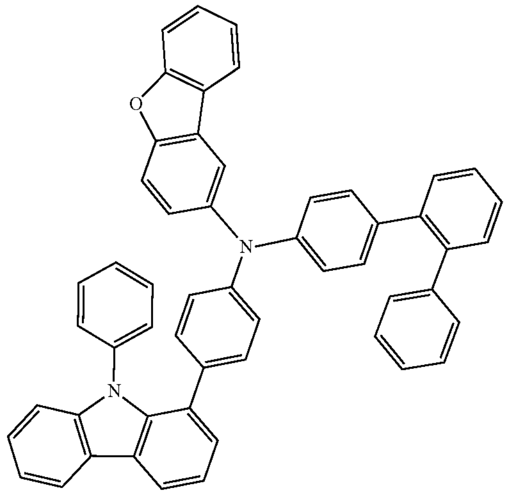
45
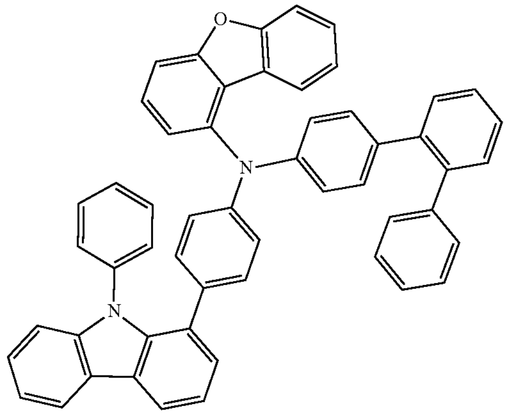
46
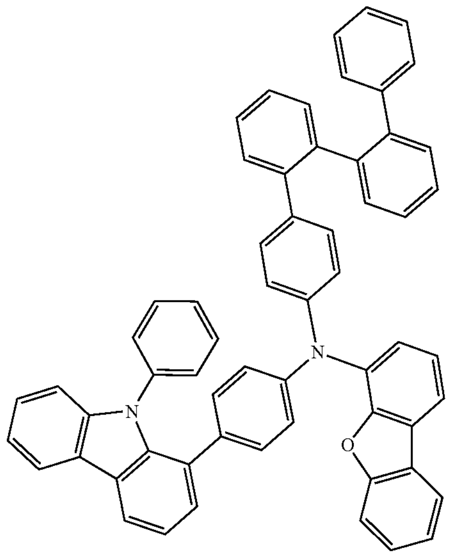

-continued
47
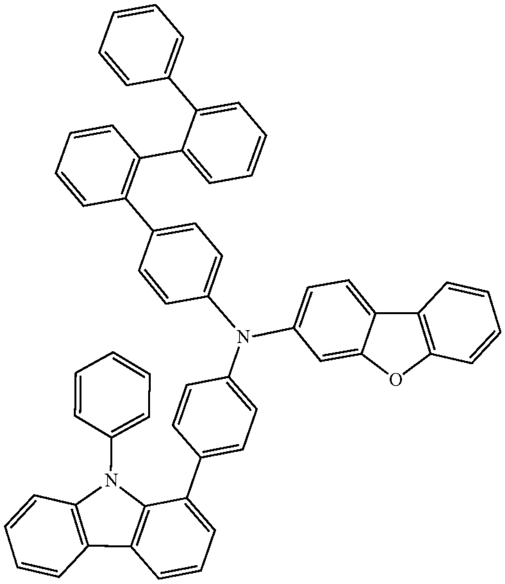
48
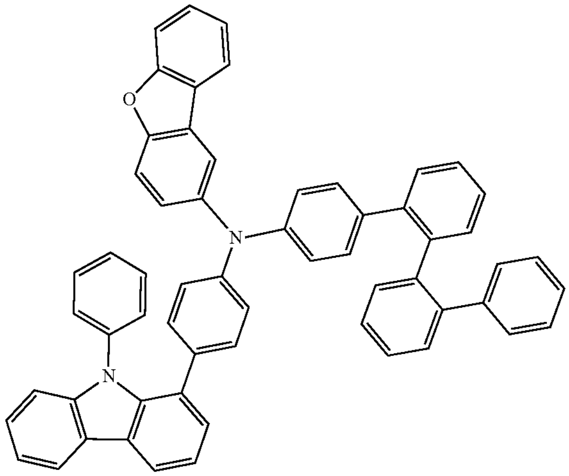
49
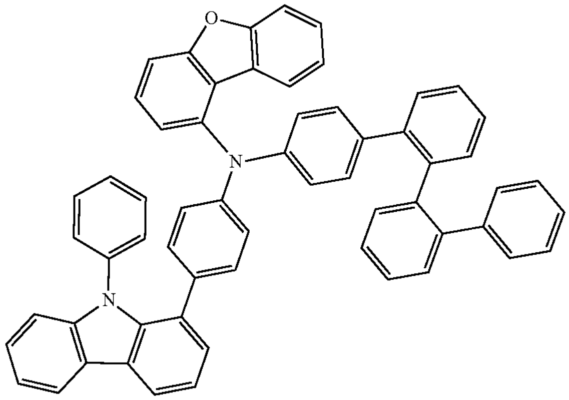
-continued
50
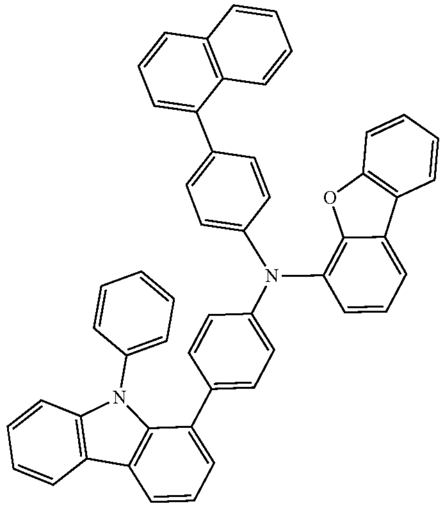
51
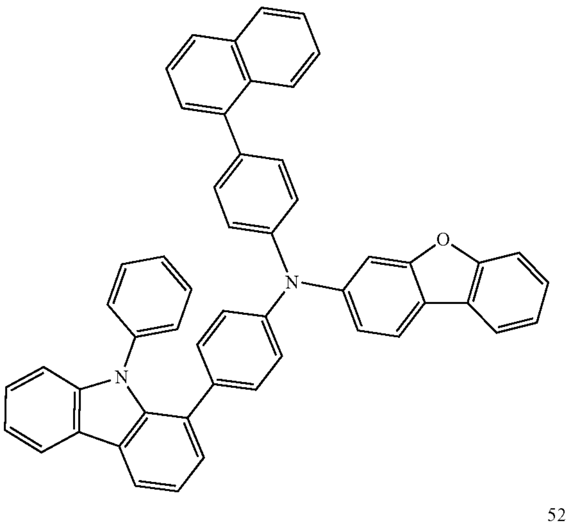
52
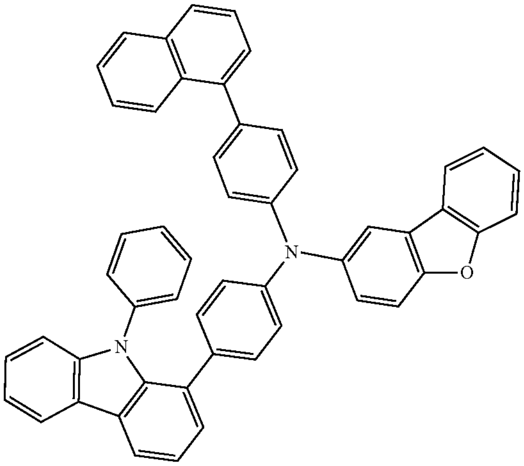

-continued
53
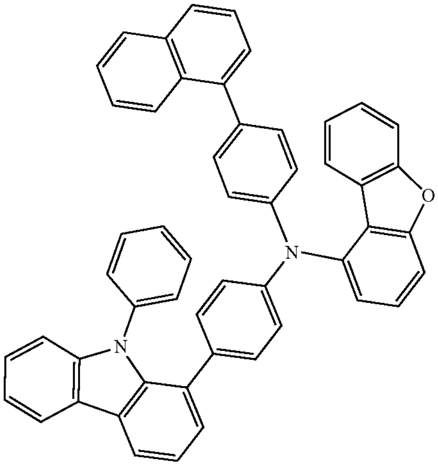
54
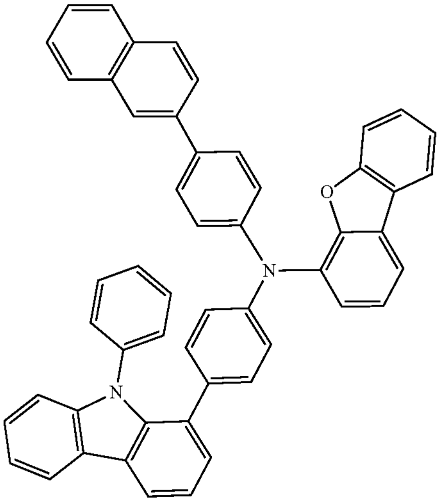
55
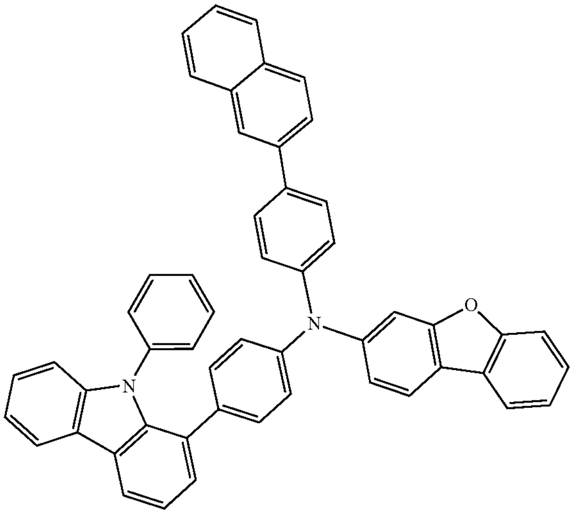
-continued
56
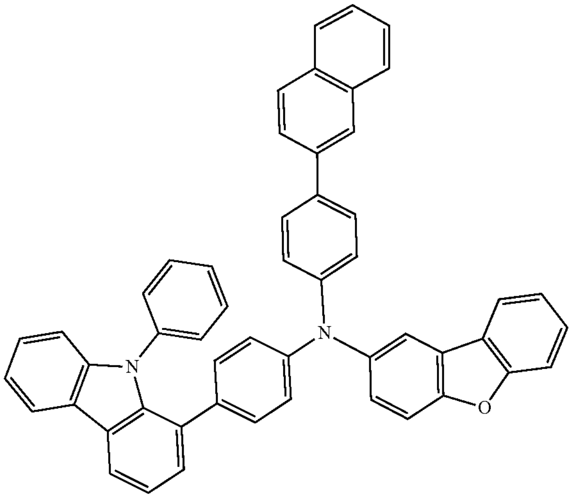
57
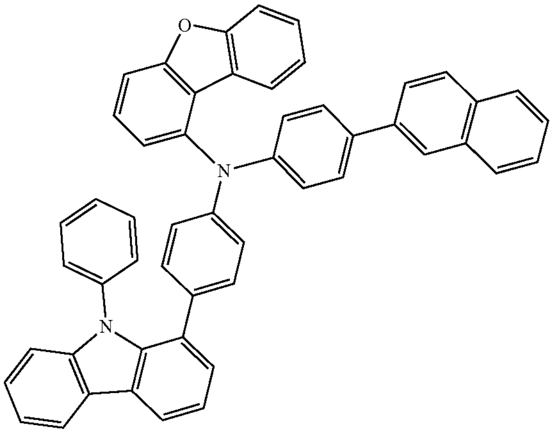
58
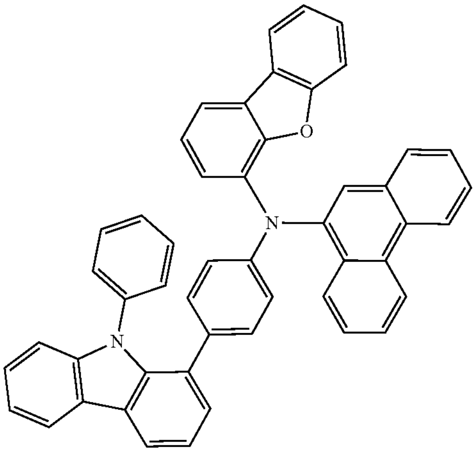

-continued
59
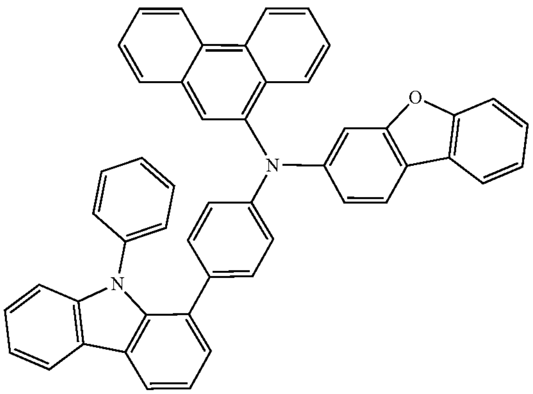
60
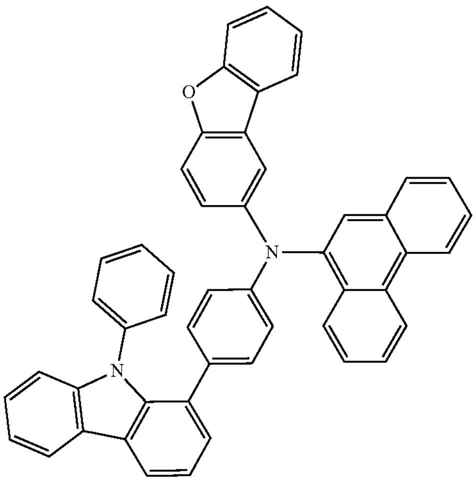
61
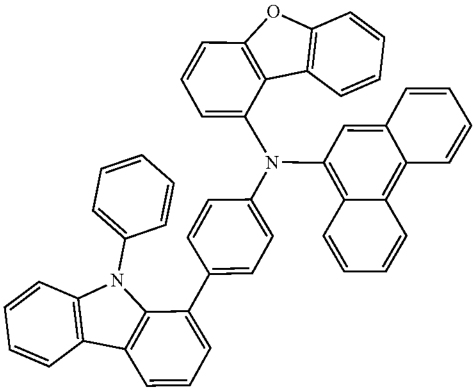
-continued
62
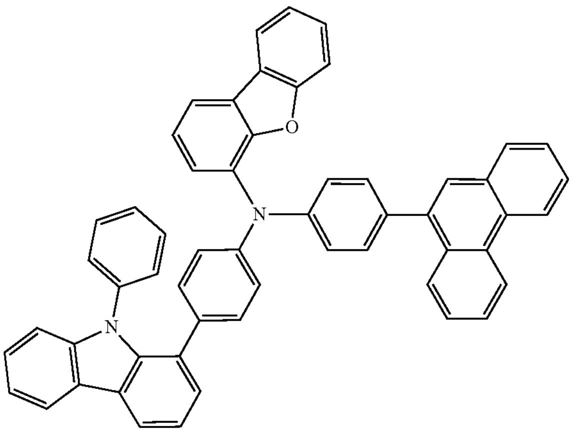
63
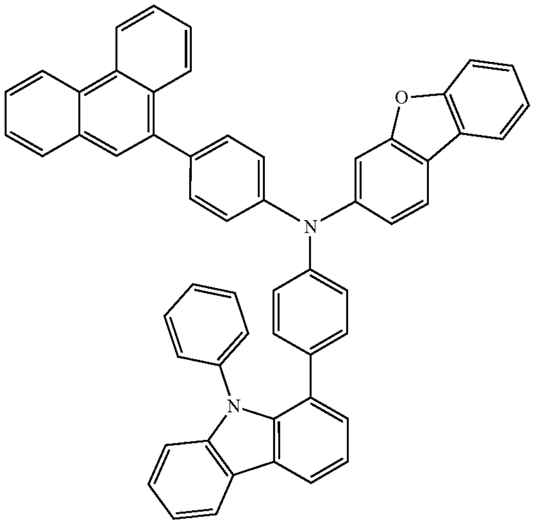
64
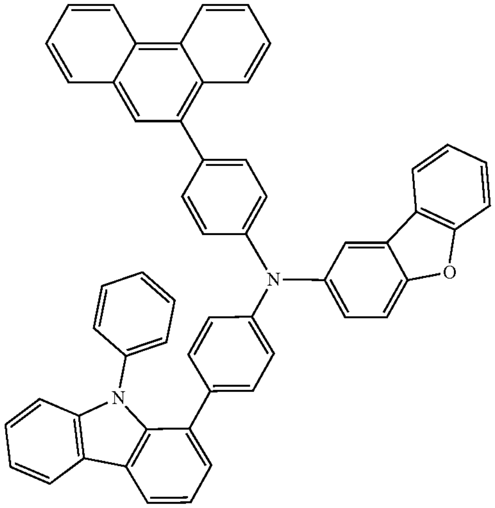

65
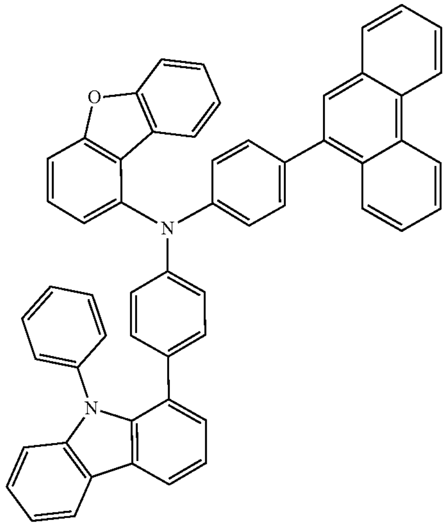
66
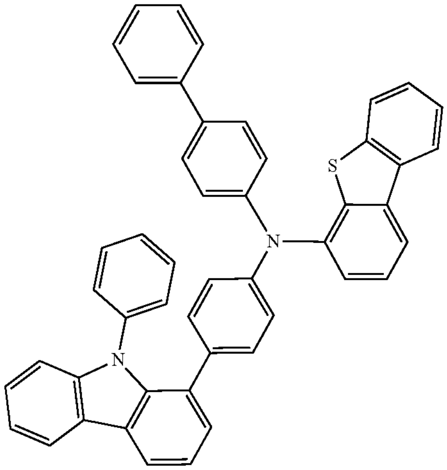
67
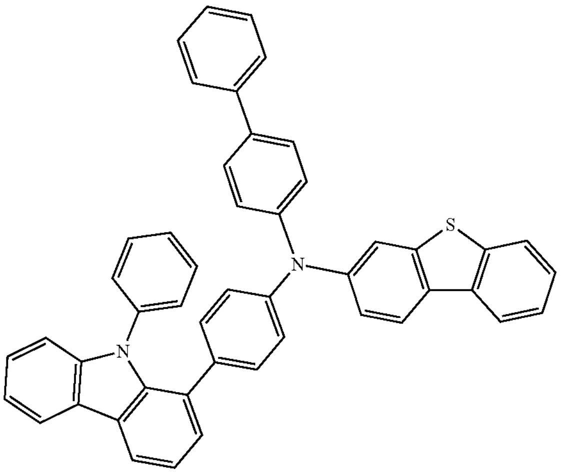
68
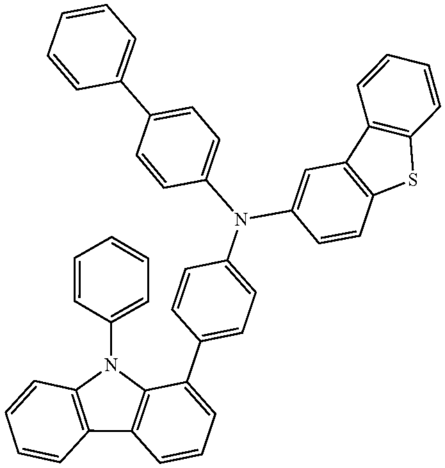
69
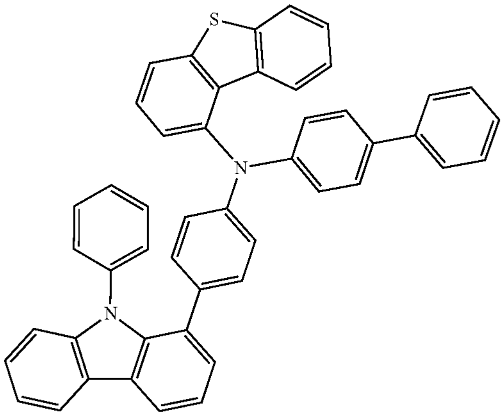
70
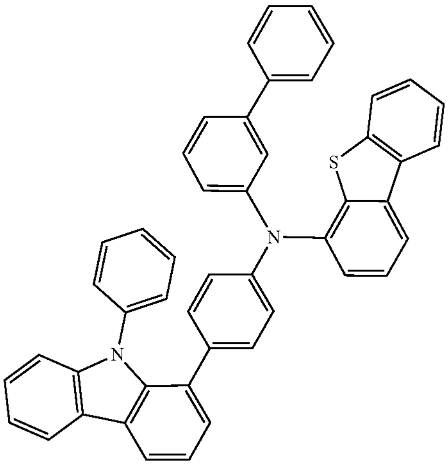

-continued
71
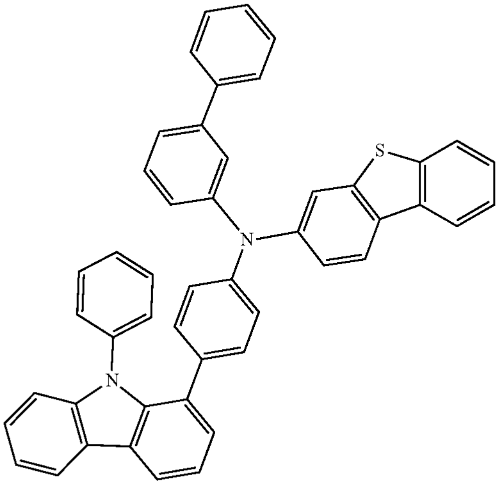
72
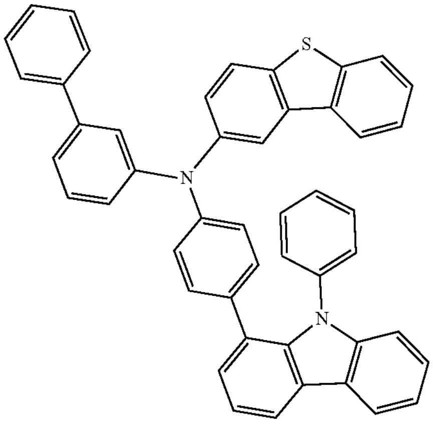
73
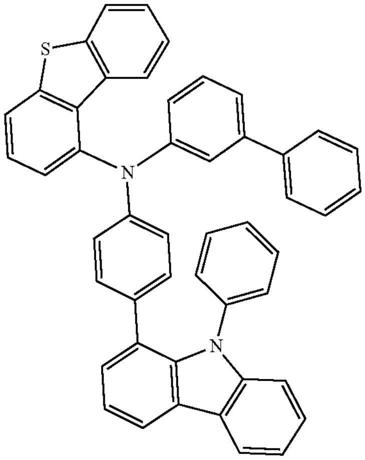
-continued
74
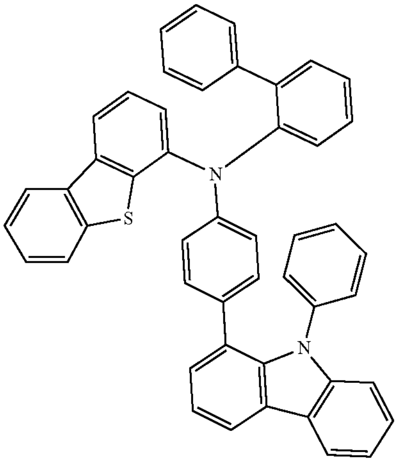
75
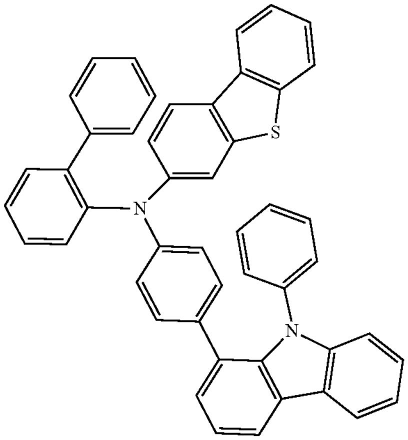
76
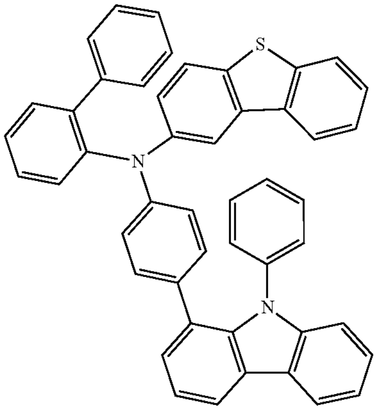

-continued
77
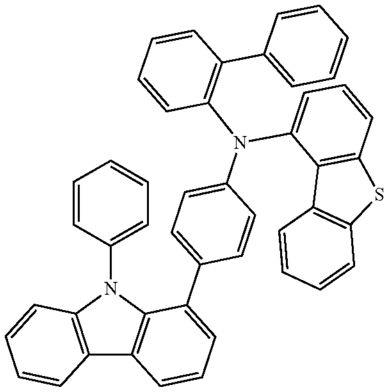
78
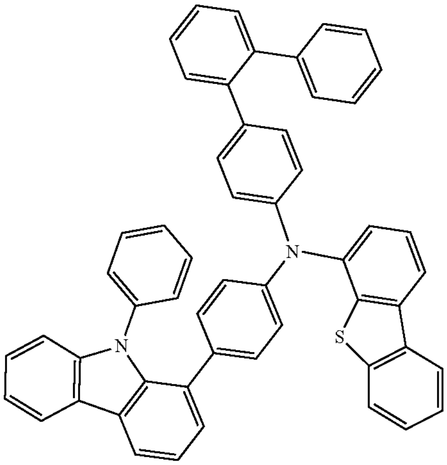
79
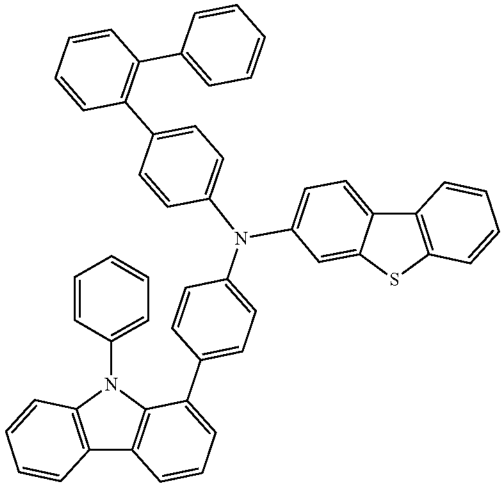
-continued
80
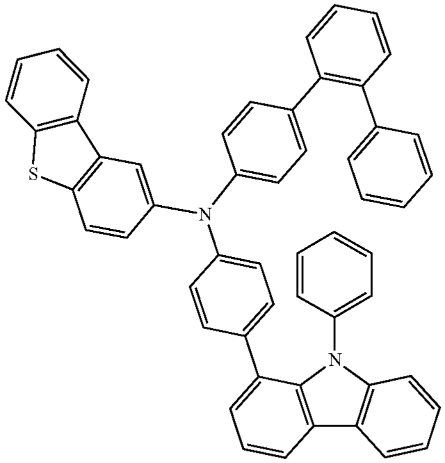
81
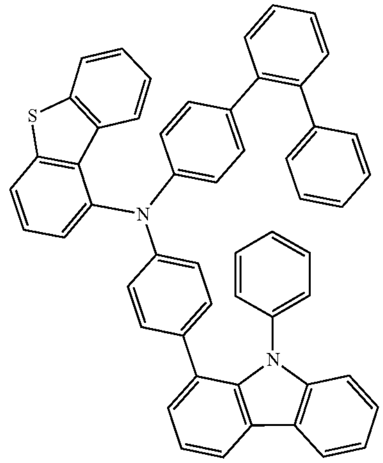
82
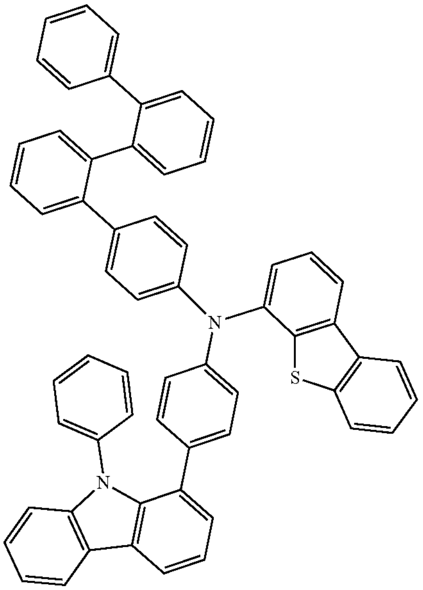

-continued
83
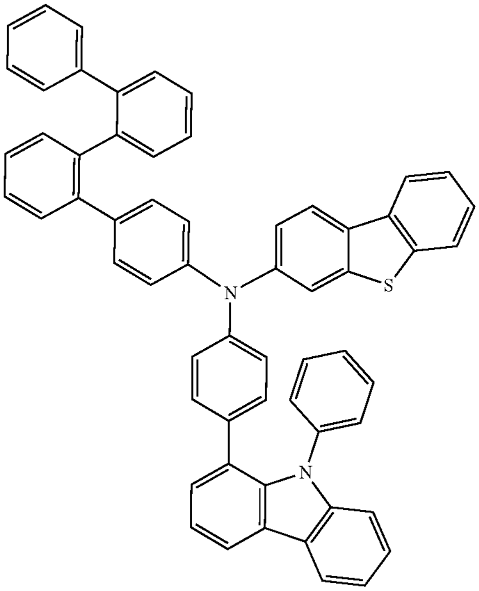
84
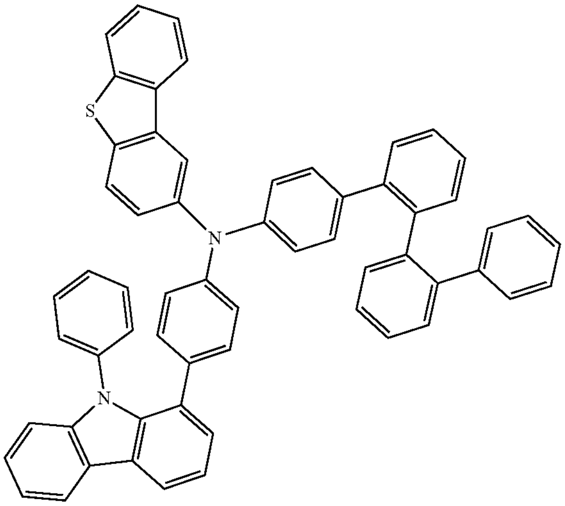
85
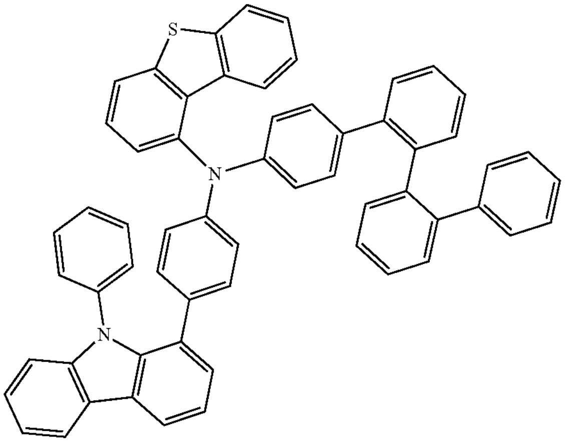
-continued
86
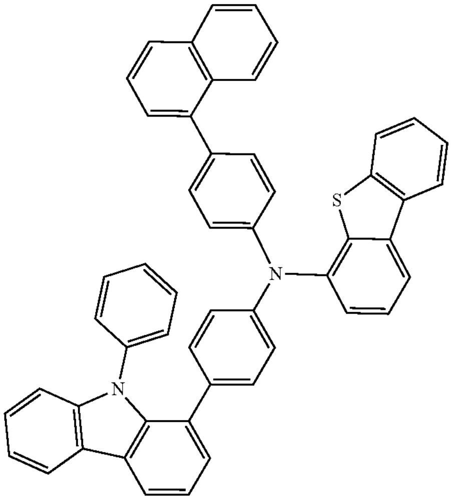
87
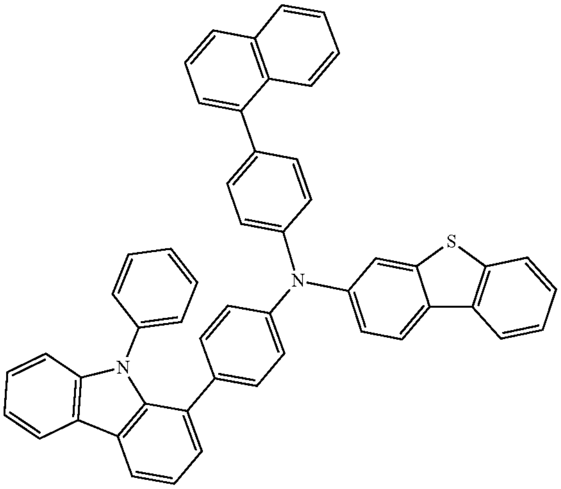
88
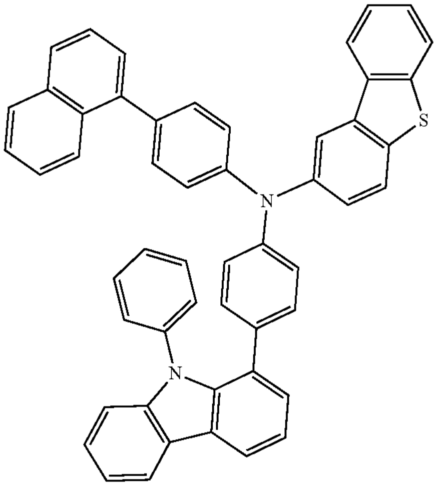

-continued
89
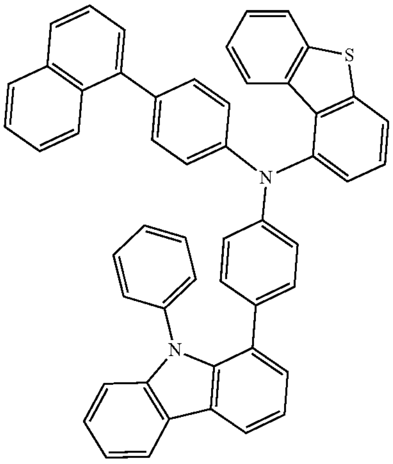
90
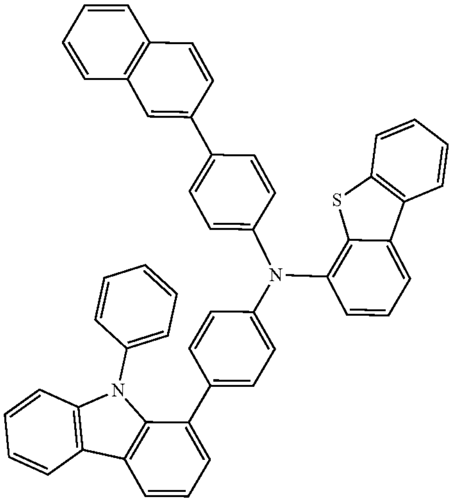
91
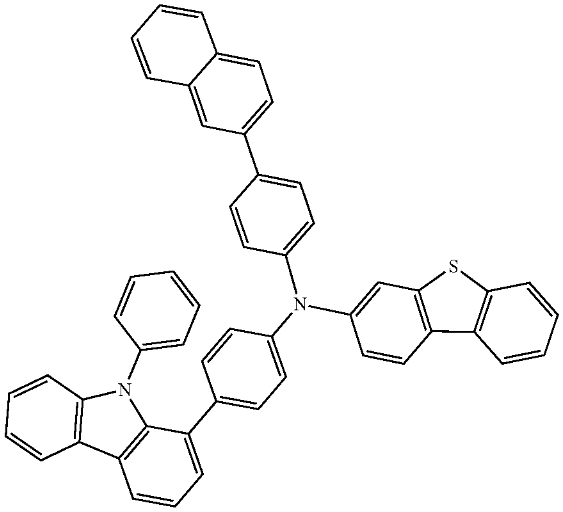
-continued
92
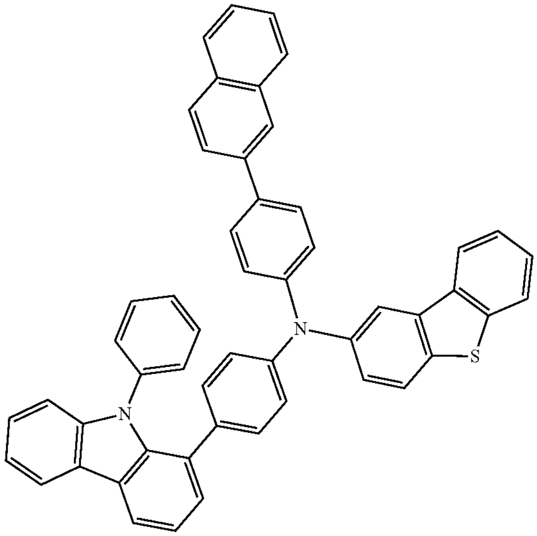
93
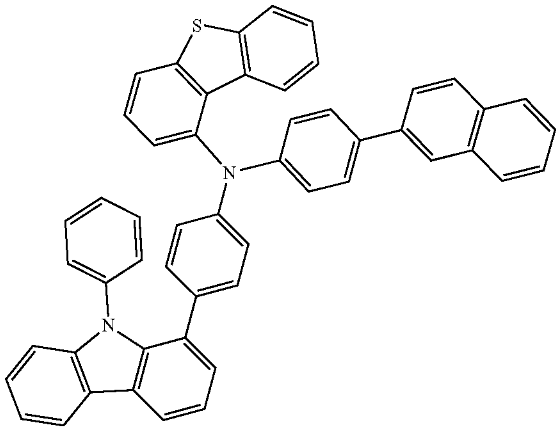
94
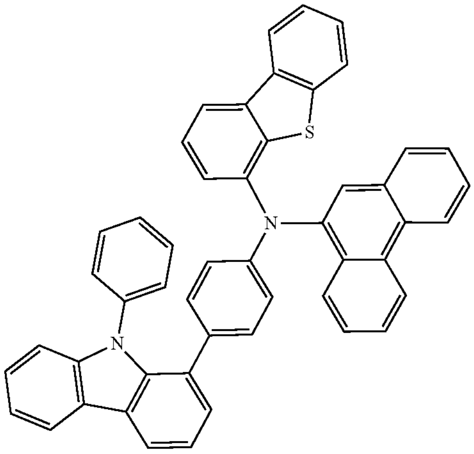

95
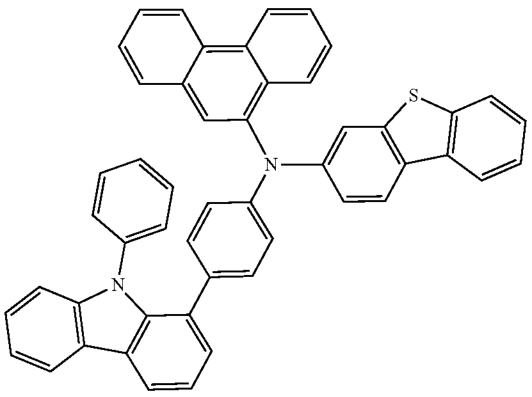
96
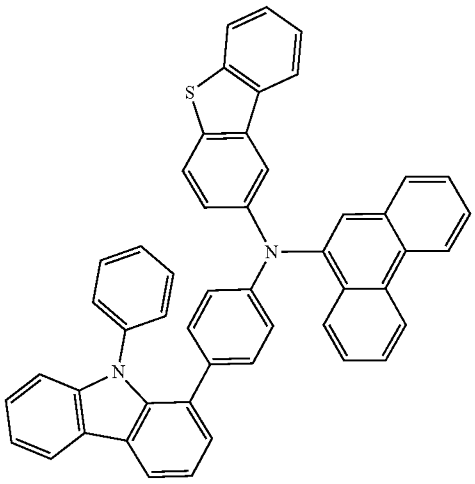
97
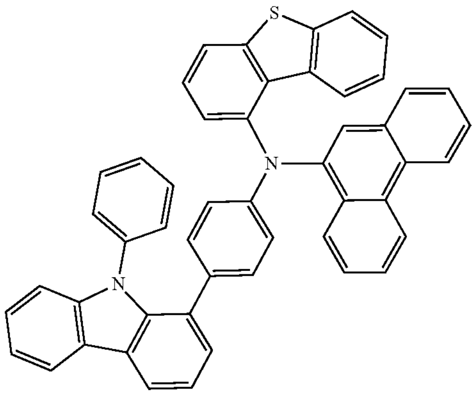
98
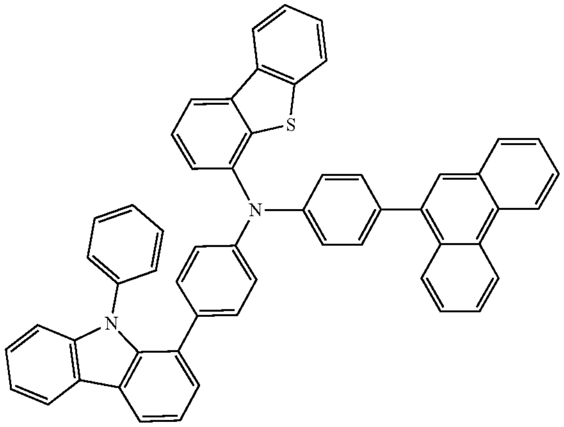
99
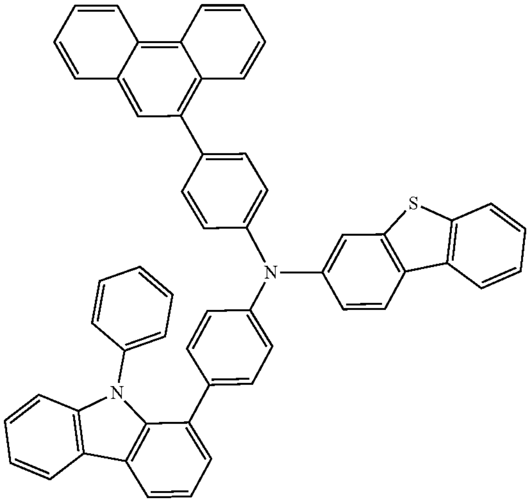
100
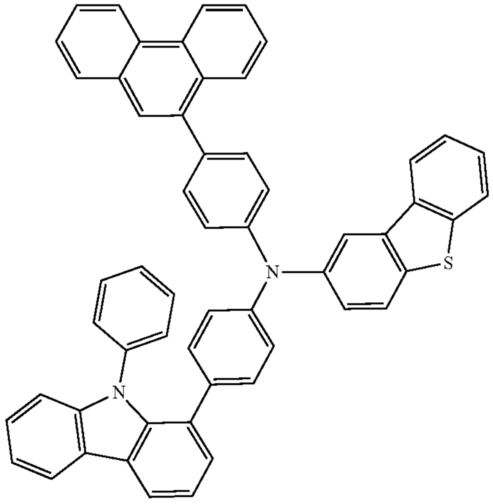

-continued
101
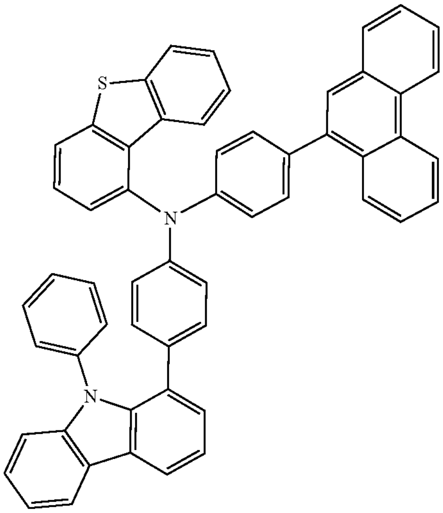
102
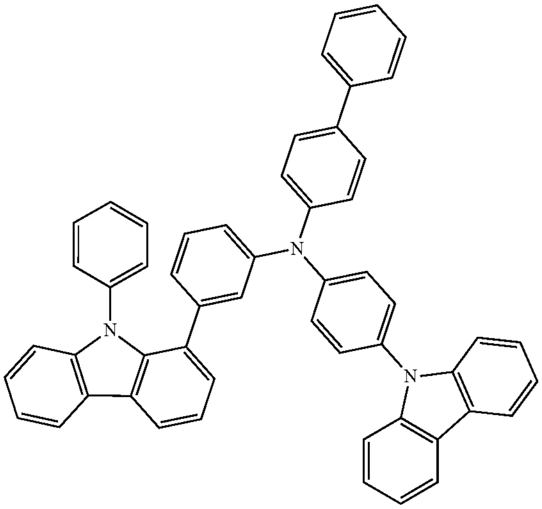
103
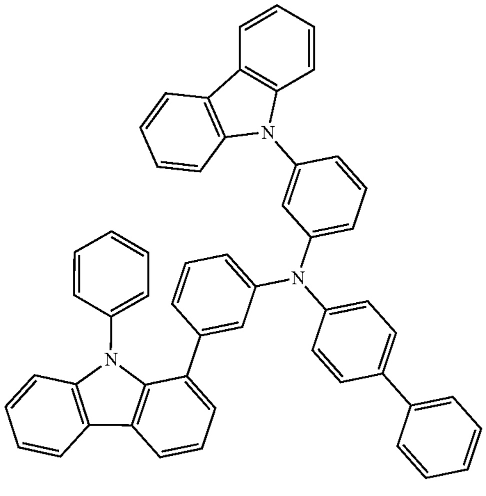
-continued
103
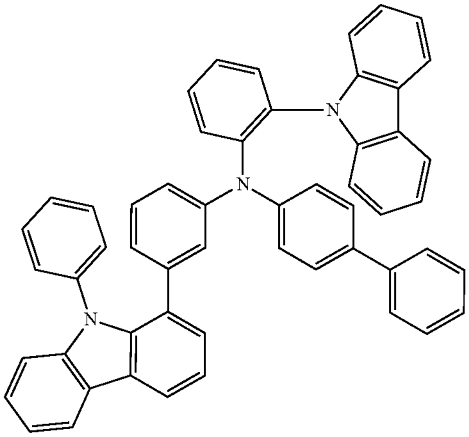
104
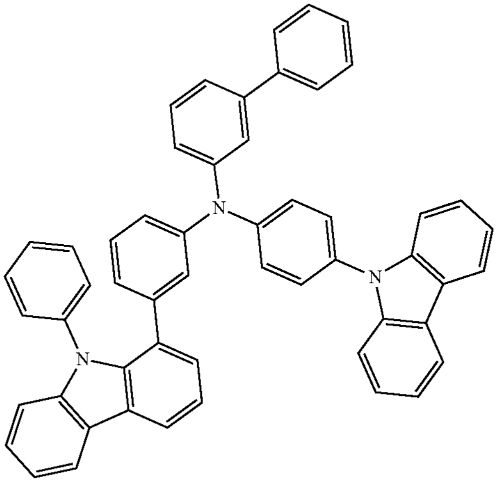
105
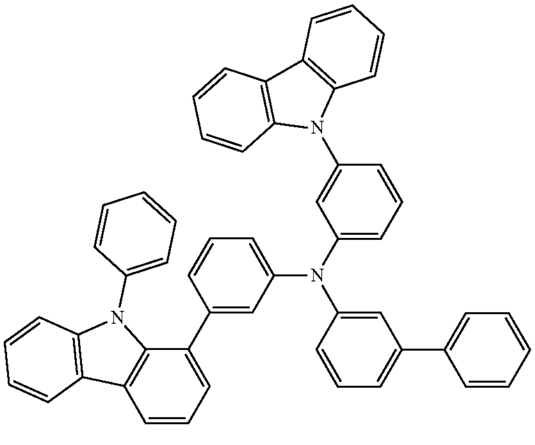

-continued
106
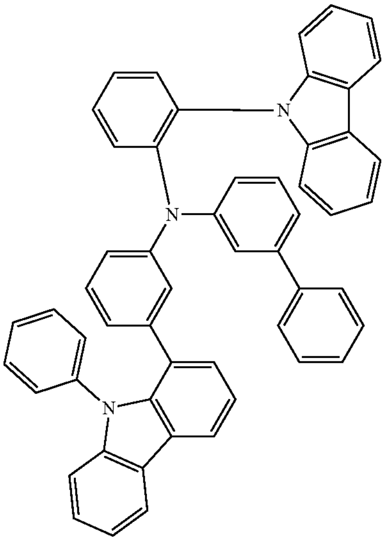
107
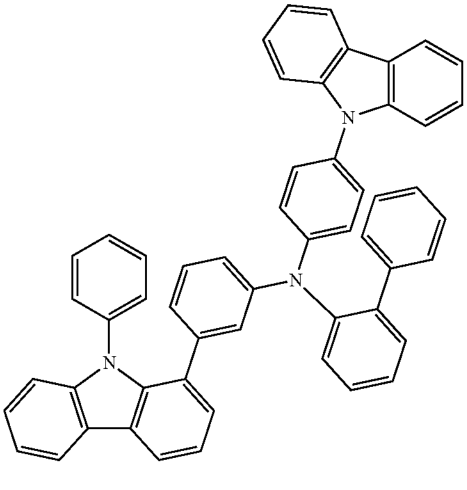
108
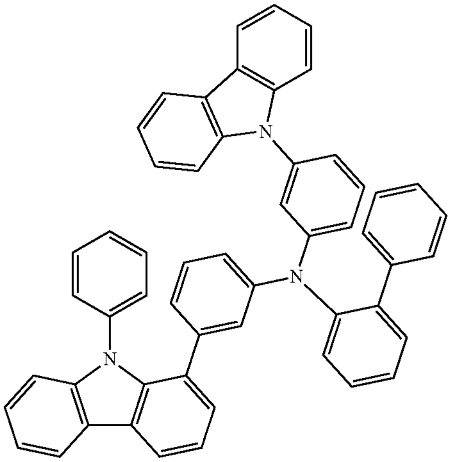
-continued
109
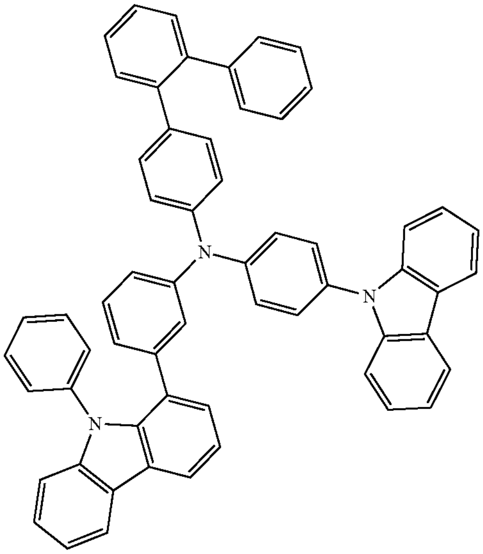
110
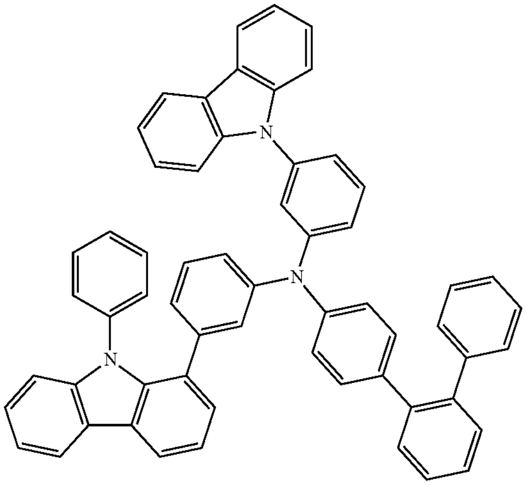
111
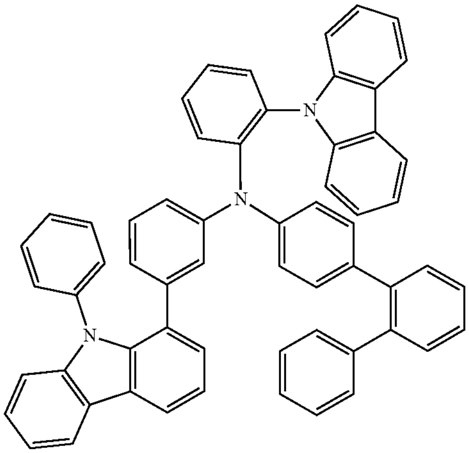

-continued
112
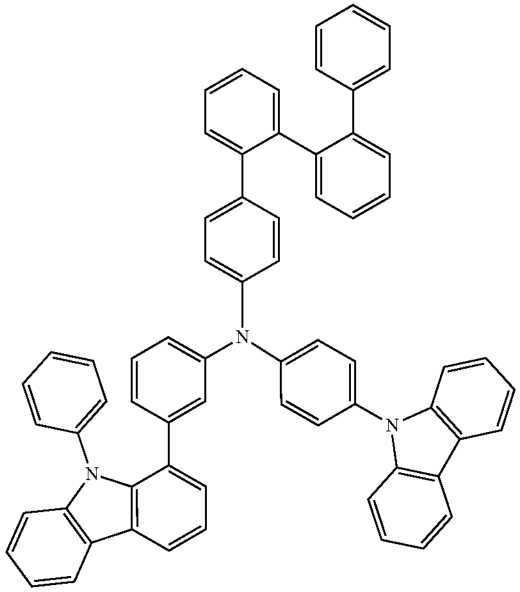
113
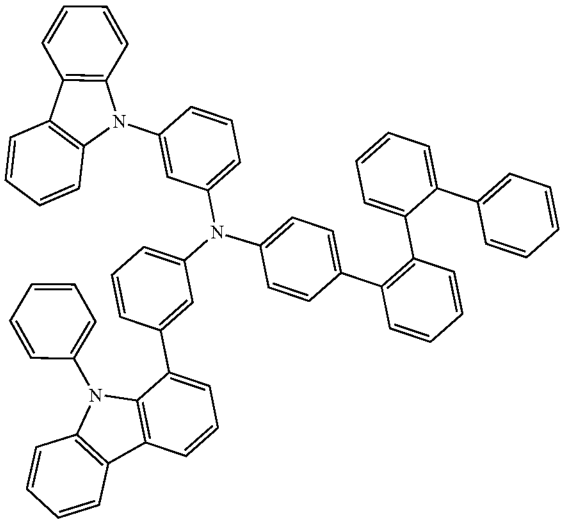
-continued
114
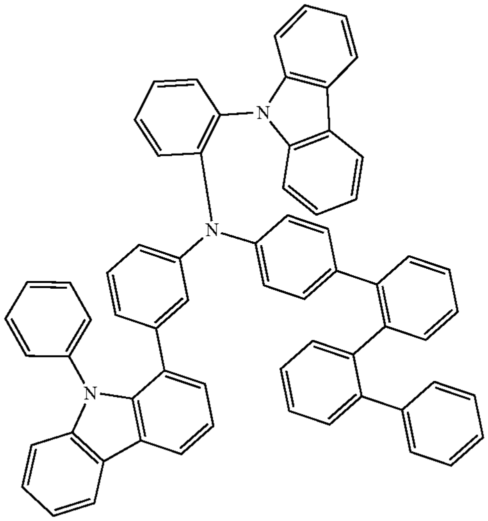
115
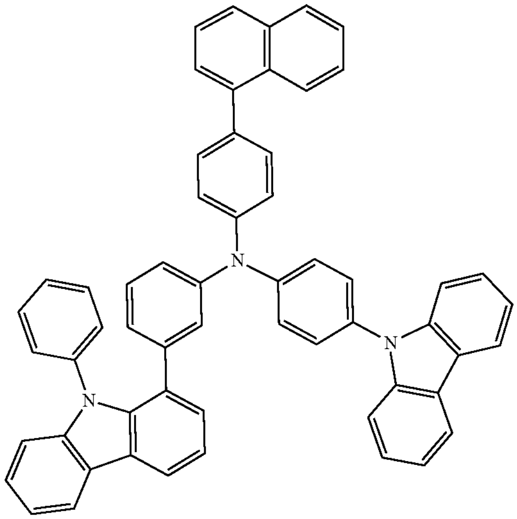
116
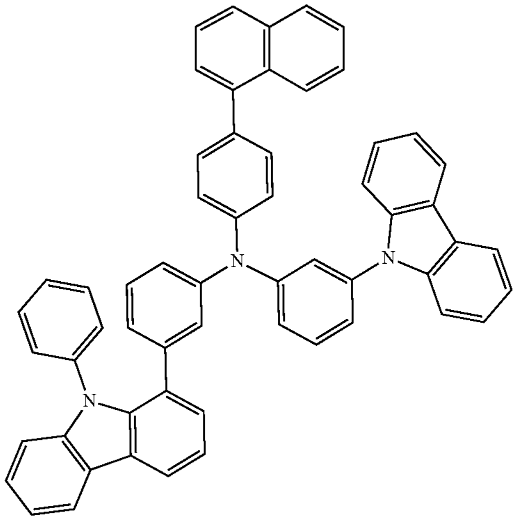

-continued
117
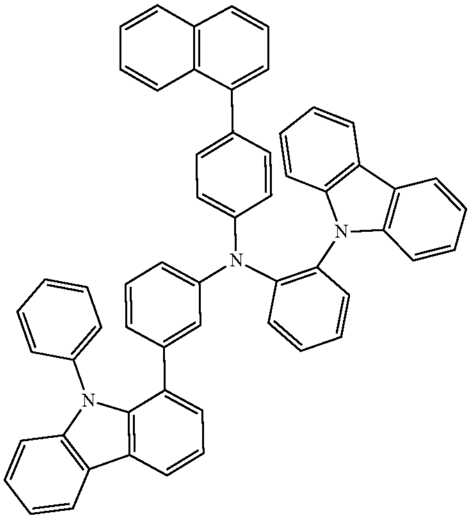
118
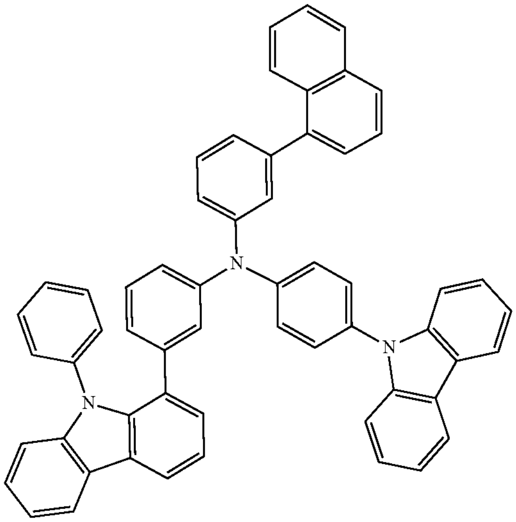
119
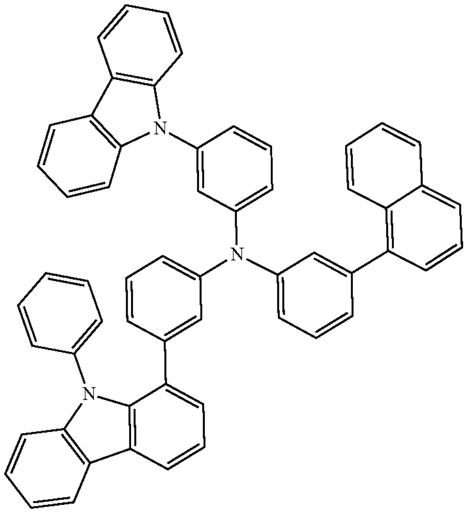
-continued
120
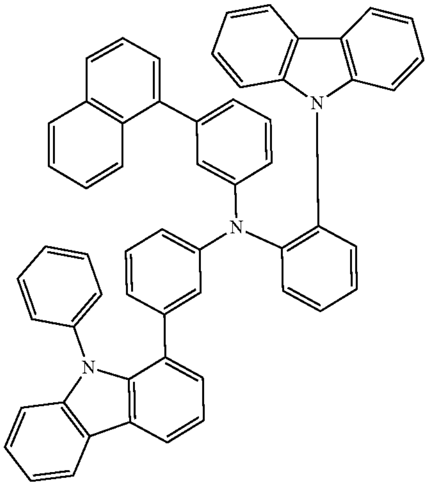
121
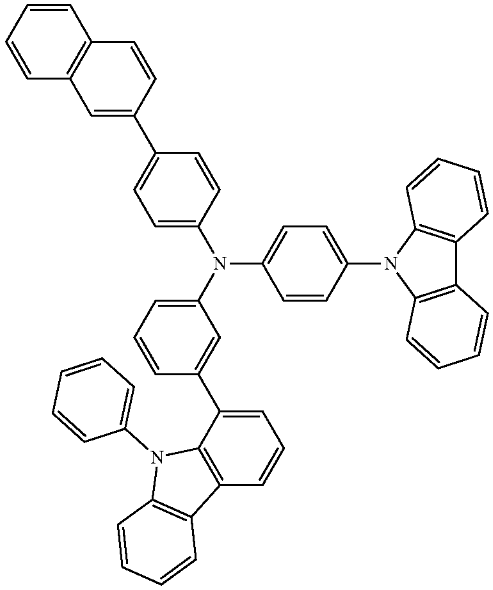
122
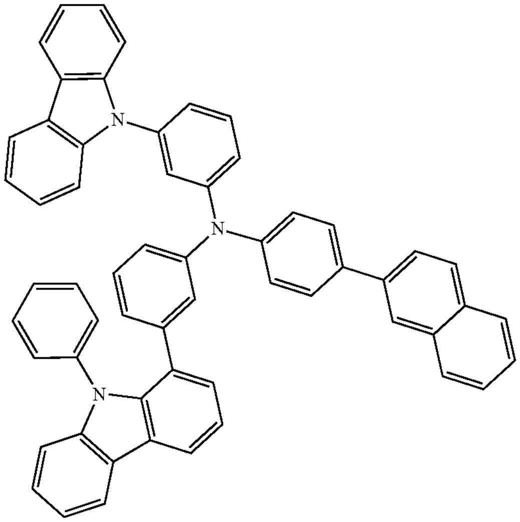

-continued
123
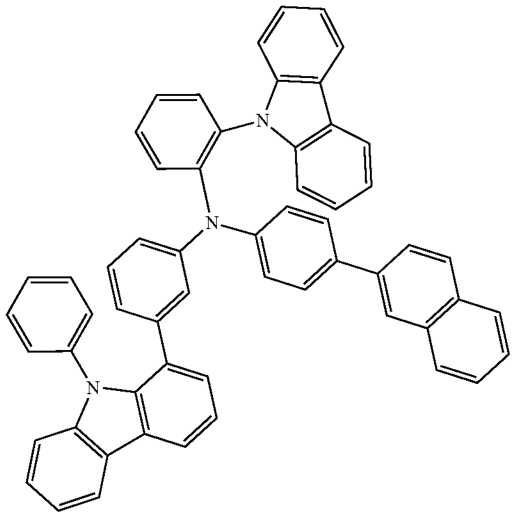
124
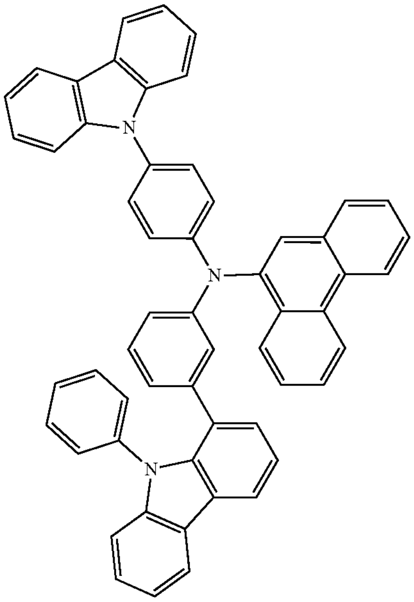
125
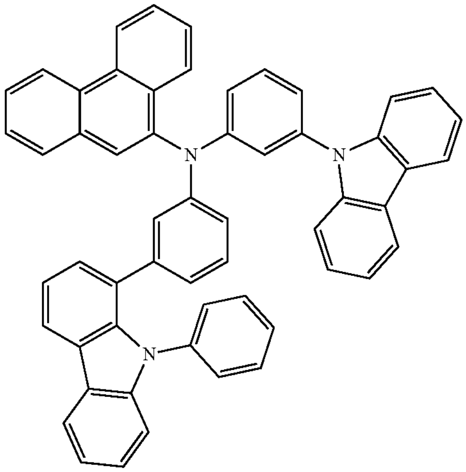
-continued
126
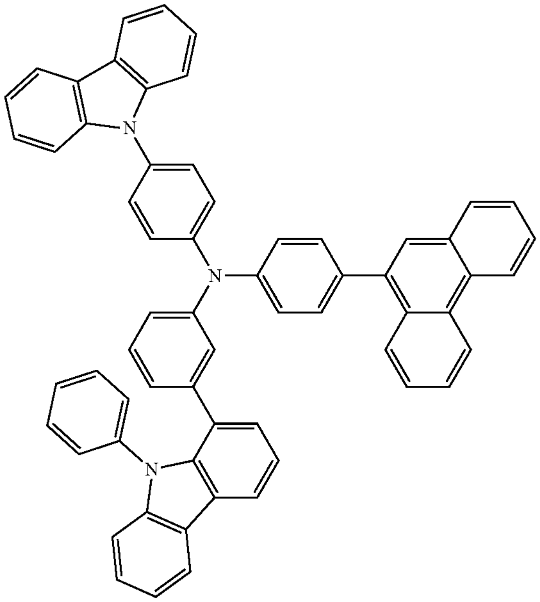
127
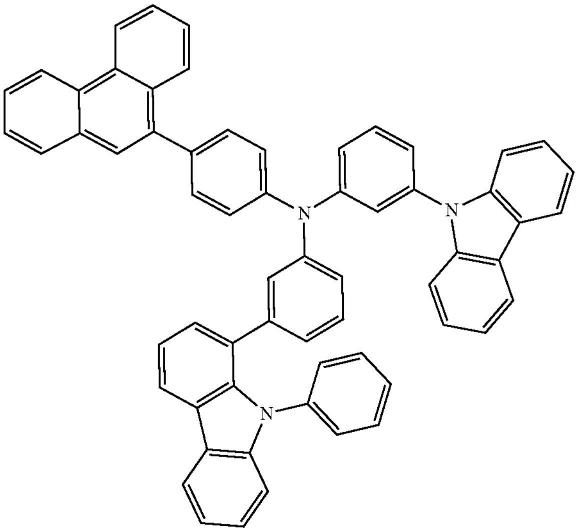

-continued
128
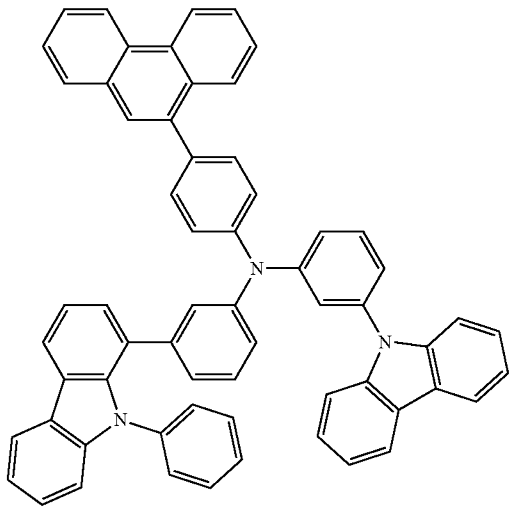
129
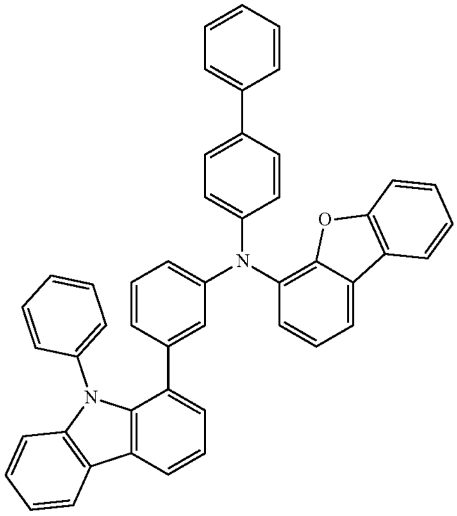
130
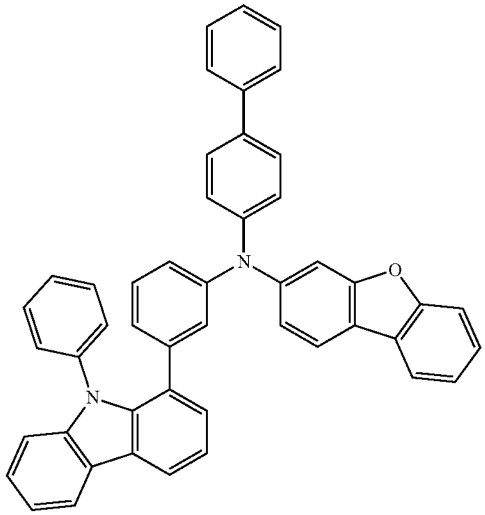
-continued
131
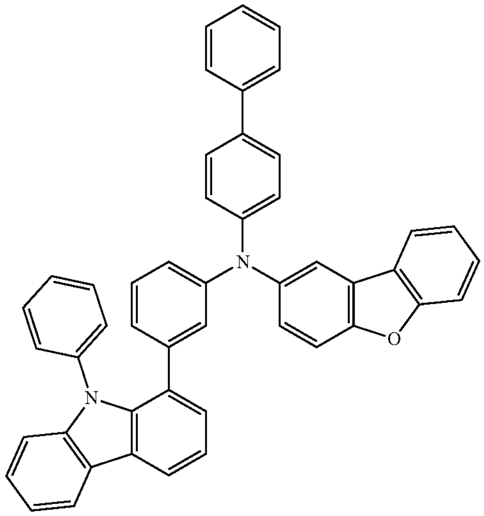
132
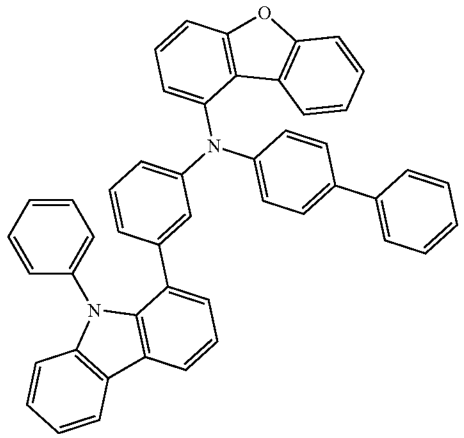
133
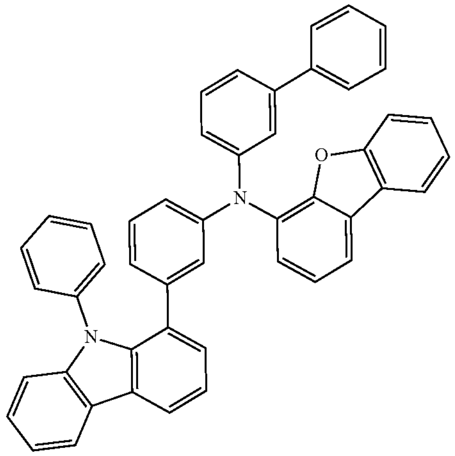

-continued
134
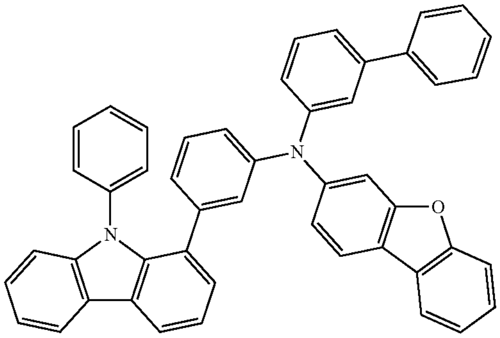
135
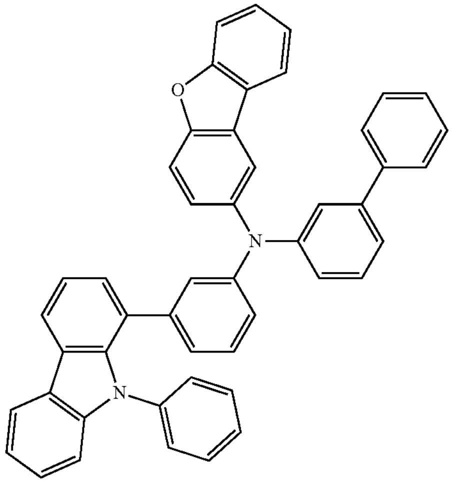
136
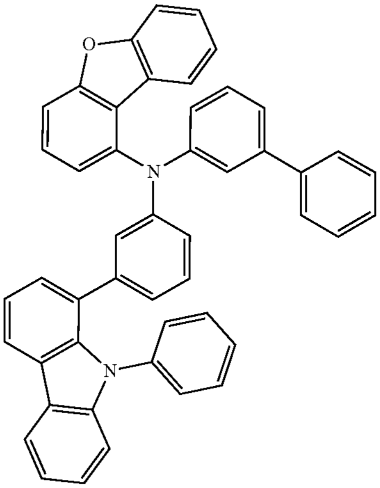
-continued
137
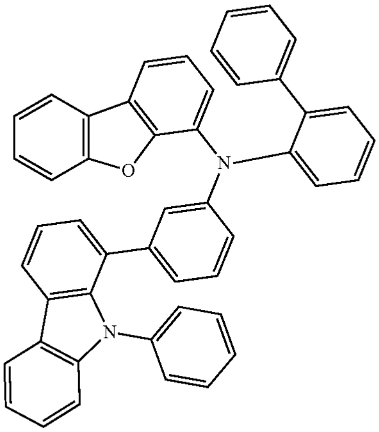
138
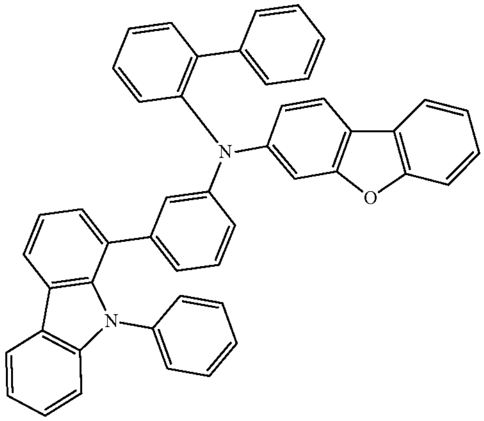
139
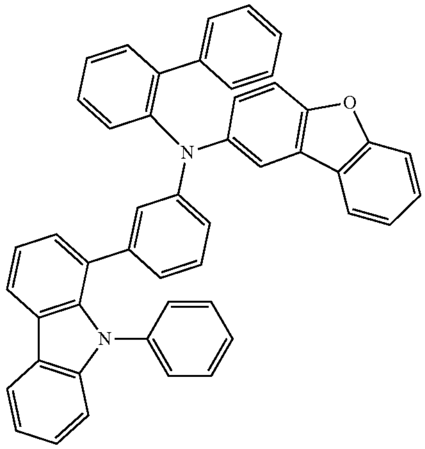
140
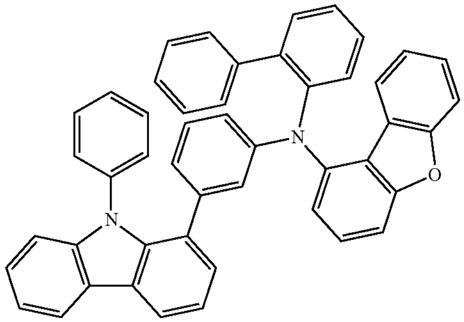

-continued
141
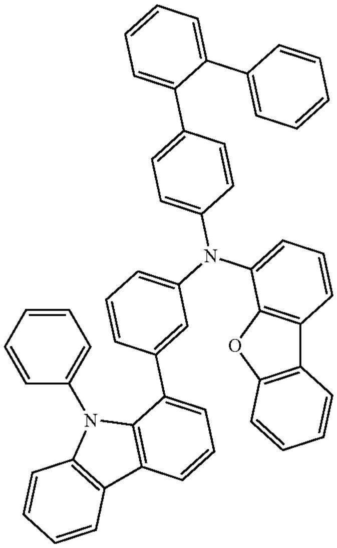
142
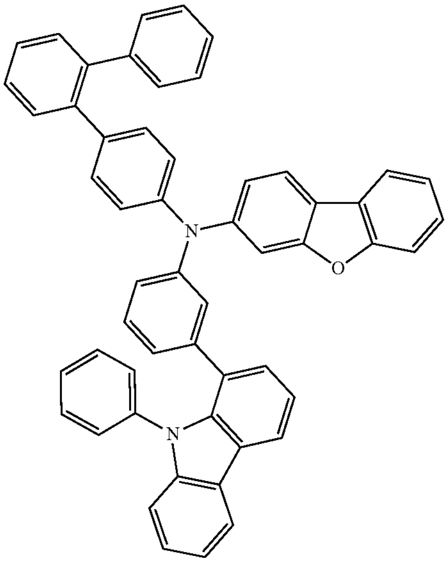
-continued
143
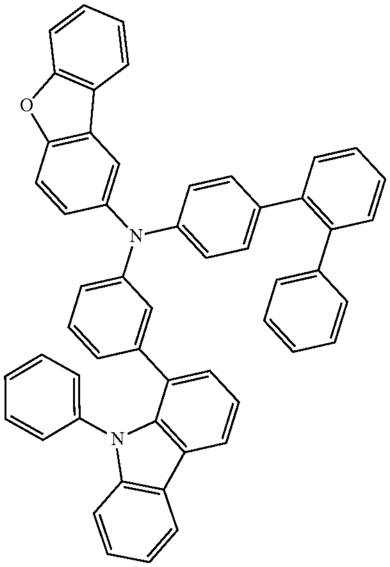
144
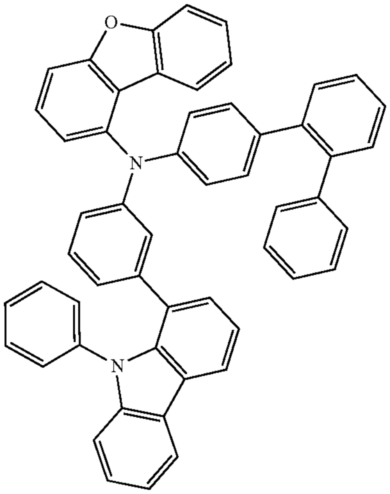
145
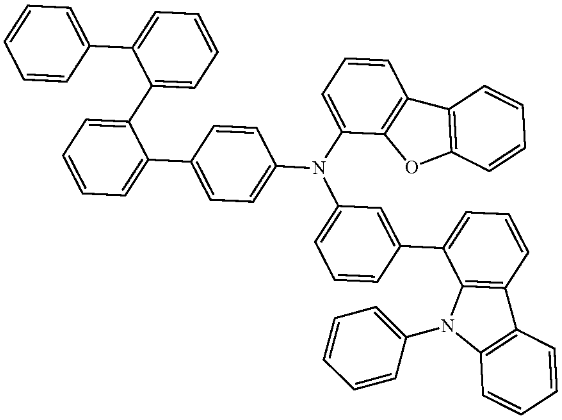

-continued
146
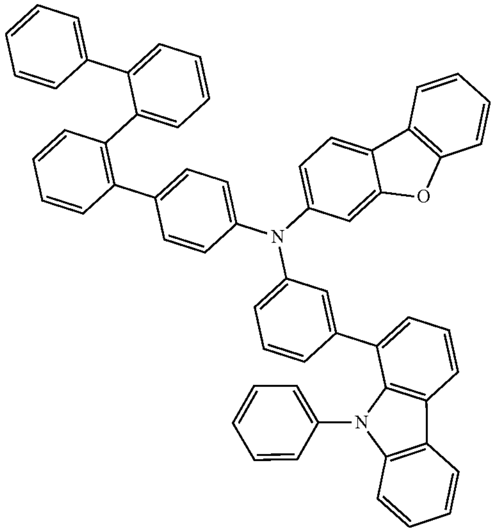
147
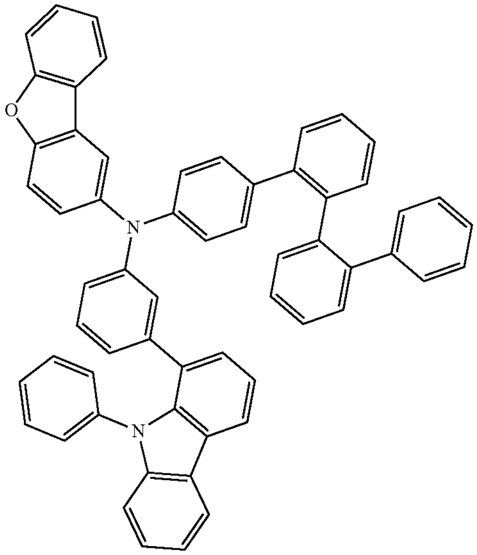
148
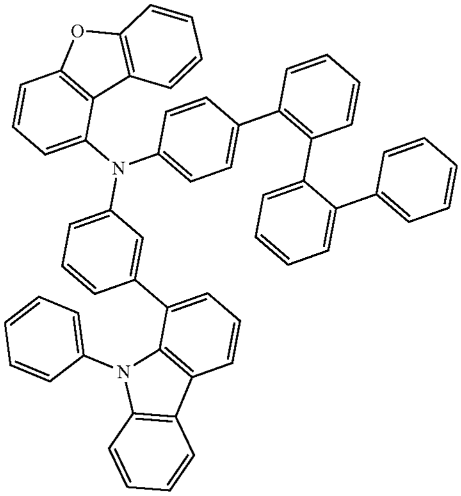
-continued
149
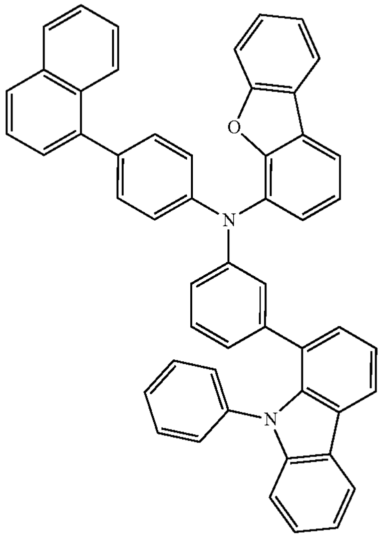
150
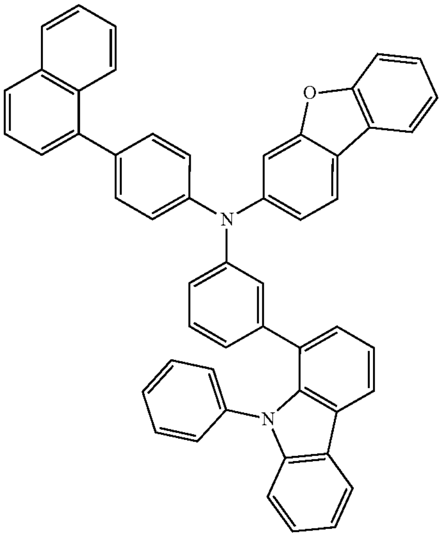
151
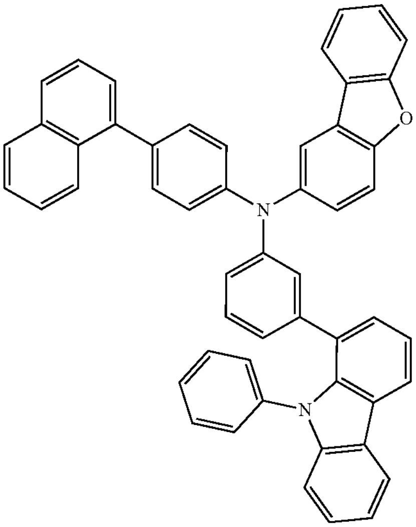

-continued
152
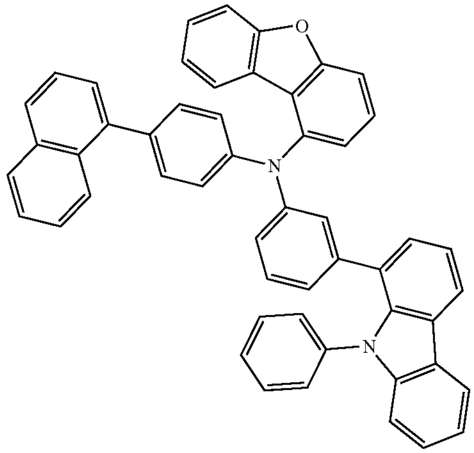
153
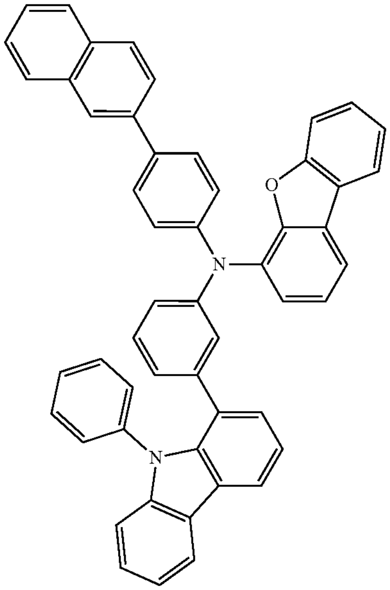
154
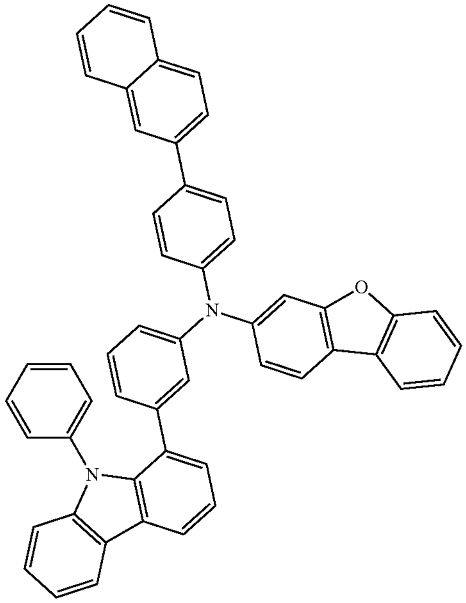
-continued
155
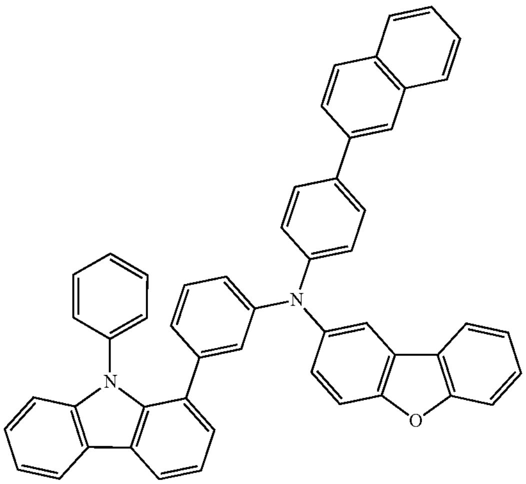
156
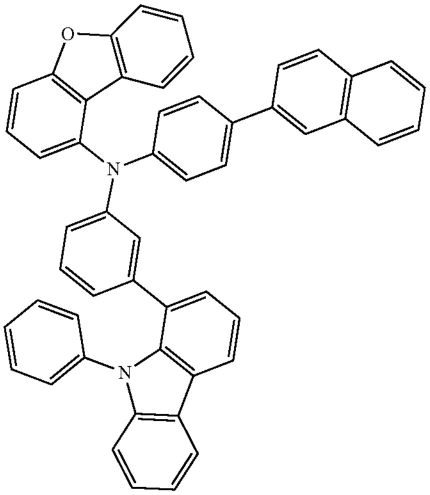
157
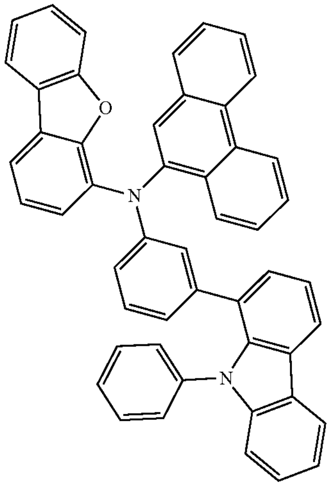

-continued
158
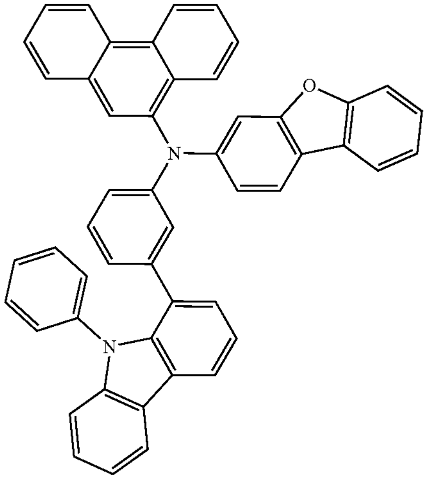
159
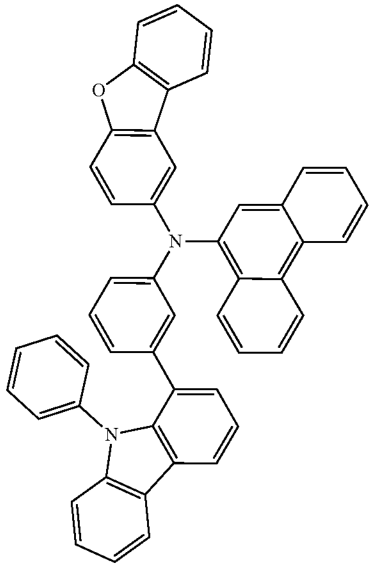
160
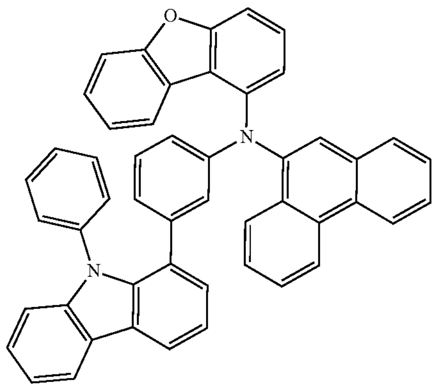
-continued
161
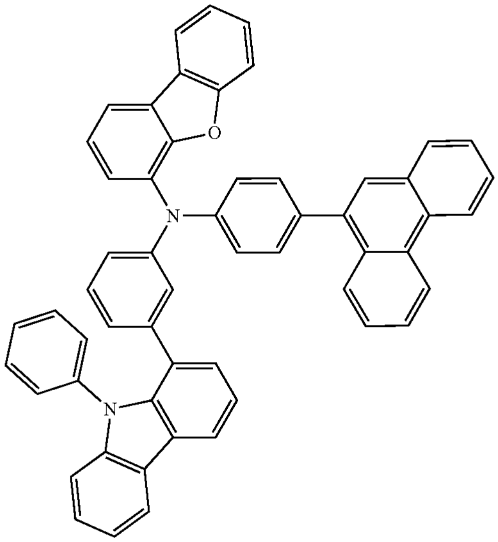
162
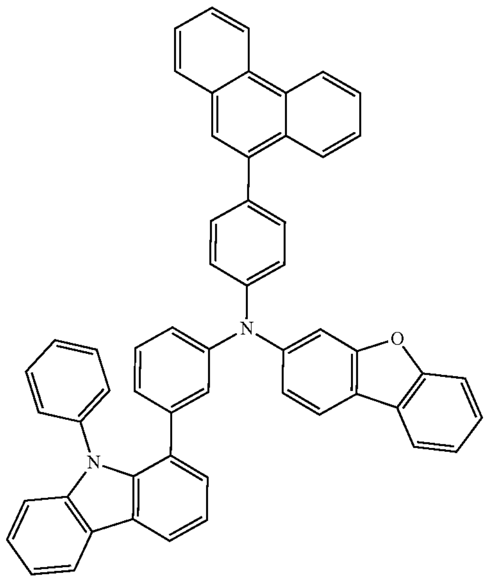

-continued
163
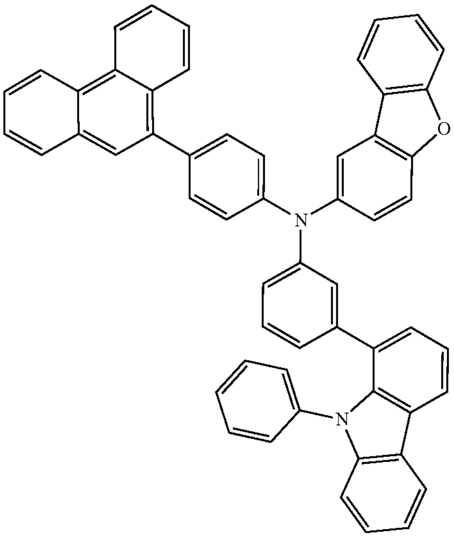
164
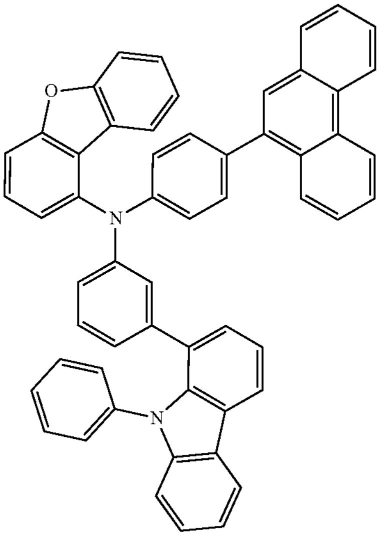
165
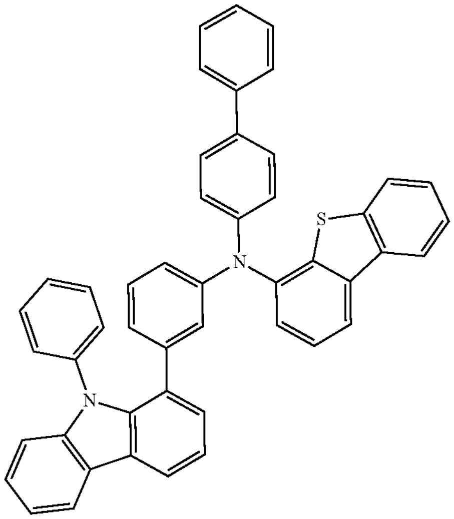
-continued
166
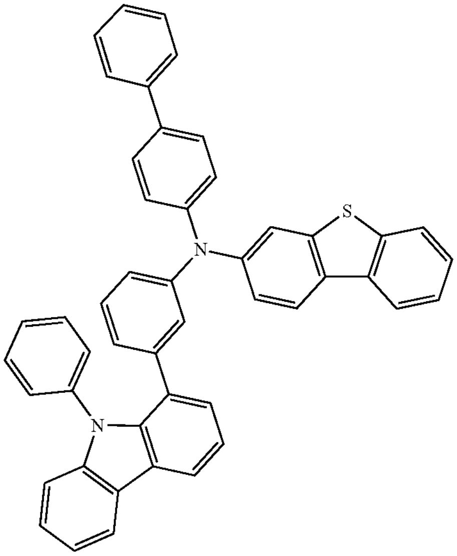
167
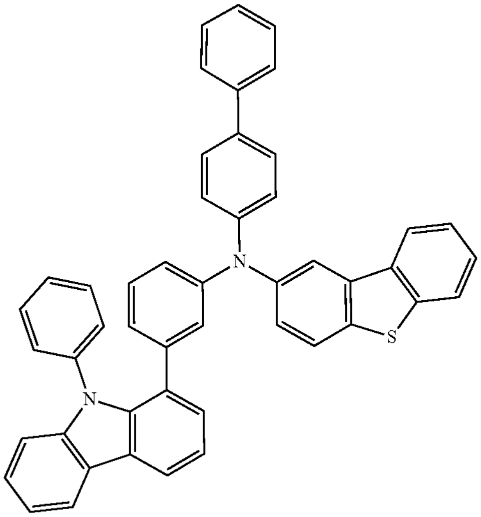
168
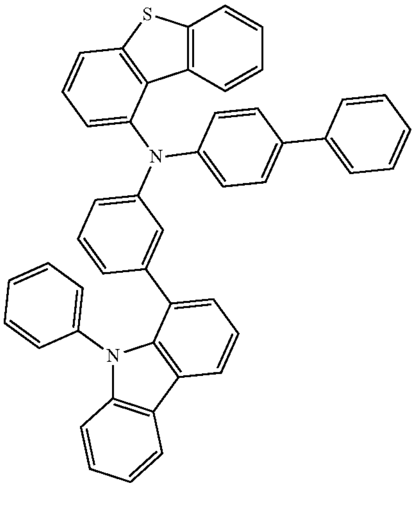

-continued
169
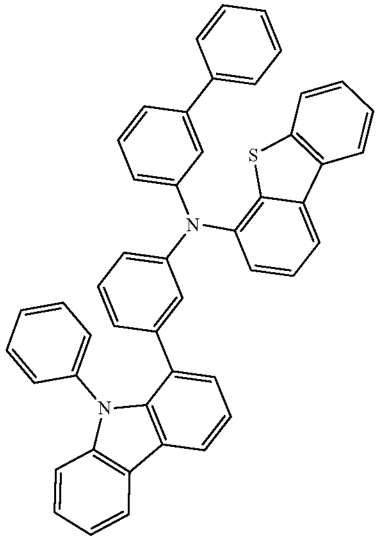
170
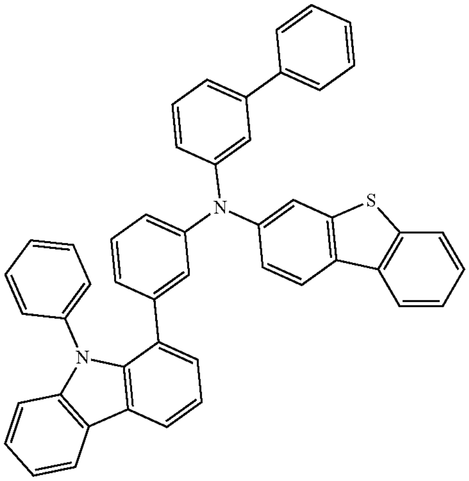
171
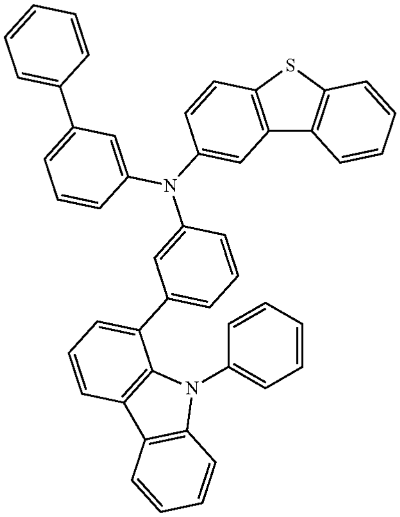
-continued
172
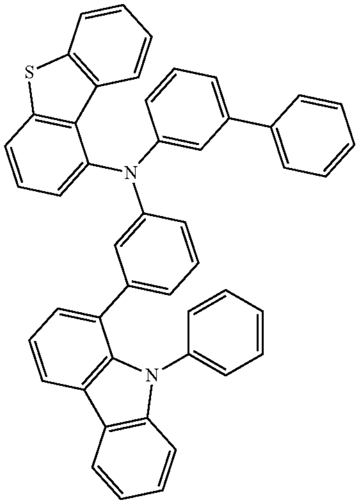
173
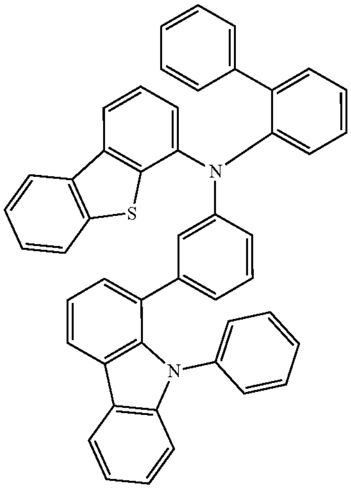
174
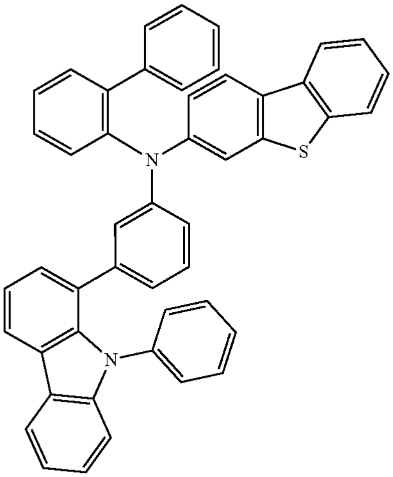

-continued
175
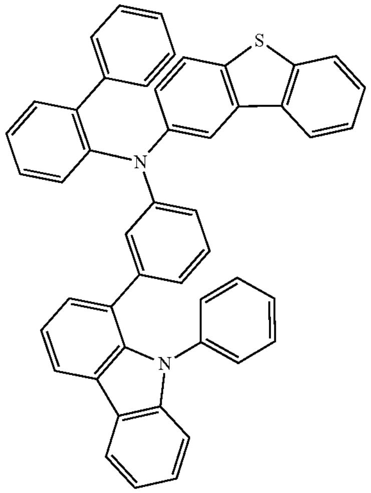
176
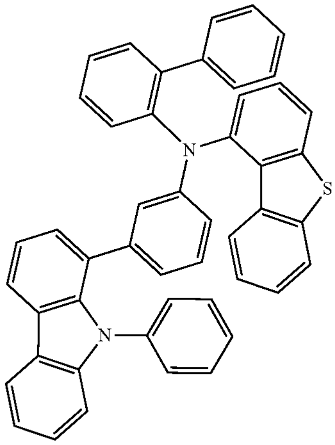
177
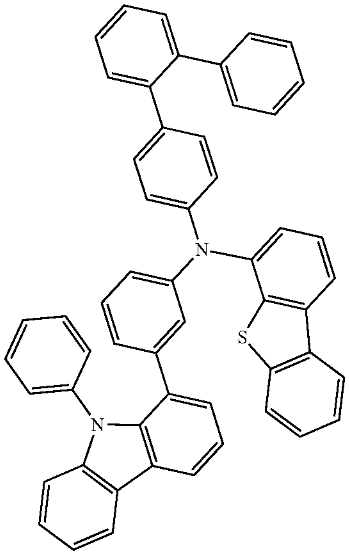
-continued
178
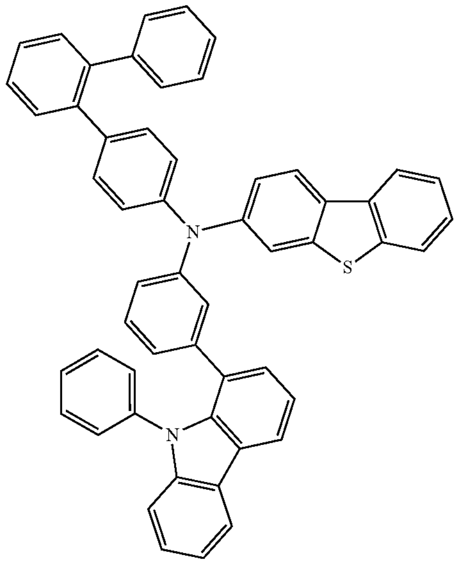
179
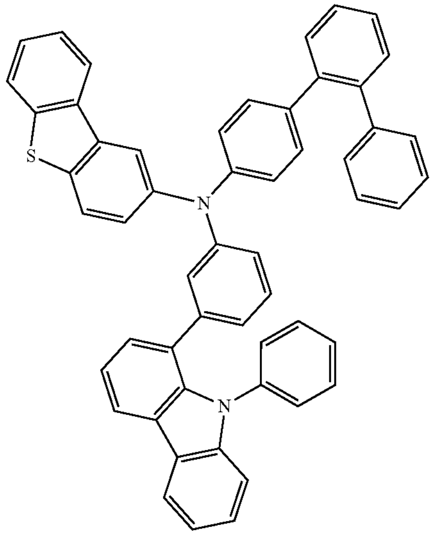
180
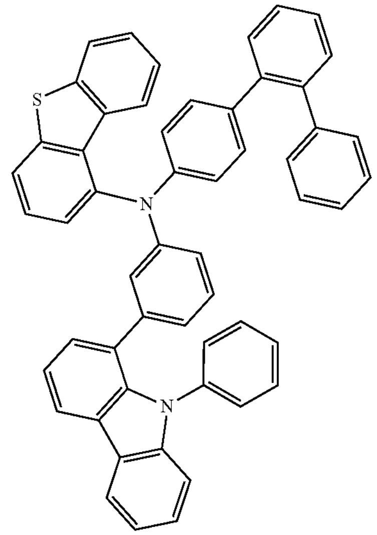

-continued
181
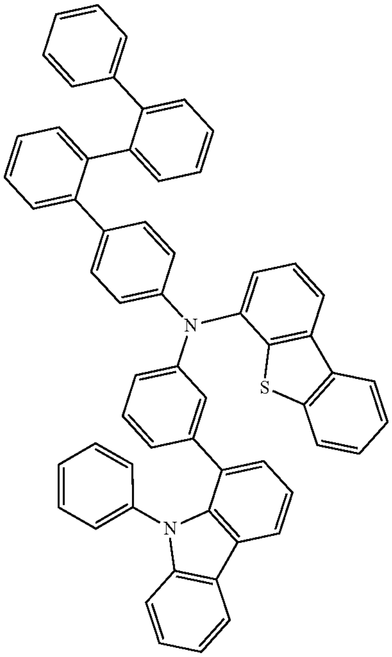
182
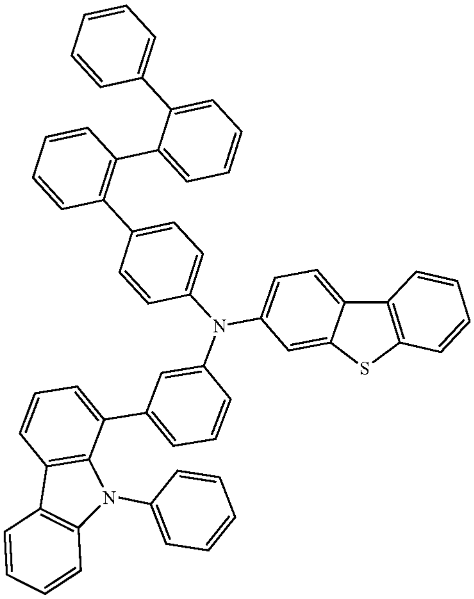
-continued
183
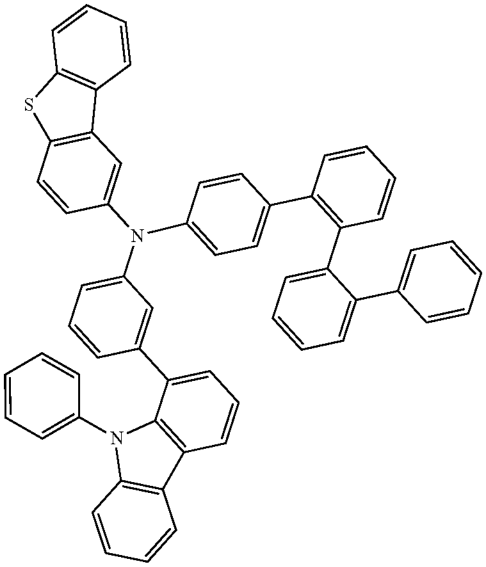
184
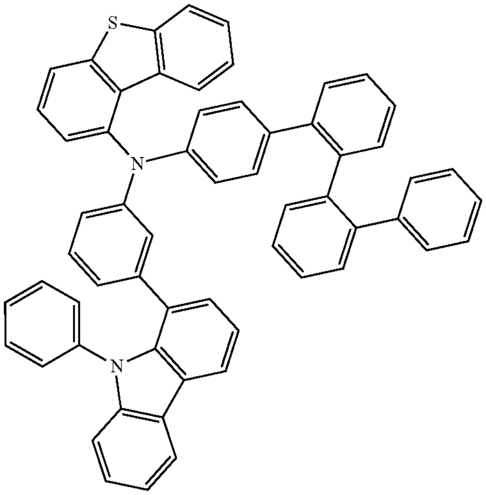
185
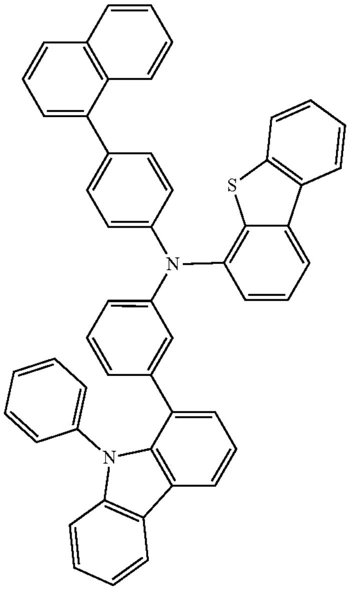

-continued
186
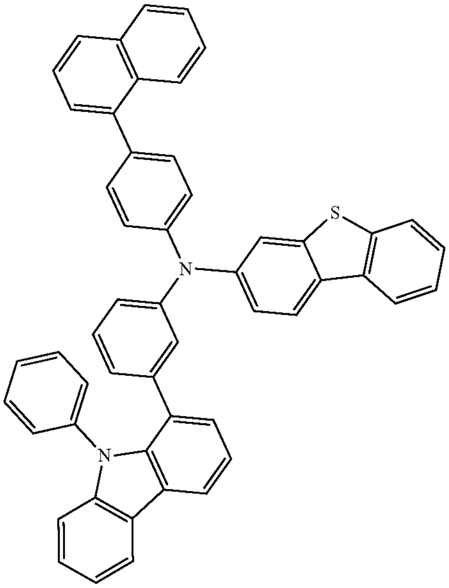
187
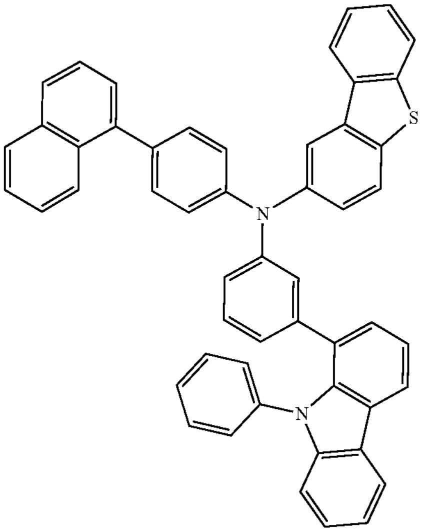
188
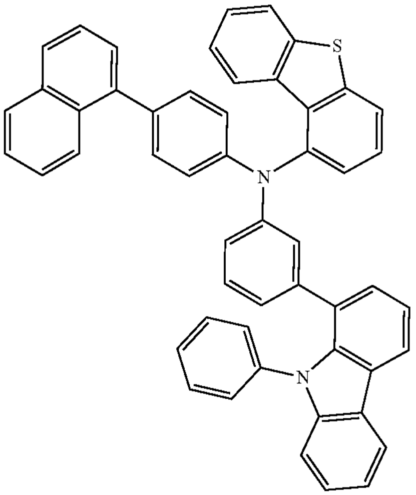
-continued
189
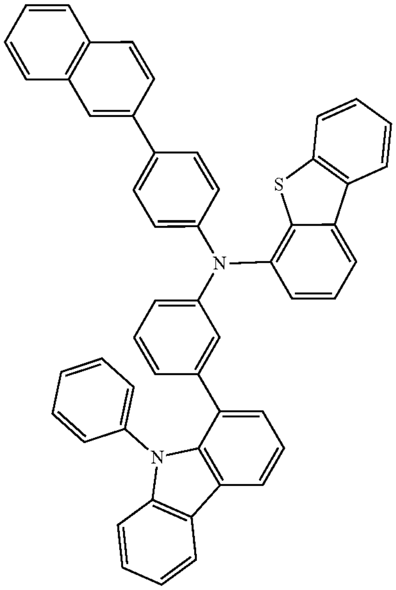
190
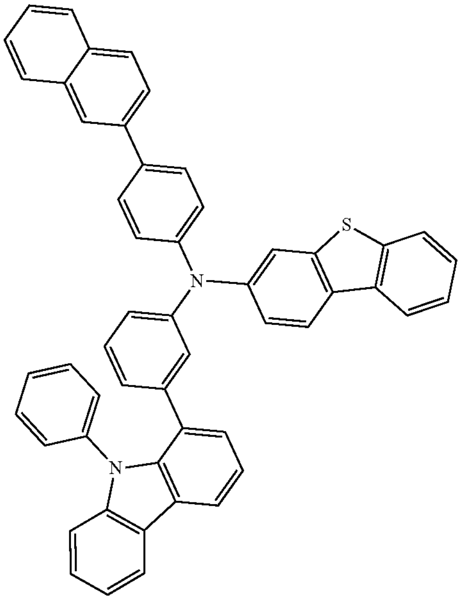

-continued
191
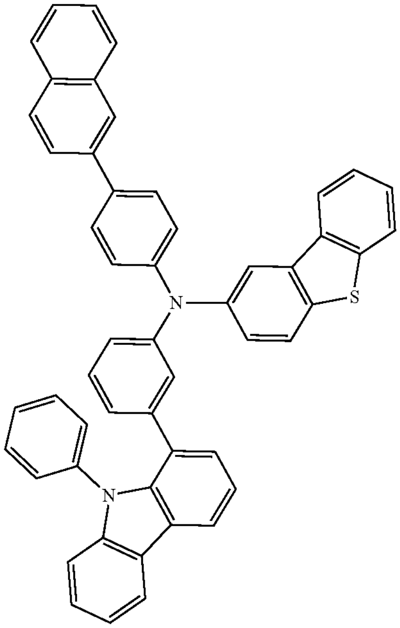
192
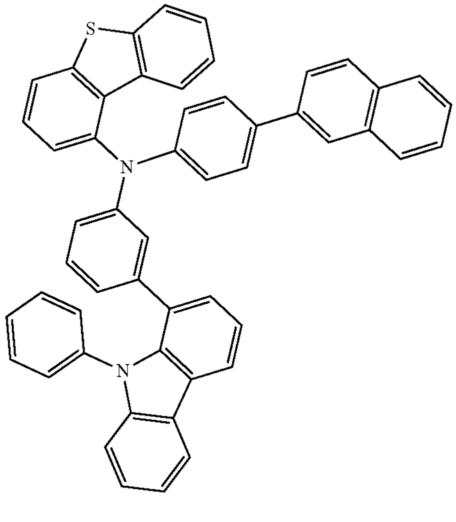
-continued
193
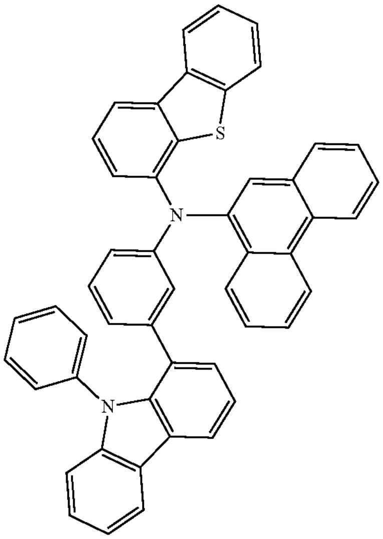
194
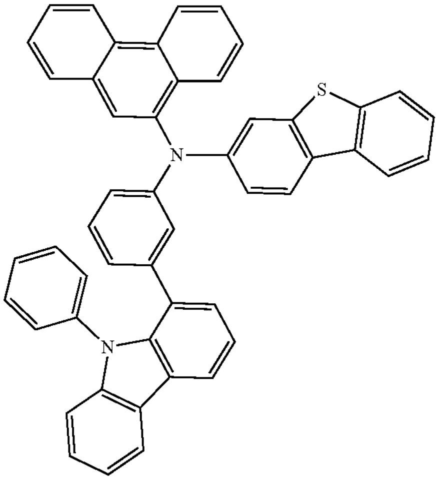
195
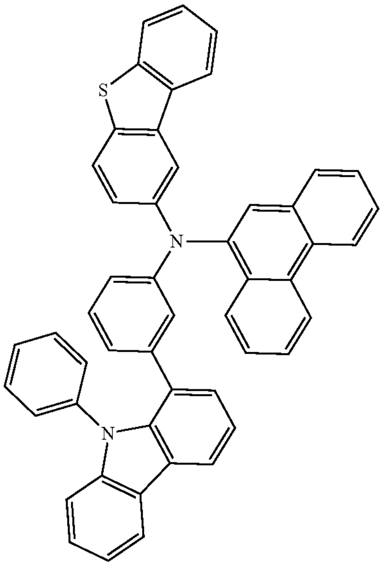

-continued
196
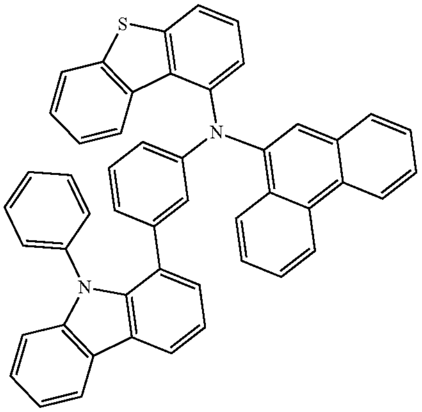
197
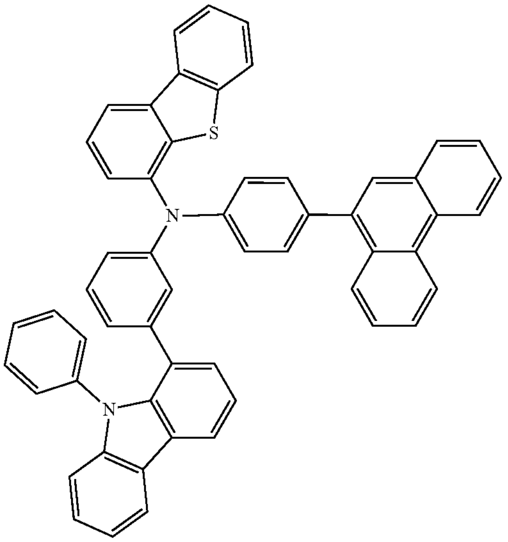
198
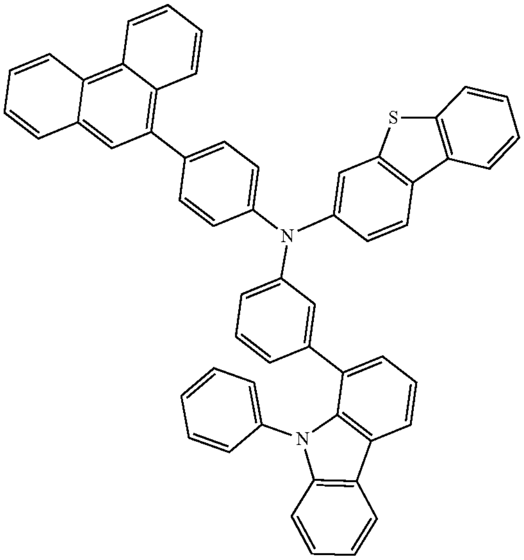
-continued
199
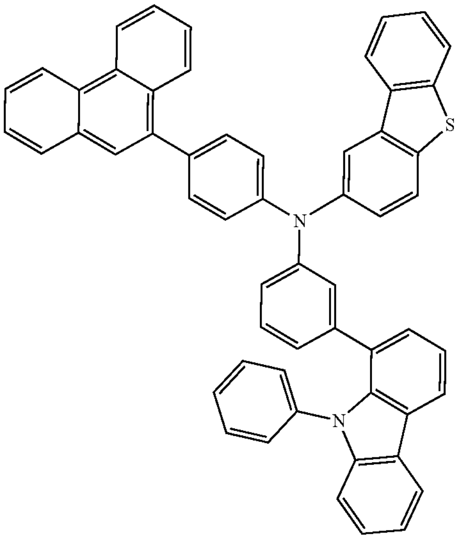
200
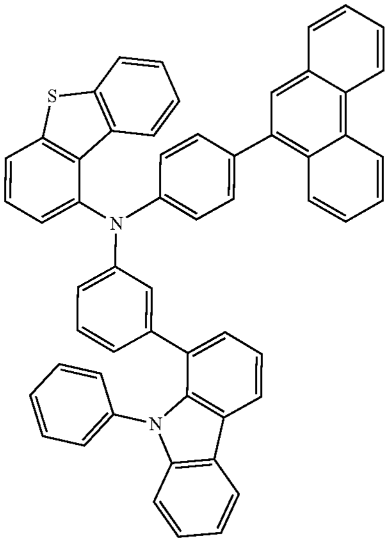
201
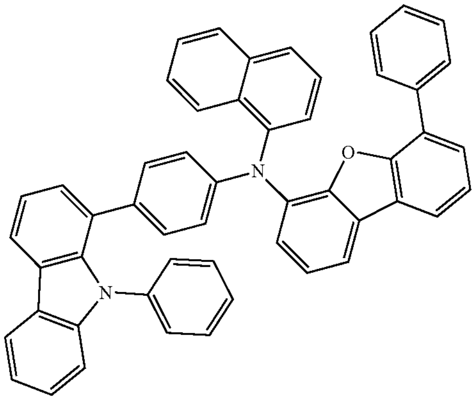

-continued
202
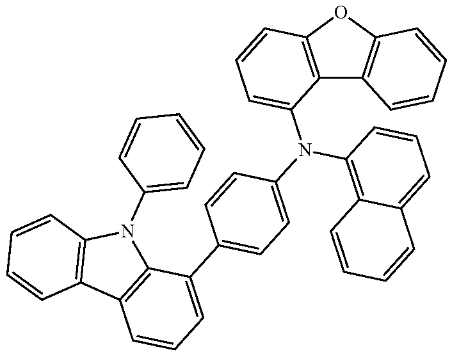
203
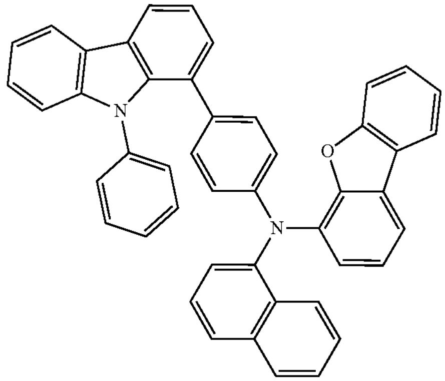
204
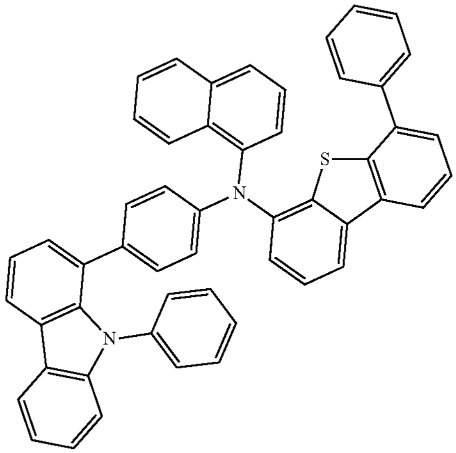
205
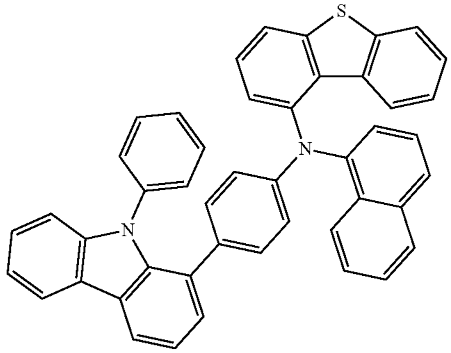
-continued
206
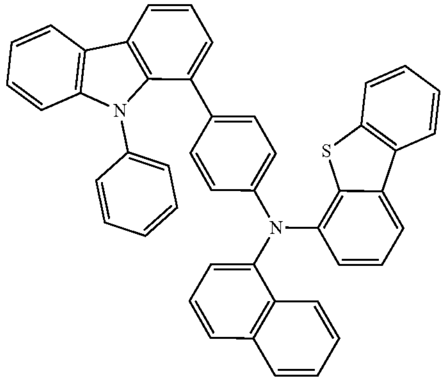
207
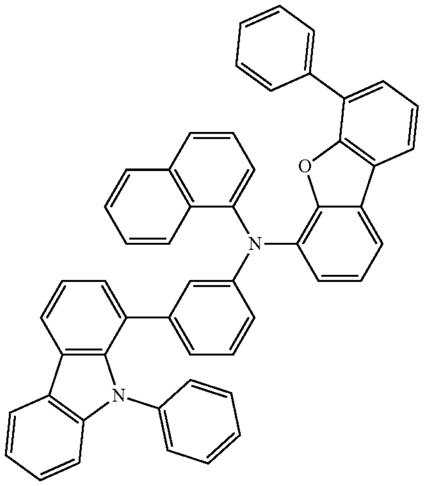
208
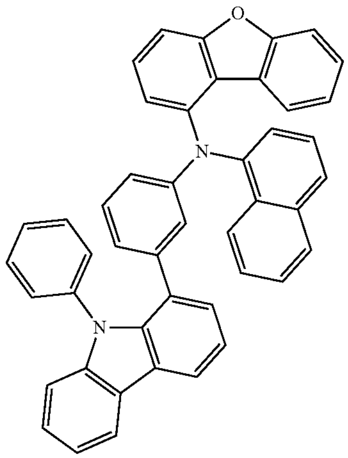

-continued
209
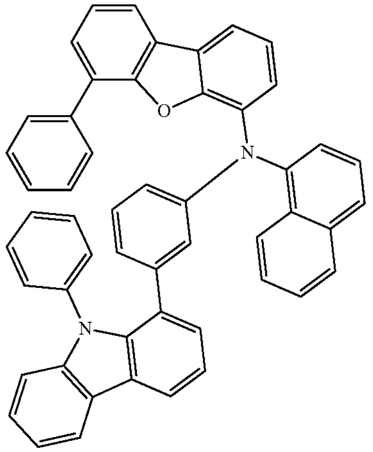
210
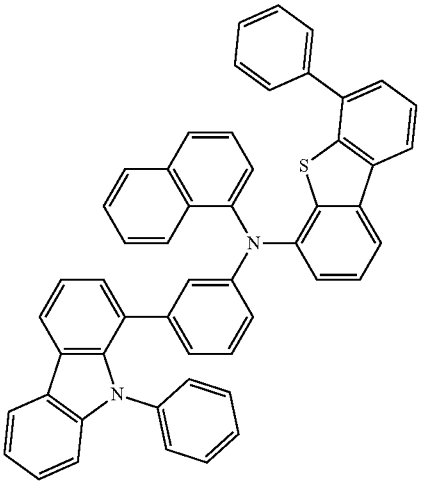
211
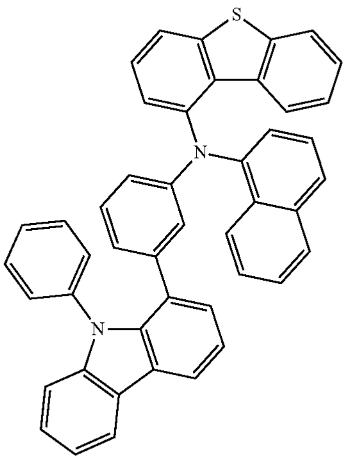
-continued
212
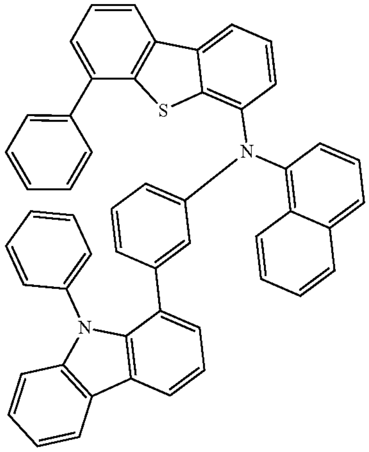
213
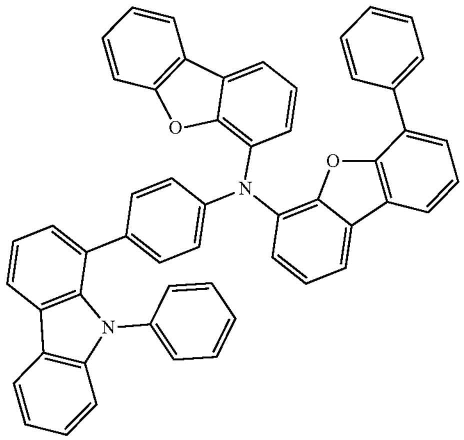
214
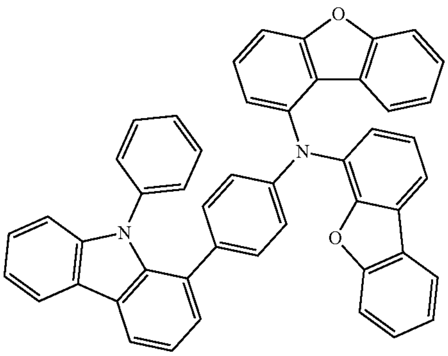

-continued
215
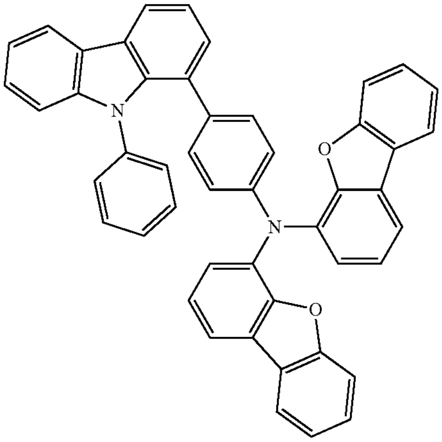
216
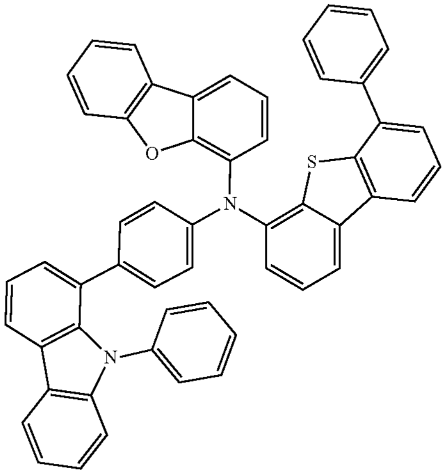
217
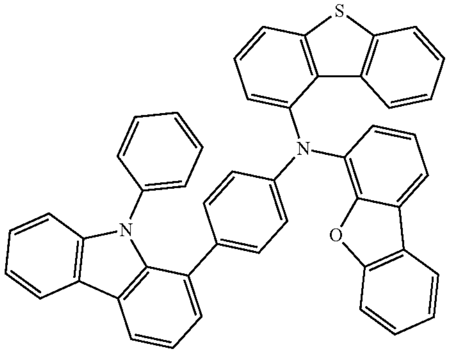
-continued
218
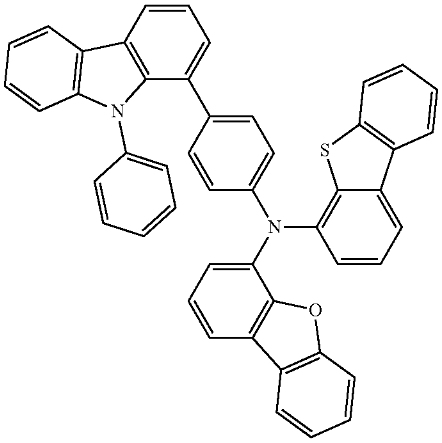
219
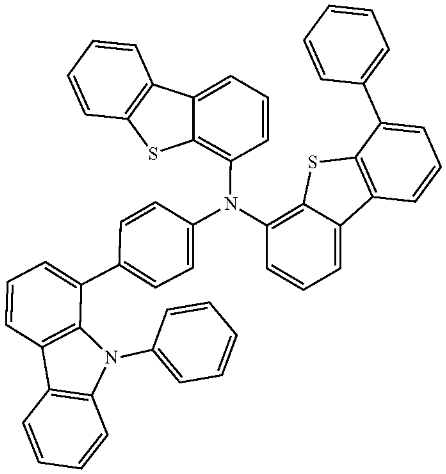
220
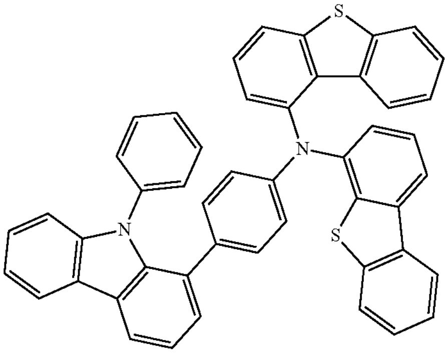

-continued
221
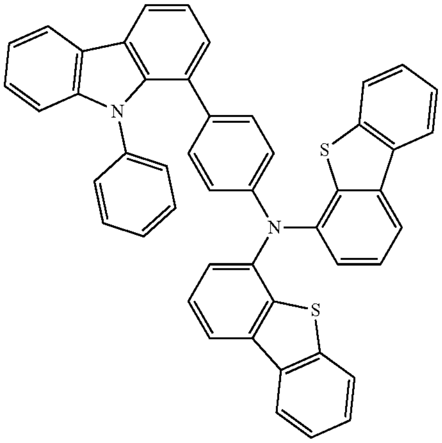
222
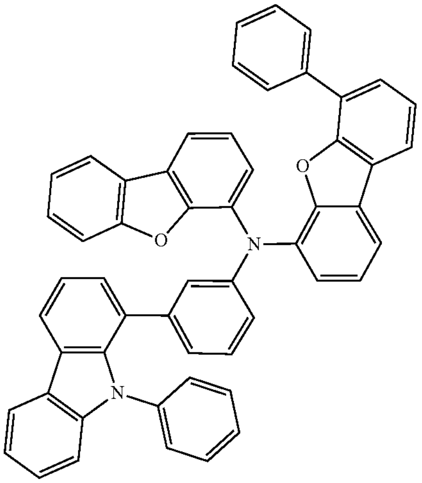
223
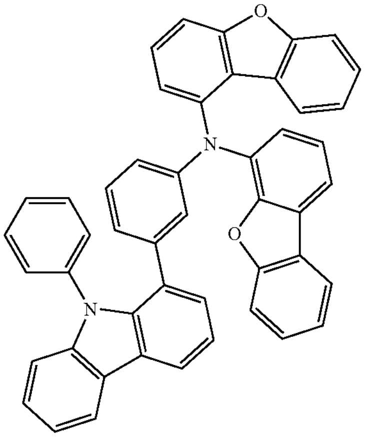
-continued
224
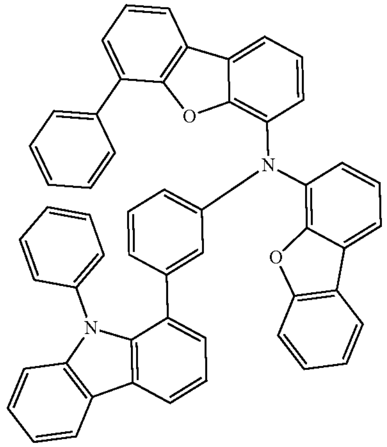
225
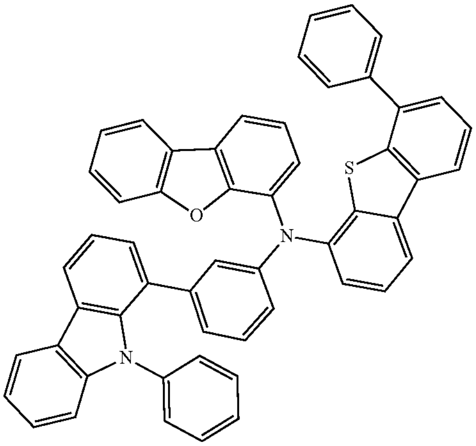
226
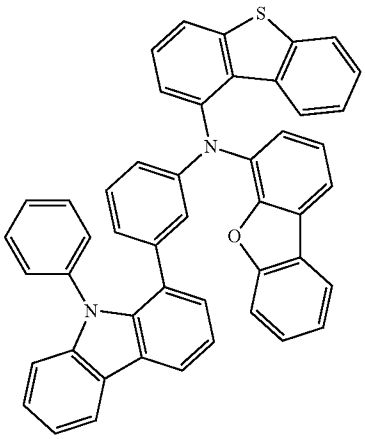

-continued
227
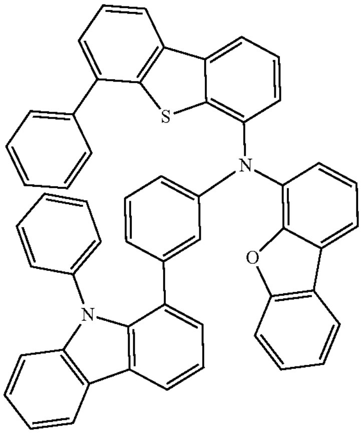
228
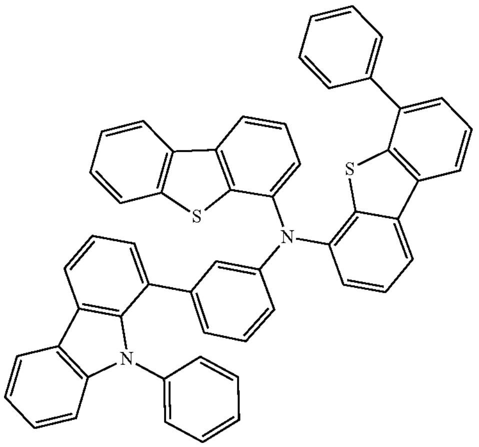
229
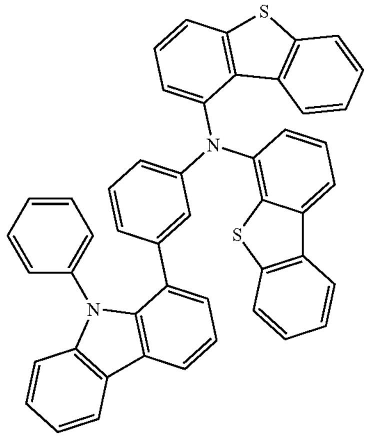
230
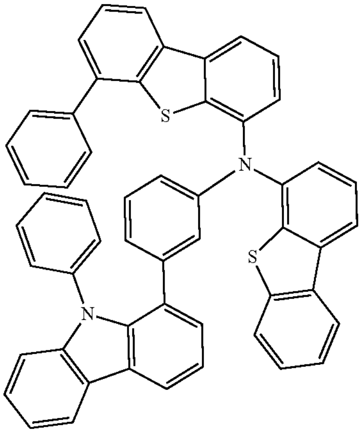
231
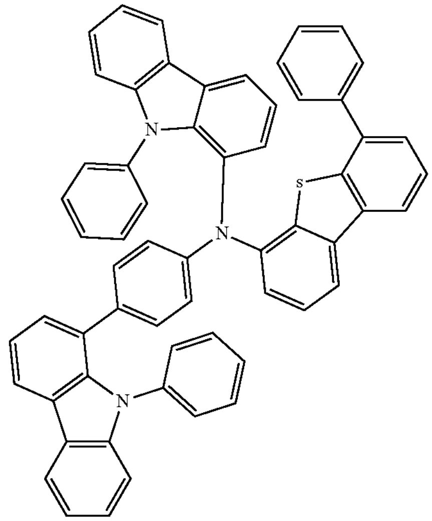
232
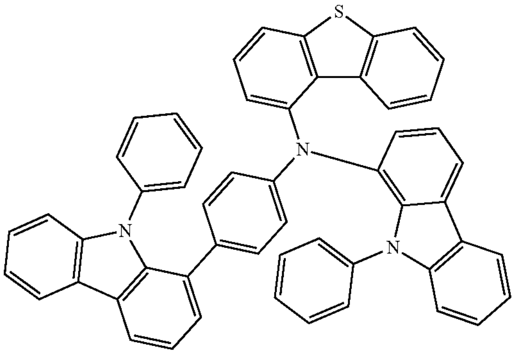

-continued
233
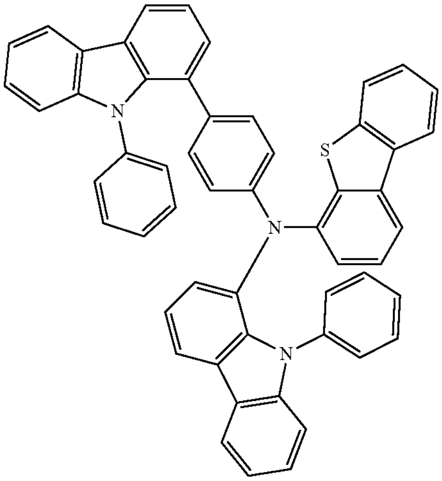
234
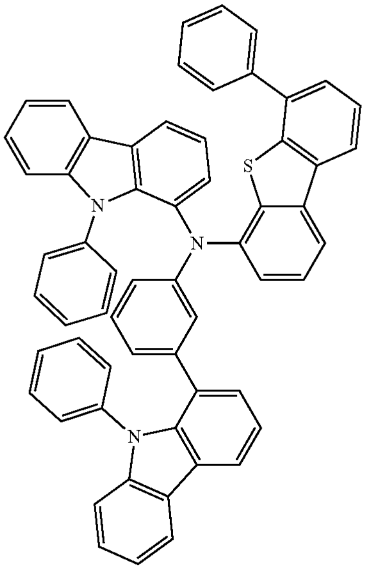
235
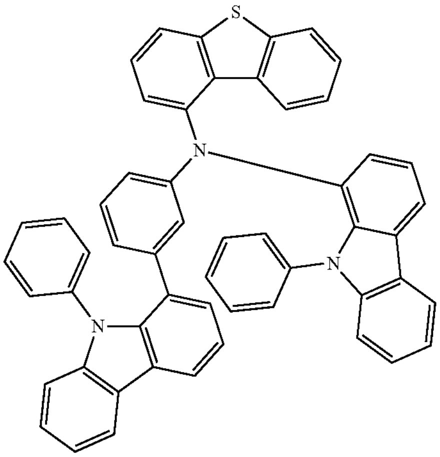
-continued
236
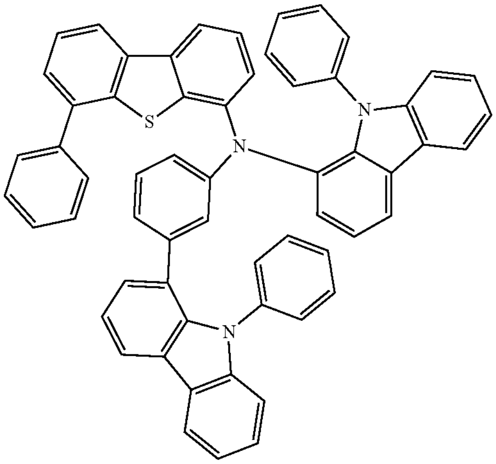
237
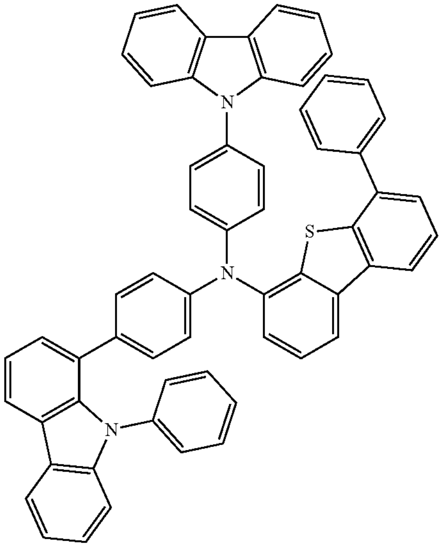
238
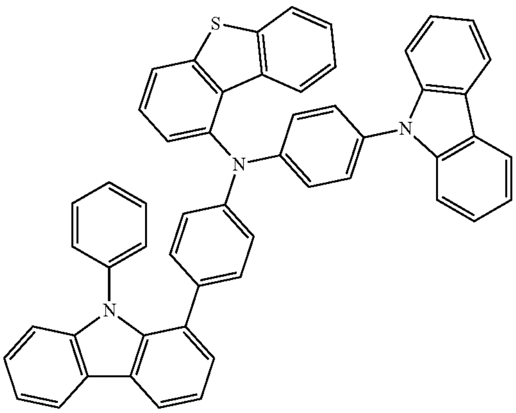

-continued
239
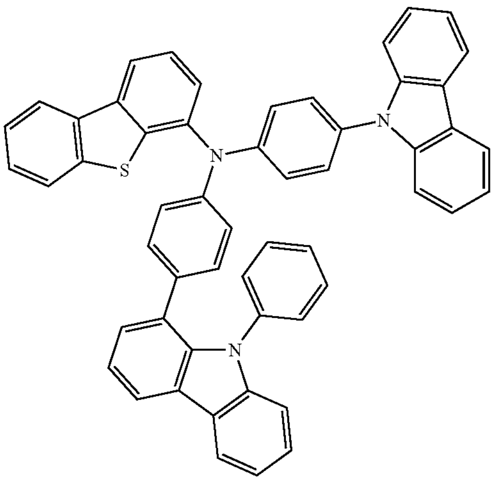
240
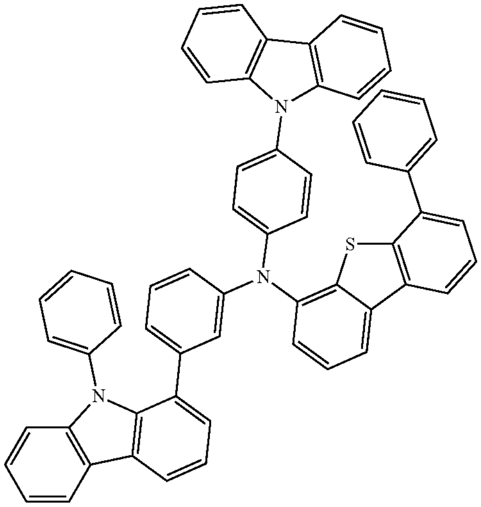
241
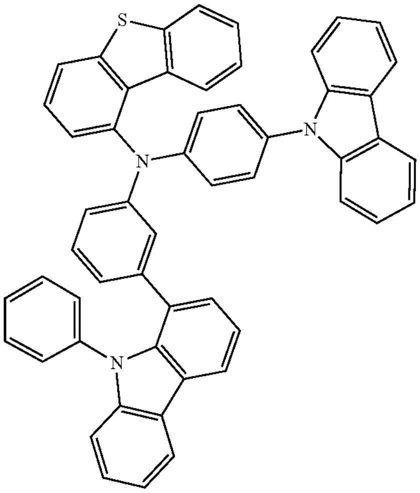
-continued
242
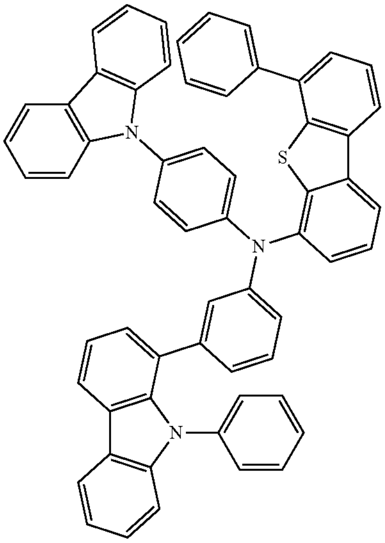
243
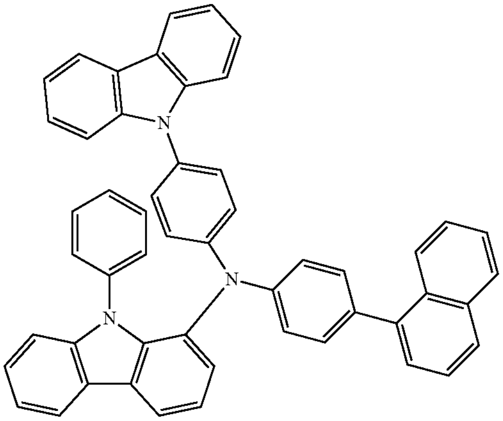
244
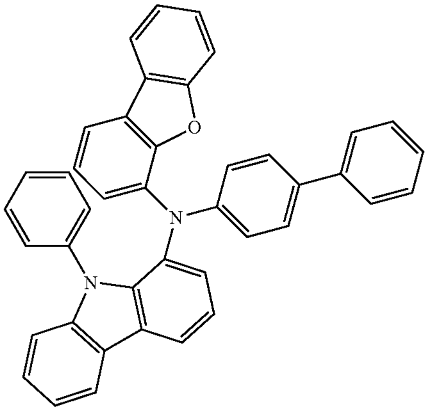

-continued
245
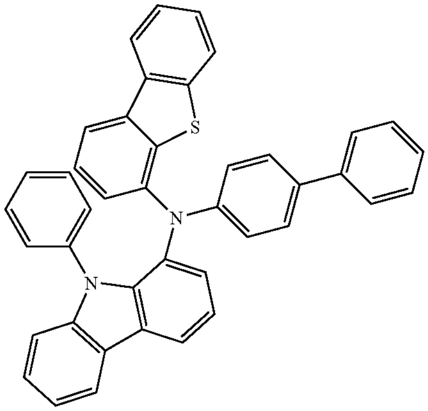
246
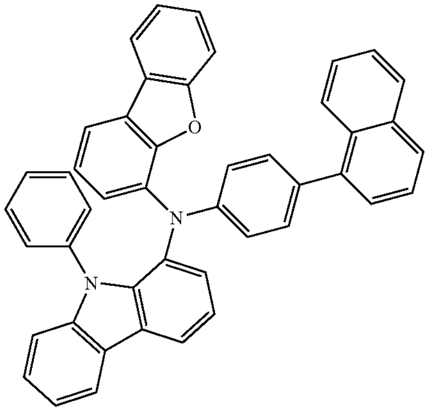
247
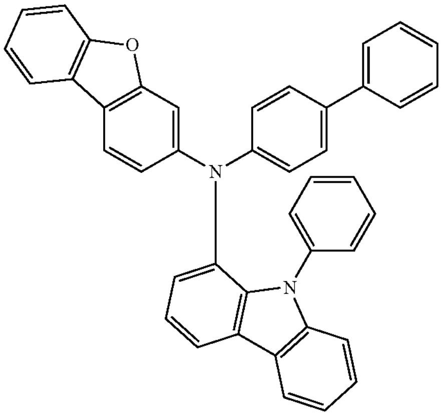
-continued
248
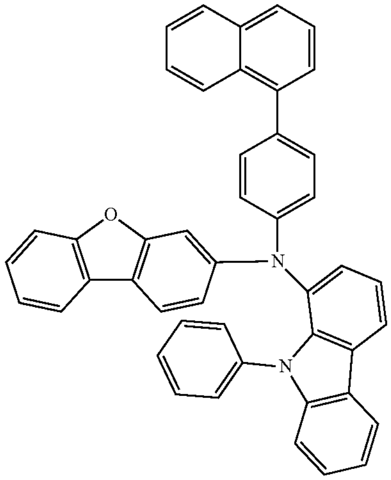
249
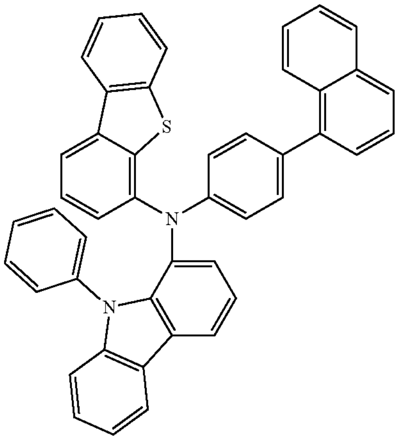
250
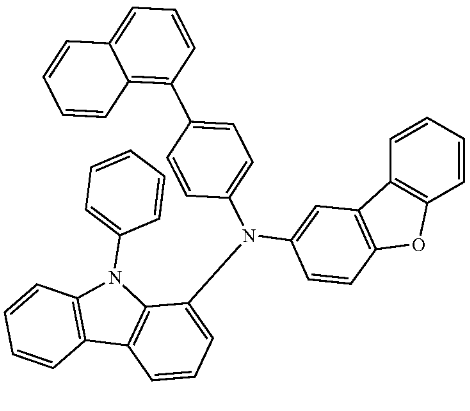

-continued
251
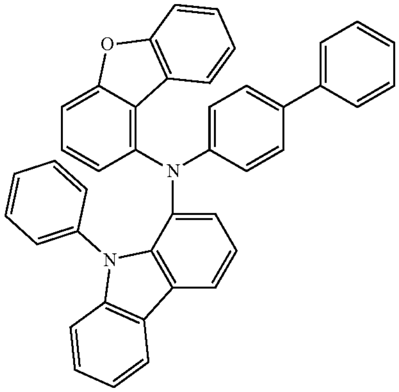
252
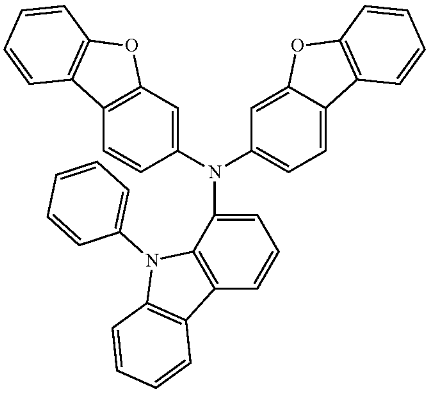
253
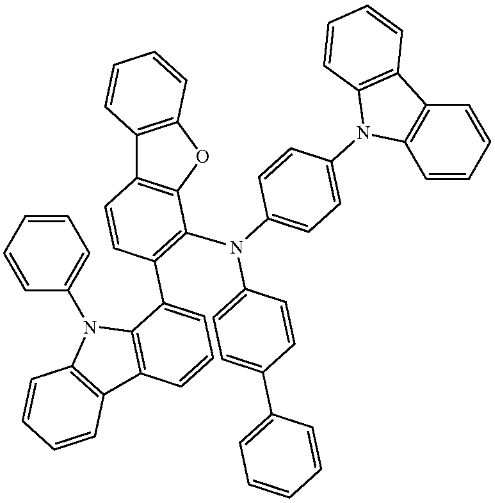
-continued
254
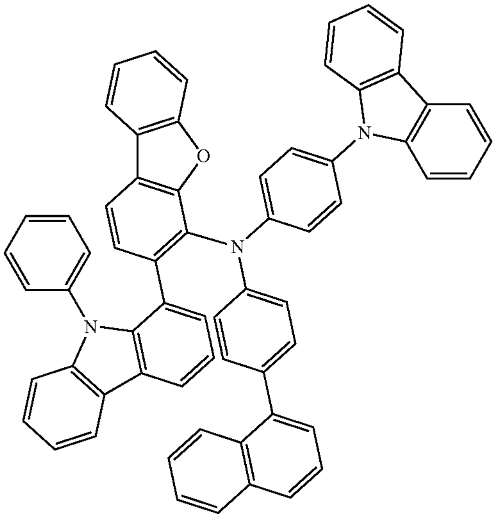
255
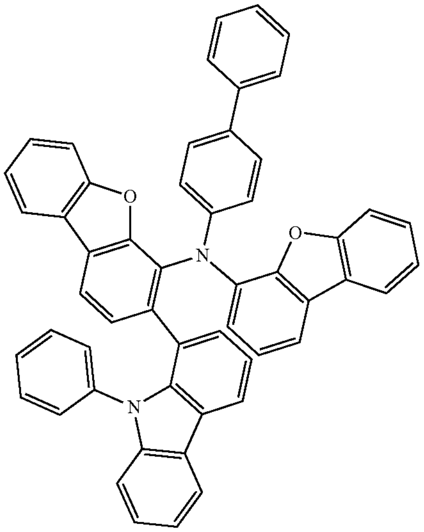
256
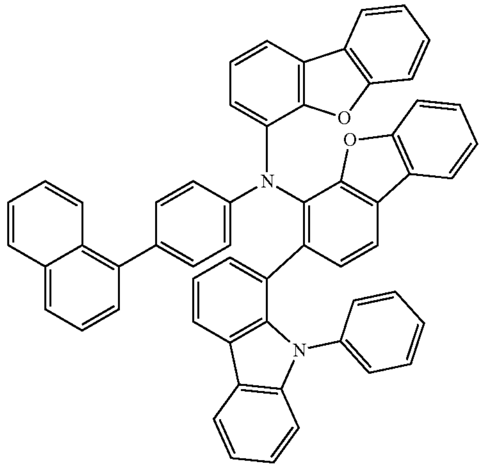

-continued
257
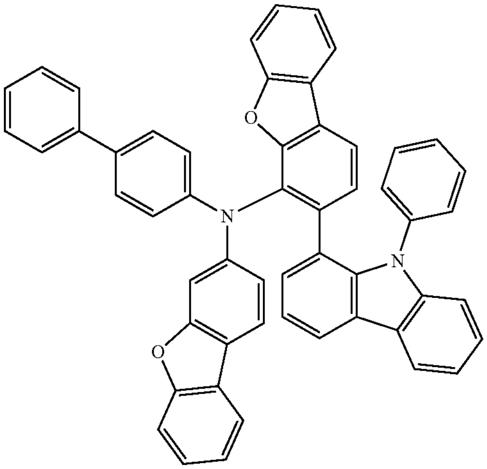
258
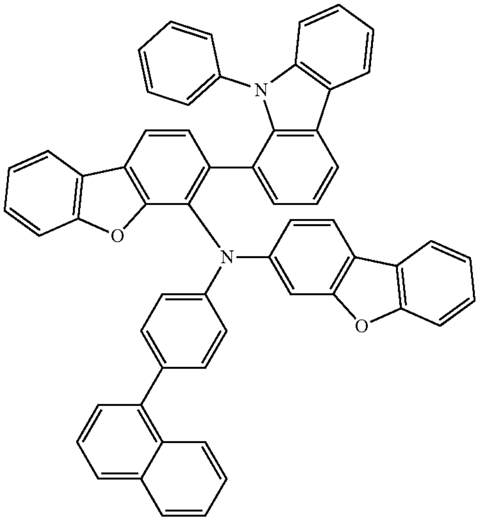
259
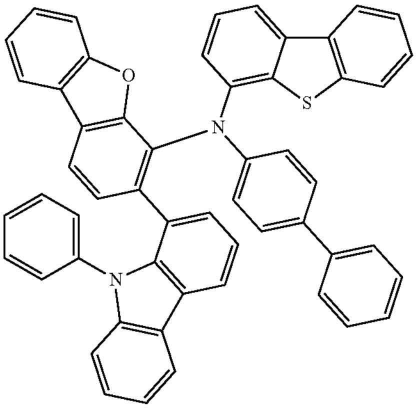
-continued
260
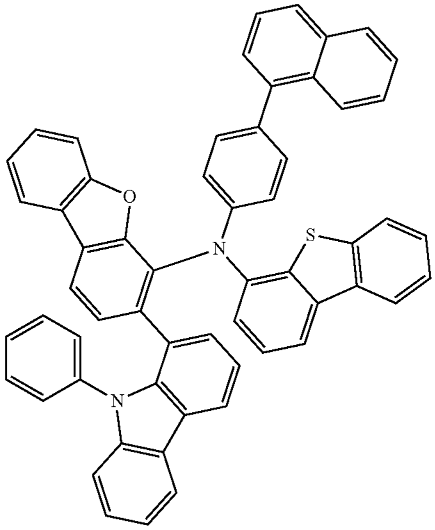
261
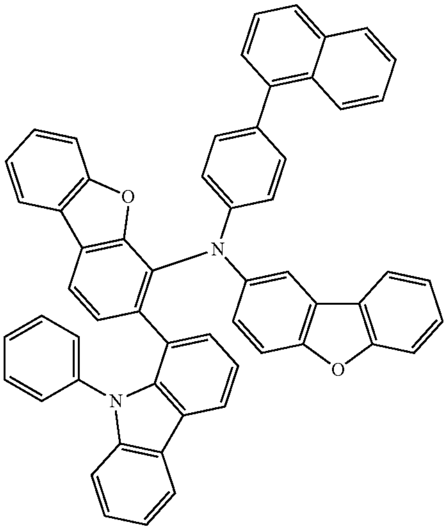
262
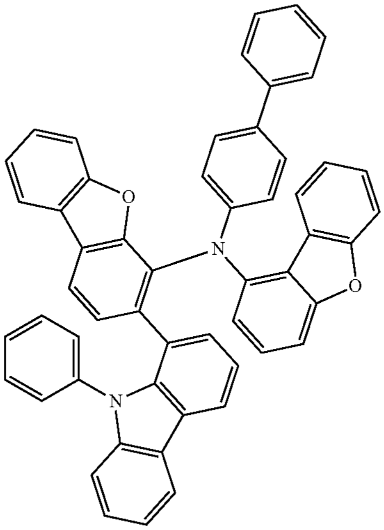

-continued
263
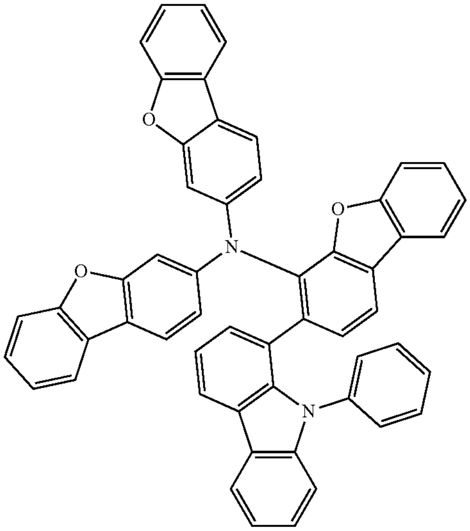
264
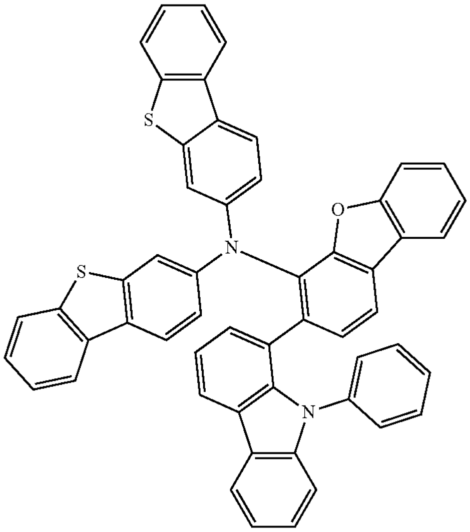
265
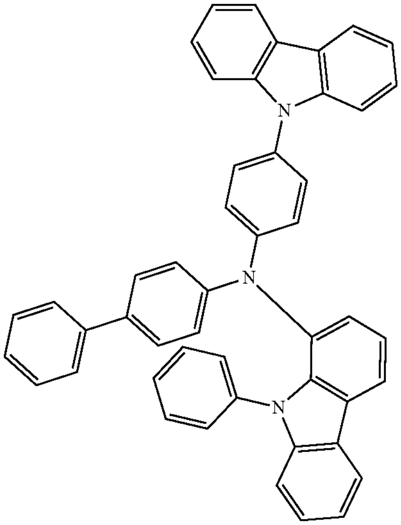
-continued
266
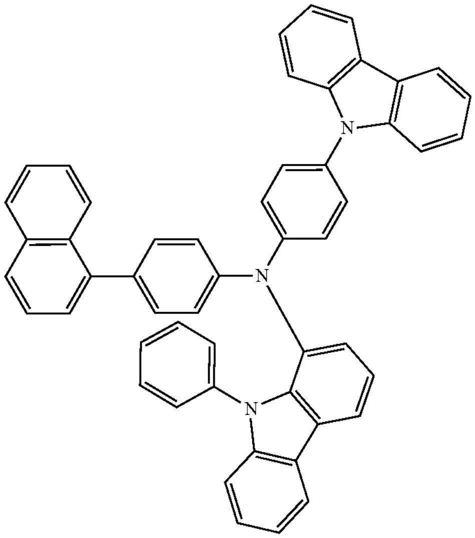
267
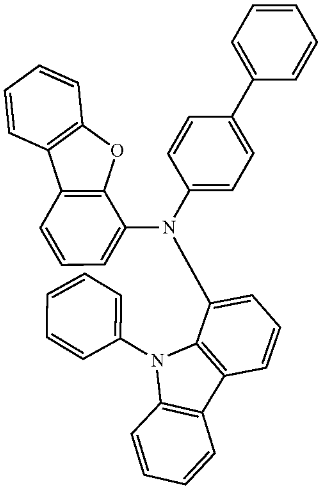
268
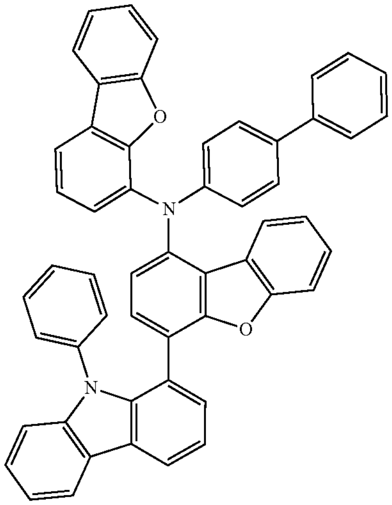

-continued
269
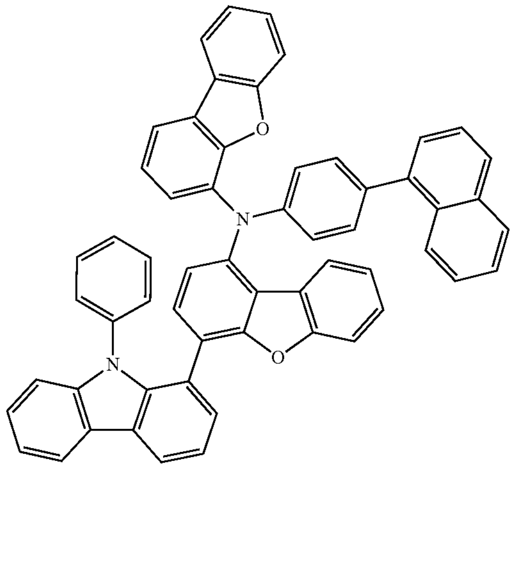
270
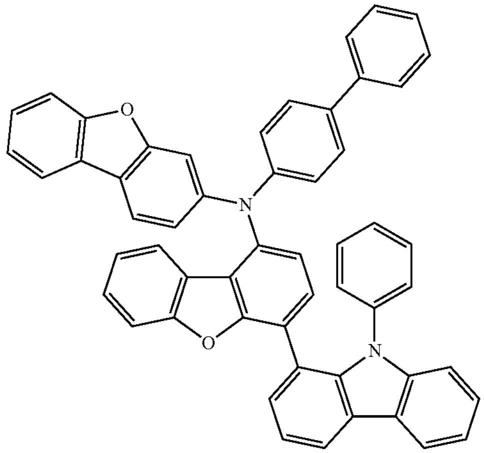
271
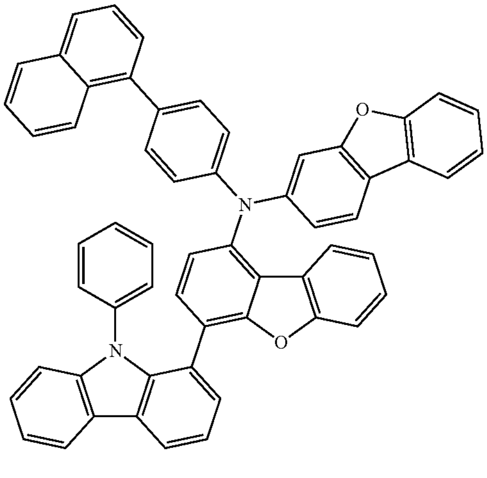
-continued
272
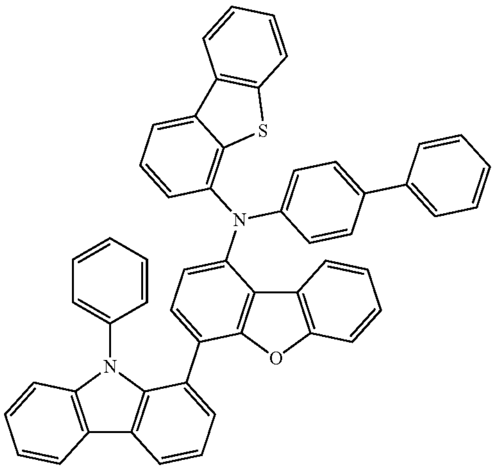
273
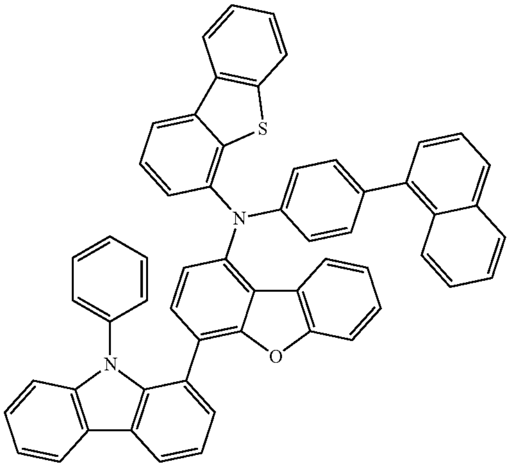
274
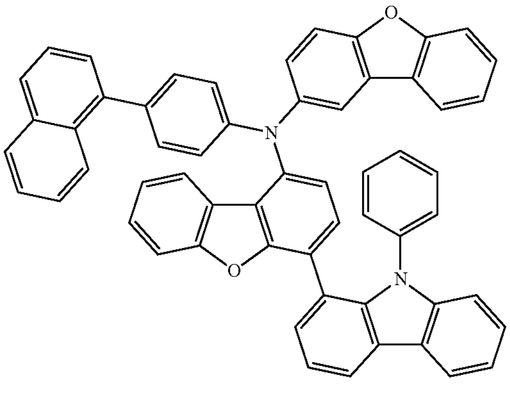

-continued
275
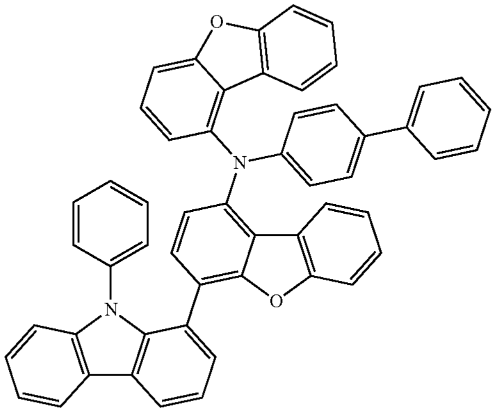
276
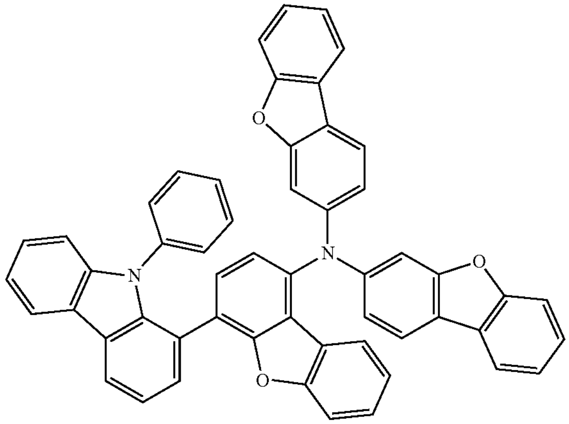
277
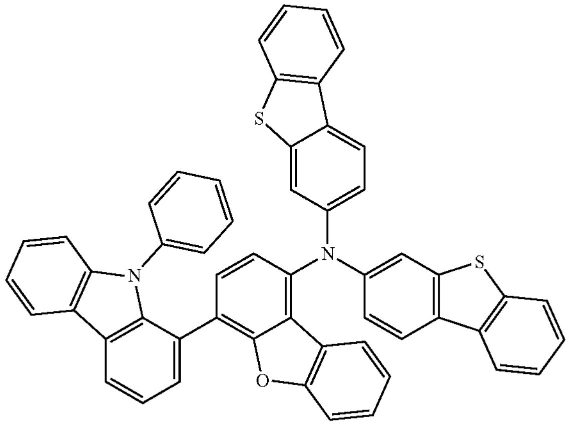
-continued
278
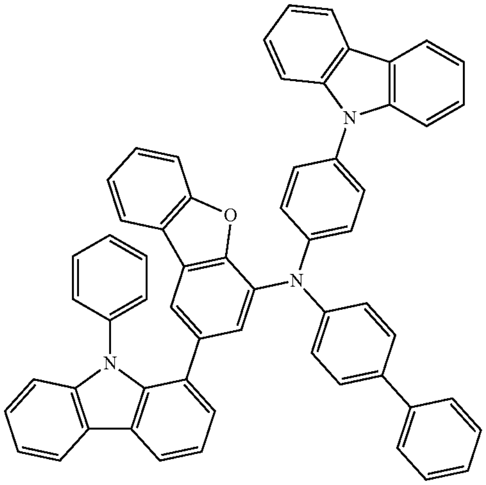
279
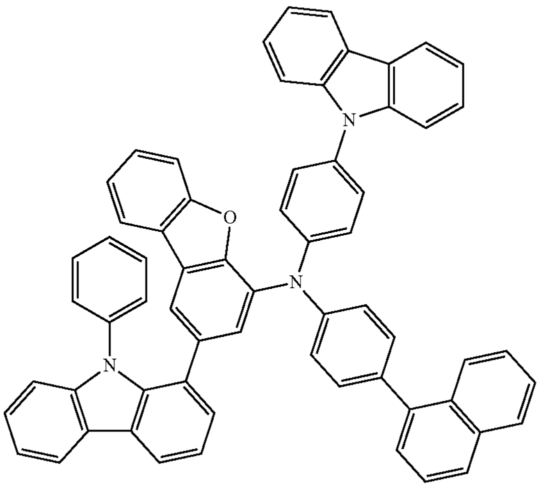
280
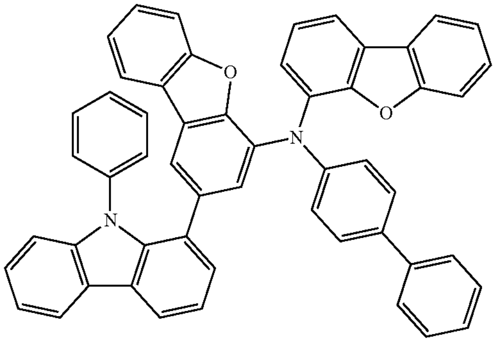

-continued
281
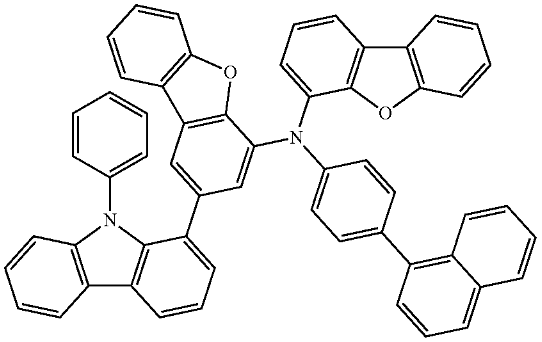
282
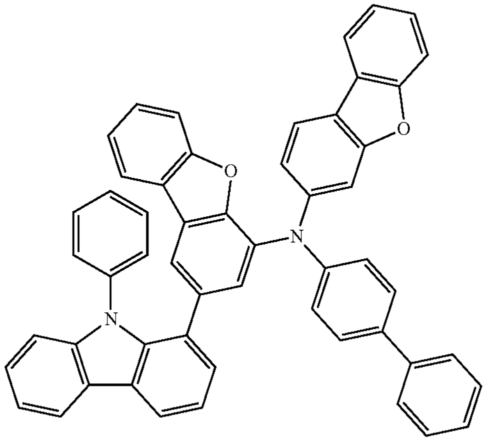
283
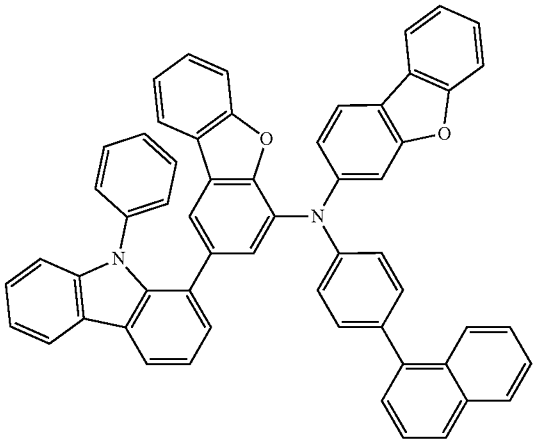
284
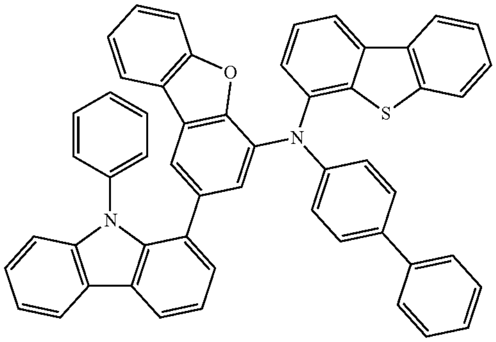
-continued
285
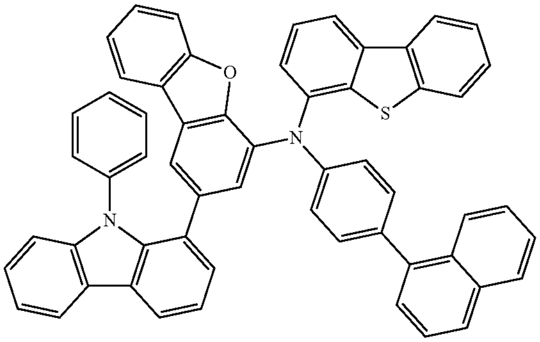
286
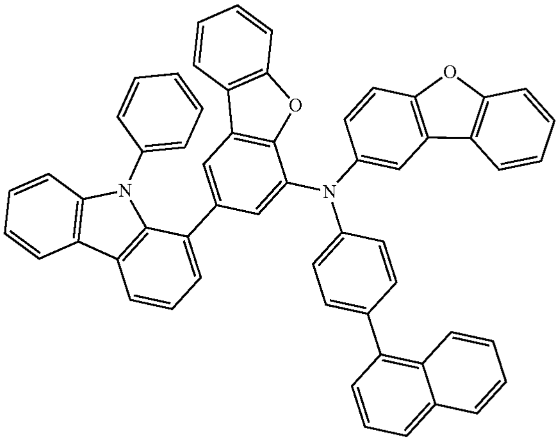
287
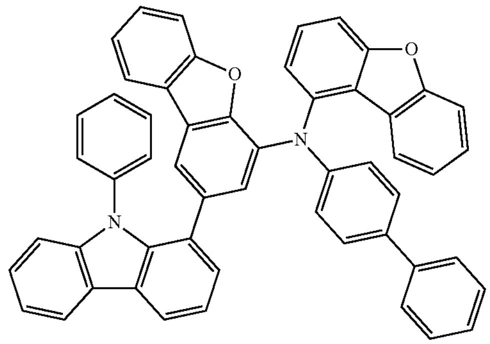
288
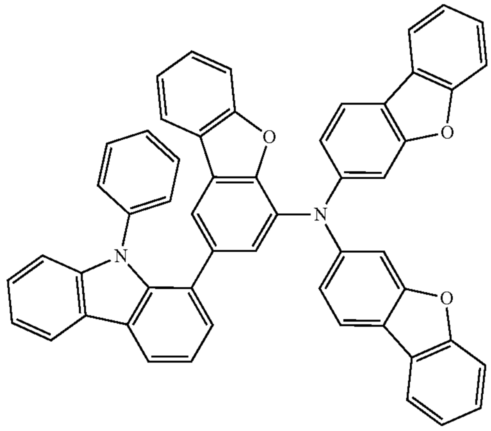

-continued
289
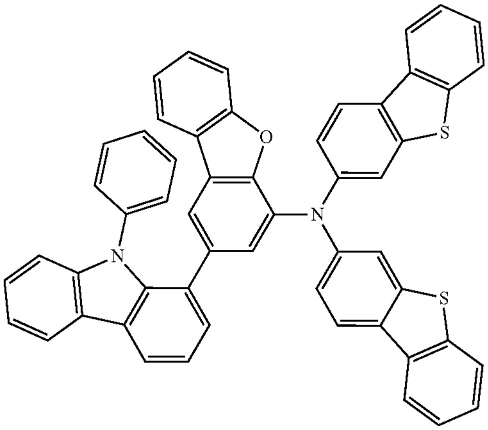
290
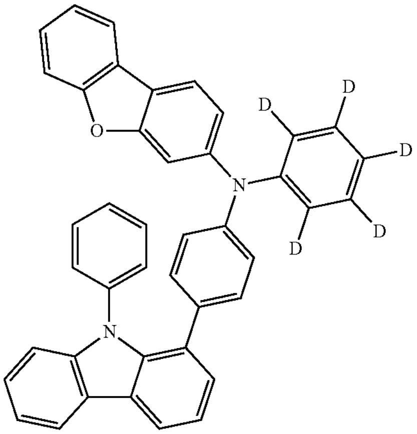
291
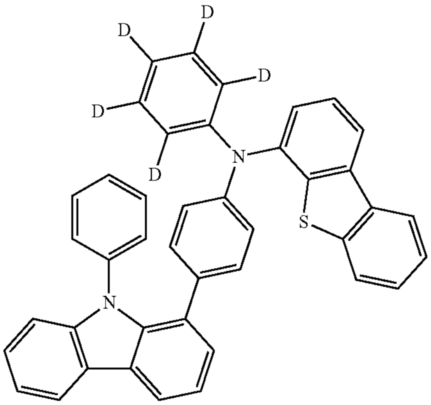
-continued
292
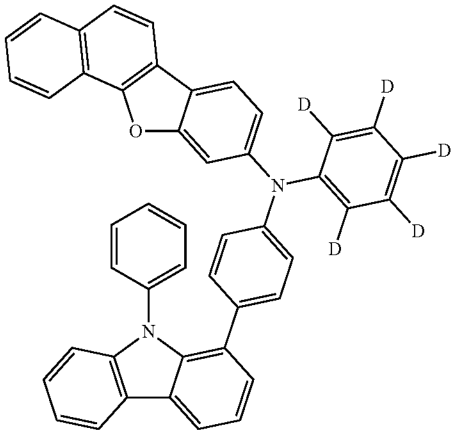
293
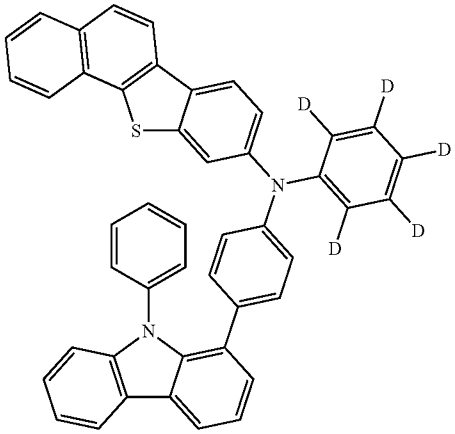
294
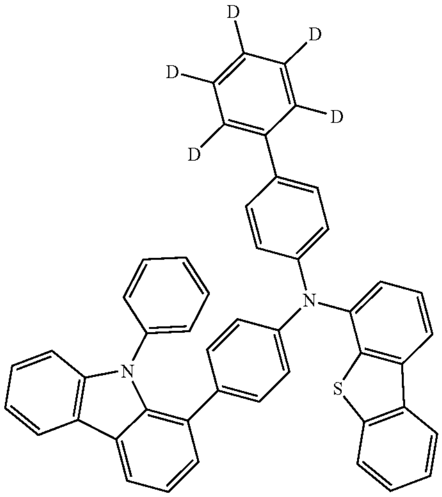

-continued

295

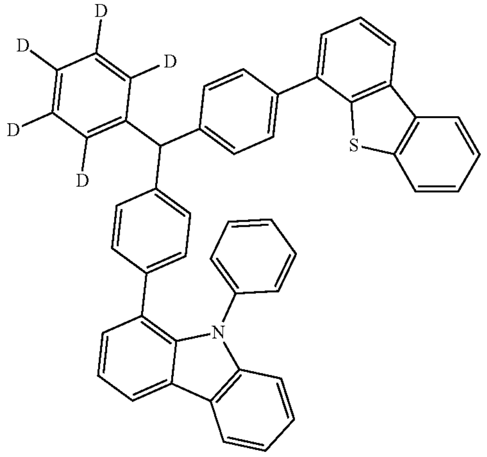

296

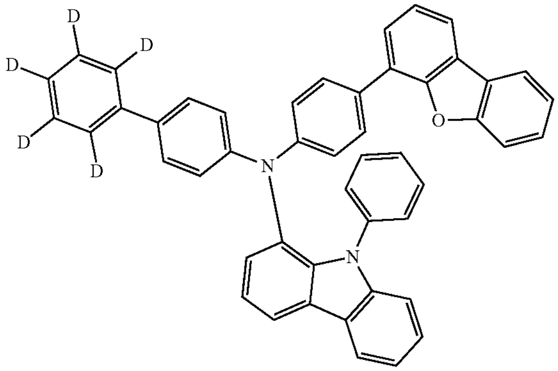

The amine compound represented by Formula 1 according to an embodiment includes a carbazole moiety and amine derivative directly or indirectly bonded to the carbazole moiety at an ortho-position to the nitrogen atom of the carbazole moiety, and has a molecular structure in which the amine derivative includes at least one dibenzoheterole group, and thus may have excellent hole transport ability and good material stability. Accordingly, the light emitting device according to an embodiment including the amine compound of an embodiment may exhibit improved luminous efficiency and excellent service life characteristics.

For example, when the amine compound of an embodiment is used in the hole transport region, the hole transport property may be increased to improve the recombination probability of holes and electrons in the emission layer, thereby improving luminous efficiency. The amine compound of an embodiment includes a carbazole moiety having a high heat and a charge resistance, and thus may be used as a hole transport material having improved service life characteristics while maintaining the hole transport property of the amine derivative.

The light emitting device ED of an embodiment may further include materials for the hole transport region, which will be described below, in addition to the above-described amine compound of an embodiment.

The hole transport region HTR may include a compound represented by Formula H-1 below:

[Formula H-1]

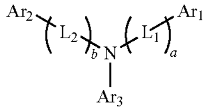

In Formula H-1 above, $L_2$ and $L_2$ may each independently be a direct linkage, a substituted or unsubstituted arylene group having 6 to 30 ring-forming carbon atoms, or a substituted or unsubstituted heteroarylene group having 2 to 30 ring-forming carbon atoms. In Formula H-1, a and b may each independently be an integer from 0 to 10. When a or b is 2 or greater, multiple $L_1$ groups and multiple $L_2$ groups may each independently be a substituted or unsubstituted arylene group having 6 to 30 ring-forming carbon atoms, or a substituted or unsubstituted heteroarylene group having 2 to 30 ring-forming carbon atoms.

In Formula H-1, $Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. In Formula H-1, $Ar_3$ may be a substituted or unsubstituted aryl group having 6 to 30 ring-forming carbon atoms, or a substituted or unsubstituted heteroaryl group having 2 to 30 ring-forming carbon atoms.

The compound represented by Formula H-1 above may be a monoamine compound. In another embodiment, the compound represented by Formula H-1 above may be a diamine compound in which at least one among Ar to $Ar_3$ includes an amine group as a substituent. The compound represented by Formula H-1 above may be a carbazole-based compound including a substituted or unsubstituted carbazole group in at least one of $Ar_1$ or $Ar_2$, or a fluorene-based compound including a substituted or unsubstituted fluorene group in at least one of $Ar_1$ or $Ar_2$.

The compound represented by Formula H-1 may be any one selected from Compound Group H below. However, the compounds listed in Compound Group H below are examples, and the compounds represented by Formula H-1 are not limited to those represented by Compound Group H below:

[Compound Group H]

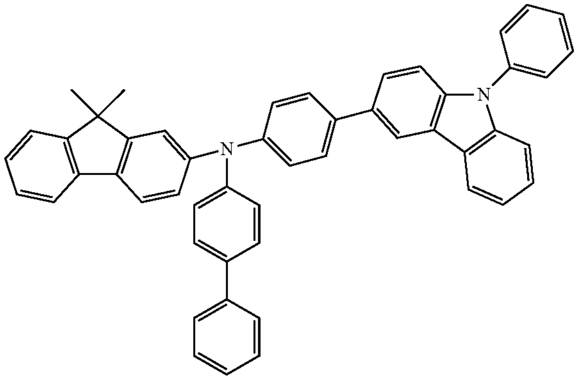

-continued
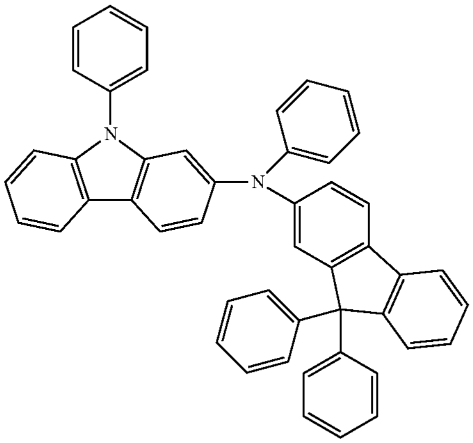
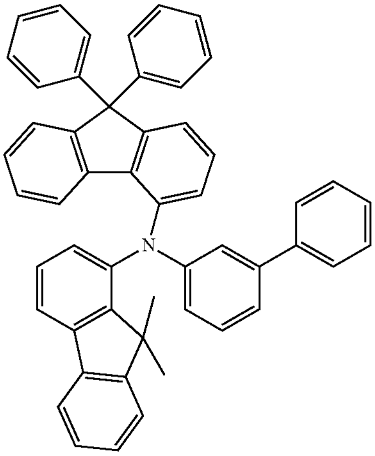
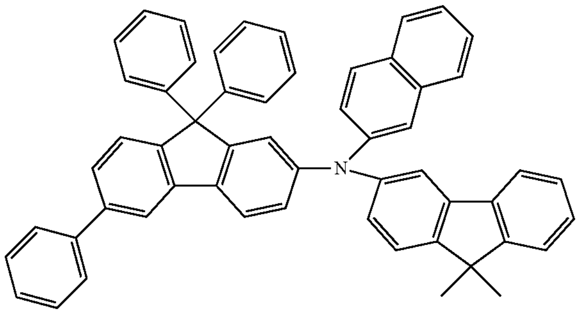
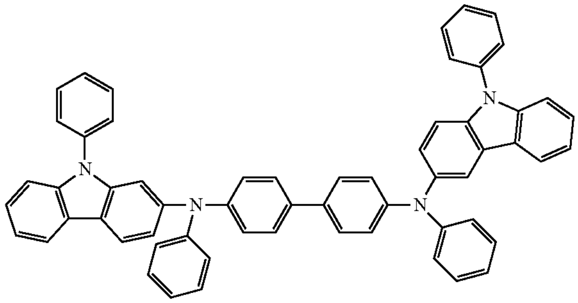
-continued
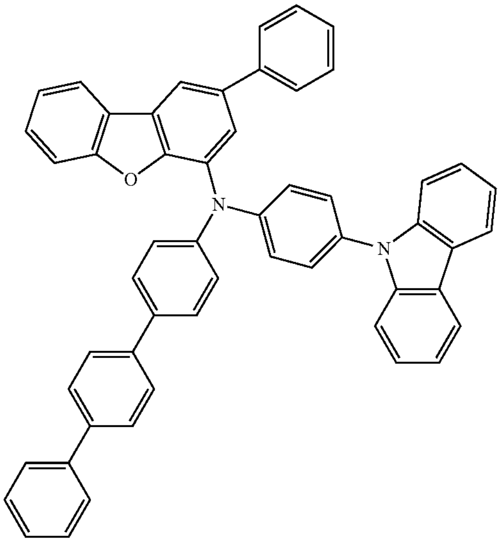
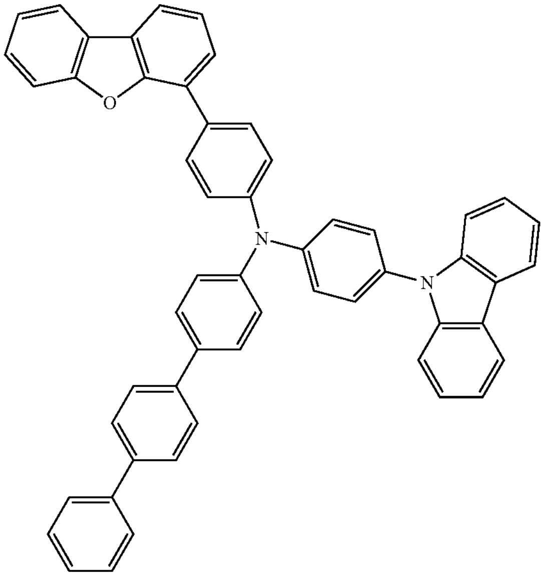
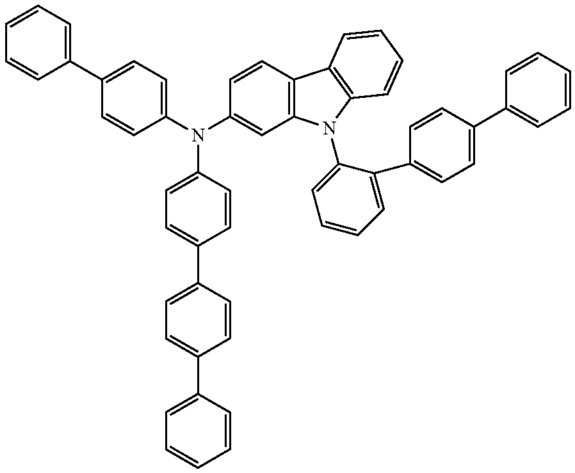

-continued
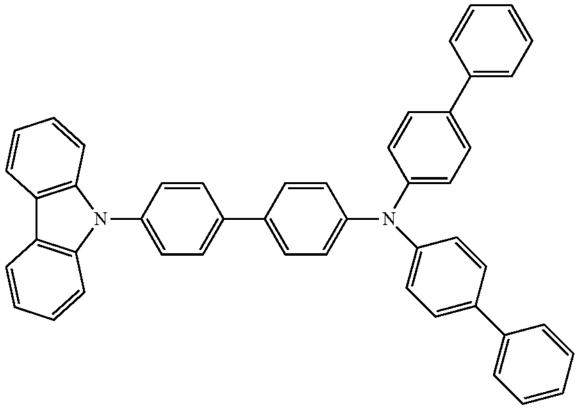
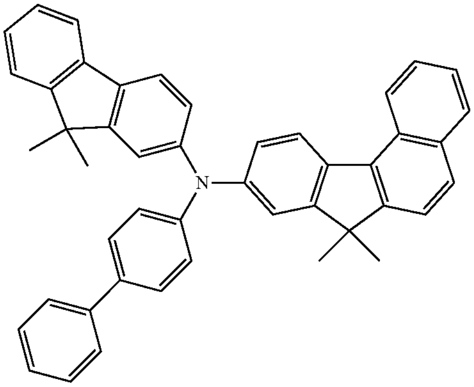
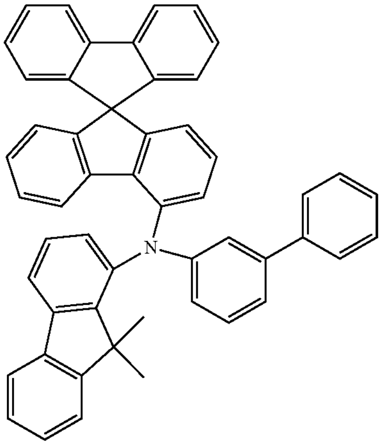
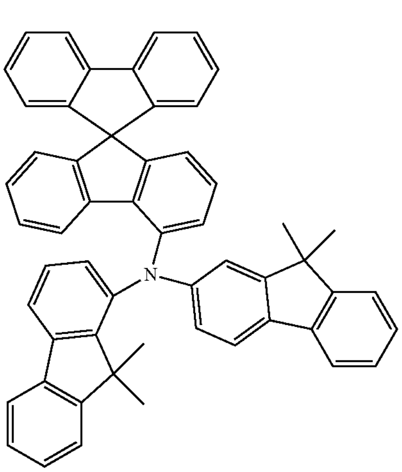
-continued
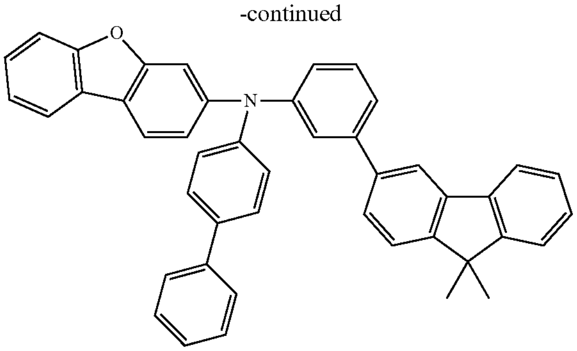
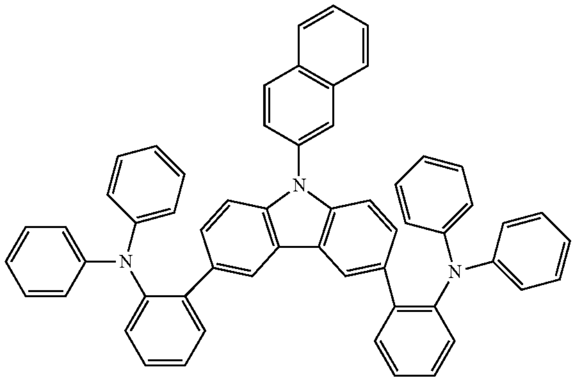
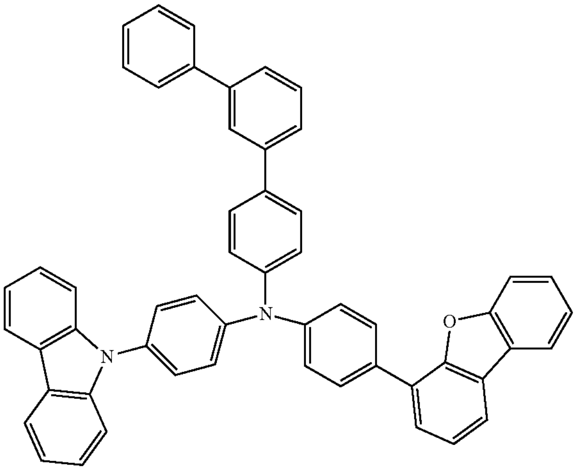

-continued
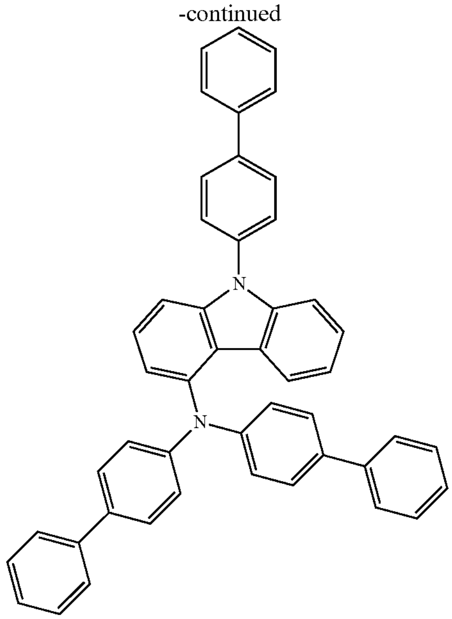
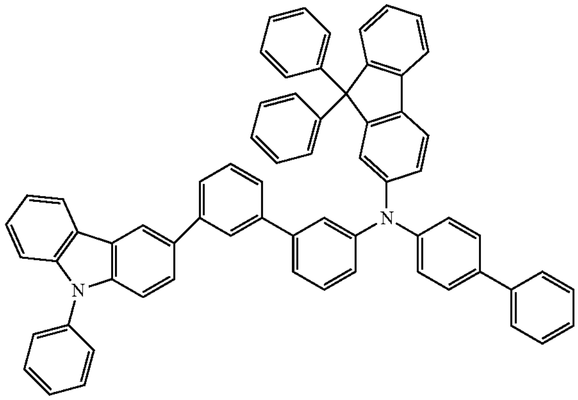
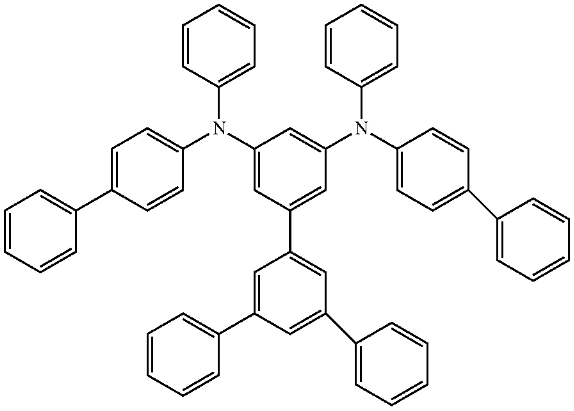
-continued
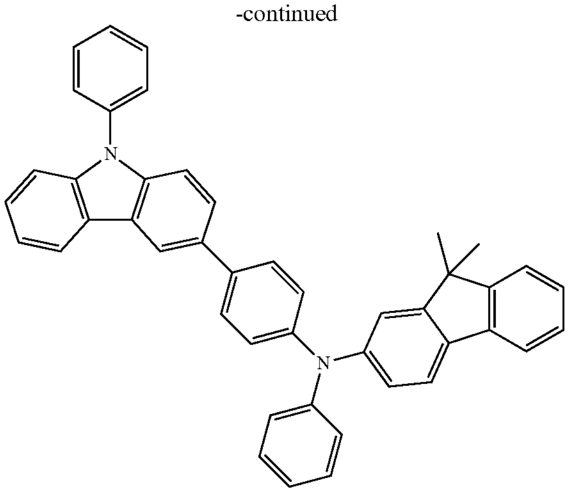
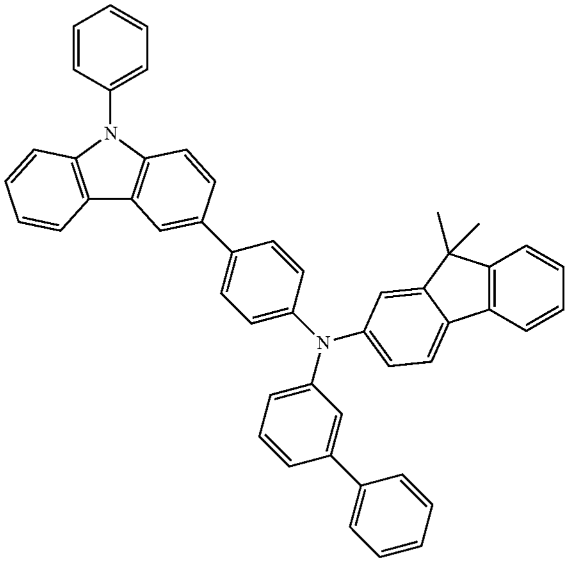
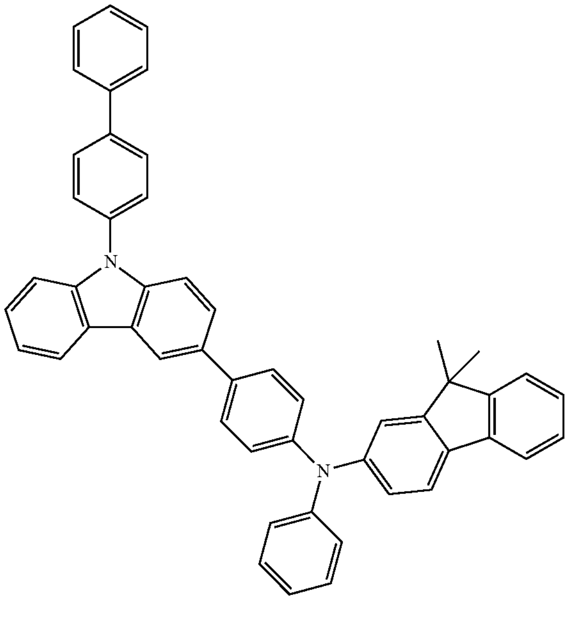

-continued
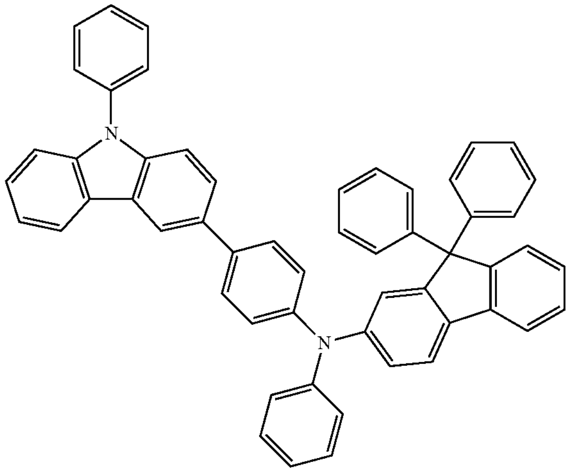
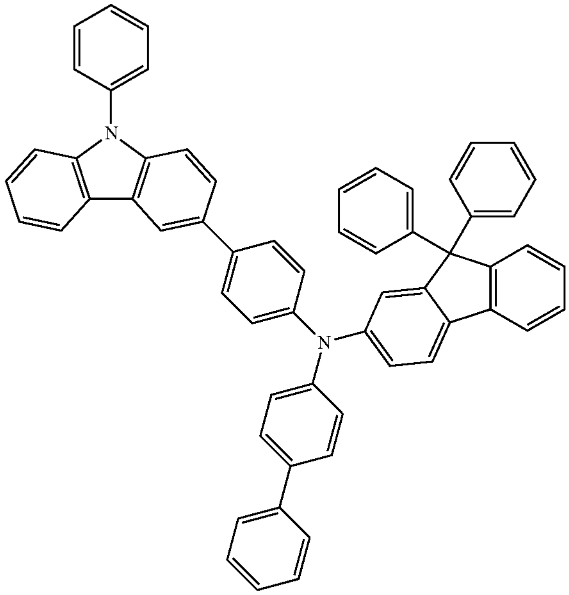
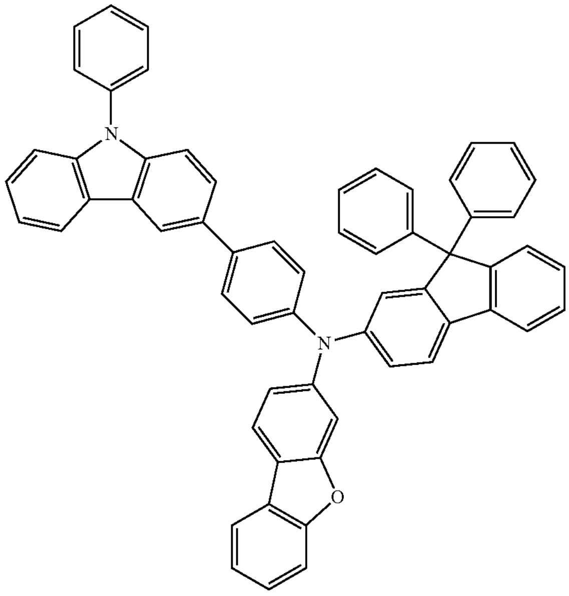
-continued
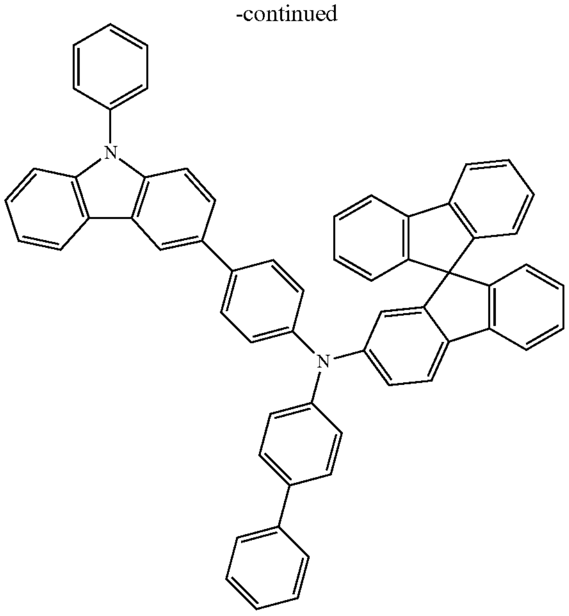
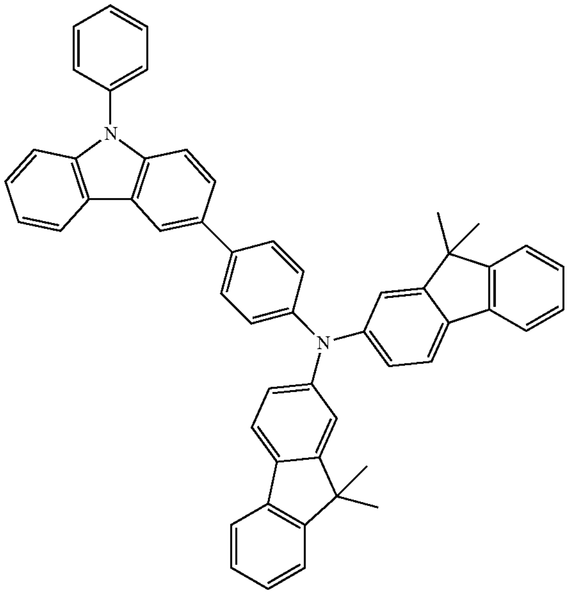

-continued
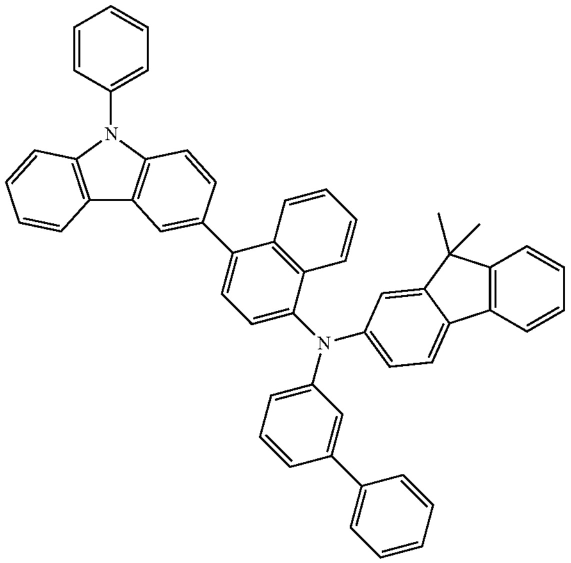
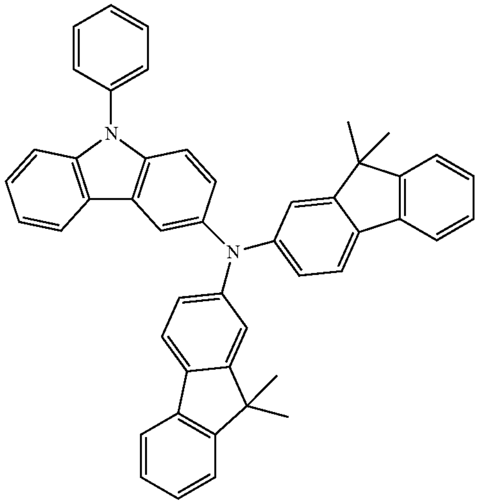
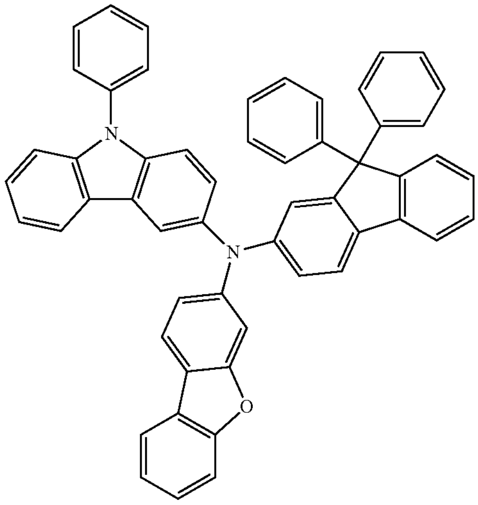
-continued
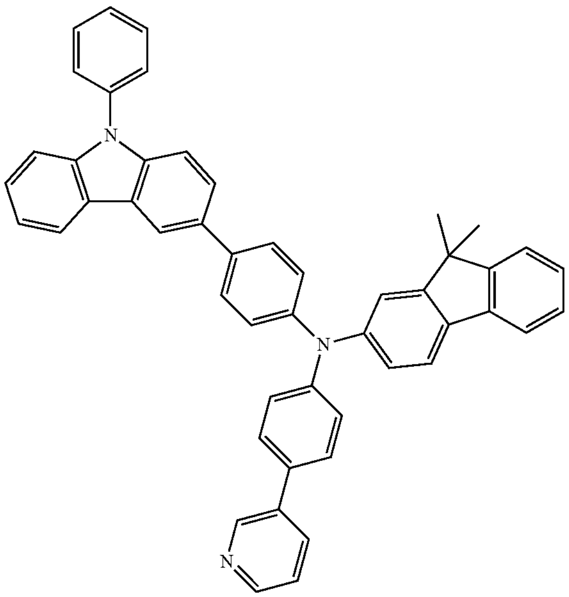
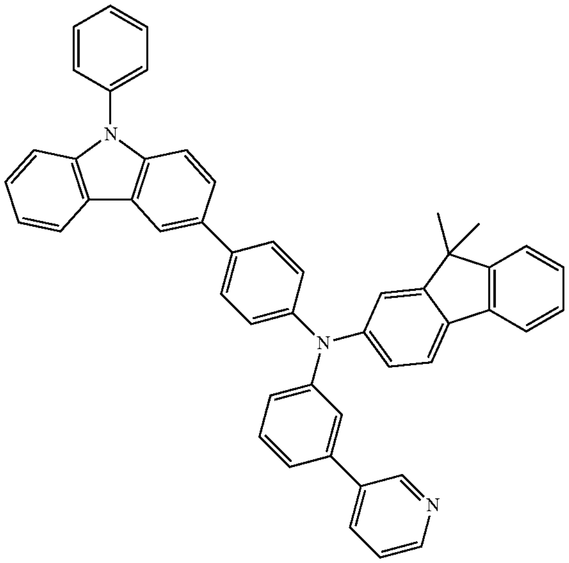
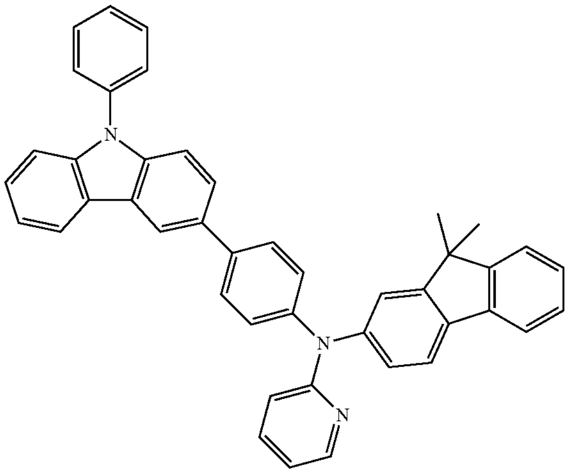

-continued
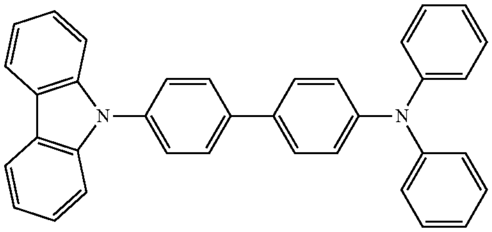
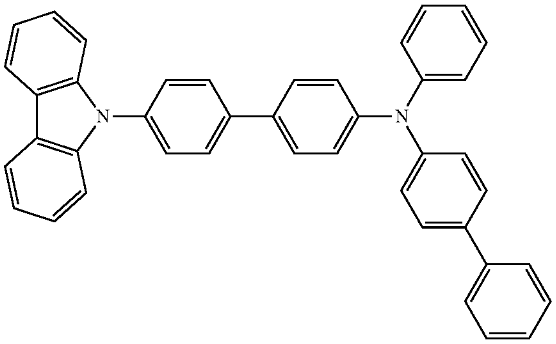
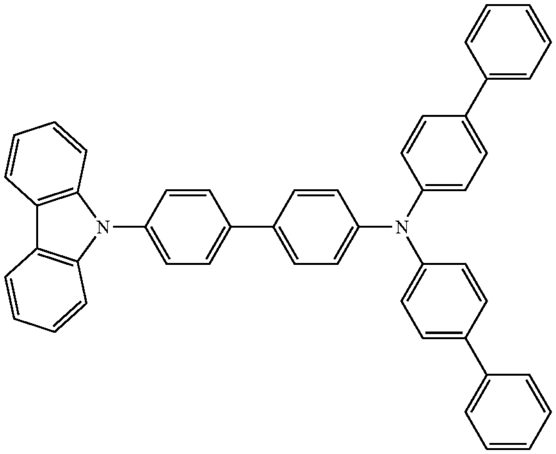
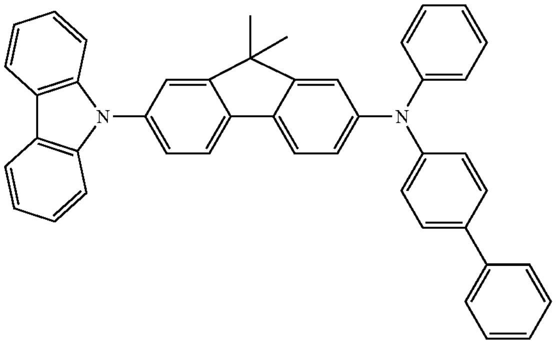
-continued
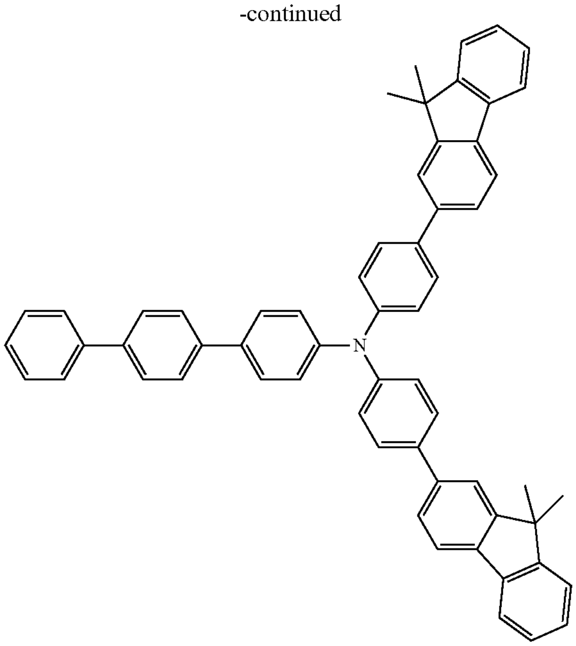
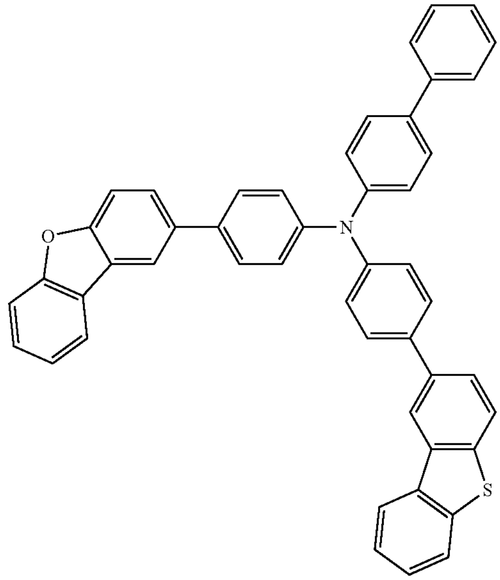
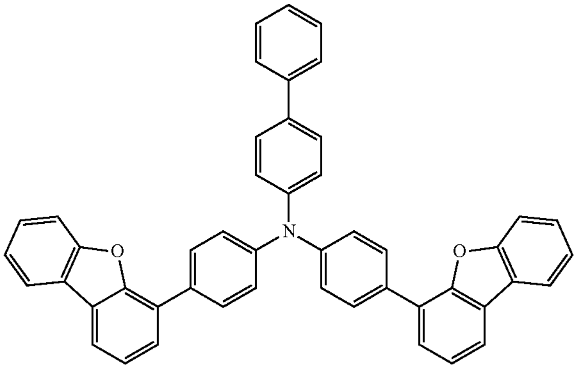

-continued
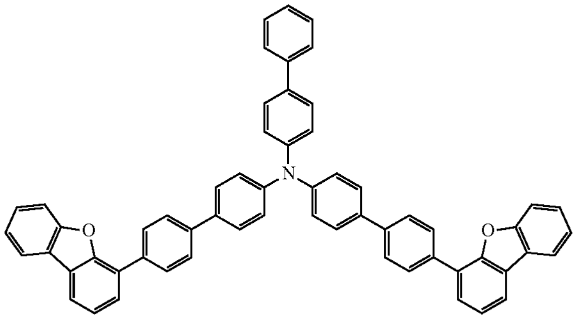
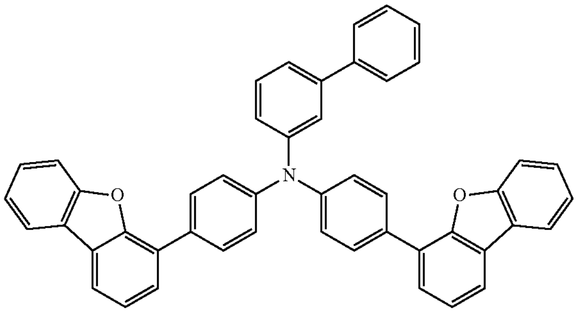
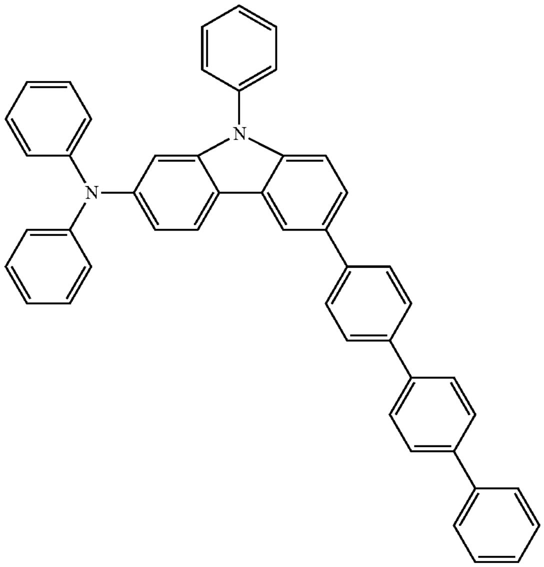
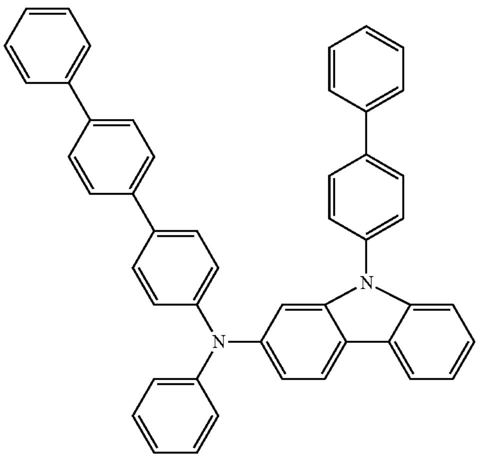
-continued
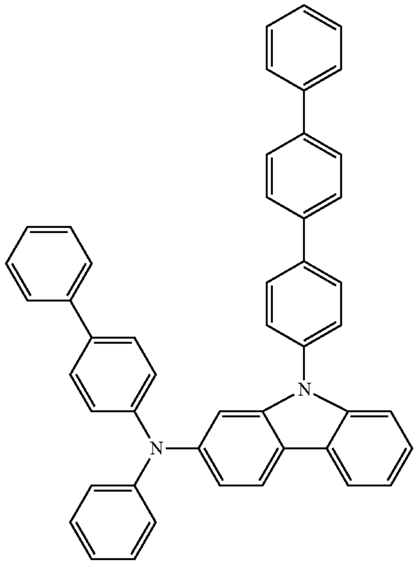
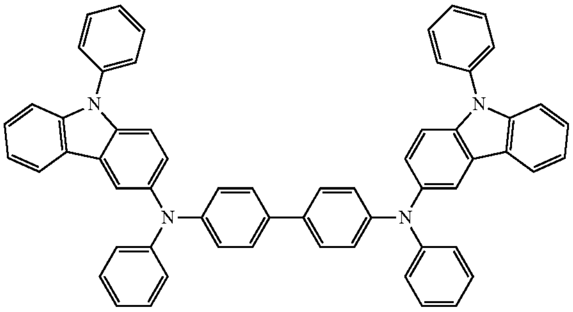
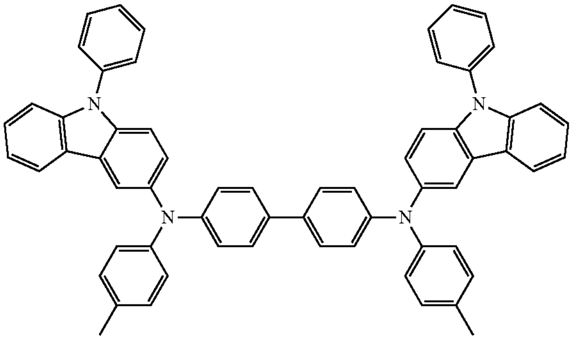
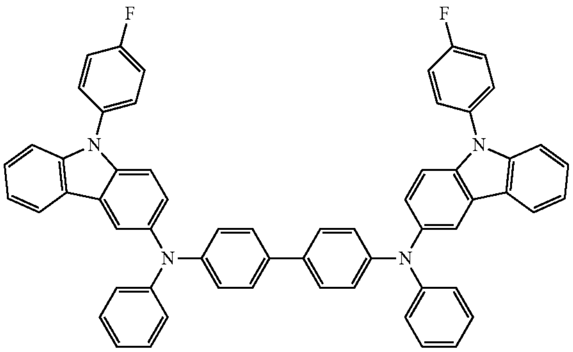

-continued
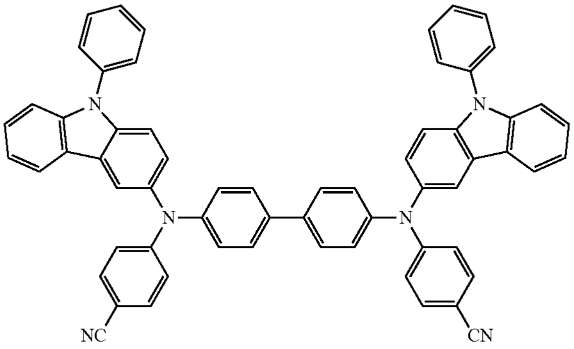
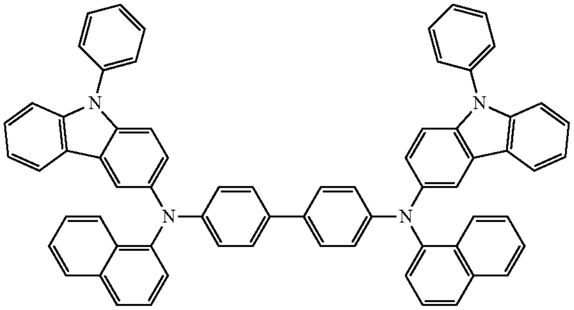
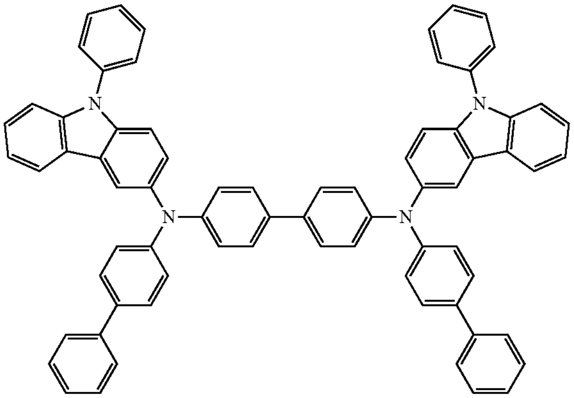
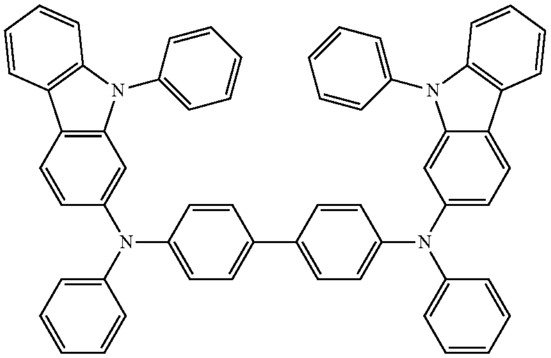
-continued
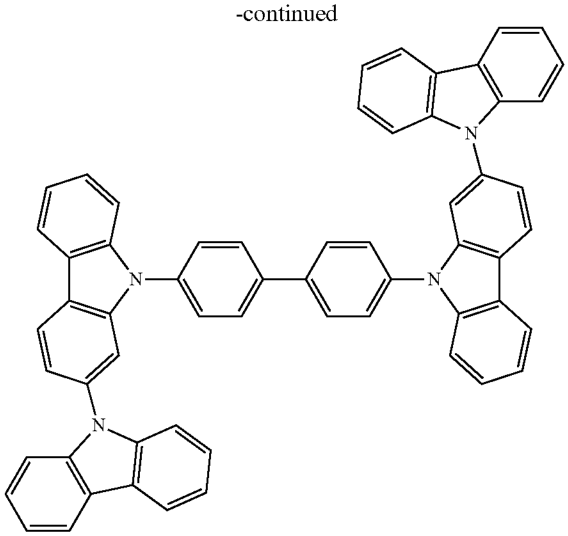
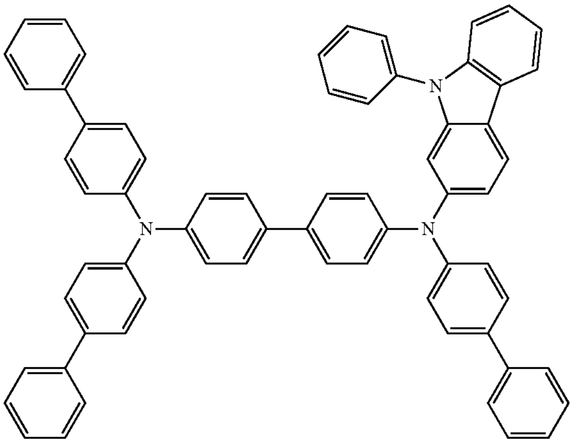
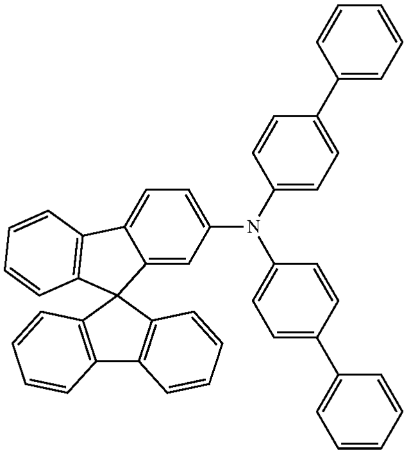

-continued

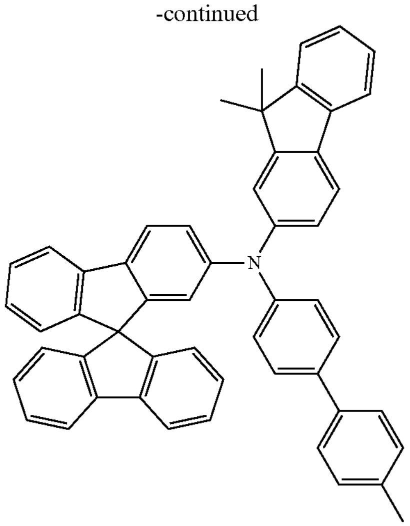

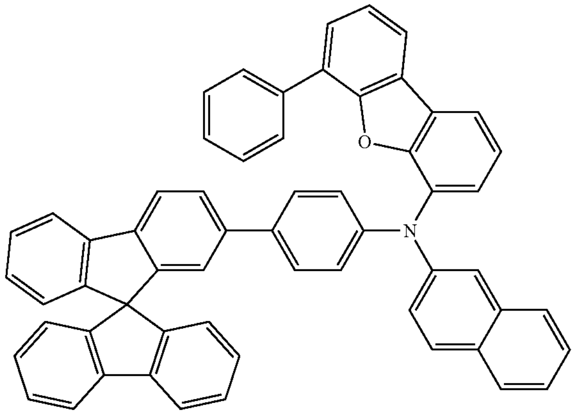

The hole transport region HTR may include a phthalocyanine compound such as copper phthalocyanine; $N^1$,$N^{1\prime}$-([1,1'-biphenyl]-4,4'-diyl)bis($N^1$-phenyl-$N^4$,$N^4$-di-m-tolyl-benzene-1,4-diamine) (DNTPD), 4,4'4"-tris(N,N-diphenylamino)triphenylamine (TDATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], dipyrazino[2,3-f: 2',3'-h]quinoxaline-2,3,6,7,10,11-hexacarbonitrile (HATCN), etc.

The hole transport region HTR may include carbazole derivatives such as N-phenyl carbazole and polyvinyl carbazole, fluorene derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl) triphenylamine (TCTA), N,N'-di(naphthalene-1-yl)-N,N'-diplienyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 9-(4-tert-butylphenyl)-3,6-bis(triphenylsilyl)-9H-carbazole (CzSi), 9-phenyl-9H-3,9'-bicarbazole (CCP), 1,3-bis(N-carbazolyl) benzene (mCP), 1,3-bis(1,8-dimethyl-9H-carbazol-9-yl) benzene (mDCP), etc.

The hole transport region HTR may include the above-described compound of the hole transport region in at least one of a hole injection layer HIL, a hole transport layer HTL, and an electron blocking layer EBL.

A thickness of the hole transport region HTR may be in a range of about 100 Å to about 10,000 Å. For example, the thickness of the hole transport region HTR may be in a range of about 100 Å to about 5,000 Å. When the hole transport region HTR includes a hole injection layer HIL, the hole injection layer HIL may have, for example, a thickness in a range of about 30 Å to about 1,000 Å. When the hole transport region HTR includes a hole transport layer HTL, the hole transport layer HTL may have a thickness in a range of about 30 Å to about 1,000 Å. When the hole transport region HTR includes an electron blocking layer EBL, the electron blocking layer EBL may have a thickness in a range of about 10 Å to about 1,000 Å. If the thicknesses of the hole transport region HTR, the hole injection layer HIL, the hole transport layer HTL and the electron blocking layer EBL satisfy the above-described ranges, satisfactory hole transport characteristic may be achieved without a substantial increase in a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may include at least one of a halogenated metal compound, a quinone derivative, a metal oxide, or a cyano group-containing compound, but embodiments are not limited thereto. For example, the p-dopant may include metal halides such as CuI and RbI, quinone derivatives such as tetracyanoquinodimethane (TCNQ) and 2,3,5,6-tetrafluoro-7,7',8,8'-tetracyanoquinodimethane (F4-TCNQ), metal oxides such as tungsten oxide and molybdenum oxide, dipyrazino[2,3-f: 2',3'-h]quinoxaline-2,3,6,7,10,11-hexacarbonitrile (HATCN), 4-[[2,3-bis[cyano-(4-cyano-2,3,5,6-tetrafluorophenyl)methylidene]cyclopropylidene]-cyanom ethyl]-2,3,5,6-tetrafluorobenzonitrile, etc., but embodiments are not limited thereto.

As described above, the hole transport region HTR may further include at least one of a buffer layer (not shown) and an electron blocking layer EBL in addition to the hole injection layer HIL and the hole transport layer HTL. The buffer layer (not shown) may compensate a resonance distance according to the wavelength of light emitted from the emission layer EML and may thus increase light emission efficiency. Materials which may be included in the hole transport region HTR may be used as materials included in the buffer layer (not shown). The electron blocking layer EBL may prevent electrons from being injected from the electron transport region ETR to the hole transport region HTR.

The emission layer EML is provided on the hole transport region HTR. The emission layer EML may have a thickness, for example, in a range of about 100 Å to about 1,000 Å. For example, the emission layer EML may have a thickness in a range of about 100 Å to about 300 Å. The emission layer EML may have a single layer formed of a single material, a single layer formed of different materials, or a multilayer structure having layers formed of different materials.

In the light emitting device ED of an embodiment, the emission layer EML may include anthracene derivatives, pyrene derivatives, fluoranthene derivatives, chrysene derivatives, dihydrobenzanthracene derivatives, or triphenylene derivatives. In an embodiment, the emission layer EML may include anthracene derivatives or pyrene derivatives.

In the light emitting devices ED of embodiments as illustrated in FIGS. 3 to 6, the emission layer EML may include a host and a dopant, and the emission layer EML may include a compound represented by Formula E-1 below. The compound represented by Formula E-1 below may be used as a fluorescence host material.

[Formula E-1]

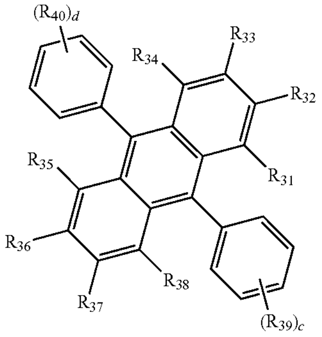

In Formula E-1, $R_{31}$ to $R_{40}$ may each independently be a hydrogen atom, a deuterium atom, a halogen atom, a substituted or unsubstituted silyl group, a substituted or unsubstituted alkyl group having 1 to 10 carbon atoms, a substituted or unsubstituted alkenyl group having 2 to 20 carbon atoms, a substituted or unsubstituted oxy group, a substituted or unsubstituted thiol group, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula E-1, $R_{31}$ to $R_{40}$ may be bonded to an adjacent group to form a saturated hydrocarbon ring or an unsaturated hydrocarbon ring.

In Formula E-1, c and d may each independently be an integer from 0 to 5.

The compound represented by Formula E-1 may be selected from any one among Compound E1 to Compound E19 below:

E1

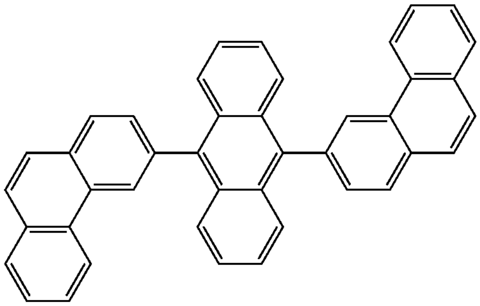

E2

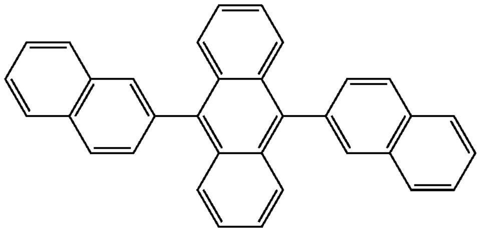

-continued

E3

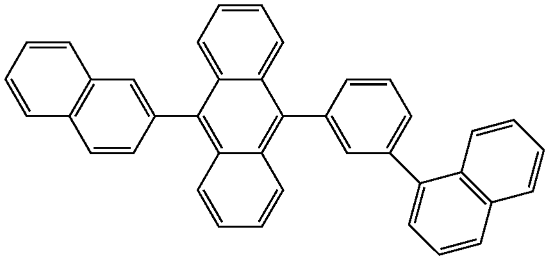

E4

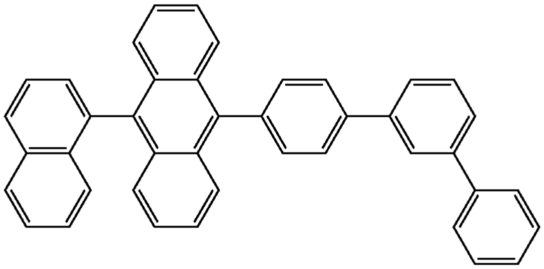

E5

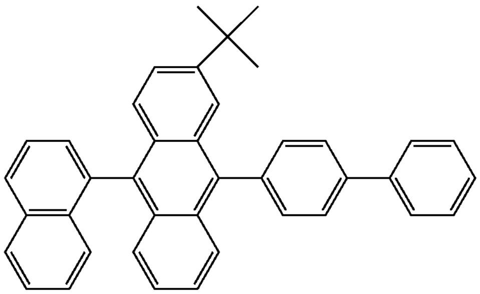

E6

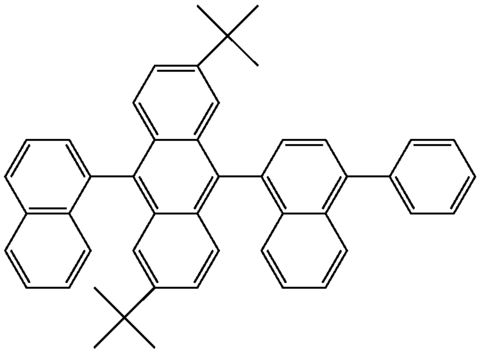

E7

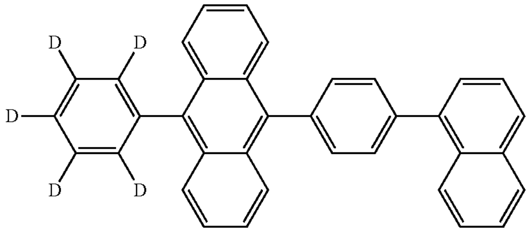

-continued
E8
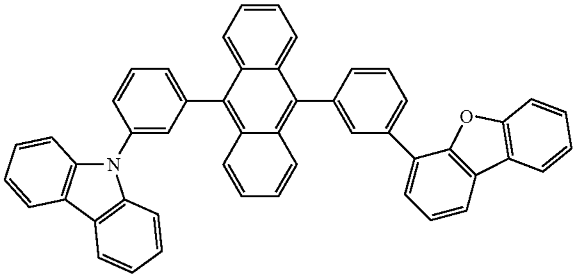
E9
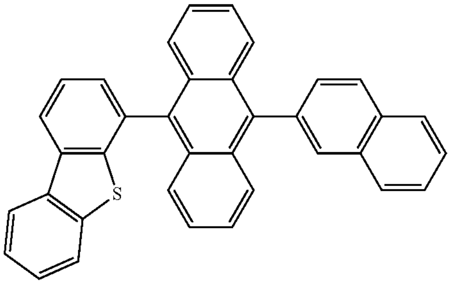
E10
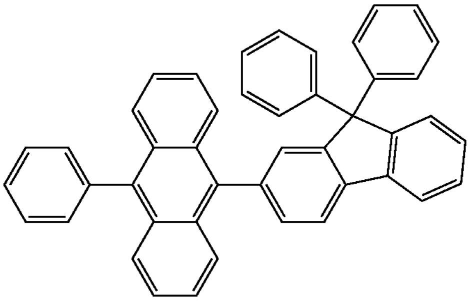
E11
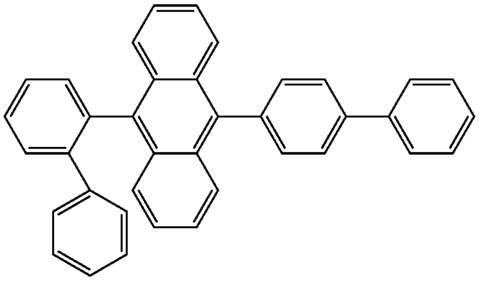
E12
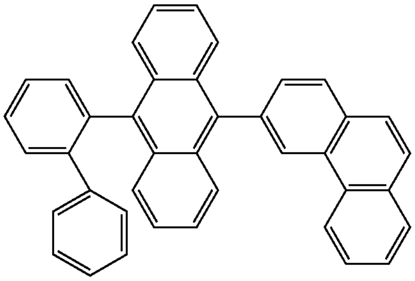
-continued
E13
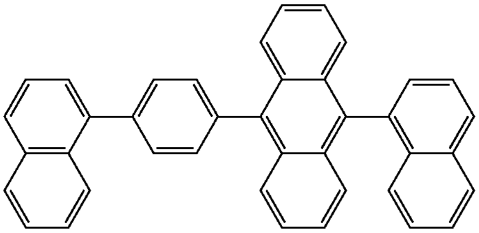
E14
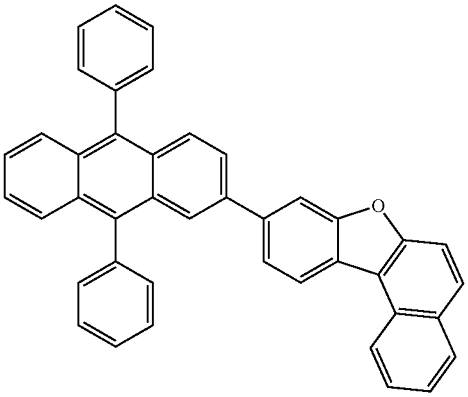
E15
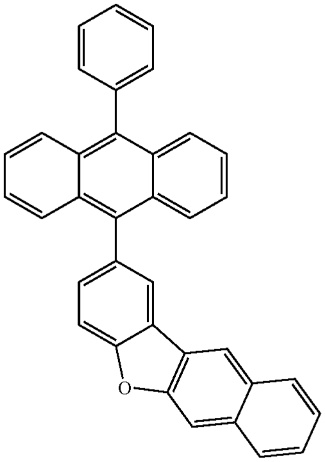
E16
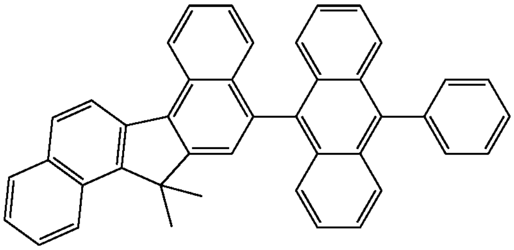

-continued
E17
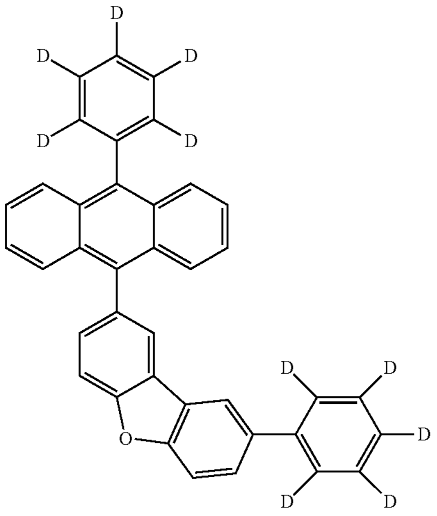
E18
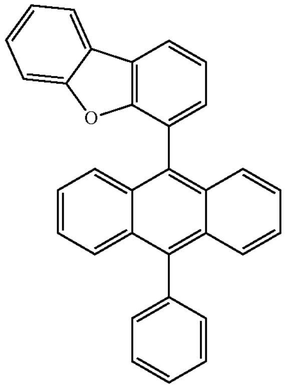
E19
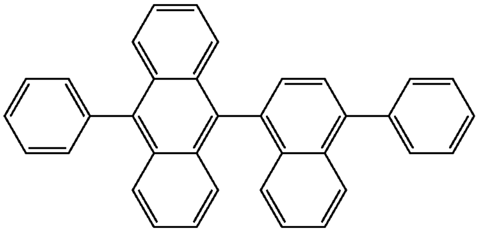
In an embodiment, the compound represented by Formula E-1 above may be selected from any one among the compounds below:
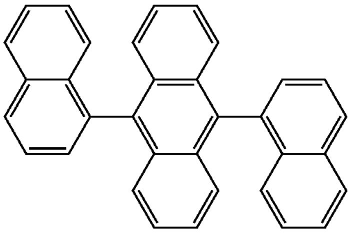
-continued
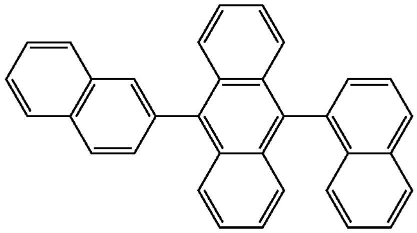
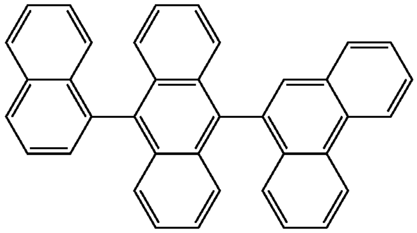
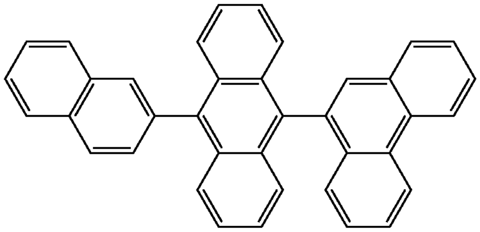
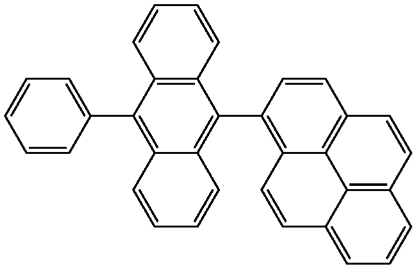
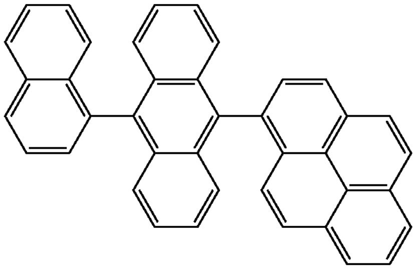
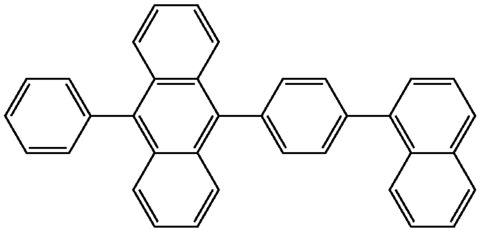
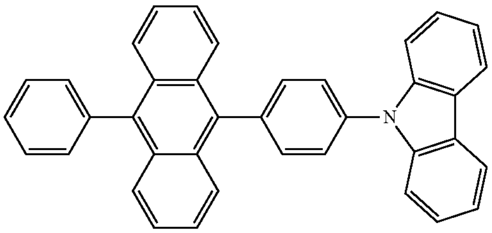

-continued
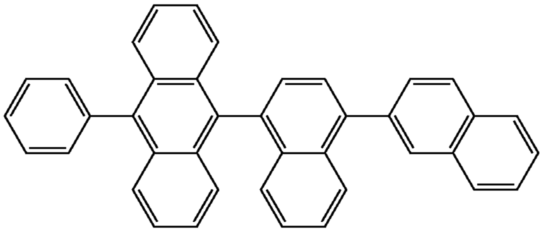
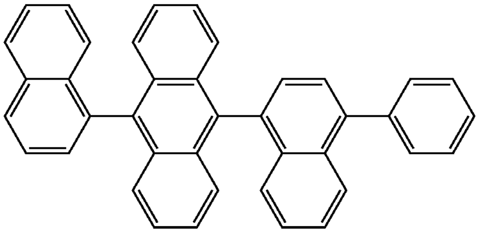
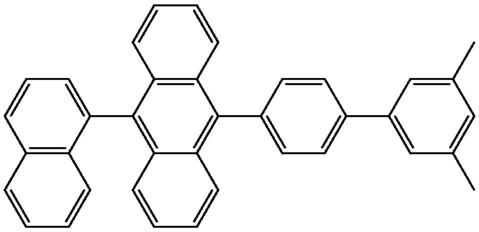
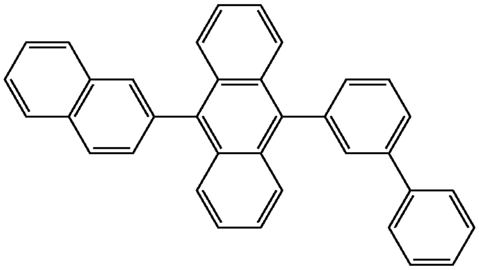
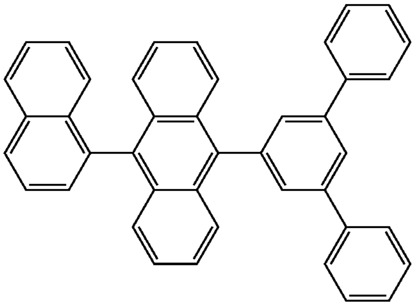
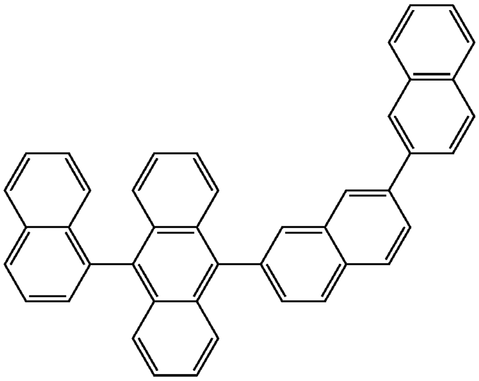
-continued
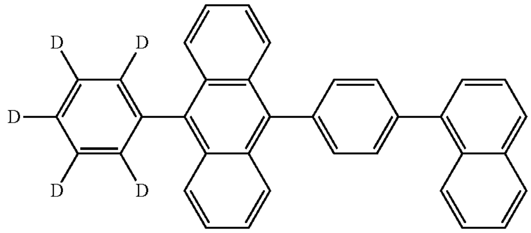
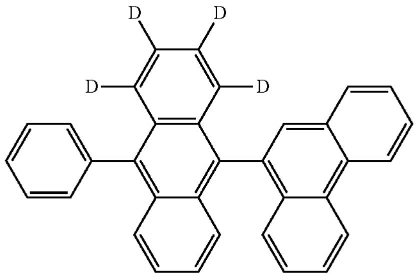
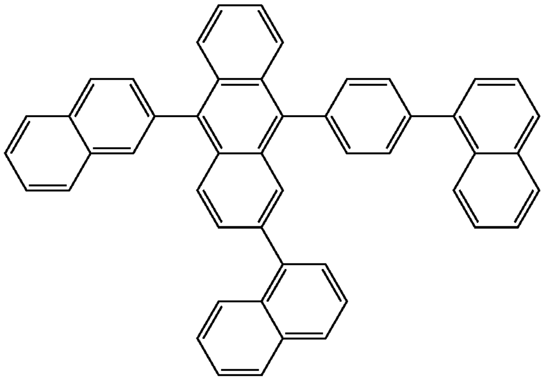
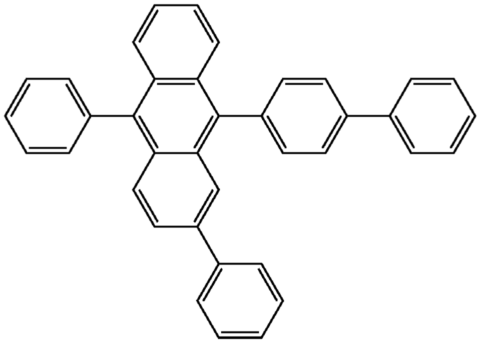
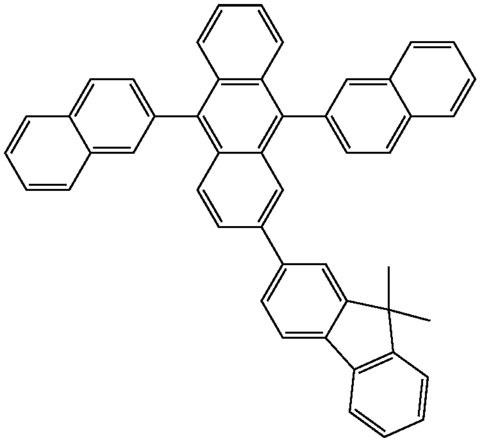

-continued

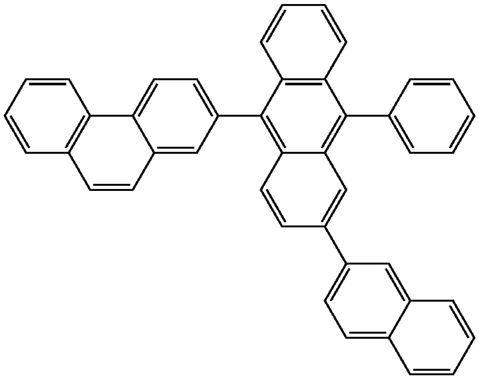

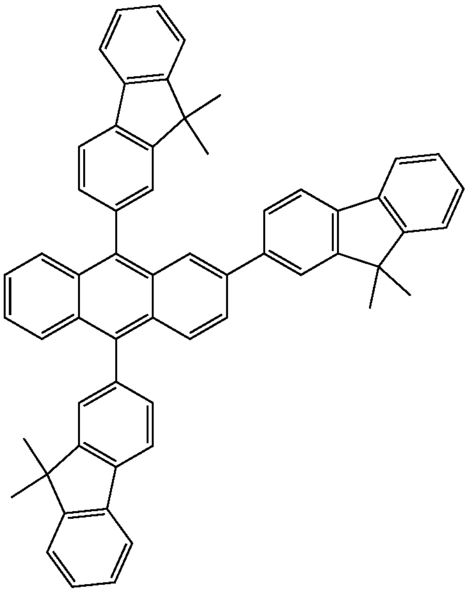

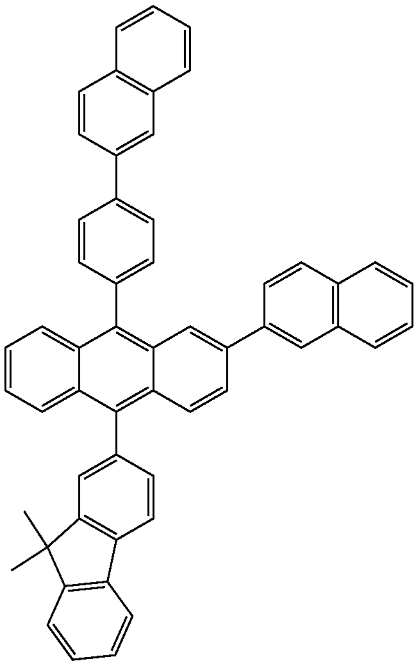

-continued

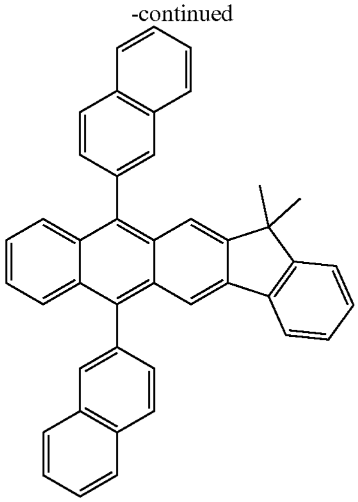

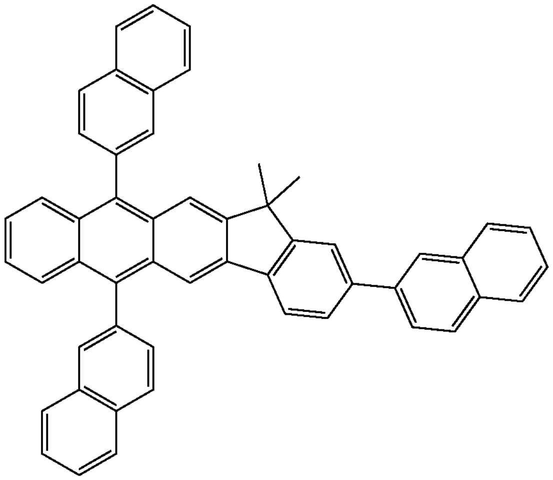

In an embodiment, the emission layer EML may include a compound represented by Formula E-2a or Formula E-2b below. The compound represented by Formula E-2a or Formula E-2b below may be used as a phosphorescence host material.

[Formula E-2a]

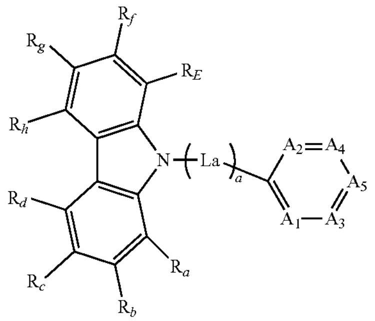

In Formula E-2a, a may be an integer from 0 to 10, and $L_a$ may be a direct linkage, a substituted or unsubstituted arylene group having 6 to 30 ring-forming carbon atoms, or a substituted or unsubstituted heteroarylene group having 2 to 30 ring-forming carbon atoms. In Formula E-2a, when a is 2 or greater, multiple $L_a$ groups may each independently be a substituted or unsubstituted arylene group having 6 to 30 ring-forming carbon atoms, or a substituted or unsubstituted heteroarylene group having 2 to 30 ring-forming carbon atoms.

In Formula E-2a, $A_1$ to $A_5$ may each independently be N or $C(R_i)$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. $R_a$ to $R_i$ may be bonded to an adjacent group to form a hydrocarbon ring or a heterocycle containing N, O, S, etc. as a ring-forming atom.

In Formula E-2a, two or three of $A_1$ to $A_5$ may be N, and the remainder of $A_1$ to $A_5$ may be $C(R_i)$.

[Formula E-2b]

$$(Cbz1)-(L_b)_b-(Cbz2)$$

In Formula E-2b, Cbz1 and Cbz2 may each independently be an unsubstituted carbazole group, or a carbazole group substituted with an aryl group having 6 to 30 ring-forming carbon atoms. In Formula E-2b, $L_b$ may be a direct linkage, a substituted or unsubstituted arylene group having 6 to 30 ring-forming carbon atoms, or a substituted or unsubstituted heteroarylene group having 2 to 30 ring-forming carbon atoms. In Formula E-2b, b may be an integer from 0 to 10, and when b is 2 or more, multiple $L_b$ groups may each independently be a substituted or unsubstituted arylene group having 6 to 30 ring-forming carbon atoms, or a substituted or unsubstituted heteroarylene group having 2 to 30 ring-forming carbon atoms.

The compound represented by Formula E-2a or Formula E-2b may be any one selected from Compound Group E-2 below. However, the compounds listed in Compound Group E-2 below are examples, and the compound represented by Formula E-2a or Formula E-2b is not limited to those listed in Compound Group E-2 below.

[Compound Group E-2]

E-2-1

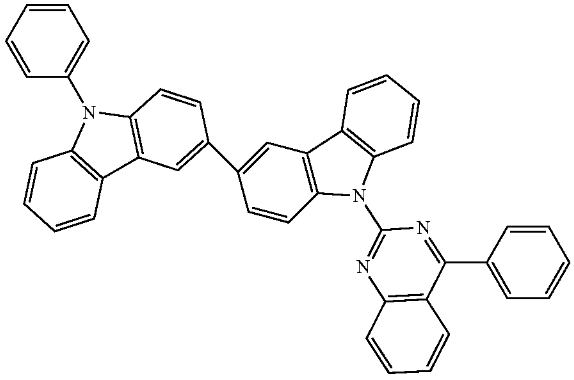

-continued

E-2-2

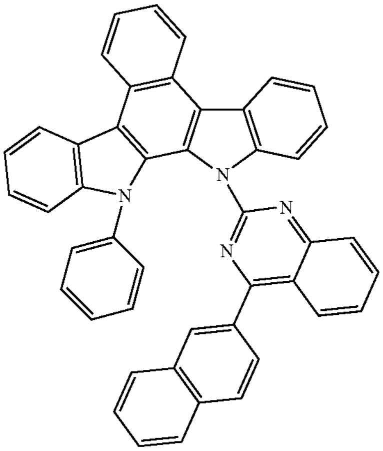

E-2-3

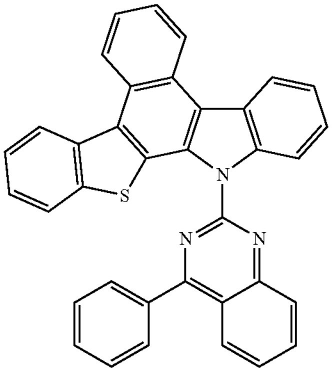

E-2-4

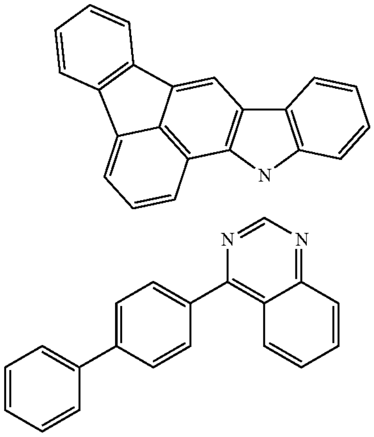

E-2-5

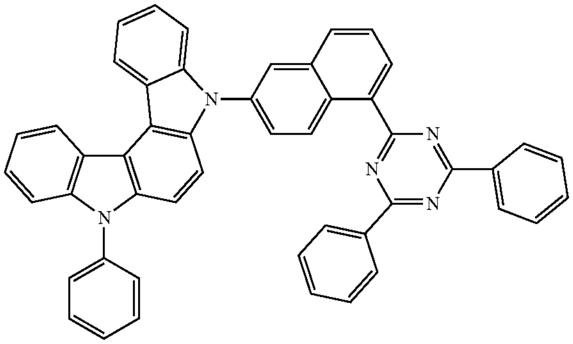

E-2-6
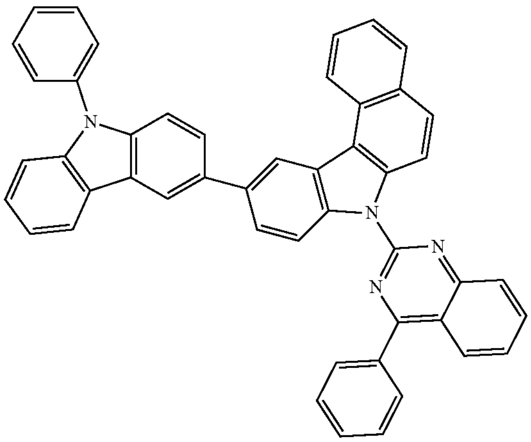
E-2-7
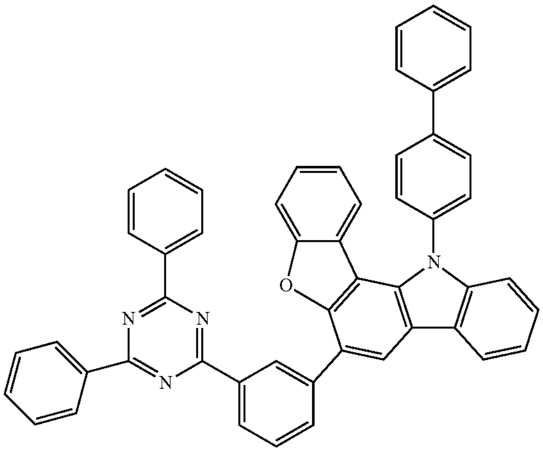
E-2-8
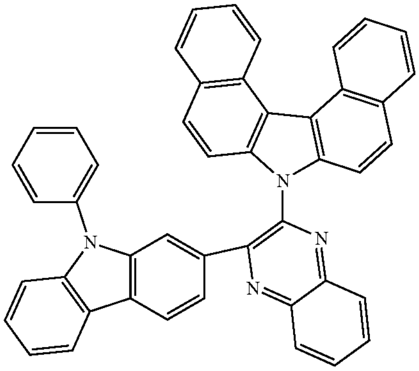
E-2-9
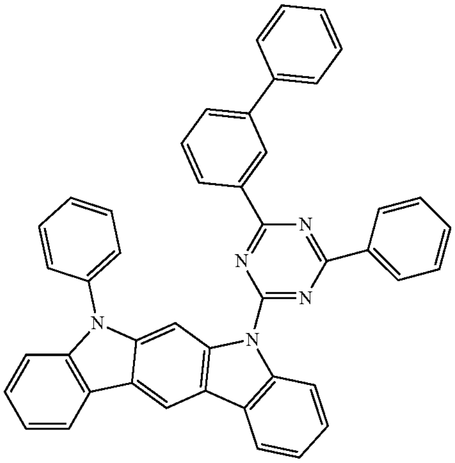
E-2-10
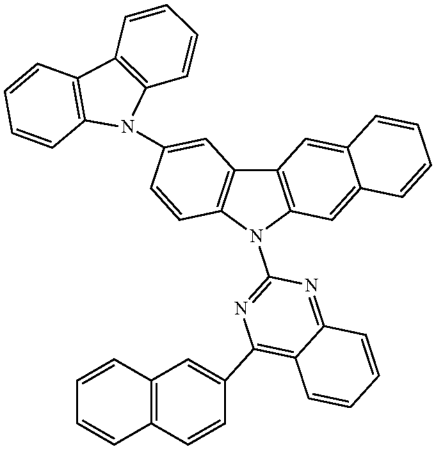
E-2-11
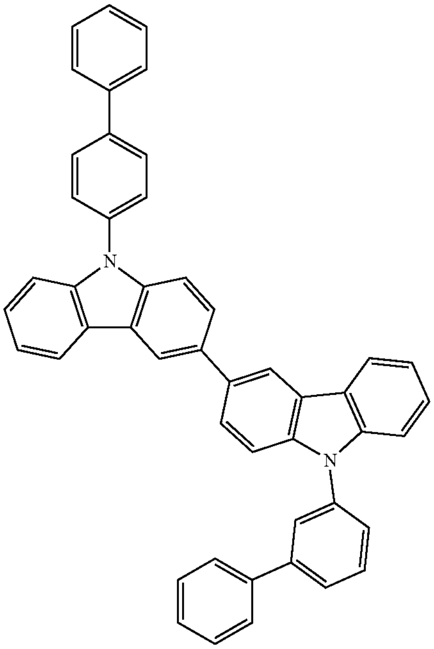

-continued
E-2-12
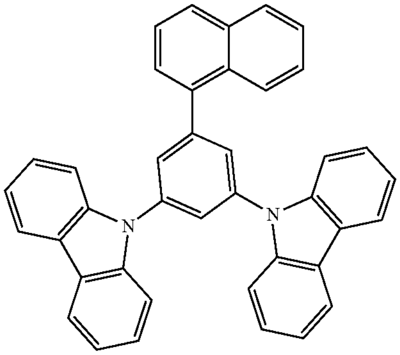
E-2-13
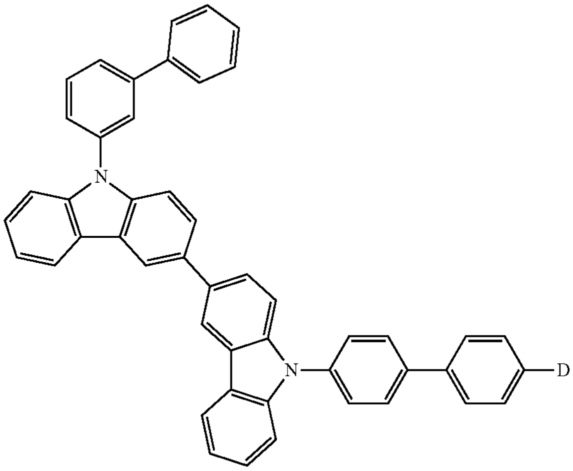
E-2-14
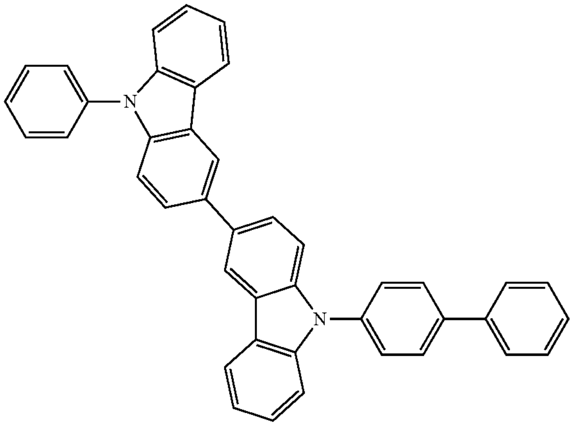
-continued
E-2-15
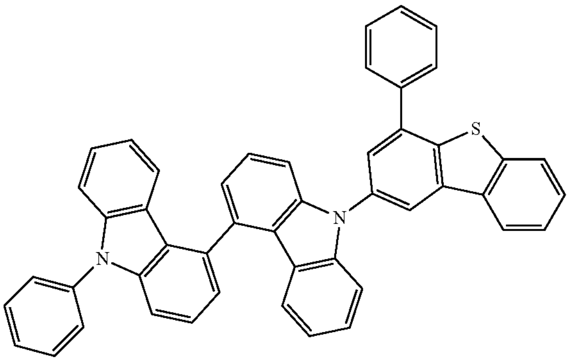
E-2-16
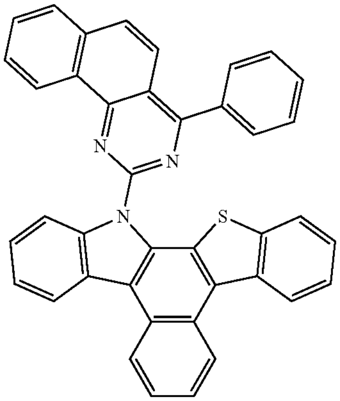
E-2-17
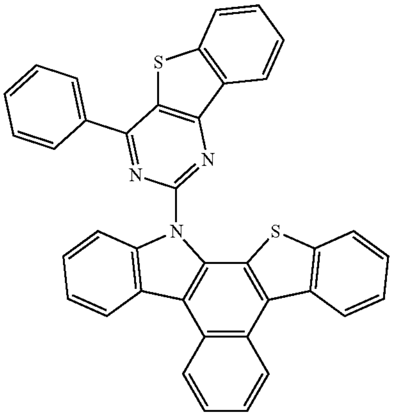
E-2-18
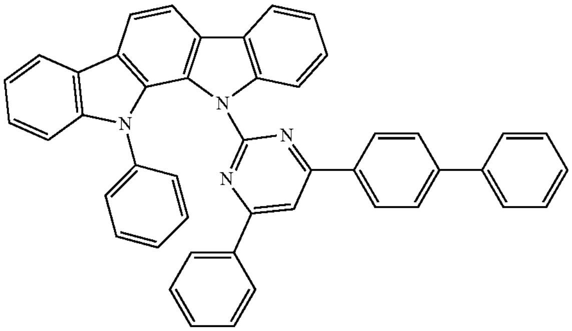

-continued

E-2-19

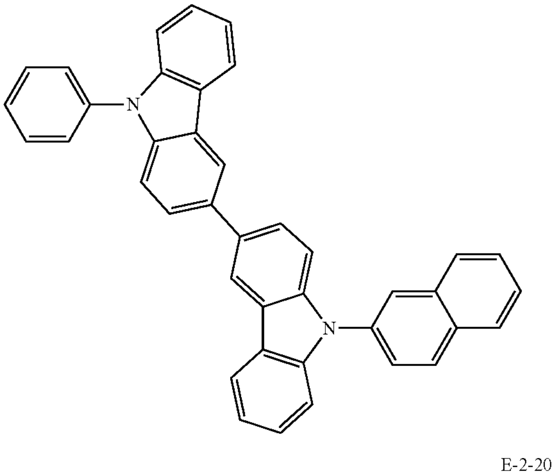

E-2-20

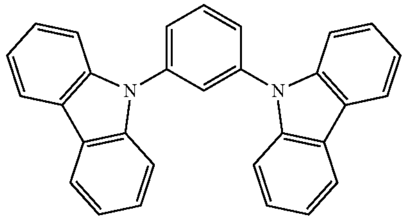

E-2-21

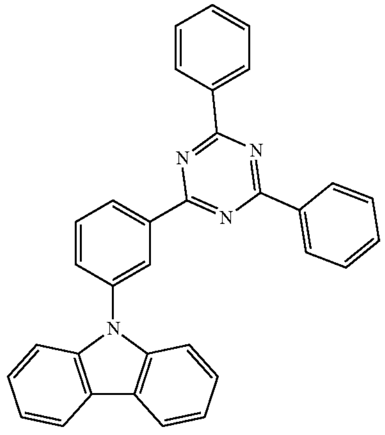

E-2-22

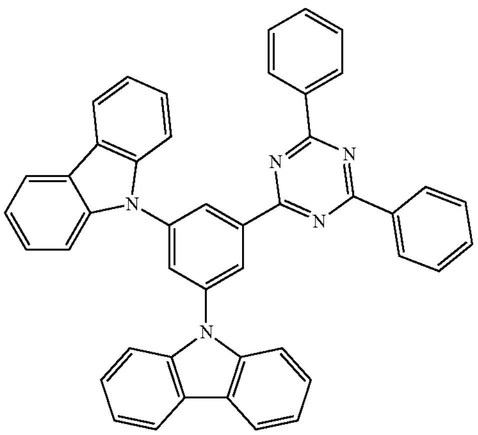

-continued

E-2-23

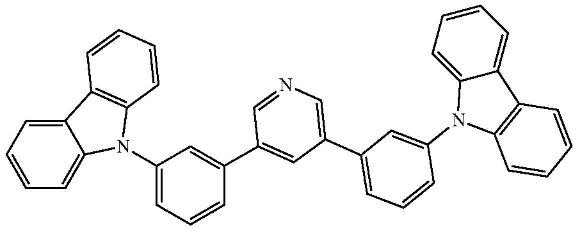

E-2-24

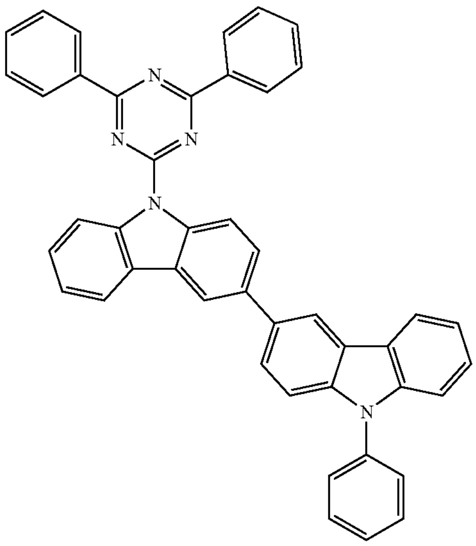

The emission layer EML may further include a general material in the art as a host material. For example, the emission layer EML may include, as a host material, at least one of bis[2-(diphenylphosphino)phenyl]ether oxide (DPEPO), 4,4'-bis(N-carbazolyl)-1,1'-biphenyl (CBP), 1,3-bis(carazol-9-yl)benzene (mCP), 2,8-bis(diphenylphosphoryl)dibenzo[b,d]furan (PPF), 4,4',4"-tris(carbazol-9-yl)-triphenylamine (TCTA), or 1,3,5-tris(1-phenyl-1H-benzo[d]imidazole-2-yl)benzene (TPBi). However, embodiments are not limited thereto. For example, tris(8-hydroxyquinolino) aluminum ($Alq_3$), 9,10-di(naphthalene-2-yl)anthracene (ADN), 2-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), etc. may be used as a host material.

The emission layer EML may include a compound represented by Formula M-a or Formula M-b below. The compound represented by Formula M-a or Formula M-b below may be used as a phosphorescence dopant material.

[Formula M-a]

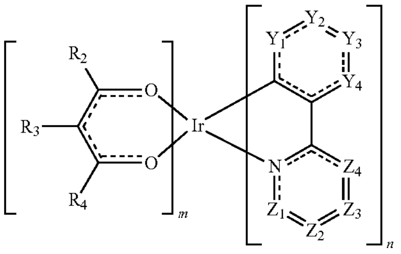

In Formula M-a above, $Y_1$ to $Y_4$ and $Z_1$ to $Z_4$ may each independently be $C(R_1)$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring. In Formula M-a, m may be 0 or 1, and n may be 2 or 3. In Formula M-a, when m is 0, n may be 3, and when m is 1, n may be 2.

The compound represented by Formula M-a may be used as a phosphorescence dopant.

The compound represented by Formula M-a may be selected from any one among Compound M-a1 to Compound M-a23 below. However, Compounds M-a1 to M-a23 below are examples, and the compound represented by Formula M-a is not limited to those represented by Compounds M-a1 to M-a23 below.

M-a1

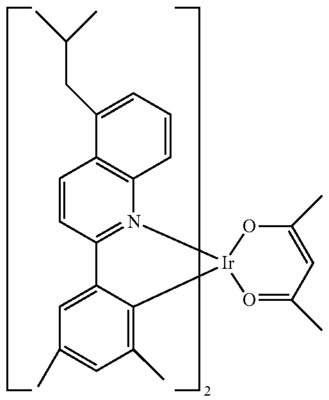

-continued

M-a2

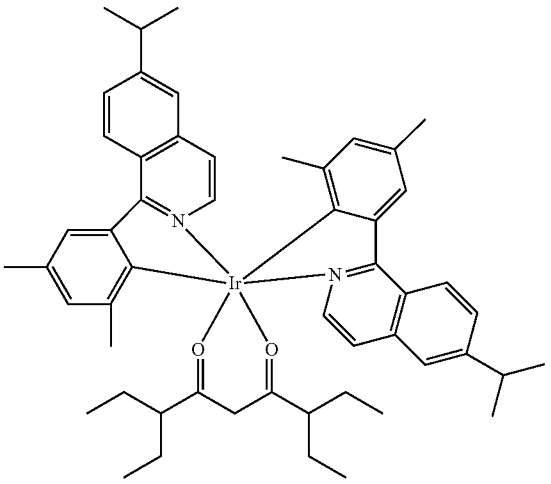

M-a3

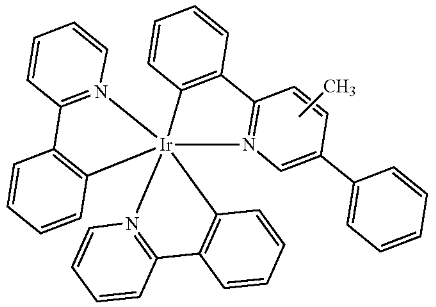

M-a4

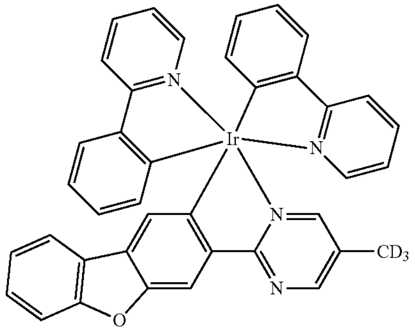

M-a5

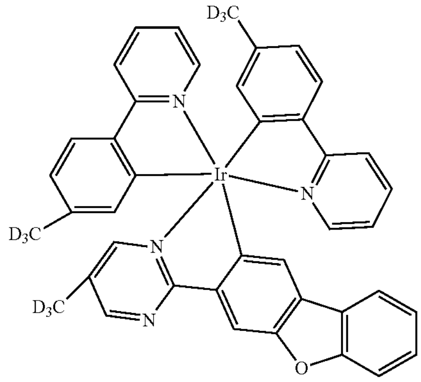

-continued
M-a6
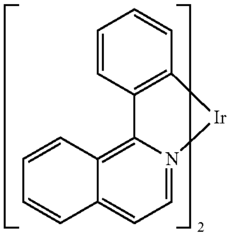
M-a7
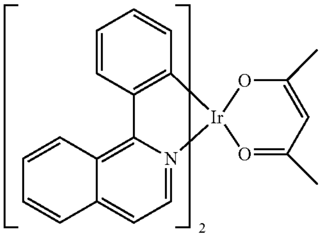
M-a8
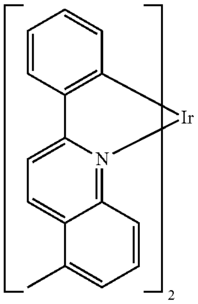
M-a9
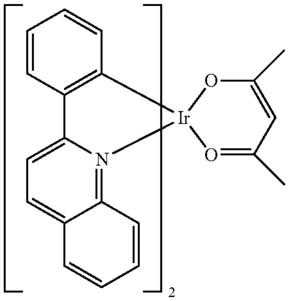
M-a10
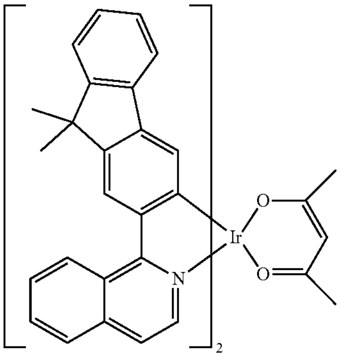
-continued
M-a11
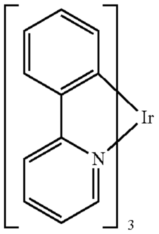
M-a12
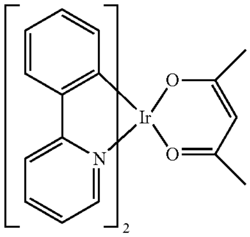
M-a13
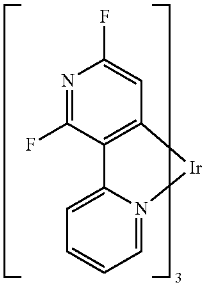
M-a14
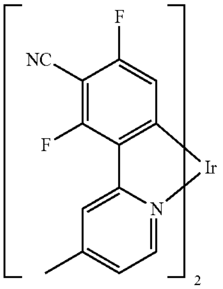
M-a15
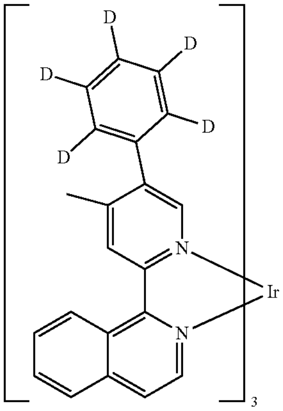

-continued
M-a16
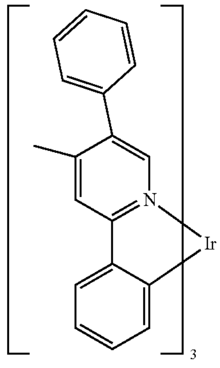
M-a17
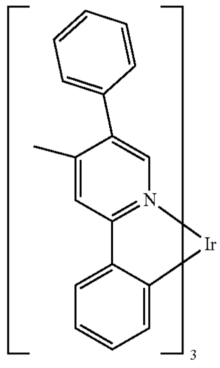
M-a18
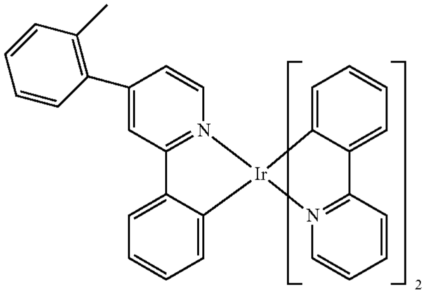
M-a19
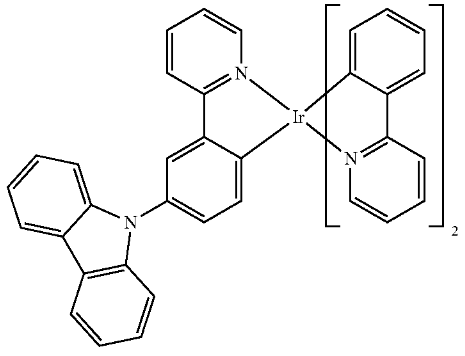
-continued
M-a20
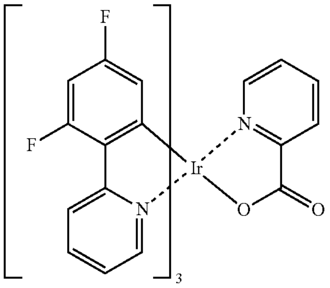
M-a21
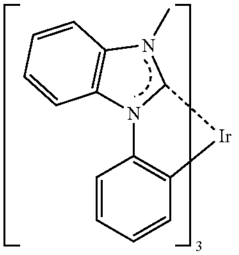
M-a22
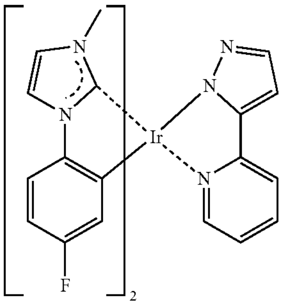
M-a23
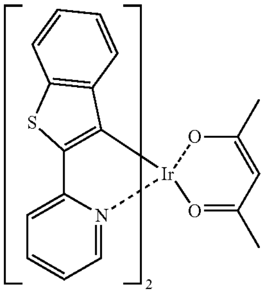
Compound M-a1 and Compound M-a2 may be used as a red dopant material, and Compound M-a3 to Compound M-a5 may be used as a green dopant material.

[Formula M-b]

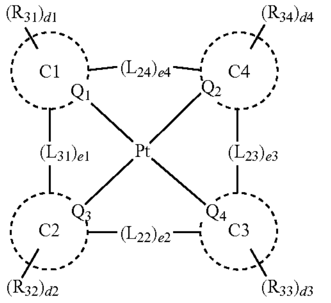

In Formula M-b, $Q_1$ to $Q_4$ may each independently be C or N, and $C_1$ to $C_4$ may each independently be a substituted or unsubstituted hydrocarbon ring having 5 to 30 ring-forming carbon atoms, or a substituted or unsubstituted heterocycle having 2 to 30 ring-forming carbon atoms. $L_{21}$ to $L_{24}$ may each independently be a direct linkage,

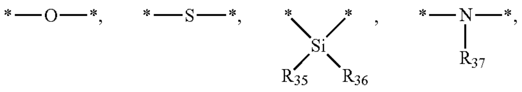

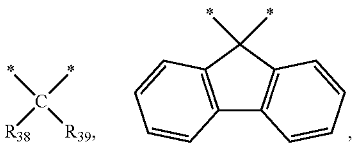

a substituted or unsubstituted divalent alkyl group having 1 to 20 carbon atoms, a substituted or unsubstituted arylene group having 6 to 30 ring-forming carbon atoms, or a substituted or unsubstituted heteroarylene group having 2 to 30 ring-forming carbon atoms, and e1 to e4 may each independently be 0 or 1. In Formula M-b, $R_{31}$ to $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring, and dl to d4 may each independently be an integer from 0 to 4.

The compound represented by Formula M-b may be used as a blue phosphorescence dopant or a green phosphorescence dopant.

The compound represented by Formula M-b may be selected from any one among the compounds below. However, the compounds below are examples, and the compound represented by Formula M-b is not limited to those represented by the compounds below.

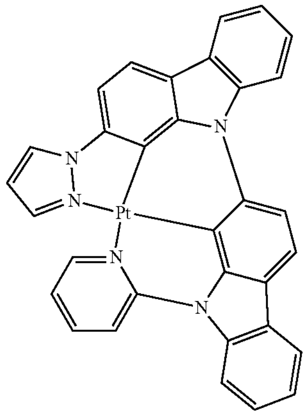

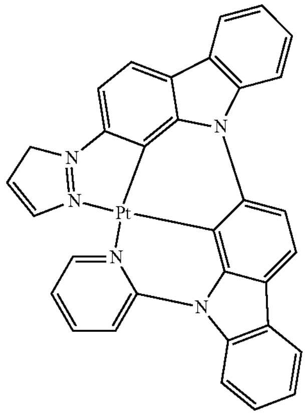

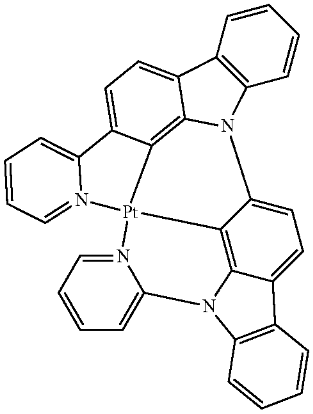

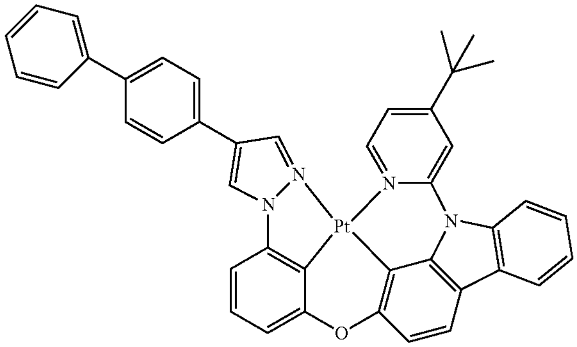

-continued

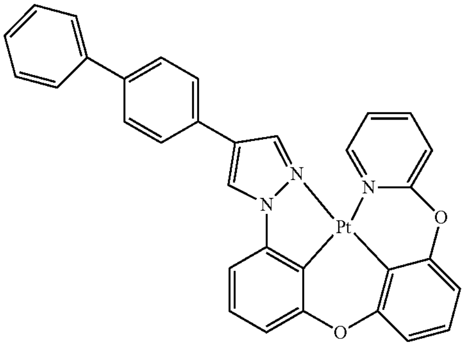

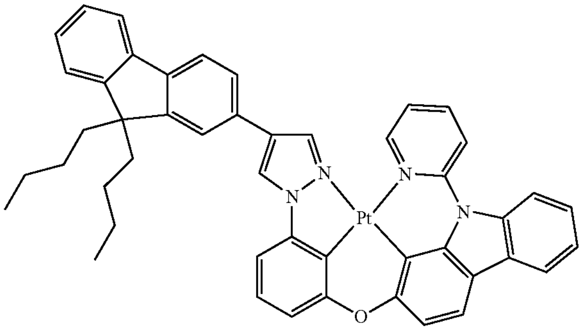

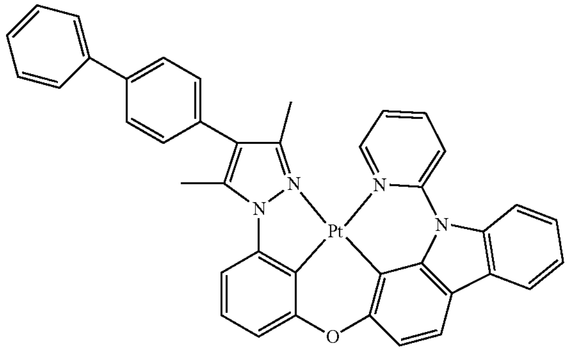

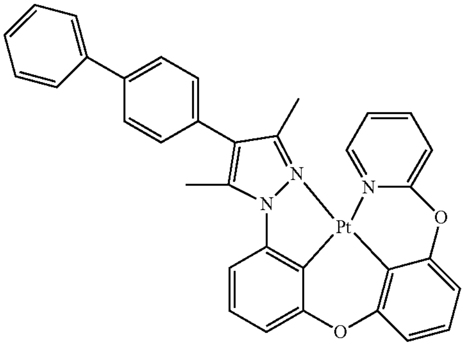

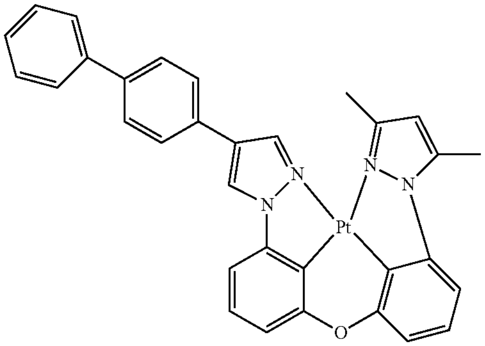

-continued

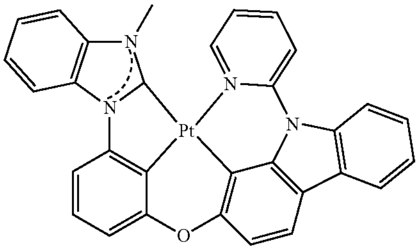

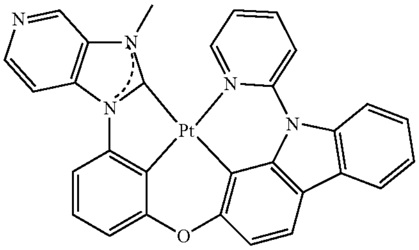

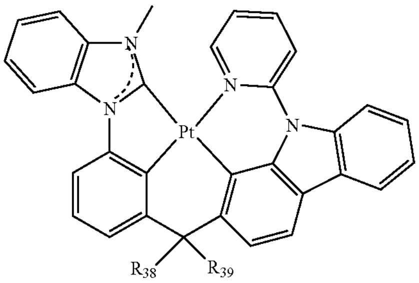

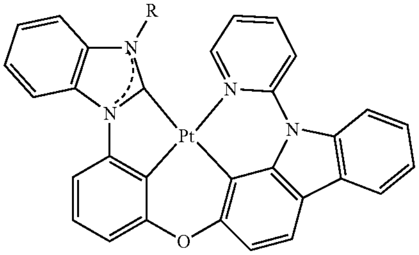

In the compounds above, R, $R_{38}$, and $R_{39}$ may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted heteroaryl group having 2 to 30 ring-forming carbon atoms.

A dopant material including Pt as a central metal may be selected from at least one among the compounds below:

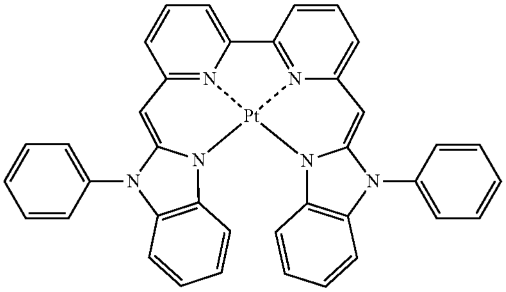

-continued

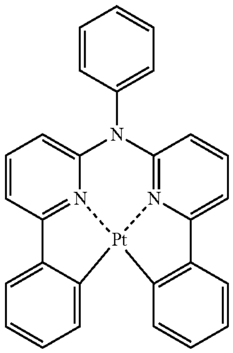

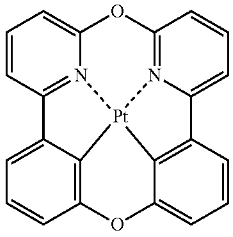

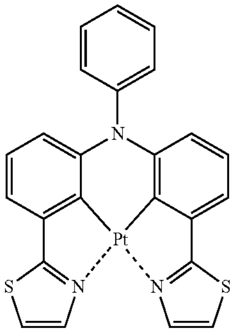

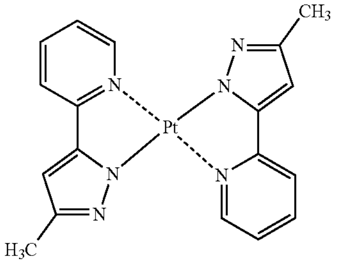

The emission layer EML may include a compound represented by any one among Formula F-a to Formula F-c below. The compound represented by Formula F-a to Formula F-c below may be used as a fluorescence dopant material.

[Formula F-a]

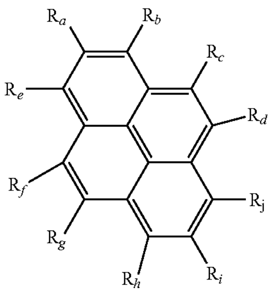

In Formula F-a, two selected from among $R_a$ to $R_j$ may each independently be substituted with $$*{-}NAr_1Ar_2.$$

The remainder of $R_a$ to $R_j$ which are not substituted with $$*{-}NAr_1Ar_2,$$

may each independently be a hydrogen atom, a deuterium atom, a halogen atom, a cyano group, a substituted or unsubstituted amine group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In Formula F-a, in the moiety represented by $$*{-}NAr_1Ar_2,$$

$Ar_1$ and $Ar_2$ may each independently be a substituted or unsubstituted aryl group having 6 to 30 ring-forming carbon atoms, or a substituted or unsubstituted heteroaryl group having 2 to 30 ring-forming carbon atoms. For example, at least one of $Ar_1$ or $Ar_2$ may be a heteroaryl group containing O or S as a ring-forming atom.

The emission layer may include, as a fluorescence dopant, at least one among Compound FD1 to Compound FD22 below.

FD1

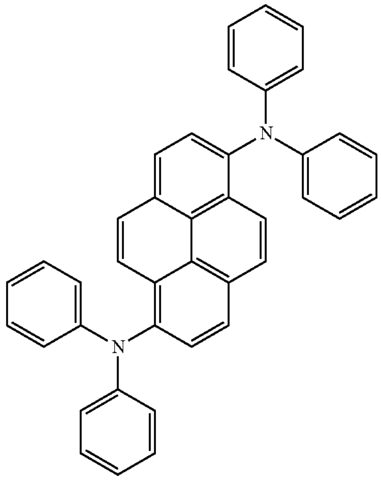

FD2

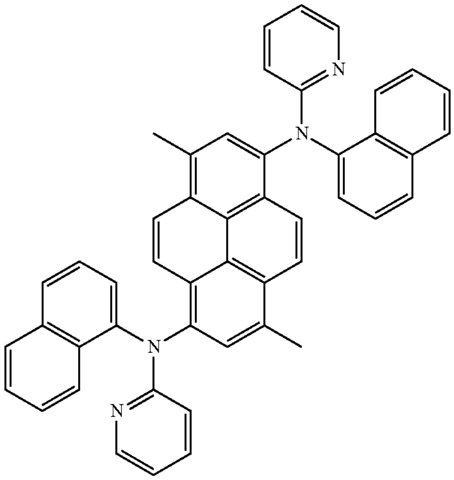

-continued
FD3
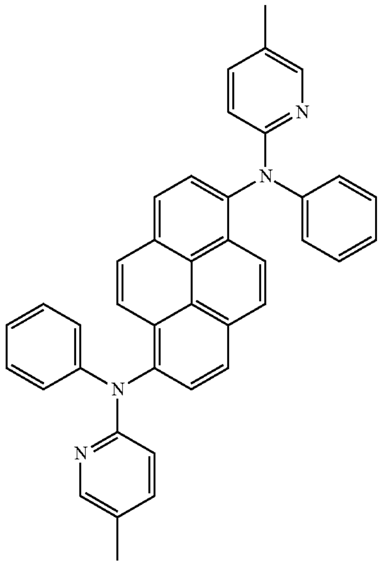
FD4
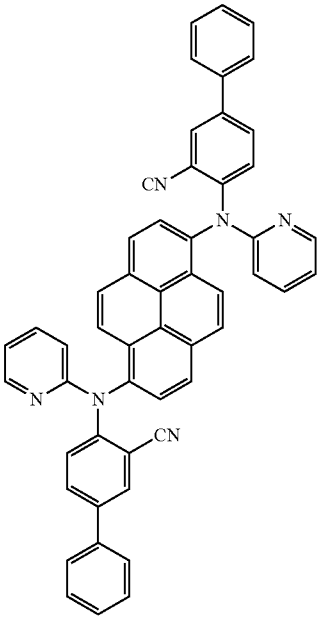
-continued
FD5
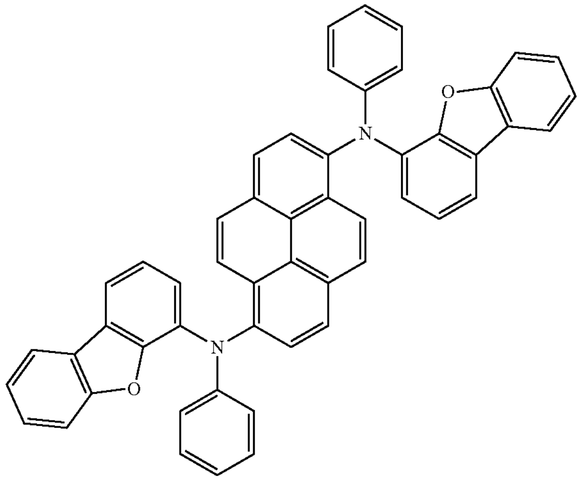
FD6
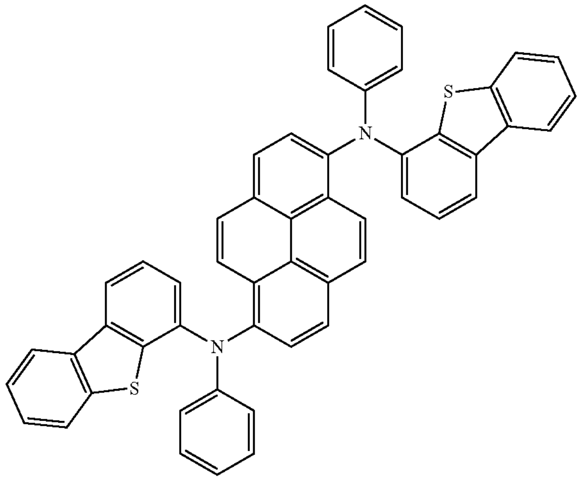
FD7
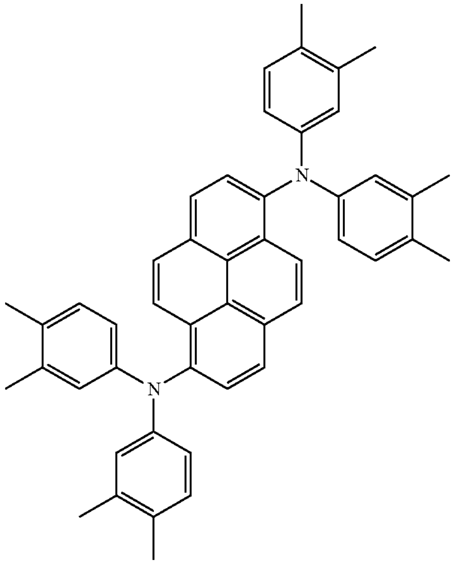

-continued
FD8
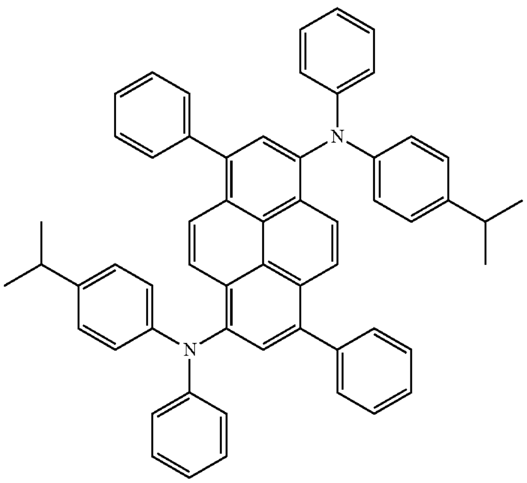
FD9
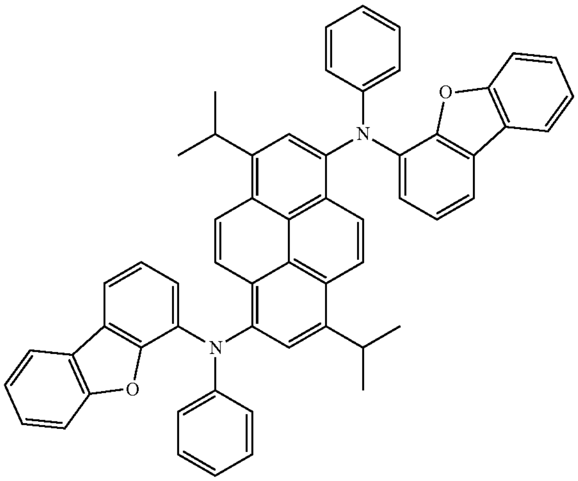
FD10
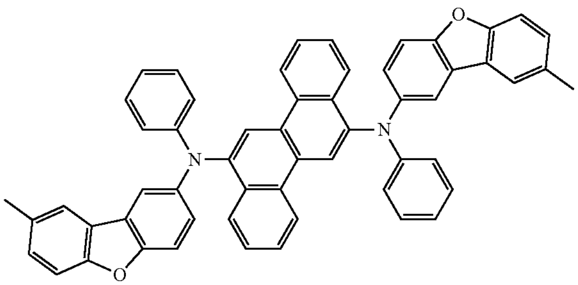
FD11
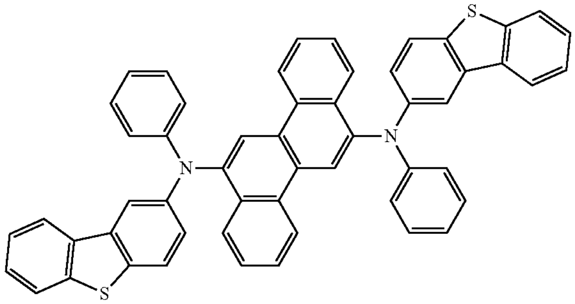
-continued
FD12
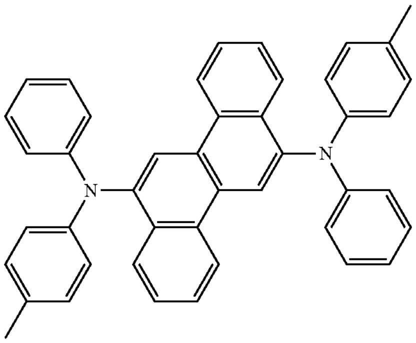
FD13
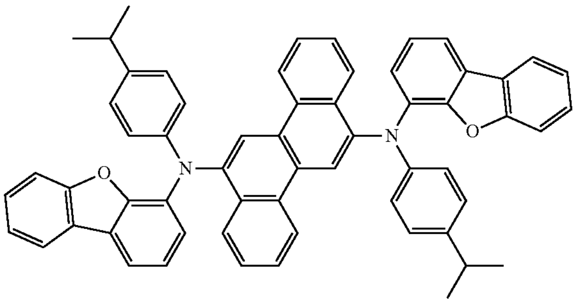
FD14
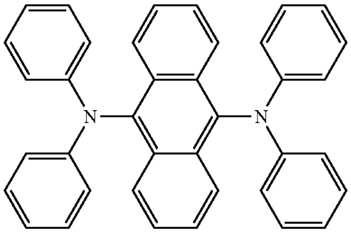
FD15
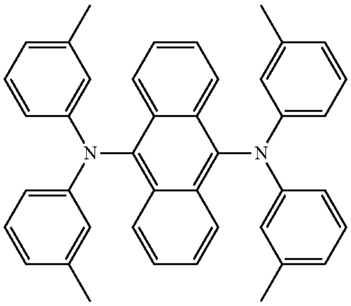
FD16
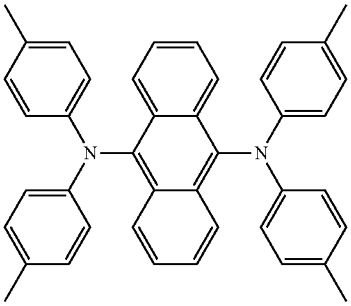

-continued

FD17

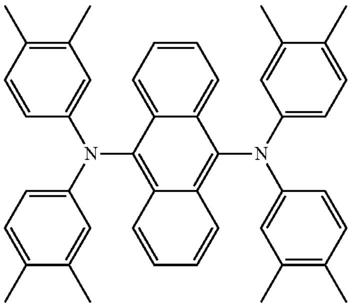

FD18

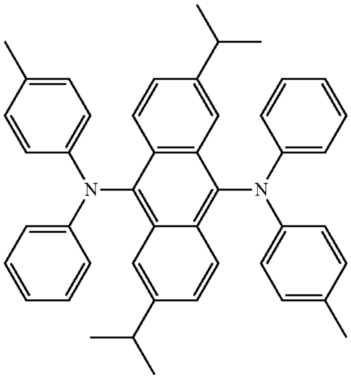

FD19

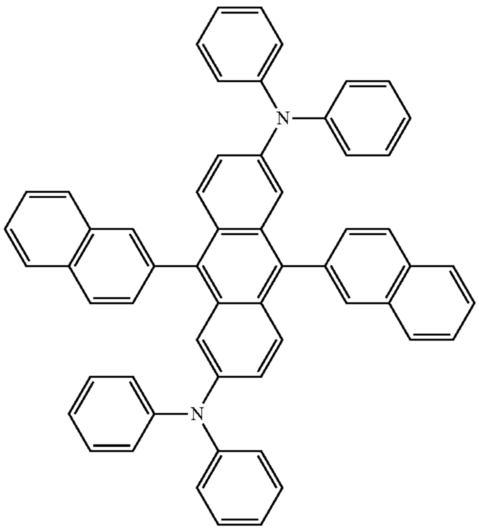

FD20

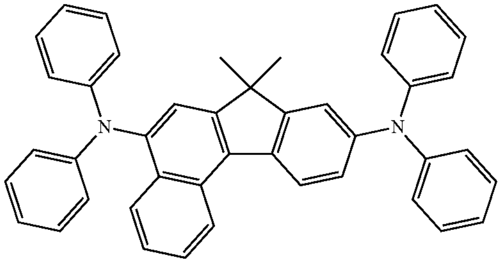

-continued

FD21

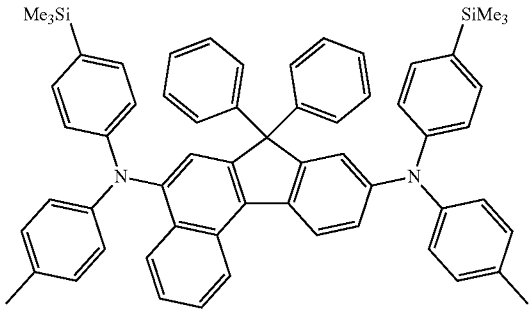

FD22

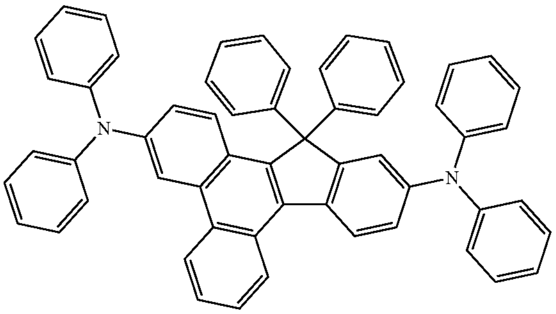

[Formula F-b]

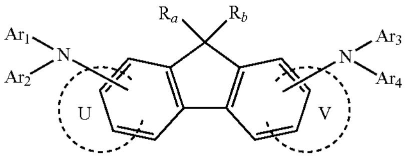

In formula F-b, $R_a$ and $R_b$ may each independently be a hydrogen atom, a deuterium atom, a substituted or unsubstituted alkyl group having 1 to 20 carbon atoms, a substituted or unsubstituted alkenyl group having 2 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-b, U and V may each independently be a substituted or unsubstituted hydrocarbon ring having 5 to 30 ring-forming carbon atoms, or a substituted or unsubstituted heterocycle having 2 to 30 ring-forming carbon atoms.

In Formula F-b, the number of rings represented by U and V may each independently be 0 or 1. For example, in Formula F-b, when the number of U or V is 1, one ring may form a condensed ring at a part described as U or V, and when the number of U or V is 0, a ring may not be present at a part described as U or V. For example, when the number of U is 0 and the number of V is 1, or when the number of U is 1 and the number of V is 0, the condensed ring having a fluorene core of Formula F-b may be a four-ring cyclic compound. When the number of U and V is each 0, the condensed ring of Formula F-b may be a three-ring cyclic compound. When the number of U and V is each 1, the condensed ring having a fluorene core of Formula F-b may be a five-ring cyclic compound.

[Formula F-c]

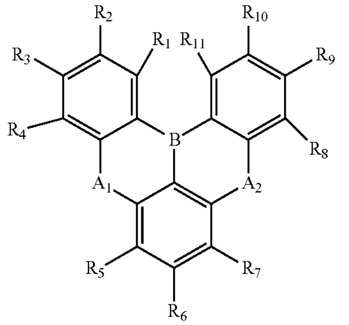

In Formula F-c, $A_1$ and $A_2$ may each independently be O, S, Se, or $N(R_m)$, and $R_m$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In Formula F-c, $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms, or may be bonded to an adjacent group to form a ring.

In Formula F-c, $A_1$ and $A_2$ may each independently be bonded to substituents of an adjacent group to form a condensed ring. For example, when $A_1$ and $A_2$ are each independently $N(R_m)$, $A_1$ may be bonded to $R_4$ or $R_5$ to form a ring. For example, $A_2$ may be bonded to $R_7$ or $R_8$ to form a ring.

In an embodiment, the emission layer EML may include, as a dopant material, styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), and N-(4-((E)-2-(6-((E)-4-(diphenylamino)styryl)naphthalen-2-yl)vinyl)phenyl)-N-phenylbenzenamine (N-BDAVBi), 4,4'-bis[2-(4-(N,N-diphenylamino)phenyl)vinyl]biphenyl (DPAVBi), perylene and the derivatives thereof (e.g., 2,5,8,11-tetra-t-butylperylene (TBP)), pyrene and the derivatives thereof (e.g., 1,1-dipyrene, 1,4-dipyrenylbenzene, 1,4-bis(N,N-diphenylamino)pyrene), etc.

The emission layer EML may include a phosphorescence dopant material. For example, a metal complex including iridium (Ir), platinum (Pt), osmium (Os), aurum (Au), titanium (Ti), zirconium (Zr), hafnium (Hf), europium (Eu), terbium (Tb), or thulium (Tm) may be used as a phosphorescence dopant. In an embodiment, iridium (III) bis(4,6-difluorophenylpyridinato-N,C2') (FIrpic), bis(2,4-difluorophenylpyridinato)-tetrakis(1-pyrazolyl)borate iridium (III) (Fir6), or platinum octaethyl porphyrin (PtOEP) may be used as a phosphorescence dopant. However, embodiments are not limited thereto.

The emission layer EML may include a quantum dot material. The core of the quantum dot may be selected from a Group II-VI compound, a Group III-VI compound, a Group 1-III-VI compound, a Group III-V compound, a Group III-II-V compound, a Group IV-VI compound, a Group IV element, a Group IV compound, or a combination thereof.

A Group II-VI compound may be selected from the group consisting of a binary compound selected from the group consisting of CdSe, CdTe, CdS, ZnS, ZnSe, ZnTe, ZnO, HgS, HgSe, HgTe, MgSe, MgS, and a mixture thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-VI compound may include a binary compound such as $In_2S_3$ and $In_2Se_3$, a ternary compound such as $InGaS_3$ and $InGaSe_3$, or any combination thereof.

A Group 1-III-VI compound may be selected from a ternary compound selected from the group consisting of AgInS, $AgInS_2$, CuInS, $CuInS_2$, $AgGaS_2$, $CuGaS_2$ $CuGaO_2$, $AgGaO_2$, $AgAlO_2$, and a mixture thereof, or a quaternary compound such as $AgInGaS_2$ and $CuInGaS_2$.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and a mixture thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof. The Group III-V compound may further include a Group II metal. For example, InZnP, etc. may be selected as a Group III-II-V compound.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

A binary compound, a ternary compound, or a quaternary compound may be present in particles at a uniform concentration distribution, or may be present in the same particle at a partially different concentration distribution. The quantum dot may have a core/shell structure in which one quantum dot surrounds another quantum dot. An interface between the core and the shell may have a concentration gradient in which the concentration of an element present in the shell may decrease towards the core.

In an embodiment, a quantum dot may have the above-described core-shell structure including a core containing a nanocrystal and a shell surrounding the core. The shell of the quantum dot may serve as a protection layer to prevent the chemical deformation of the core so as to maintain semiconductor properties, and/or as a charging layer to impart electrophoresis properties to the quantum dot. The shell may be a single layer or a multilayer. An interface between the core and the shell may have a concentration gradient in which the concentration of an element present in the shell may decrease towards the core. An example of the shell of the quantum dot may include a metal or non-metal oxide, a semiconductor compound, or a combination thereof.

For example, the metal or non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and NiO, or a ternary compound such as $MgAl_2O_4$, $CoFe_2O_4$, $NiFe_2O_4$, and $CoMn_2O_4$, but embodiments are not limited thereto.

The semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

The quantum dot may have a full width of half maximum (FWHM) of a light emission wavelength spectrum equal to or less than about 45 nm. For example, the quantum dot may have a FWHM of a light emission wavelength spectrum equal to or less than about 40 nm. For example, the quantum dot may have a FWHM of a light emission wavelength spectrum equal to or less than about 30 nm. Within these ranges, color purity or color reproducibility may be improved. Light emitted through the quantum dot may be emitted in all directions, and thus a wide viewing angle may be improved.

The form of a quantum dot may be a form used in the art, without limitation. For example, the quantum dot may have a spherical, a pyramidal, a multi-arm, or a cubic shape, or the quantum dot may be in the form of nanoparticles, nanotubes, nanowires, nanofibers, nanoparticles, etc.

The quantum dot may control the color of emitted light according to the particle size thereof. Accordingly, the quantum dot may have various light emission colors such as blue, red, and green.

In each light emitting device ED of embodiments illustrated in FIGS. 2 to 6, the electron transport region ETR is provided on the emission layer EML. The electron transport region ETR may include at least one of a hole blocking layer HBL, an electron transport layer ETL, and an electron injection layer EIL, but embodiments are not limited thereto.

The electron transport region ETR may have a single layer formed of a single material, a single layer formed of different materials, or a multilayer structure including layers formed of different materials.

For example, the electron transport region ETR may have a single layer structure of the electron injection layer EIL or the electron transport layer ETL, and may have a single layer structure formed of an electron injection material and an electron transport material. The electron transport region ETR may have a single layer structure formed of different materials, or may have a structure in which an electron transport layer ETL/electron injection layer EIL and a hole blocking layer HBL/electron transport layer ETL/electron injection layer EIL are stacked in order from the emission layer EML, but embodiments are not limited thereto. The electron transport region ETR may have a thickness, for example, in a range of about 1,000 Å to about 1,500 Å.

The electron transport region ETR may be formed by using various methods such as a vacuum deposition method, a spin coating method, a cast method, a Langmuir-Blodgett (LB) method, an inkjet printing method, a laser printing method, a laser induced thermal imaging (LITI) method, etc.

The electron transport region ETR may include a compound represented by Formula ET-1 below:

[Formula ET-1]

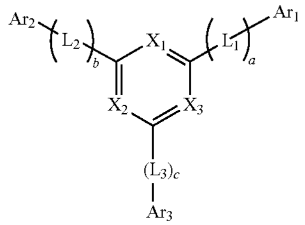

In Formula ET-1, at least one among $X_1$ to $X_3$ may be N, and the remainder of $X_1$ to $X_3$ may be $C(R_a)$. $R_a$ may be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms. In Formula ET-1, $Ar_1$ to $Ar_3$ may each independently be a hydrogen atom, a deuterium atom, a substituted or unsubstituted alkyl group having 1 to 20 carbon atoms, a substituted or unsubstituted aryl group having 6 to 30 ring-forming carbon atoms, or a substituted or unsubstituted heteroaryl group having 2 to 30 ring-forming carbon atoms.

In Formula ET-1, a to c may each independently be an integer from 0 to 10. In Formula ET-1, $L_1$ to $L_3$ may each independently be a direct linkage, a substituted or unsubstituted arylene group having 6 to 30 ring-forming carbon atoms, or a substituted or unsubstituted heteroarylene group having 2 to 30 ring-forming carbon atoms. In Formula ET-1, when a to c are 2 or more, $L_1$ to $L_3$ may each independently be a substituted or unsubstituted arylene group having 6 to 30 ring-forming carbon atoms, or a substituted or unsubstituted heteroarylene group having 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazol-1-yl)phenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebq_2$), 9,10-di(naphthalene-2-yl)anthracene (ADN), 1,3-Bis[3,5-di(pyridin-3-yl)phenyl]benzene (BmPyPhB), or a mixture thereof.

The electron transport region ETR may include at least one among Compound ET1 to Compound ET36 below:

-continued
ET1
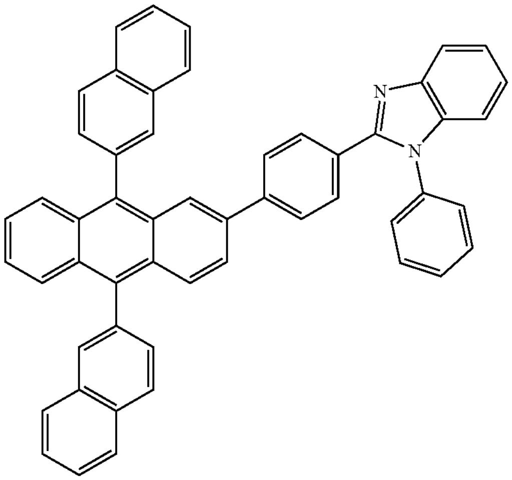
ET2
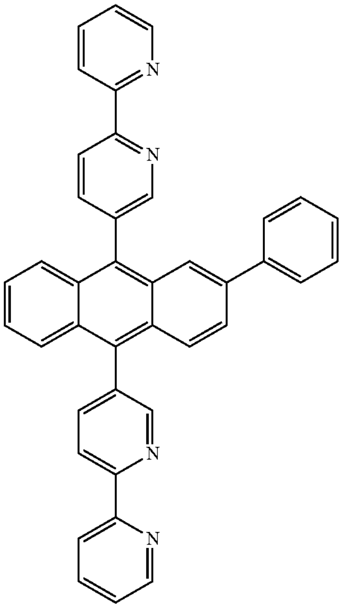
ET3
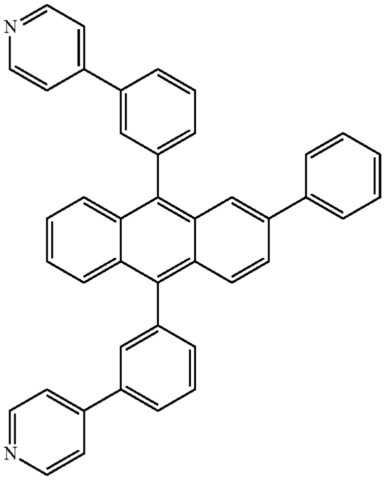
ET4
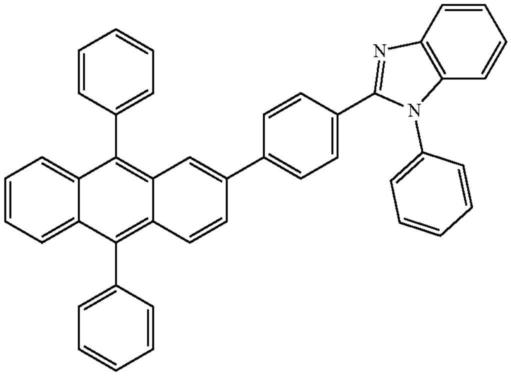
ET5
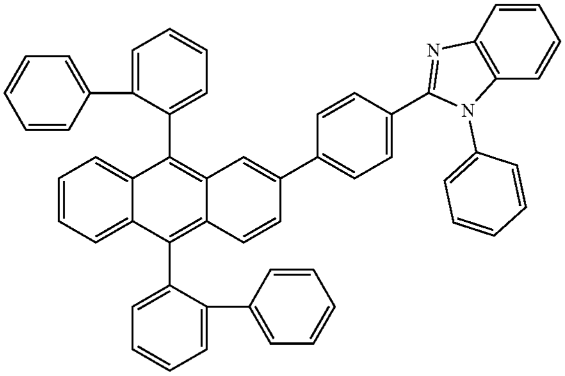
ET6
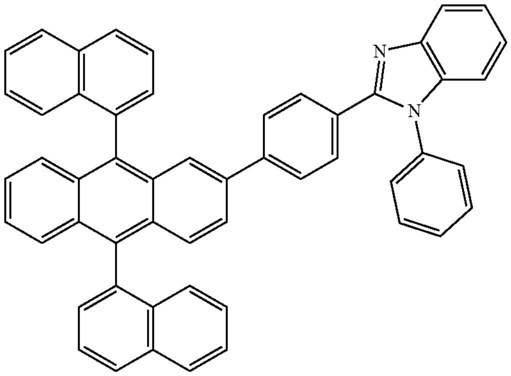

-continued
ET7
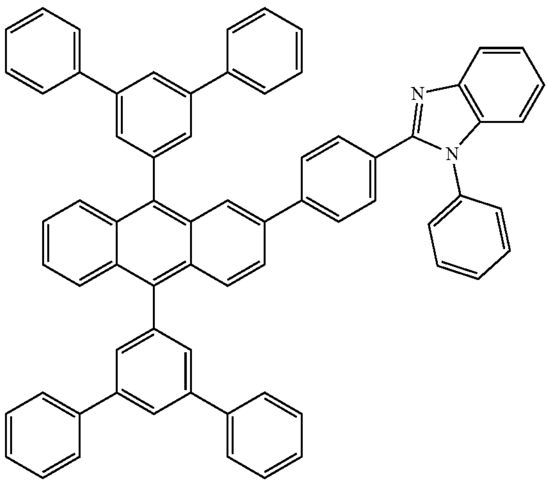
ET8
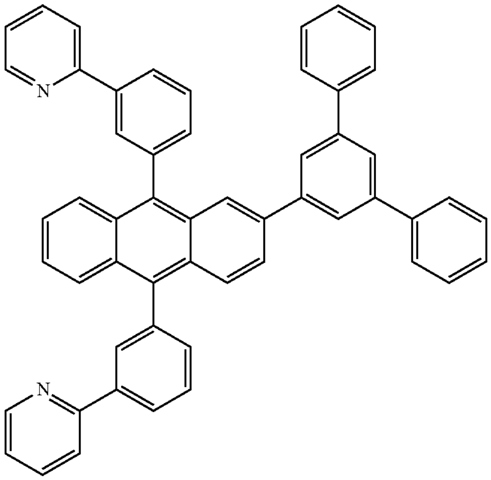
ET9
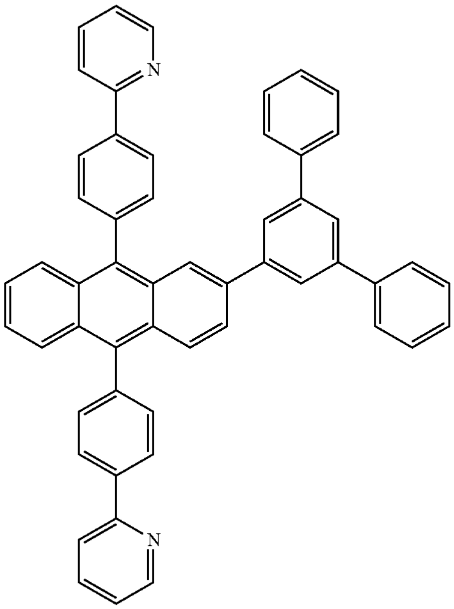
-continued
ET10
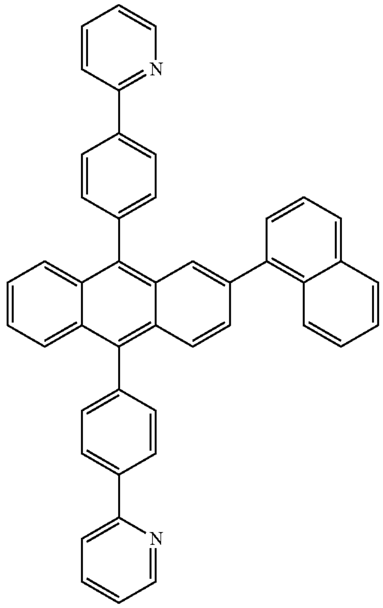
ET11
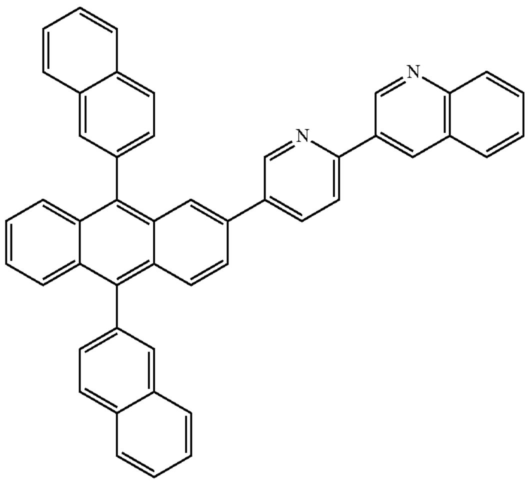
ET12
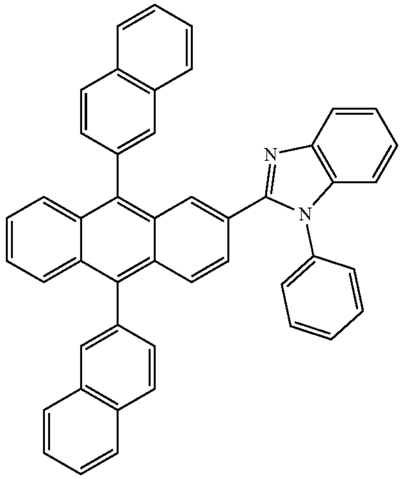

-continued
ET13
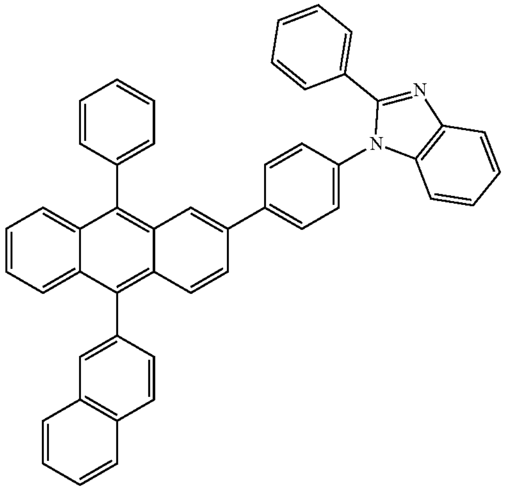
ET14
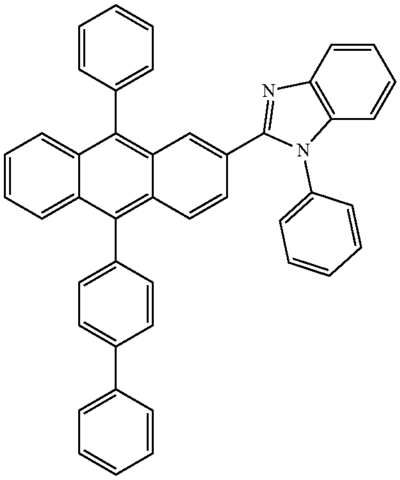
ET15
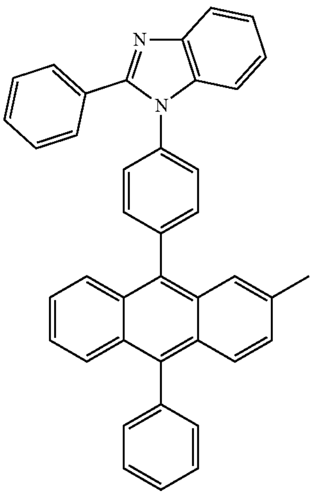
-continued
ET16
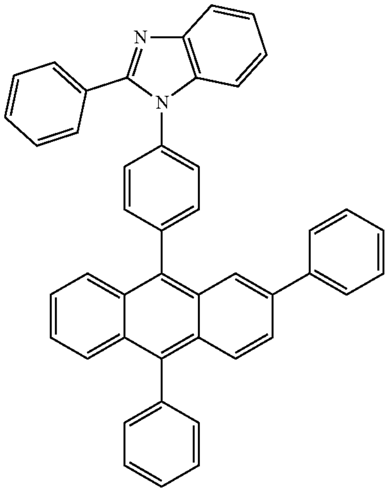
ET17
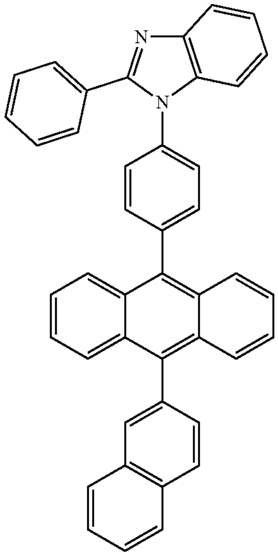
ET18
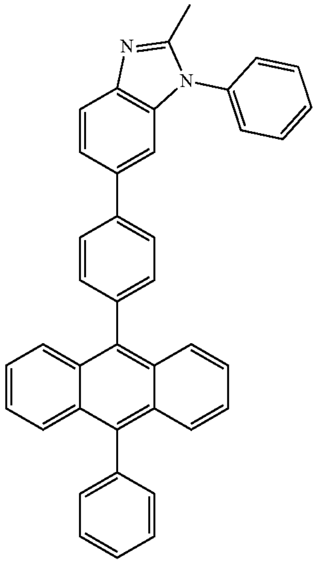

-continued
ET19
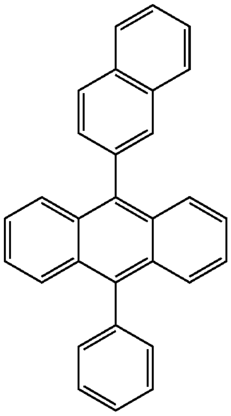
ET20
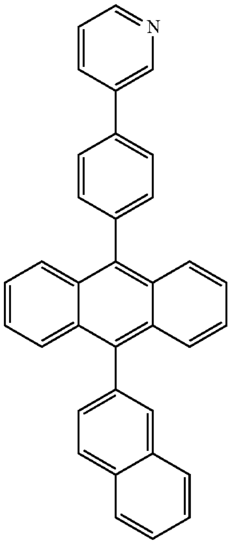
ET21
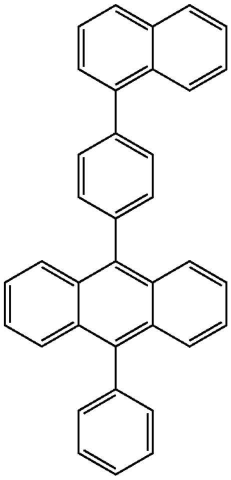
-continued
ET22
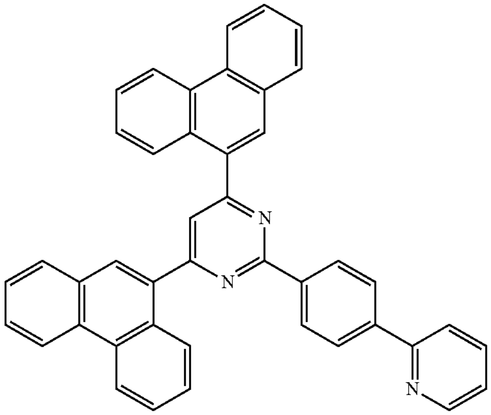
ET23
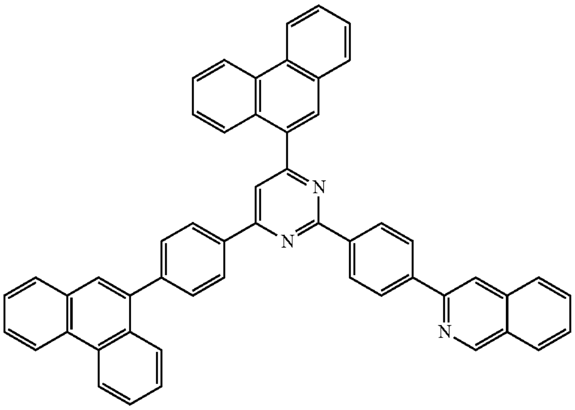
ET24
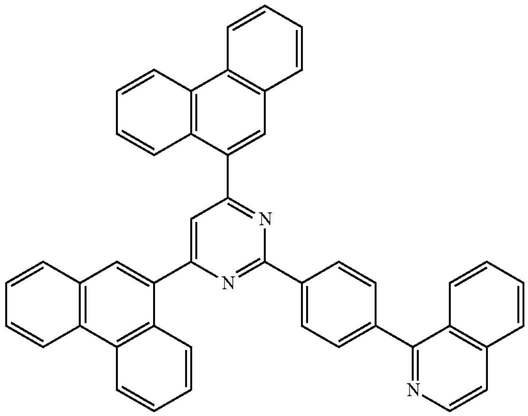

-continued
ET25
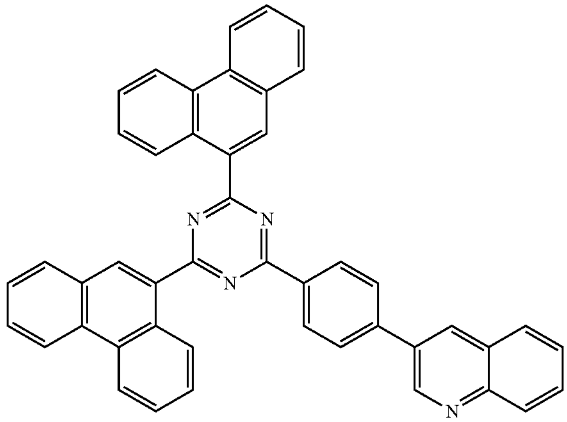
ET26
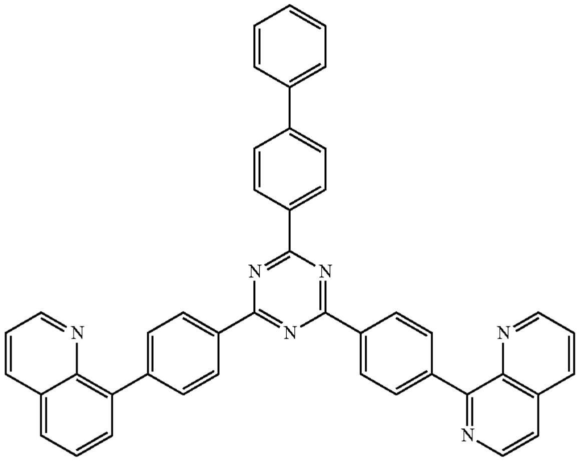
ET27
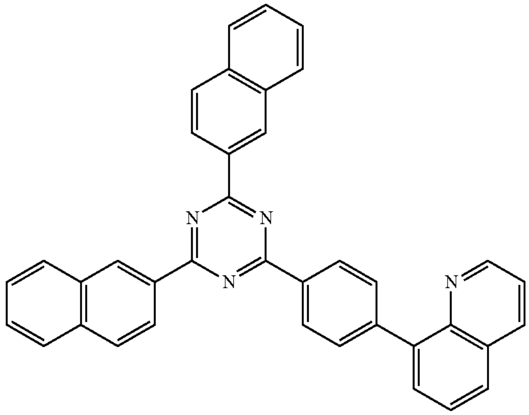
-continued
ET28
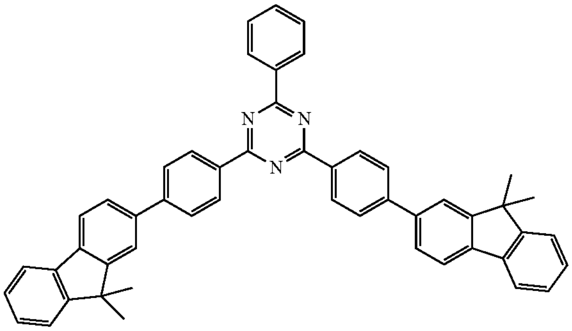
ET29
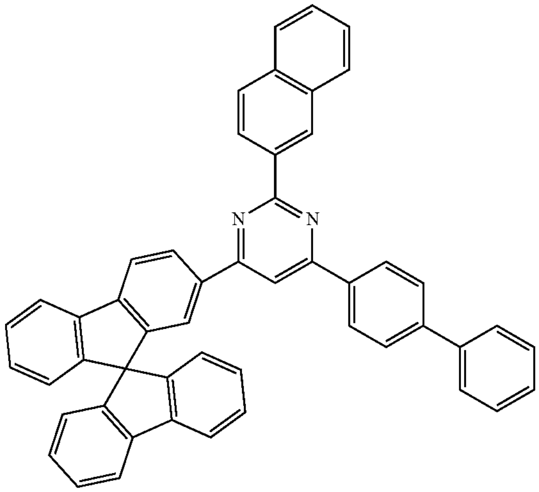
ET30
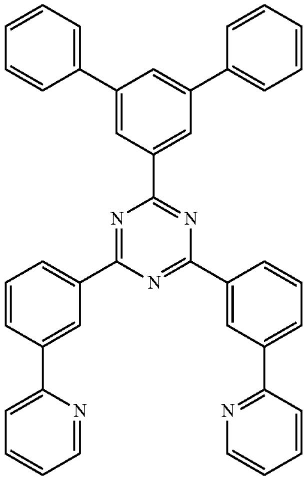

-continued

ET31

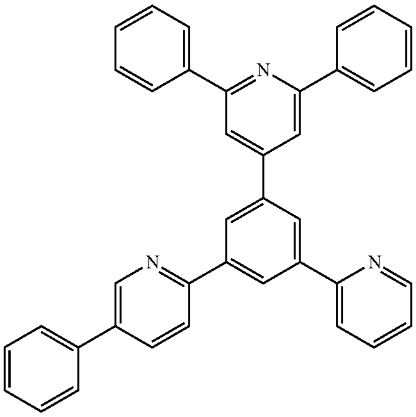

ET32

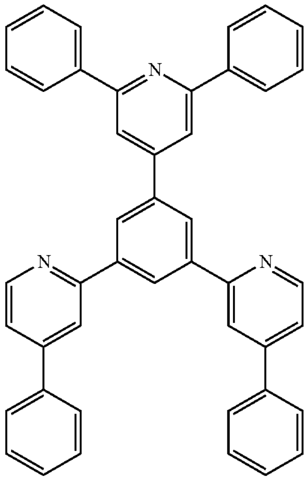

ET33

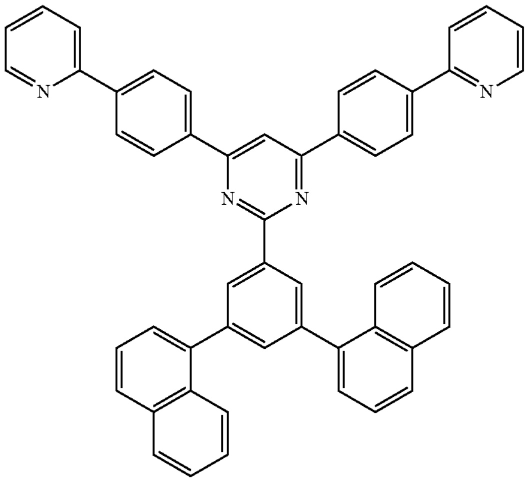

-continued

ET34

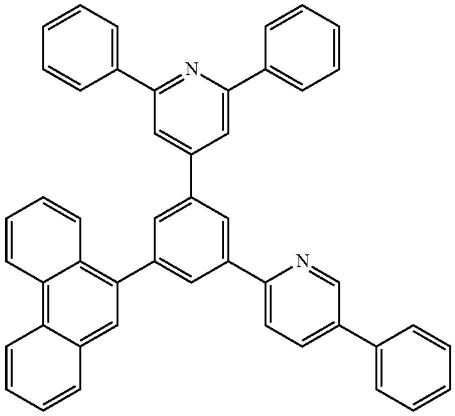

ET35

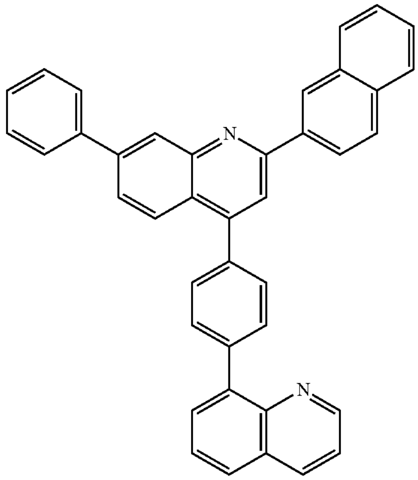

ET36

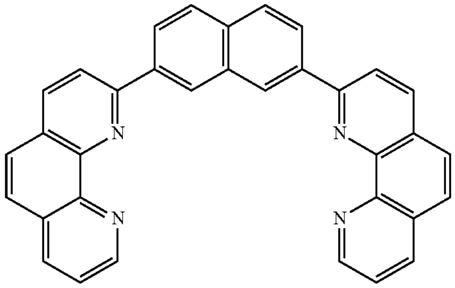

The electron transport regions ETR may include a metal halide such as LiF, NaCl, CsF, RbCl, RbI, CuI, or KI, a lanthanide such as Yb, and a co-deposited material of the metal halide and the lanthanide. For example, the electron transport region ETR may include KI:Yb, RbI:Yb, etc. as a co-deposited material. The electron transport region ETR may include a metal oxide such as $Li_2O$ or BaO, or 8-hydroxyl-lithium quinolate (Liq), etc., but embodiments are not limited thereto. The electron transport region ETR may as include a mixture of an electron transport material and an insulating organometallic salt. The organometallic salt may be a material having an energy band gap equal to or greater than about 4 eV. In an embodiment, the organometallic salt may include, for example, metal acetates, metal benzoates, metal acetoacetates, metal acetylacetonates, or metal stearates.

The electron transport region ETR may further include at least one of 2,9-dimethyl-4,7-diphenyl-1,10-phenanthroline (BCP), or 4,7-diphenyl-1,10-phenanthroline (Bphen) in addition to the above-described materials, but embodiments are not limited thereto.

The electron transport region ETR may include the above-described compounds of the hole transport region in at least one of the electron injection layer EIL, the electron transport layer ETL, or the hole blocking layer HBL.

When the electron transport region ETR includes an electron transport layer ETL, the electron transport layer ETL may have a thickness in a range of about 100 Å to about 1,000 Å. For example, the electron transport layer ETL may have a thickness in a range of about 150 Å to about 500 Å. If the thickness of the electron transport layer ETL satisfies the aforementioned range, satisfactory electron transport characteristics may be obtained without a substantial increase in driving voltage. When the electron transport region ETR includes an electron injection layer EIL, the electron injection layer EIL may have a thickness in a range of about 1 Å to about 100 Å. For example, the electron injection layer EIL may have a thickness in a range of about 3 Å to about 90 Å. If the thickness of the electron injection layer EIL satisfies the above-described range, satisfactory electron injection characteristics may be obtained without a substantial increase in driving voltage.

The second electrode EL2 is provided on the electron transport region ETR. The second electrode EL2 may be a common electrode. The second electrode EL2 may be a cathode or an anode, but embodiments are not limited thereto. For example, when the first electrode EL1 is an anode, the second electrode EL2 may be a cathode, and when the first electrode EL1 is a cathode, the second electrode EL2 may be an anode.

The second electrode EL2 may be a transmissive electrode, a transflective electrode, or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

If the second electrode EL2 is a transflective electrode or a reflective electrode, the second electrode EL2 may include Ag, Mg, Cu, Al, Pt, Pd, Au, Ni, Nd, Ir, Cr, Li, Ca, LiF, Mo, Ti, W, a compound thereof, or a mixture thereof (e.g., a mixture of Ag and Mg, a mixture of LiF and Ca, a mixture of LiF and Al, etc.). In another embodiment, the second electrode EL2 may have a multilayer structure including a reflective film or a transflective film formed of the above-described materials, and a transparent conductive film formed of ITO, IZO, ZnO, ITZO, etc. For example, the second electrode EL2 may include the above-described metal materials, combinations of at least two metal materials of the above-described metal materials, oxides of the above-described metal materials, or the like.

Although not shown in the drawings, the second electrode EL2 may be electrically connected to an auxiliary electrode. If the second electrode EL2 is electrically connected to the auxiliary electrode, the resistance of the second electrode EL2 may decrease.

The light emitting device ED of an embodiment may further include a capping layer CPL disposed on the second electrode EL2. The capping layer CPL may include a multilayer or a single layer.

In an embodiment, the capping layer CPL may include an organic layer or an inorganic layer. For example, when the capping layer CPL includes an inorganic material, the inorganic material may include an alkaline metal compound such as LiF, an alkaline earth metal compound such as $MgF_2$, SiON, $SiN_x$, SiOy, etc.

For example, when the capping layer CPL includes an organic material, the organic material may include α-NPD, NPB, TPD, m-MTDATA, $Alq_3$, CuPc, N4,N4,N4',N4'-tetra (biphenyl-4-yl)biphenyl-4,4'-diamine (TPD15), 4,4',4"-tris (carbazol-9-yl)triphenylamine (TCTA), etc., or an epoxy resin, or acrylate such as methacrylate. However, embodiments are not limited thereto, and the capping layer CPL may include at least one among Compounds P1 to P5 below:

P1

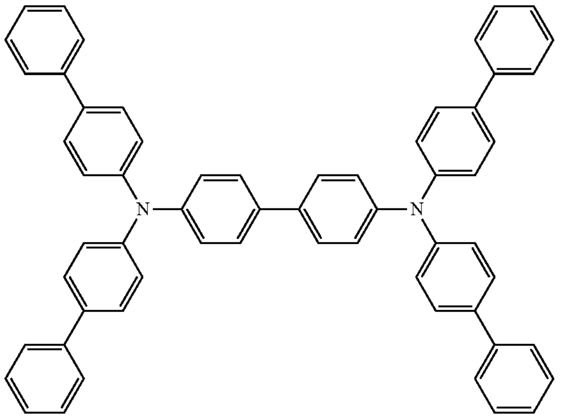

P2

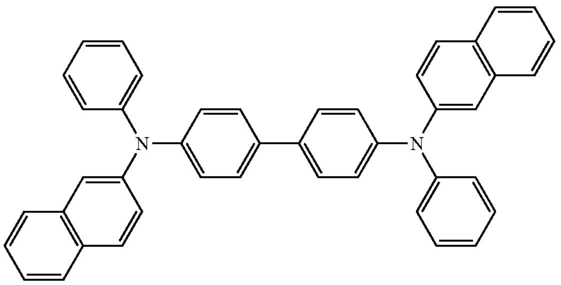

P3

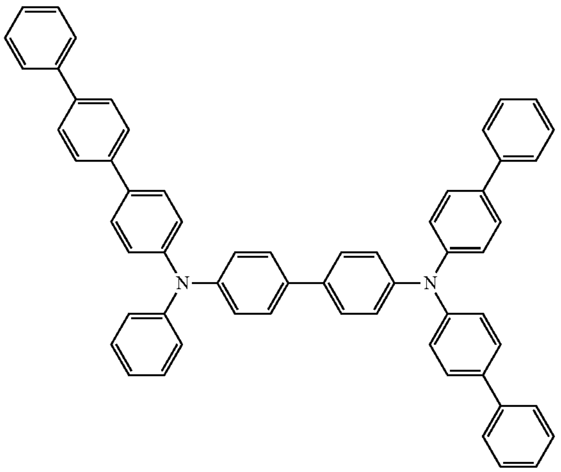

-continued

P4

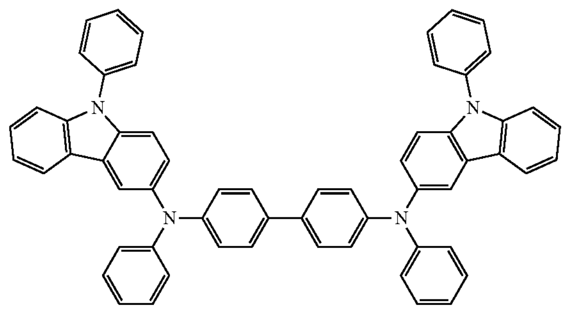

P5

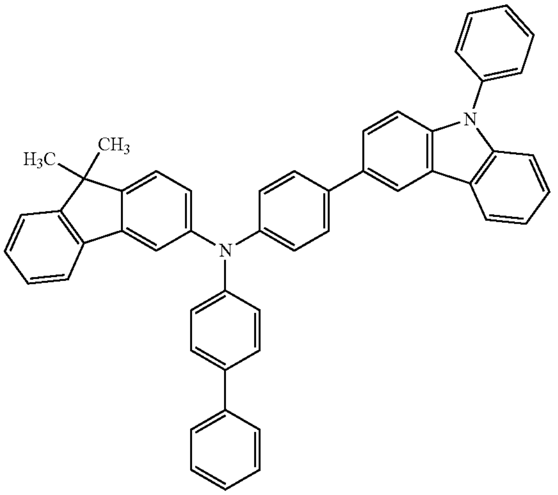

A refractive index of the capping layer CPL may be equal to or greater than about 1.6. For example, a refractive index of the capping layer CPL may be equal to or greater than about 1.6 with respect to light in a wavelength range of about 550 nm to about 660 nm.

Figure 7:
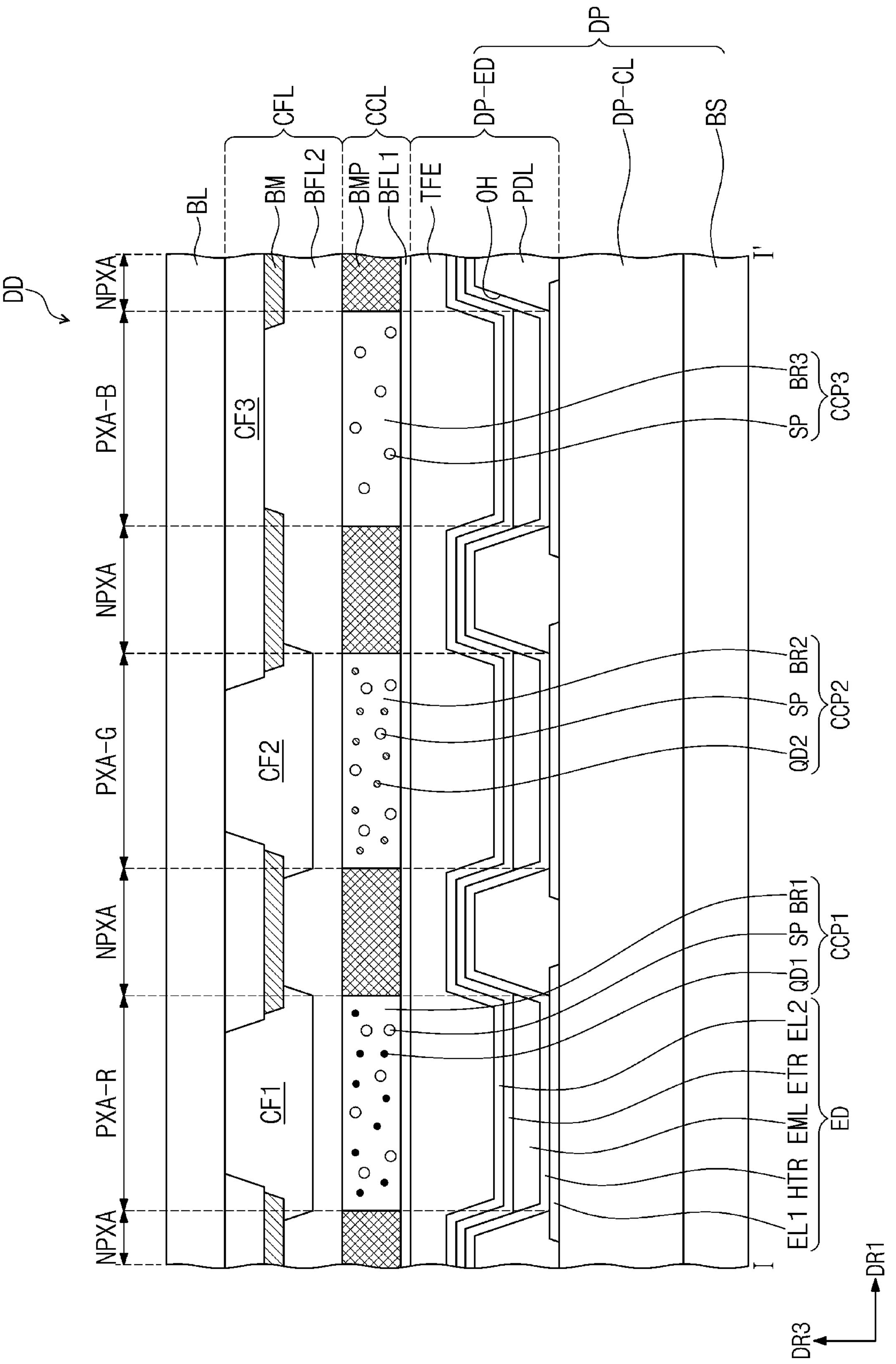
FIG. 7 is a schematic cross-sectional view of a display apparatus according to an embodiment.
Figure 8:
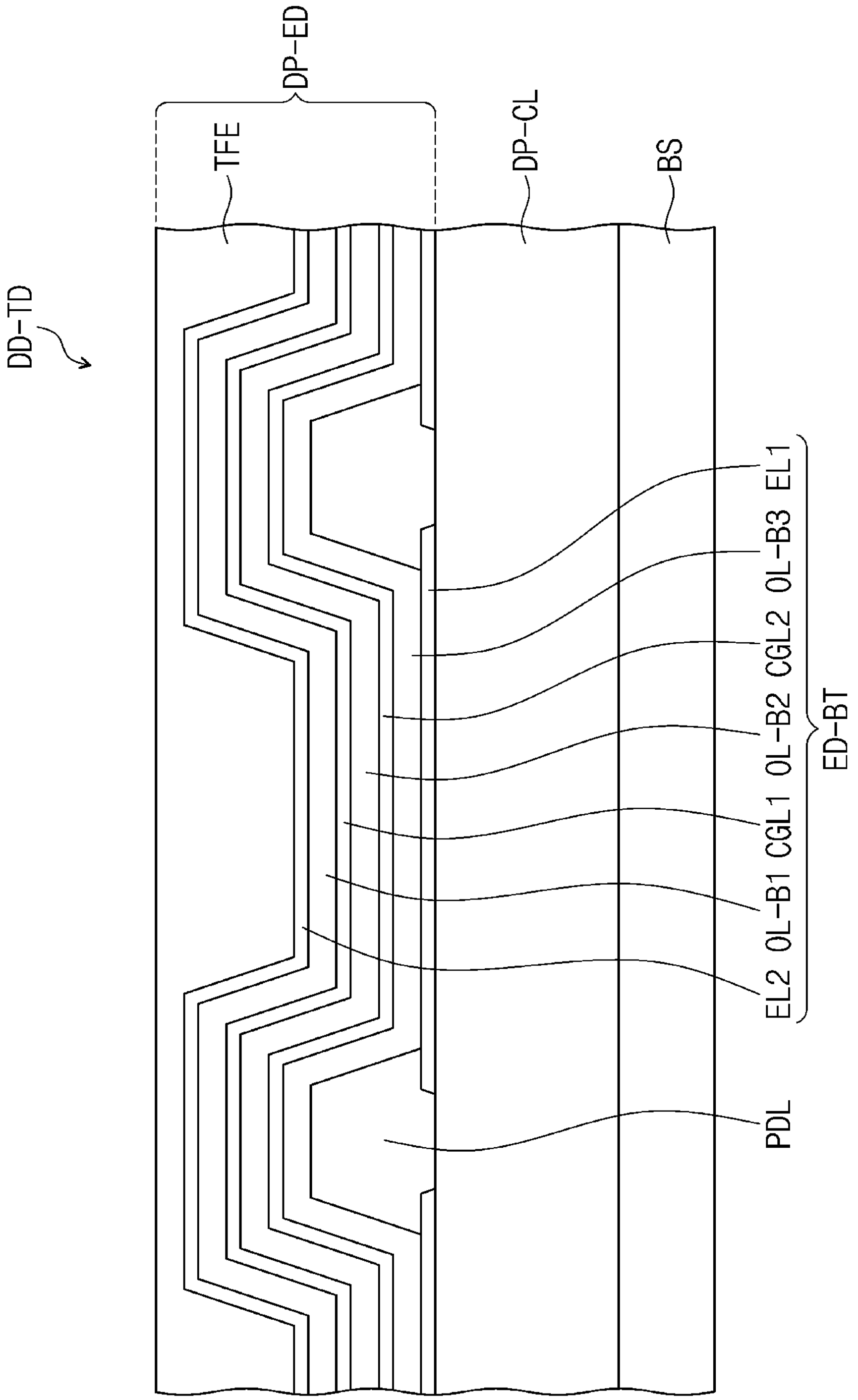
FIG. 8 is a schematic cross-sectional view of a display apparatus according to an embodiment.

FIGS. 7 and 8 each are a schematic cross-sectional view of a display apparatus according to an embodiment. Hereinafter, in describing the display apparatus of an embodiment with reference to FIGS. 7 and 8, the duplicated features which have been described in FIGS. 1 to 6 will not be described again, but their differences will be described.

Referring to FIG. 7, the display apparatus DD according to an embodiment may include a display panel DP including a display element layer DP-ED, a light control layer CCL disposed on the display panel DP, and a color filter layer CFL.

In an embodiment illustrated in FIG. 7, the display panel DP may include a base layer BS, a circuit layer DP-CL provided on the base layer BS, and the display element layer DP-ED, and the display element layer DP-ED may include a light emitting device ED.

The light emitting device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. The structures of the light emitting devices of FIGS. 3 to 6 as described above may be applied to the structure of the light emitting device ED shown in FIG. 7.

Referring to FIG. 7, the emission layer EML may be disposed in an opening OH defined in a pixel defining film PDL. For example, the emission layer EML which may be divided by the pixel defining film PDL and provided corresponding to each light emitting regions PXA-R, PXA-G, and PXA-B, may emit light in a same wavelength range. In the display apparatus DD of an embodiment, the emission layer EML may emit blue light. Although not shown in the drawing, in an embodiment, the emission layer EML may be provided as a common layer for all light emitting regions PXA-R, PXA-G, and PXA-B.

The light control layer CCL may be disposed on the display panel DP. The light control layer CCL may include a light conversion body. The light conversion body may include a quantum dot, a phosphor, or the like. The light conversion body may convert the wavelength of a provided light and emit the converted light. For example, the light control layer CCL may be a layer containing a quantum dot or a layer containing a phosphor.

The light control layer CCL may include light control parts CCP1, CCP2, and CCP3. The light control parts CCP1, CCP2, and CCP3 may be spaced apart from one another.

Referring to FIG. 7, divided patterns BMP may be disposed between the light control parts CCP1, CCP2, and CCP3 which are spaced apart from each other, but embodiments are not limited thereto. FIG. 7 illustrates that the divided patterns BMP do not overlap the light control parts CCP1, CCP2, and CCP3, but at least a portion of the edges of the light control parts CCP1, CCP2, and CCP3 may overlap the divided patterns BMP.

The light control layer CCL may include a first light control part CCP1 containing a first quantum dot QD1 which converts first color light provided from the light emitting device ED into second color light, a second light control part CCP2 containing a second quantum dot QD2 which converts the first color light into third color light, and a third light control part CCP3 which transmits the first color light.

In an embodiment, the first light control part CCP1 may provide red light which is the second color light, and the second light control part CCP2 may provide green light which is the third color light. The third light control part CCP3 may provide blue light by transmitting the blue light that is the first color light provided from the light emitting device ED. For example, the first quantum dot QD1 may be a red quantum dot, and the second quantum dot QD2 may be a green quantum dot. The same description as given to the quantum dots described above may be applied with respect to the quantum dots QD1 and QD2.

The light control layer CCL may further include a scatterer SP. The first light control part CCP1 may include the first quantum dot QD1 and the scatterer SP, the second light control part CCP2 may include the second quantum dot QD2 and the scatterer SP, and the third light control part CCP3 may not include any quantum dot but include the scatterer SP.

The scatterer SP may include inorganic particles. For example, the scatterer SP may include at least one of $TiO_2$, ZnO, $Al_2O_3$, $SiO_2$, and hollow silica. The scatterer SP may include any one of $TiO_2$, ZnO, $Al_2O_3$, $SiO_2$, and hollow silica, or may be a mixture of at least two materials selected from among $TiO_2$, ZnO, $Al_2O_3$, $SiO_2$, and hollow silica.

The first light control part CCP1, the second light control part CCP2, and the third light control part CCP3 each may include base resins BR1, BR2, and BR3 in which the quantum dots QD1 and QD2 and the scatterer SP are dispersed. In an embodiment, the first light control part CCP1 may include the first quantum dot QD1 and the scatterer SP dispersed in a first base resin BR1, the second light control part CCP2 may include the second quantum dot QD2 and the scatterer SP dispersed in a second base resin BR2, and the third light control part CCP3 may include the scatterer SP dispersed in a third base resin BR3. The base resins BR1, BR2, and BR3 are media in which the quantum dots QD1 and QD2 and the scatterer SP are dispersed, and may be formed of various resin compositions, which may be generally referred to as a binder. For example, the base resins BR1, BR2, and BR3 may be acrylic-based resins, urethane-based resins, silicone-based resins, epoxy-based resins, etc. The base resins BR1, BR2, and BR3 may be transparent resins. In an embodiment, the first base resin BR1, the second base resin BR2, and the third base resin BR3 may each be the same as or different from each other.

The light control layer CCL may include a barrier layer BFL1. The barrier layer BFL1 may prevent the penetration of moisture and/or oxygen (hereinafter, referred to as 'moisture/oxygen'). The barrier layer BFL1 may be disposed on the light control parts CCP1, CCP2, and CCP3 to block the light control parts CCP1, CCP2 and CCP3 from being exposed to moisture/oxygen. The barrier layer BFL1 may cover the light control parts CCP1, CCP2, and CCP3. A barrier layer BFL2 may be provided between the light control parts CCP1, CCP2, and CCP3 and the color filter layer CFL.

The barrier layers BFL1 and BFL2 may include at least one inorganic layer. For example, the barrier layers BFL1 and BFL2 may include an inorganic material. For example, the barrier layers BFL1 and BFL2 may include a silicon nitride, an aluminum nitride, a zirconium nitride, a titanium nitride, a hafnium nitride, a tantalum nitride, a silicon oxide, an aluminum oxide, a titanium oxide, a tin oxide, a cerium oxide, a silicon oxynitride, a metal thin film which secures a transmittance, etc. The barrier layers BFL1 and BFL2 may further include an organic film. The barrier layers BFL1 and BFL2 may be formed of a single layer or of multiple layers.

In the display apparatus DD of an embodiment, the color filter layer CFL may be disposed on the light control layer CCL. For example, the color filter layer CFL may be directly disposed on the light control layer CCL. For example, in an embodiment, the barrier layer BFL2 may be omitted.

The color filter layer CFL may include a light shielding unit BM and filters CF1, CF2, and CF3. The color filter layer CFL may include a first filter CF1 that transmits the second color light, a second filter CF2 that transmits the third color light, and a third filter CF3 that transmits the first color light. For example, the first filter CF1 may be a red filter, the second filter CF2 may be a green filter, and the third filter CF3 may be a blue filter. The filters CF1, CF2, and CF3 may each include a polymeric photosensitive resin and a pigment or dye. The first filter CF1 may include a red pigment or dye, the second filter CF2 may include a green pigment or dye, and the third filter CF3 may include a blue pigment or dye. However, embodiments are not limited thereto, and the third filter CF3 may not include a pigment or dye. The third filter CF3 may include a polymeric photosensitive resin and may not include a pigment or dye. The third filter CF3 may be transparent. The third filter CF3 may be formed of a transparent photosensitive resin.

In an embodiment, the first filter CF1 and the second filter CF2 may each be a yellow filter. The first filter CF1 and the second filter CF2 may not be separated but be provided as one filter.

The light shielding unit BM may be a black matrix. The light shielding unit BM may include an organic light shielding material or an inorganic light shielding material containing a black pigment or dye. The light shielding unit BM may prevent light leakage, and may separate boundaries between the adjacent filters CF1, CF2, and CF3. In an embodiment, the light shielding unit BM may be formed of a blue filter.

The first to third filters CF1, CF2, and CF3 may be disposed corresponding to the red light emitting region PXA-R, the green light emitting region PXA-G, and the blue light emitting region PXA-B, respectively.

A base substrate BL may be disposed on the color filter layer CFL. The base substrate BL may be a member which provides a base surface on which the color filter layer CFL, the light control layer CCL, and the like are disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawing, in an embodiment, the base substrate BL may be omitted.

FIG. 8 is a schematic cross-sectional view illustrating a part of a display apparatus according to an embodiment. FIG. 8 illustrates a schematic cross-sectional view of a part corresponding to the display panel DP of FIG. 7. In the display apparatus DD-TD of an embodiment, the light emitting device ED-BT may include light emitting structures OL-B1, OL-B2, and OL-B3. The light emitting device ED-BT may include a first electrode EL1 and a second electrode EL2 which face each other, and the light emitting structures OL-B1, OL-B2, and OL-B3 sequentially stacked in a thickness direction between the first electrode EL1 and the second electrode EL2. The light emitting structures OL-B1, OL-B2, and OL-B3 may each include an emission layer EML (FIG. 7), a hole transport region HTR, and an electron transport region ETR, with the emission layer EML (FIG. 7) disposed therebetween.

The light emitting device ED-BT included in the display apparatus DD-TD of an embodiment may be a light emitting device having a tandem structure and including multiple emission layers.

In an embodiment illustrated in FIG. 8, light emitted from the light emitting structures OL-B1, OL-B2, and OL-B3 may each be blue light. However, embodiments are not limited thereto, and the light respectively emitted from the light emitting structures OL-B1, OL-B2, and OL-B3 may have wavelength ranges different from each other. For example, the light emitting device ED-BT including the light emitting structures OL-B1, OL-B2, and OL-B3 which emit light having wavelength ranges different from each other may emit white light.

Charge generation layers CGL1 and CGL2 may be disposed between neighboring light emitting structures OL-B1, OL-B2, and OL-B3. The charge generation layers CGL1 and CGL2 may each include a p-type charge generation layer and/or an n-type charge generation layer.

At least one of the light emitting structures OL-B1, OL-B2, and OL-B3 included in the display device DD-TD of an embodiment may contain the above-described amine compound of an embodiment.

The light emitting device ED according to an embodiment may include the above-described amine compound of an embodiment in at least one functional layer disposed between the first electrode EL1 and the second electrode EL2, thereby exhibiting improved luminous efficiency and service life characteristics. The light emitting device ED according to an embodiment may include the above-described amine compound of an embodiment in at least one of the hole transport region HTR, the emission layer EML, or the electron transport region ETR disposed between the first electrode EL1 and the second electrode EL2, or in a capping layer CPL.

For example, the amine compound according to an embodiment may be included in the hole transport region HTR of the light emitting device ED of an embodiment, and the light emitting device of an embodiment may exhibit excellent luminous efficiency and long service life characteristics.

The above-described amine compound of an embodiment includes a carbazole moiety and an amine derivative having at least one dibenzoheterole group, and has a molecular structure in which the amine derivative is directly or indirectly bonded to the carbazole moiety at an ortho-position to the nitrogen atom of the carbazole moiety, thereby exhibiting excellent film properties and excellent electron resistance and heat stability characteristics due to the steric structure of the amine compound. Owing to such molecular structural characteristics of the amine compound, the amine compound of an embodiment has excellent hole transport ability and improved material stability, and if the amine compound is used as a material of the light emitting device, it may improve luminous efficiency and may increase service life of the light emitting device.

Hereinafter, with reference to Examples and Comparative Examples, an amine compound according to an embodiment and a light emitting device of an embodiment will be described in detail. However, the Examples shown below are illustrated only for the understanding of the disclosure, and the scope of the embodiments are not limited thereto.

EXAMPLES

1. Synthesis of Amine Compound

First, a synthesis method of an amine compound according to an embodiment will be described in detail by illustrating the synthesis methods of Compounds 1, 30, 43, 93, 109, 204, 277, and 290 of Compound Group 1. In the following descriptions, the synthesis method of the amine compound is provided as an example, but the synthesis method according to an embodiment is not limited to Examples below.

Synthesis of Compound 1

Amine Compound 1 according to an example may be synthesized by, for example, the steps shown in Reaction Scheme 1 below:

[Reaction Scheme 1]

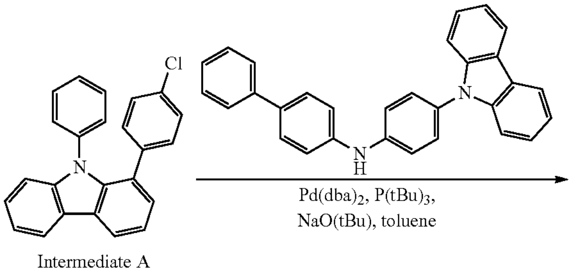

Intermediate A

-continued

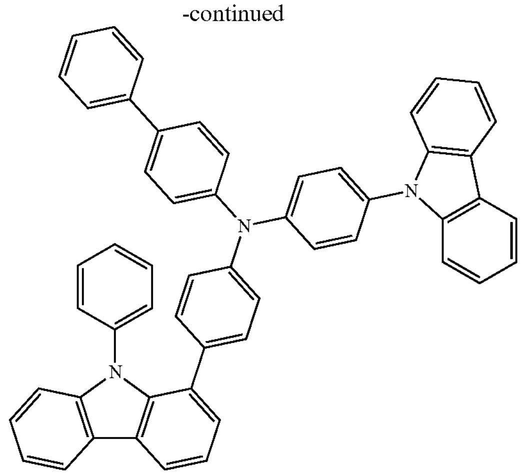

1

In an argon (Ar) atmosphere, in a 300 mL three-neck flask, Intermediate A (10.0 g, 28.32 mmol), Pd(dba)$_2$ (0.81 g, 0.05 equiv, 1.42 mmol), NaO$^t$Bu (2.72 g, 1 equiv, 28.32 mmol), toluene (283 mL), N-biphenyl-N—[N-(p-phenyl) carbazole]amine (11.63 g, 28.32 mmol), and $^t$Bu$_3$P (1.15 g, 0.2 equiv, 3.0 mmol) were sequentially added, and the resulting mixture was heated and stirred under reflux for about 6 hours. After air cooling to room temperature, organic layers were separated and obtained by adding water to the reaction solvent. The organic layers were further extracted by adding toluene to a water layer, and the extracted organic layers were combined and washed with saline and dried over $MgSO_4$. $MgSO_4$ was filtered and the organic layers were concentrated, and the resulting crude product was purified by silica gel column chromatography to obtain Compound 1 which is a white solid (6.5 g, yield 70%).

By measuring FAB-MS, a mass number of m/z=727 was observed by molecular ion peak, thereby identifying Compound 1.

Synthesis of Compound 30

Amine Compound 30 according to an example may be synthesized by, for example, the steps shown in Reaction Scheme 2 below:

[Reaction Scheme 2]

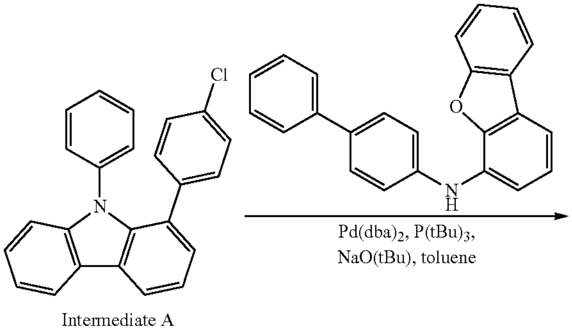

Intermediate A

-continued

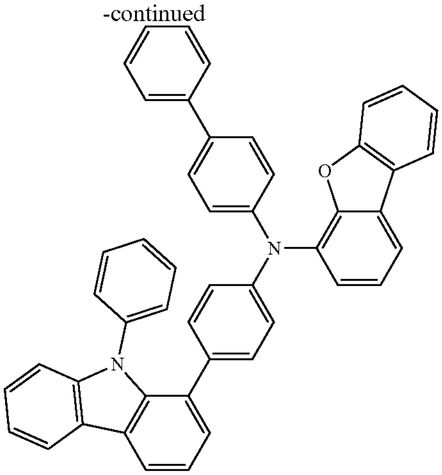

30

Compound 30 was synthesized in the same manner as the synthesis method of Compound 1 except for using N-[(4-biphenyl)-N'-(4-dibenzofuran)]amine instead of N-biphenyl-N—[N-(p-phenyl)carbazole]amine.

By measuring FAB-MS, a mass number of m/z=652 was observed by molecular ion peak, thereby identifying Compound 30.

Synthesis of Compound 43

Amine Compound 43 according to an example may be synthesized by, for example, the steps shown in Reaction Scheme 3 below:

[Reaction Scheme 3]

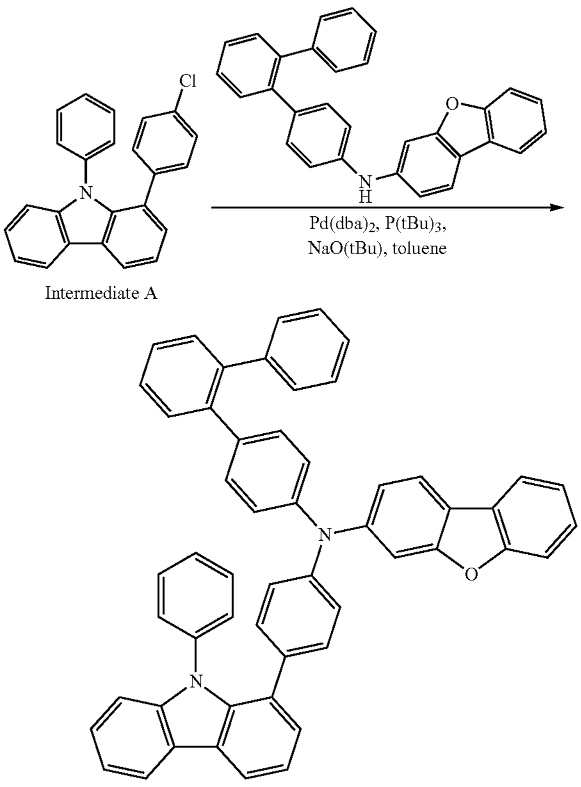

43

Compound 43 was synthesized in the same manner as the synthesis method of Compound 1 except for using N-[4-(2-phenyl)biphenyl-N-(3-dibenzofuran)]amine instead of N-biphenyl-N—[N-(p-phenyl)carbazole]amine.

By measuring FAB-MS, a mass number of m/z=728 was observed by molecular ion peak, thereby identifying Compound 43.

Synthesis of Compound 93

Amine Compound 93 according to an example may be synthesized by, for example, the steps shown in Reaction Scheme 4 below:

[Reaction Scheme 4]

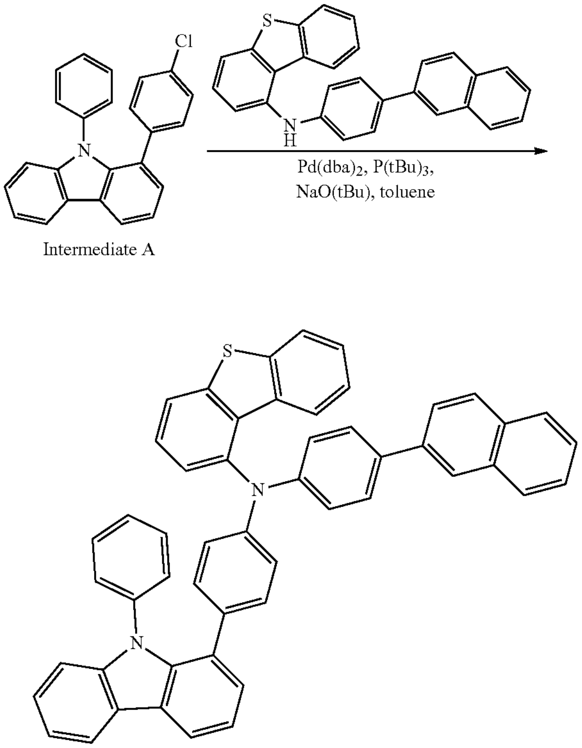

93

Synthesis of Intermediate IM-4

Compound 93 was synthesized in the same manner as the synthesis method of Compound 1 except for using N-[4-(2-naphthalenyl)phenyl]-N-(1-dibenzothiophenyl)amine instead of N-biphenyl-N—[N-(p-phenyl)carbazole]amine.

By measuring FAB-MS, a mass number of m/z=718 was observed by molecular ion peak, thereby identifying Compound 93.

Synthesis of Compound 109

Amine Compound 109 according to an example may be synthesized by, for example, the steps shown in Reaction Scheme 5 below:

[Reaction Scheme 5]

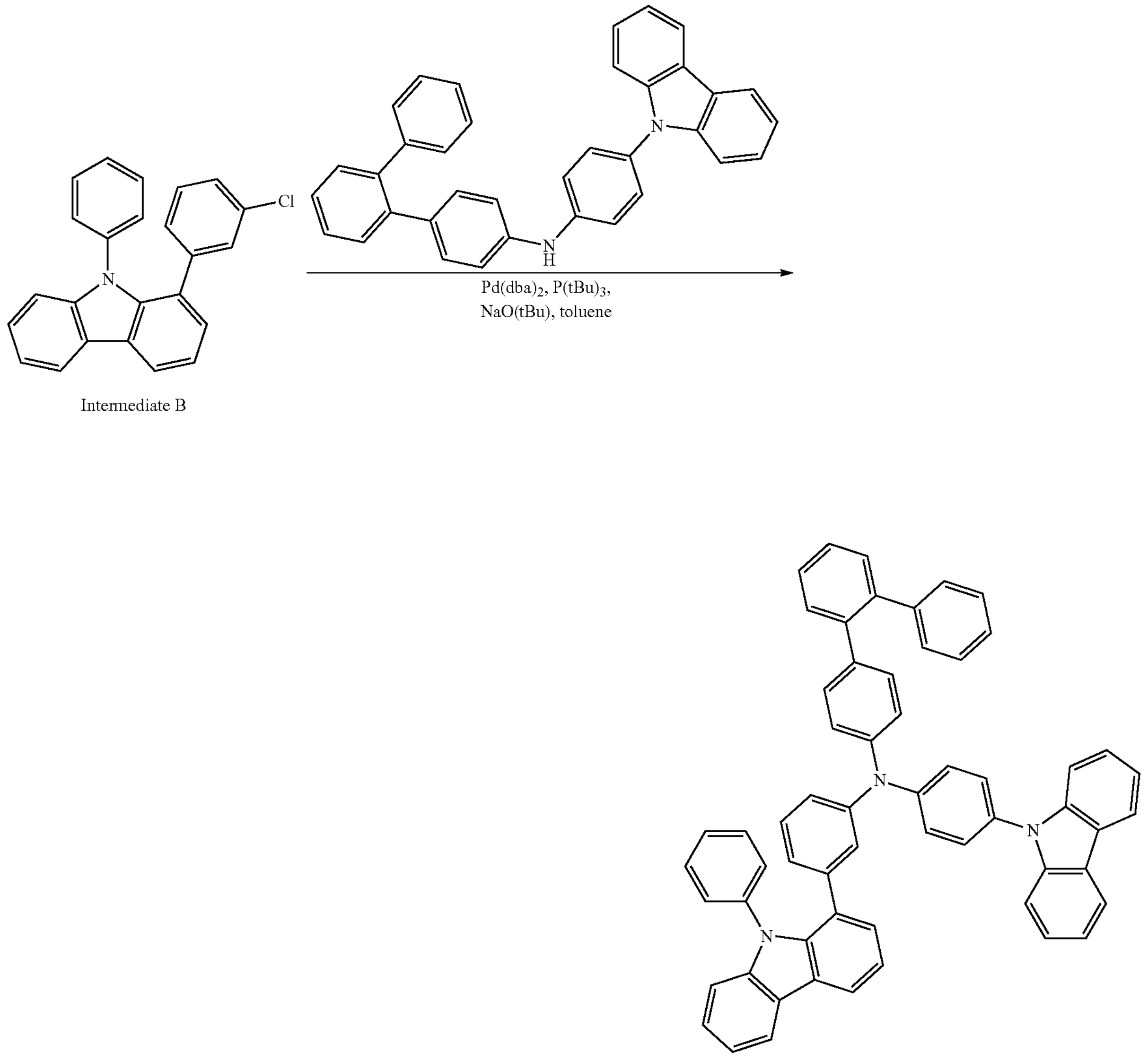

Intermediate B

109

Compound 109 was synthesized in the same manner as the synthesis method of Compound 1 except for using Intermediate B instead of Intermediate A and using N-4-(2-phenyl)biphenyl-N'—(N-(p-phenyl)carbazole)amine instead of N-biphenyl-N—[N-(p-phenyl)carbazole]amine.

By measuring FAB-MS, a mass number of m/z=804 was observed by molecular ion peak, thereby identifying Compound 109.

Synthesis of Compound 204

Amine Compound 204 according to an example may be synthesized by, for example, the steps shown in Reaction Scheme 6 below:

[Reaction Scheme 6]

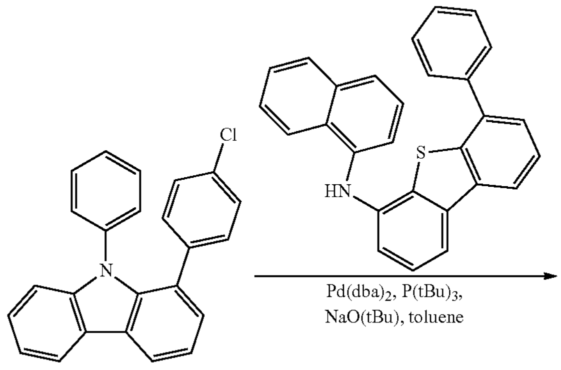

Intermediate A

-continued

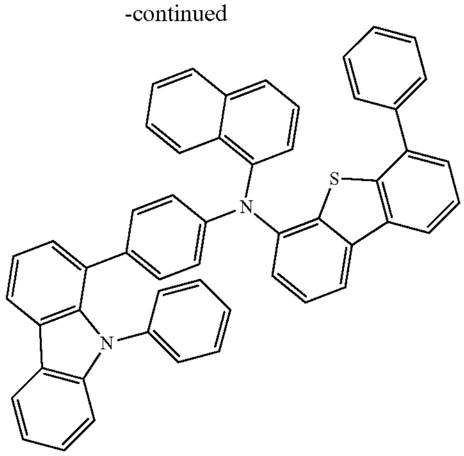

204

Compound 204 was synthesized in the same manner as the synthesis method of Compound 1 except for using N-(1-naphthalenyl)-N-(6-phenyldibenzothiophenyl)amine instead of Intermediate A and N-biphenyl-N—[N-(p-phenyl) carbazole]amine.

By measuring FAB-MS, a mass number of m/z=718 was observed by molecular ion peak, thereby identifying Compound 204.

Synthesis of Compound 277

Amine Compound 277 according to an example may be synthesized by, for example, the steps shown in Reaction Scheme 7 below:

[Reaction Scheme 7]

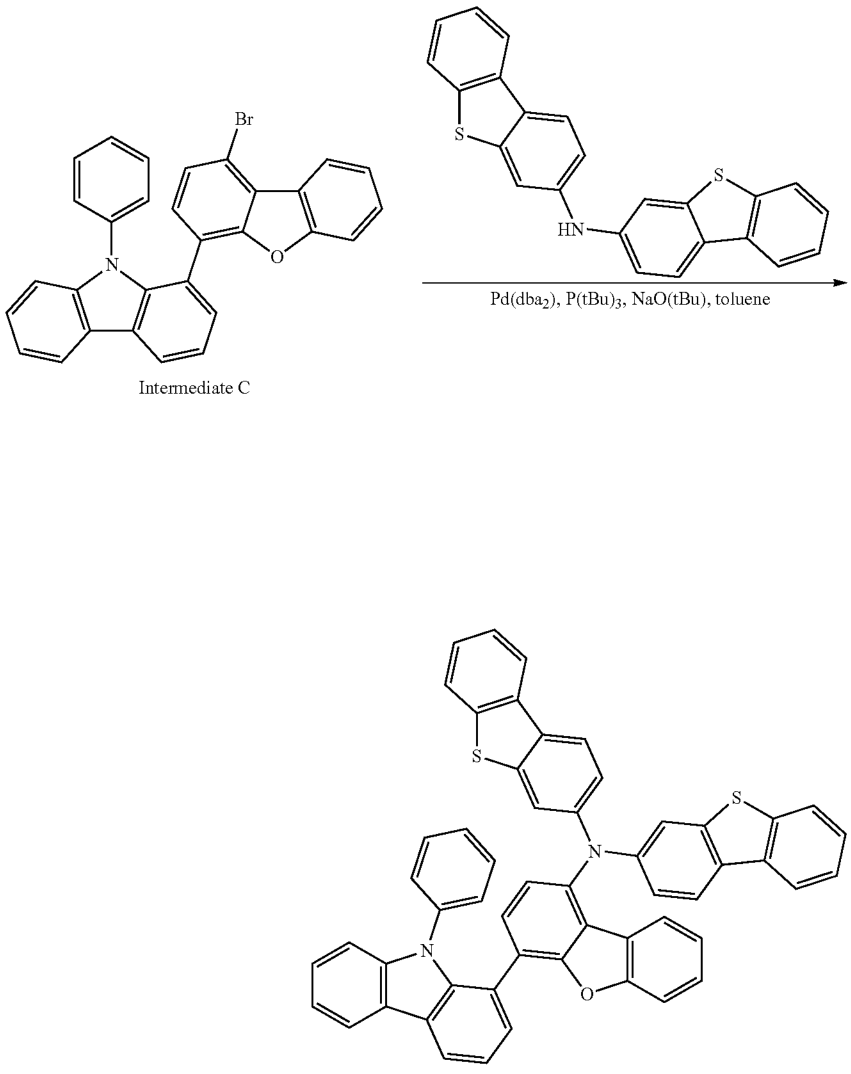

Intermediate C

277

Compound 277 was synthesized in the same manner as the synthesis method of Compound 1 except for using Intermediate C instead of Intermediate A and using N-bis (3-dibenzothiophene)amine instead of N-biphenyl-N—[N-(p-phenyl)carbazole]amine.

By measuring FAB-MS, a mass number of m/z=788 was observed by molecular ion peak, thereby identifying Compound 277.

Synthesis of Compound 290

Amine Compound 290 according to an example may be synthesized by, for example, the steps shown in Reaction Scheme 8 below:

[Reaction Scheme 8]

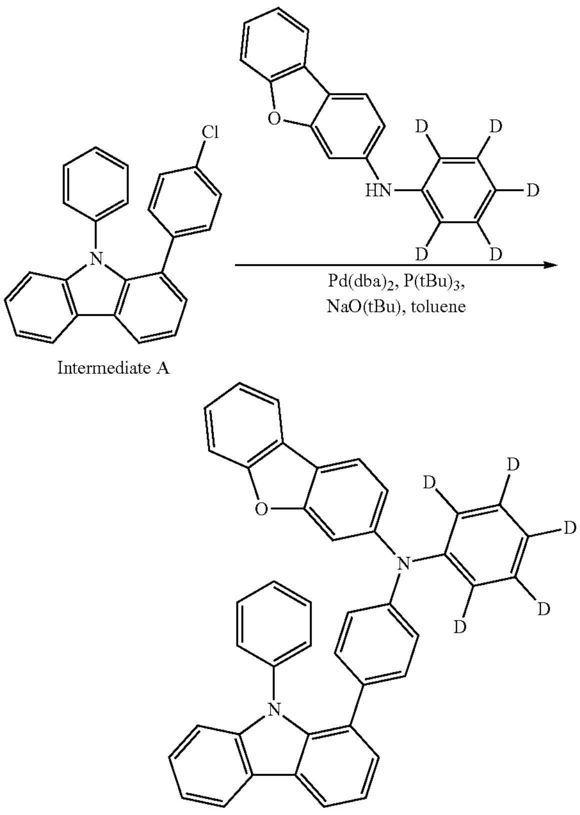

290

Compound 290 was synthesized in the same manner as the synthesis method of Compound 1 except for using N-2,3,4,5,6-d5-phenyl-N-[3-dibenzofuran]amine instead of N-biphenyl-N—[N-(p-phenyl)carbazole]amine.

By measuring FAB-MS, a mass number of m/z=581 was observed by molecular ion peak, thereby identifying Compound 290.

2. Manufacture and Evaluation of Light Emitting Device

Manufacture of Light Emitting Device

The light emitting device of an embodiment including the amine compound of an embodiment in a hole transport layer was manufactured as follows. Amine compounds of Compound 1, Compound 30, Compound 43, Compound 93, Compound 109, Compound 204, Compound 277, and Compound 290 as described above were used as a hole transport layer material to manufacture the light emitting devices of Examples 1 to 8, respectively. Comparative Example Compounds R1 to R5 were used as hole transport layer materials to manufacture the light emitting devices of Comparative Examples 1 to 5, respectively.

Compounds used in the hole transport layers in Examples 1 to 8 and Comparative Examples 1 to 5 are shown as follows.

Example Compounds Used to Manufacture Devices

1

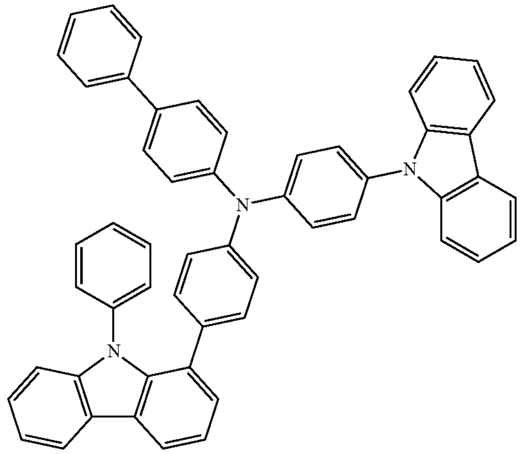

30

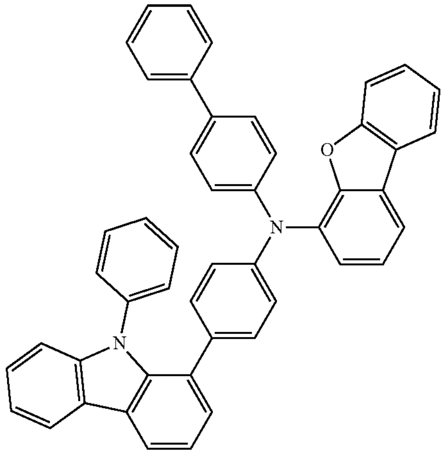

-continued
43
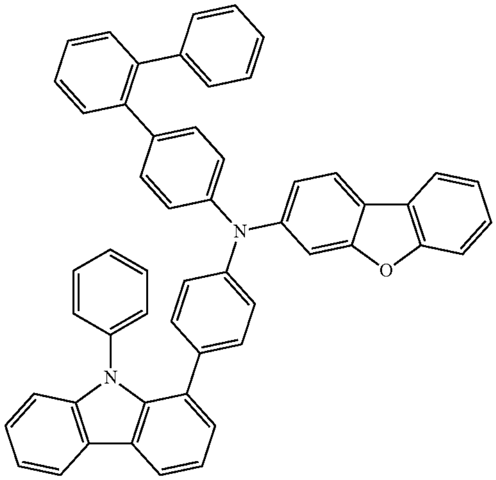
93
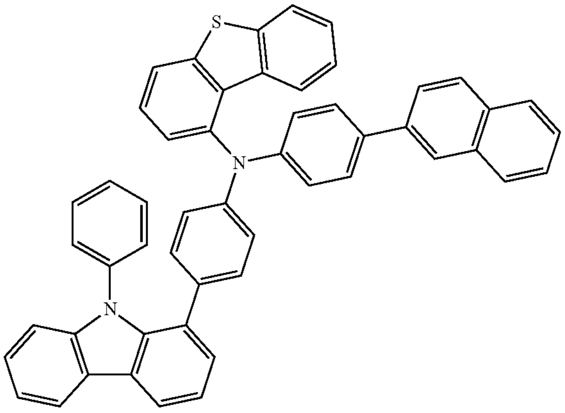
108
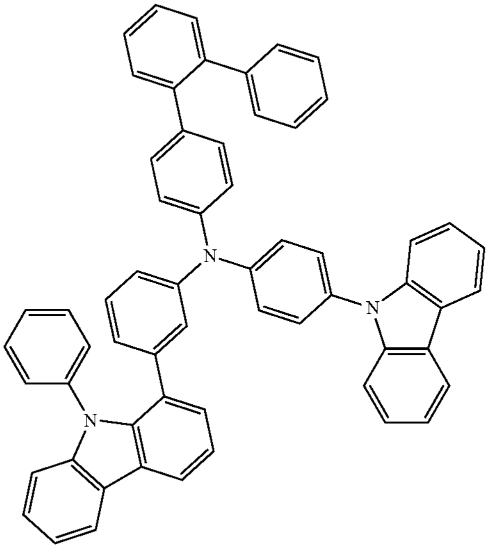
-continued
204
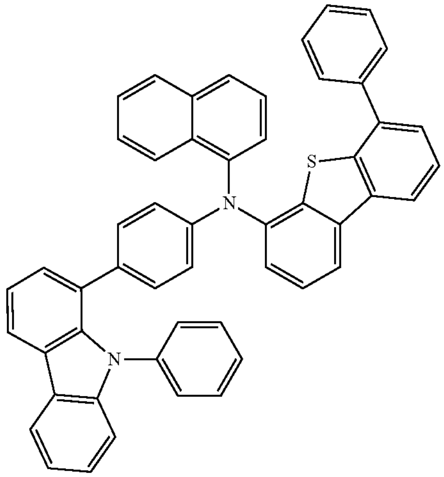
277
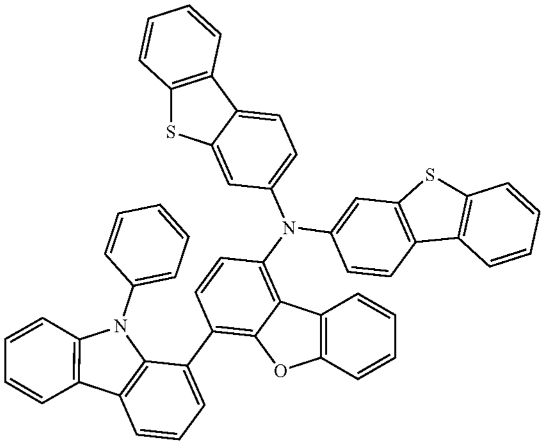
290
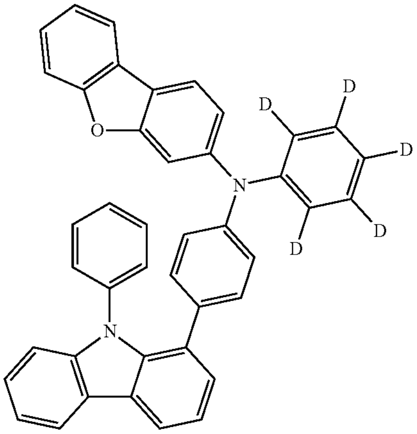

Comparative Example Compounds Used to Manufacture Devices

R1

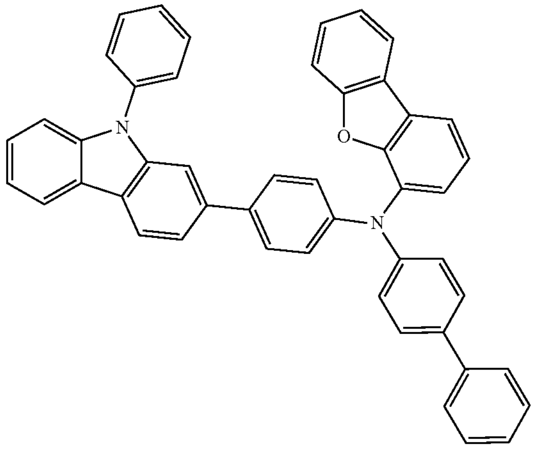

R2

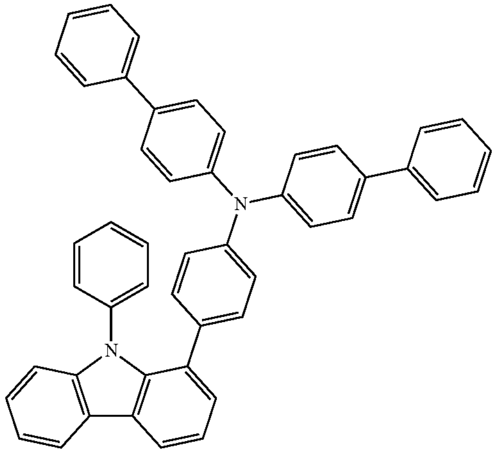

R3

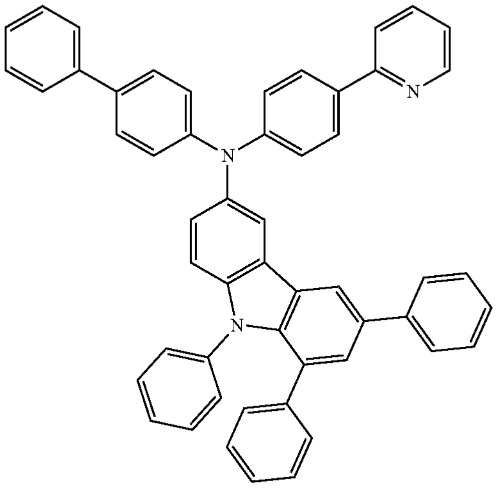

-continued

R4

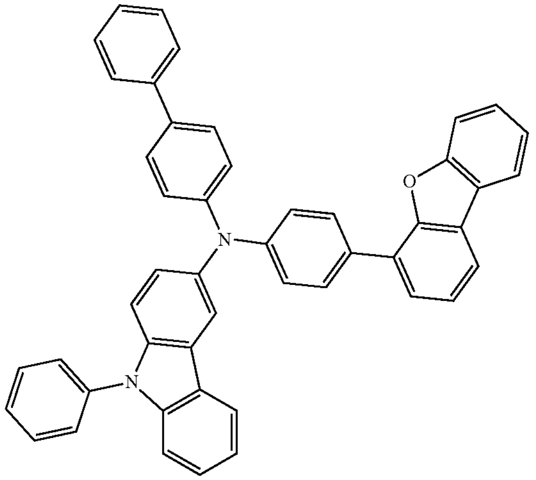

R5

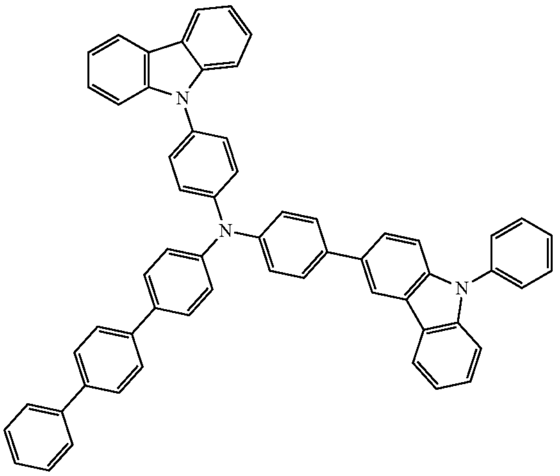

A 1500 Å-thick ITO was patterned on a glass substrate, washed with ultrapure water, and UV ozone-treated for about 10 minutes. 2-TNATA was deposited to form a 600 Å-thick hole injection layer. The Example Compound or Comparative Example Compound was deposited to form a 300 Å-thick hole transport layer.

TBP was doped to ADN by 3% to form a 250 Å-thick emission layer. $Alq_3$ was deposited to form a 250 Å-thick electron transport layer, and LiF was deposited to form a 10 Å-thick electron injection layer.

A1 was deposited to form a 1,000 Å-thick second electrode.

In the Examples, the hole injection layer, the hole transport layer, the emission layer, the electron transport layer, the electron injection layer, and the second electrode were formed by using a vacuum deposition apparatus.

(Evaluation of Light Emitting Device Characteristics)

Evaluation results of the light emitting devices of Examples 1 to 8 and Comparative Examples 1 to 5 are listed in Table 1. Driving voltages, luminous efficiencies, and device service lives of the manufactured light emitting devices are listed in comparison in Table 1. In the evaluation results of the characteristics for Examples and Comparative Examples listed in Table 1, the luminous efficiency shows an efficiency value at a current density of 10 $mA/cm^2$, and the device service life (LT50) shows a brightness half-life at an initial brightness of 1,000 cd/$m^2$.

Current densities, voltages, and luminous efficiencies of the light emitting devices of Examples and Comparative Examples were measured in a dark room by using 2400 Series Source Meter from Keithley Instruments, Inc., CS-200, Color and Luminance Meter from Konica Minolta, Inc., and PC Program LabVIEW 2.0 for the measurement from Japan National Instrument, Inc.

TABLE 1

| Device manufacturing examples | Hole transport layer material | Voltage (V) | Effi-ciency (cd/A) | Service life LT50 (h) |
|---|---|---|---|---|
| Example 1 | Example Compound 1 | 5.7 | 8.9 | 2100 |
| Example 2 | Example Compound 30 | 5.8 | 9.2 | 2000 |
| Example 3 | Example Compound 43 | 5.6 | 8.7 | 2250 |
| Example 4 | Example Compound 93 | 5.7 | 9.3 | 2200 |
| Example 5 | Example Compound 109 | 5.6 | 9.2 | 2100 |
| Example 6 | Example Compound 204 | 5.8 | 9.1 | 2050 |
| Example 7 | Example Compound 277 | 5.7 | 9.0 | 2150 |
| Example 8 | Example Compound 290 | 5.7 | 8.9 | 1900 |
| Comparative Example 1 | Comparative Example Compound R1 | 6.0 | 5.4 | 1400 |
| Comparative Example 2 | Comparative Example Compound R2 | 6.0 | 7.9 | 1600 |
| Comparative Example 3 | Comparative Example Compound R3 | 5.9 | 6.2 | 1000 |
| Comparative Example 4 | Comparative Example Compound R4 | 6.1 | 5.6 | 1200 |
| Comparative Example 5 | Comparative Example Compound R5 | 5.8 | 6.4 | 1700 |

Referring to the results of Table 1, it may be seen that Examples of the light emitting devices using the amine compounds according to examples of the disclosure as hole transport layer materials exhibit low driving voltage, excellent device efficiency, and improved device service life characteristics compared to Comparative Examples.

The amine compounds according to examples have the structure of the amine compound with an o-carbazole skeleton in which the N of the carbazole moiety and the amine derivative are bonded at an ortho-position, and thus Examples including the amine compounds of examples exhibit low driving voltage, long service life, and high efficiency characteristics. It is believed that the amine compounds of examples exhibit excellent hole transport ability and long service life characteristics by introducing the carbazole skeleton having excellent resistance against heat or charge.

The amine compounds of examples have improved hole transport ability by introducing the dibenzoheterole group containing the O, S, or N atom as a substituent of the amine derivative as well as the N atom contained in the carbazole moiety. Thus, it is believed that when the amine compounds of examples are used as a hole transport region material, the recombination probability of holes and electrons in the emission layer is improved, thereby improving luminous efficiency of the devices.

The light emitting devices of examples including the amine compounds of examples in the hole transport regions exhibited low driving voltage, high luminous efficiency, and improved service life characteristics.

Example Compound 93 used in Example 4 has, in the amine derivative, 1-dibenzothiophene as a high-efficient substituent and a b-naphthylphenyl group with a long service life characteristic, and thus Example 4 achieved high device efficiency and a long service life. This effect of improving device characteristics is achieved because an amine group is bonded to the carbazole at an ortho-position to the nitrogen atom of the carbazole in the Example Compound that is used, and thus the volume around the nitrogen atom (N) of the amine is increased and the symmetry of the entire molecule is broken to suppress crystallinity, thereby improving film characteristics of the hole transport region. It may be considered that the luminous efficiency of the light emitting device of the Example is improved because a hole transport property of Example Compound is improved, thereby improving the recombination probability of holes and electrons in the emission layer.

Comparative Example Compound R1 used in Comparative Example 1 has a different bonding position of the amine derivative in the carbazole from Example Compounds. Comparative Example Compound R1, in which the amine derivative is substituted with the N atom of the carbazole at the meta-position, molecular structurally does not have a large volume around the N atom of the amine, thereby deteriorating film characteristics during the manufacture of the device. When Comparative Example Compound R1 was used as a hole transport layer material, the characteristics of both reduced device efficiency and reduced service life were exhibited compared to the Examples.

Comparative Example Compound R2 used in Comparative Example 2 has a skeleton structure of the carbazole amine, in which the amine derivative is substituted at the ortho-position of the carbazole, but has a difference from Example Compounds in that both substituents substituted at the amine derivative are aryl groups. Comparative Example Compound R2 includes aryl groups as all substituents substituted at the amine derivative, thereby exhibiting reduced molecular planarity and reduced hole transport properties compared to Example Compounds. Accordingly, Comparative Example 2 using Comparative Example Compound R2 exhibited the characteristic of reduced both device efficiency and service life compared to Examples.

Comparative Example Compound R3 used in Comparative Example 3 has a different bonding position of the carbazole moiety and the amine derivative from Example Compounds, and also exhibits the characteristic of reduced hole transport property by introducing a pyridine substituent in the molecule compared to Example Compounds. Comparative Example 3 using Comparative Example Compound R3 exhibited the characteristic of reduced both device efficiency and service life compared to Examples.

From the comparative evaluation results of Examples and Comparative Examples listed in Table 1, it may be confirmed that in the case where the amine compound of an example is used as a hole transport layer material, the light emitting device exhibits long service life and high efficiency characteristics compared to the case of using Comparative Examples.

The amine compound of an example includes the amine derivative bonded to the carbazole skeleton at an ortho-position to the nitrogen atom of the carbazole skeleton to increase the volume around the nitrogen atom of the amine derivative, and also introduces the dibenzoheterole group as a substituent of the amine derivative, thereby exhibiting effects of improving the hole transport property of the entire molecule and improving electron resistance, heat stability, and film characteristics of the material. The light emitting device of an example includes the amine compound of an example, thereby achieving long service life and high efficiency characteristics simultaneously.

The light emitting device of an embodiment may include the amine compound of an embodiment in the hole transport region, thereby exhibiting high efficiency and long service life characteristics.

The amine compound of an embodiment may improve luminous efficiency and a device service life of the light emitting device.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. A light emitting device comprising:

a first electrode;

a second electrode disposed on the first electrode; and at least one functional layer disposed between the first electrode and the second electrode and comprising an amine compound represented by any one of Compounds 204 and 277:

204

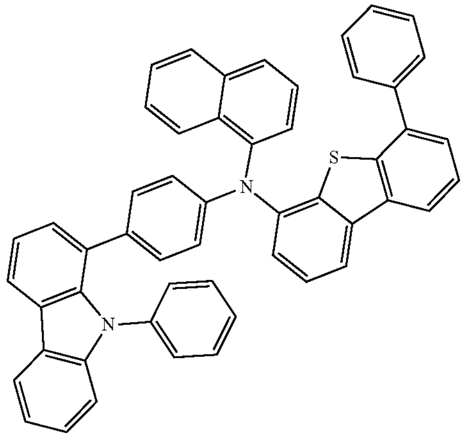

277

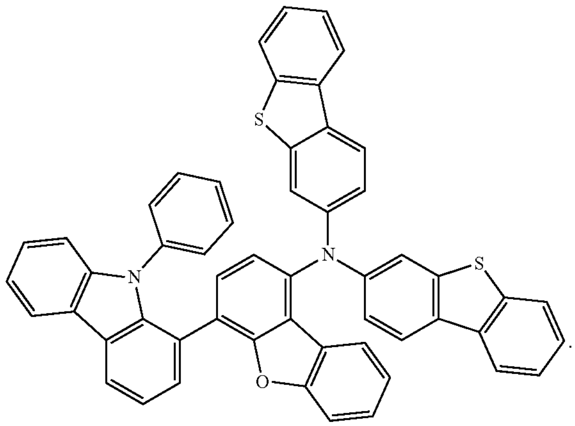

.

2. The light emitting device of claim 1, wherein the at least one functional layer comprises:

an emission layer;

a hole transport region disposed between the first electrode and the emission layer; and an electron transport region disposed between the emission layer and the second electrode, and the hole transport region comprises the amine compound.

3. The light emitting device of claim 2, wherein the hole transport region comprises at least one of a hole injection layer, a hole transport layer, and an electron blocking layer, and at least one of the hole injection layer, the hole transport layer, and the electron blocking layer comprises the amine compound.

4. The light emitting device of claim 2, wherein the emission layer further comprises a compound represented by Formula E-1:

[Formula E-1]

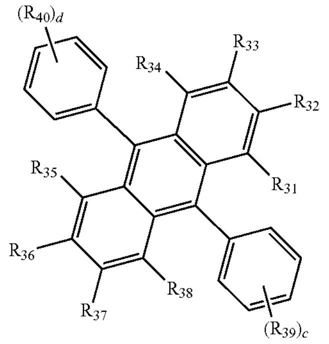

wherein in Formula E-1, c and d are each independently an integer from 0 to 5, and $R_{31}$ to $R_{40}$ are each independently a hydrogen atom, a deuterium atom, a halogen atom, a substituted or unsubstituted silyl group, a substituted or unsubstituted alkyl group having 1 to 20 carbon atoms, a substituted or unsubstituted alkenyl group having 2 to 20 carbon atoms, a substituted or unsubstituted oxy group, a substituted or unsubstituted thiol group, a substituted or unsubstituted aryl group having 6 to 30 ring-forming carbon atoms, or a substituted or unsubstituted heteroaryl group having 2 to 30 ring-forming carbon atoms, or are bonded to an adjacent group to form a ring.

5. The light emitting device of claim 2, wherein the emission layer emits blue light or green light.

6. An amine compound represented by any one of Compounds 204 and 277:

204

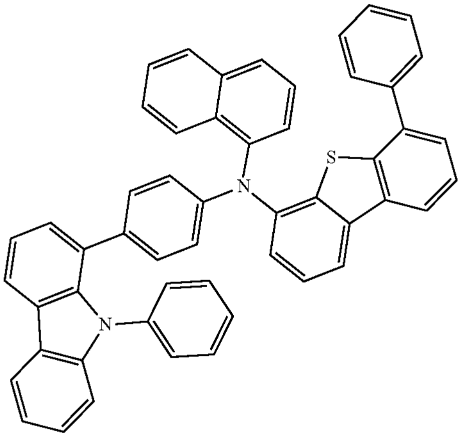

277

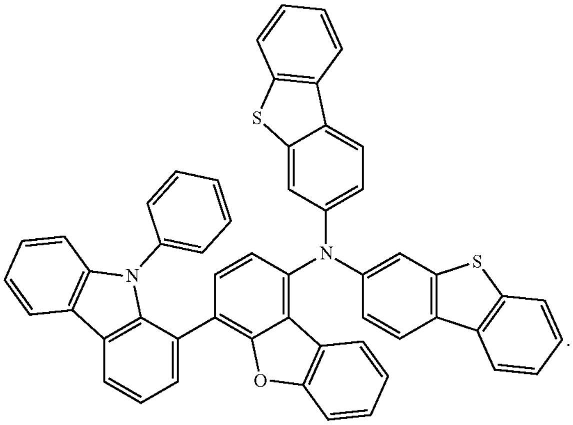

.

7. A display comprising:

a display panel including a plurality of light emitting devices, wherein at least one of the light emitting devices comprises:

a first electrode, a second electrode disposed on the first electrode, and at least one functional layer disposed between the first electrode and the second electrode and comprising an amine compound represented by any one of Compounds 204 and 277:

204

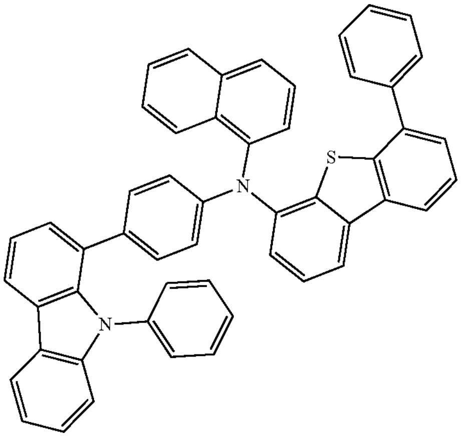

277

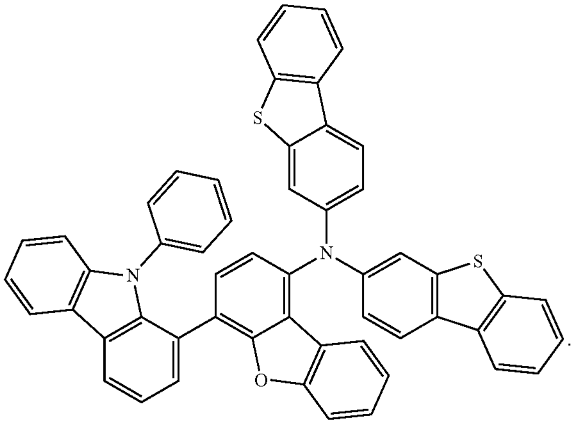

.

* * * * *